(12) United States Patent
Zhang et al.

(10) Patent No.: US 10,501,538 B2
(45) Date of Patent: Dec. 10, 2019

(54) ANTI-LILRB ANTIBODIES AND THEIR USE IN DETECTING AND TREATING CANCER

(71) Applicant: THE BOARD OF REGENTS OF THE UNIVERSITY OF TEXAS SYSTEM, Austin, TX (US)

(72) Inventors: Chengcheng Zhang, Dallas, TX (US); Mi Deng, Plano, TX (US); Wei Xiong, Pearland, TX (US); Zhiqiang An, Houston, TX (US); Ningyan Zhang, Houston, TX (US); Xun Gui, Houston, TX (US); Junke Zheng, Shanghai (CN)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 48 days.

(21) Appl. No.: 15/696,972

(22) Filed: Sep. 6, 2017

(65) Prior Publication Data
US 2018/0086829 A1 Mar. 29, 2018

Related U.S. Application Data

(63) Continuation-in-part of application No. PCT/US2016/020838, filed on Mar. 4, 2016.

(60) Provisional application No. 62/129,572, filed on Mar. 6, 2015.

(51) Int. Cl.
| | |
|---|---|
| *A61K 39/395* | (2006.01) |
| *C07K 16/28* | (2006.01) |
| *G01N 33/574* | (2006.01) |
| *C12N 15/113* | (2010.01) |
| *A61P 35/02* | (2006.01) |
| *A61K 45/06* | (2006.01) |
| *C07K 16/30* | (2006.01) |
| *A61K 39/00* | (2006.01) |

(52) U.S. Cl.
CPC ...... *C07K 16/2803* (2013.01); *A61K 39/3955* (2013.01); *A61K 45/06* (2013.01); *A61P 35/02* (2018.01); *C07K 16/3061* (2013.01); *C12N 15/1138* (2013.01); *G01N 33/57426* (2013.01); *G01N 33/57492* (2013.01); *A61K 2039/505* (2013.01); *C07K 2317/14* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C12N 2310/14* (2013.01); *C12N 2310/531* (2013.01); *G01N 2333/70503* (2013.01)

(58) Field of Classification Search
CPC .................................................. C07K 16/2803
See application file for complete search history.

(56) References Cited

U.S. PATENT DOCUMENTS

| | | |
|---|---|---|
| 9,868,777 B2 | 1/2018 | Fu et al. |
| 2002/0176855 A1 | 11/2002 | Co et al. |
| 2005/0287538 A1 | 12/2005 | Cheung |
| 2006/0223096 A1 | 10/2006 | Umana |
| 2009/0041783 A1 | 2/2009 | Takayama et al. |
| 2011/0044894 A1 | 2/2011 | Karsunky |
| 2012/0328616 A1 | 12/2012 | Li et al. |
| 2014/0356364 A1 | 12/2014 | Langermann et al. |
| 2016/0130327 A1 | 5/2016 | Fu et al. |

FOREIGN PATENT DOCUMENTS

| | | |
|---|---|---|
| JP | 2008-543317 | 12/2008 |
| WO | WO 2006/138739 | 12/2006 |
| WO | WO 2013/033734 | 3/2013 |
| WO | WO 2013/181438 | 12/2013 |
| WO | WO 2014/059028 | 4/2014 |
| WO | WO 2014/200898 | 12/2014 |

OTHER PUBLICATIONS

Paul, Fundamental Immunology, 3rd Edition, 1993, pp. 292-295 (Year: 1993).*
Rudikoff et al(Proc. Natl. Acad. Sci. USA 1982 vol. 79: p. 1979). (Year: 1982).*
Pascalis et al (The Journal of Immunology (2002) 169, 3076-3084) (Year: 2002).*
Casset et al. (2003) BBRC 307, 198-205 (Year: 2003)*
Brown et al (J. Immunol. May 1996; 156(9):3285-3291 (Year: 1996).*
Vajdos et al (J. Mol. Biol. Jul. 5, 2002;320(2); 415-428) (Year: 2002).*
International Preliminary Report on Patentability issued in International Application No. PCT/US16/20838, dated Sep. 21, 2017.
International Search Report and Written Opinion issued in International Application No. PCT/US16/20838, dated Sep. 8, 2016.
Invitation to Pay Additional Fees issued in International Application No. PCT/US16/20838, dated Jun. 14, 2016.
Kang, Xunlei, et al. "The ITIM-Containing Receptor LAIR1 is Essential for Acute Myeloid Leukaemia Development." *Nature Cell Biology* 17.5 (2015): 665.
Sun, Yuping, et al. "Expression of Ig-like Transcript 4 Inhibitory Receptor in Human Non-Small Cell Lung Cancer." *Chest* 134.4 (2008): 783-788.
Supplemental European Search Report issued in European Application No. 16762200.0, dated Oct. 8, 2018.
Zheng, Junke, et al. "Inhibitory Receptors Bind ANGPTLs and Support Blood Stem Cells and Leukaemia Development." *Nature* 485.7400 (2012): 656.

(Continued)

*Primary Examiner* — Sheela J. Huff
(74) *Attorney, Agent, or Firm* — Parker Highlander PLLC

(57) ABSTRACT

The present disclosure is directed to antibodies binding to LILRBs and methods of detecting and treating cancer therewith.

24 Claims, 116 Drawing Sheets

Specification includes a Sequence Listing.

(56) References Cited

OTHER PUBLICATIONS

Extended European Search Report issued in corresponding European Application No. 16762200.0, dated Jan. 21, 2019.
Office Communication issued in corresponding Korean Application No. 10-2017-7026448, dated Mar. 25, 2019.
Office Communication issued in corresponding Japanese Application No. 2017-546907, dated Aug. 26, 2019. English Translation.

* cited by examiner

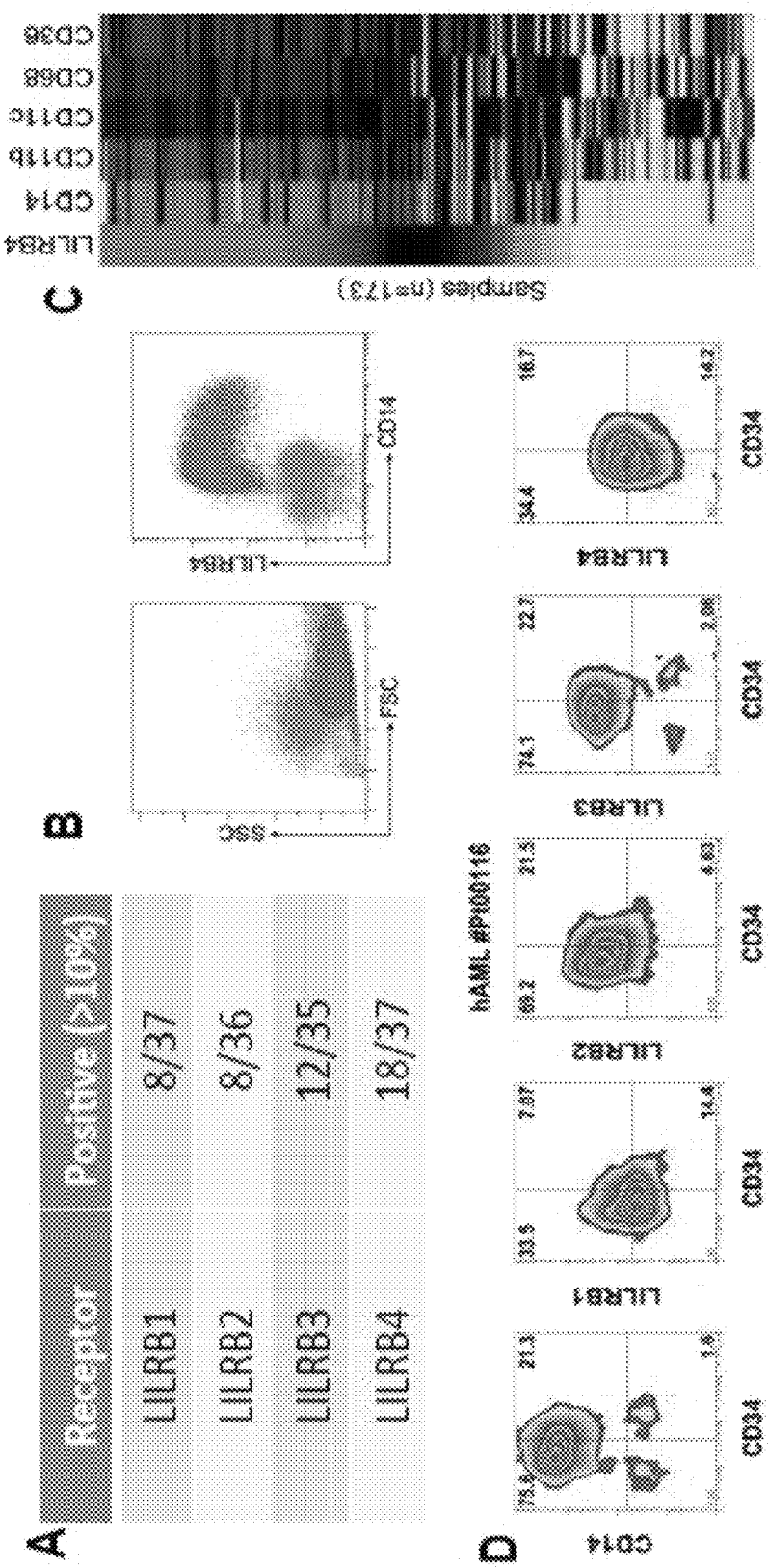
FIGS. 1A-D

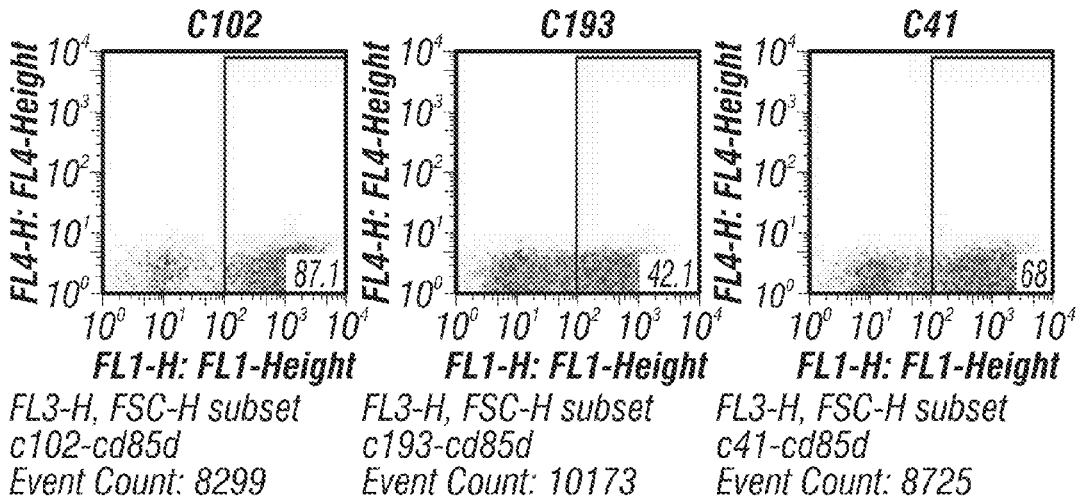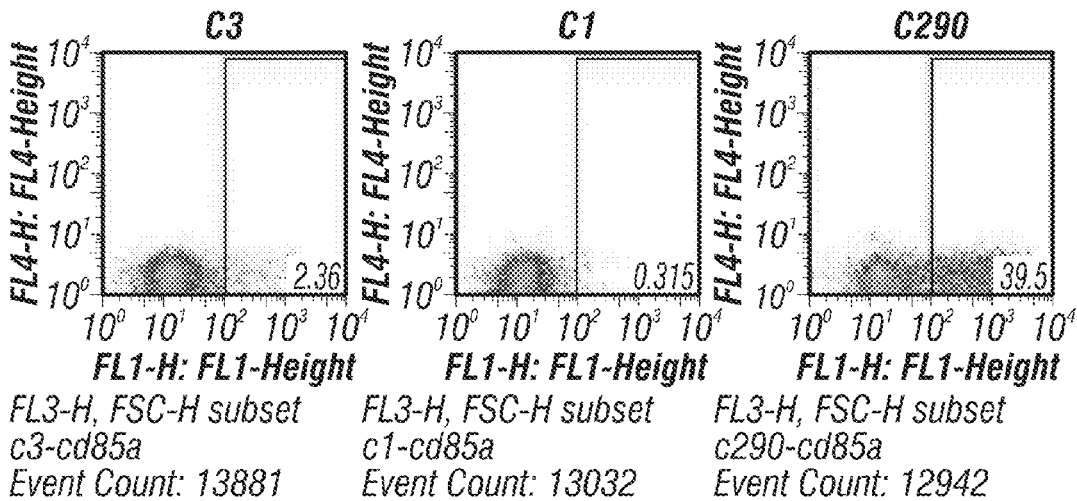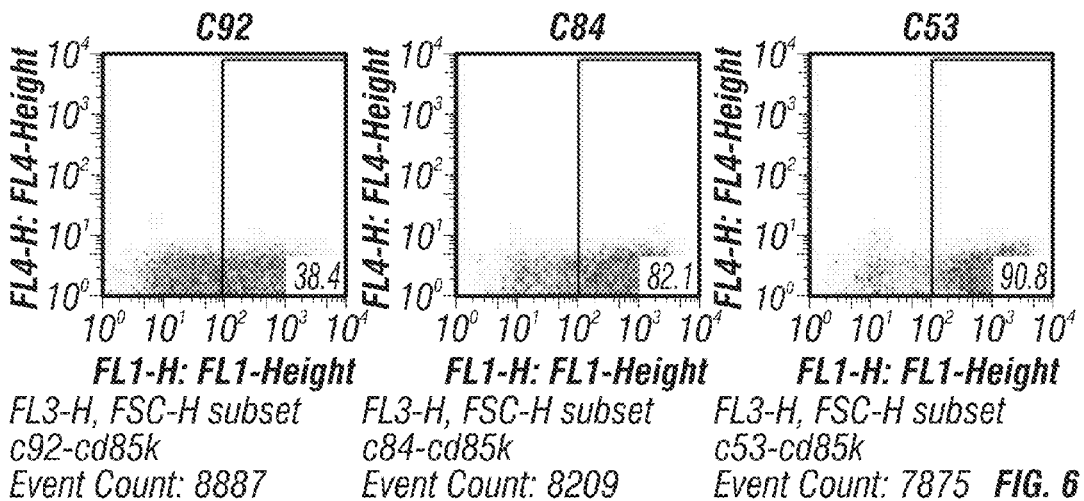
FIG. 6

*Anti-LILRB2:*
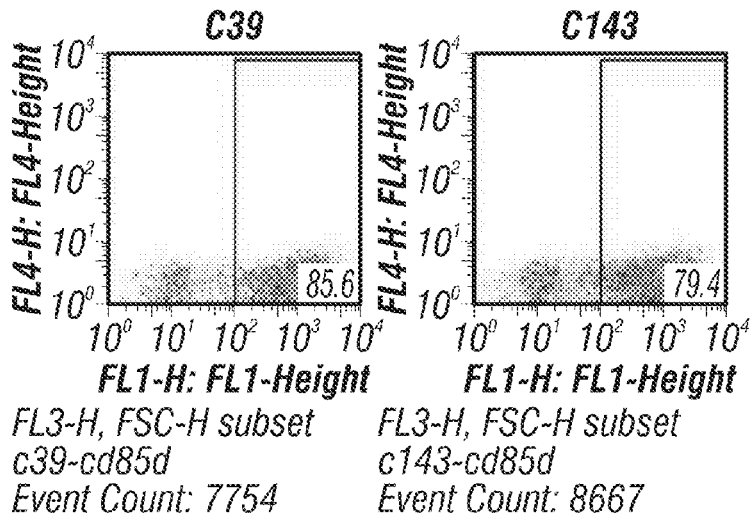
FL3-H, FSC-H subset
c39-cd85d
Event Count: 7754
FL3-H, FSC-H subset
c143-cd85d
Event Count: 8667
*Anti-LILRB3:*
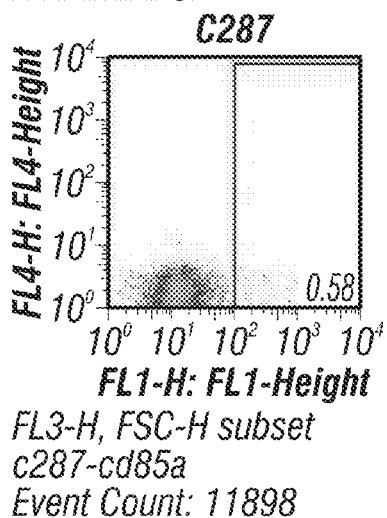
FL3-H, FSC-H subset
c287-cd85a
Event Count: 11898
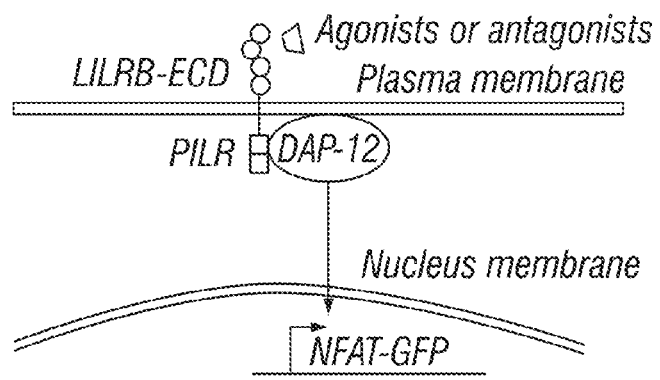
FIG. 6 (Cont'd)

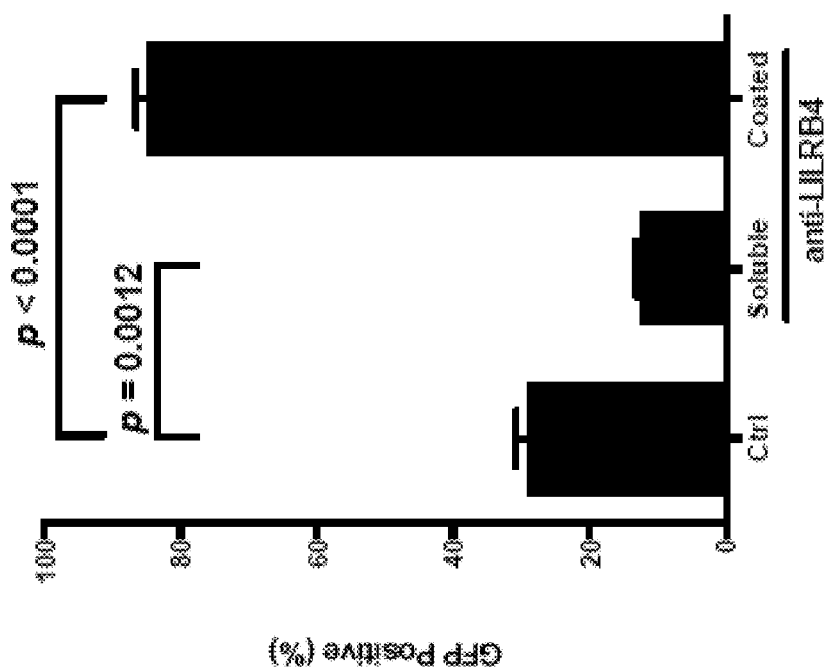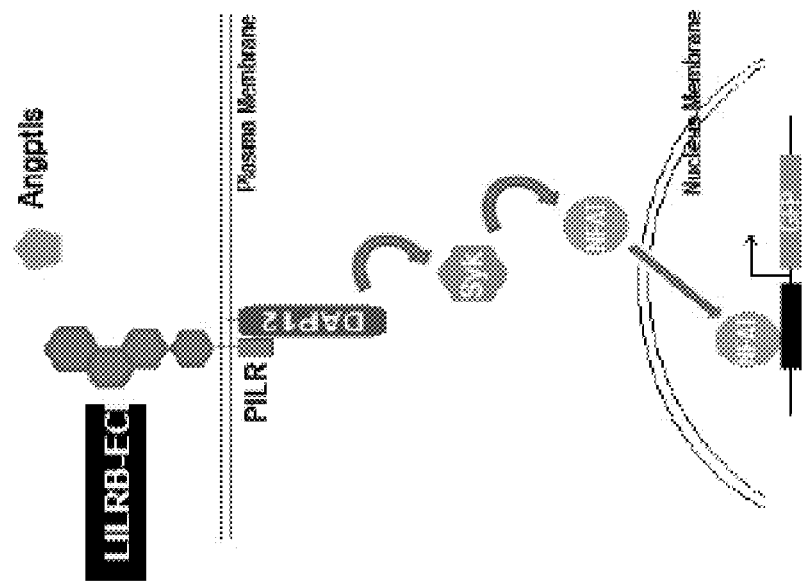
FIG. 7

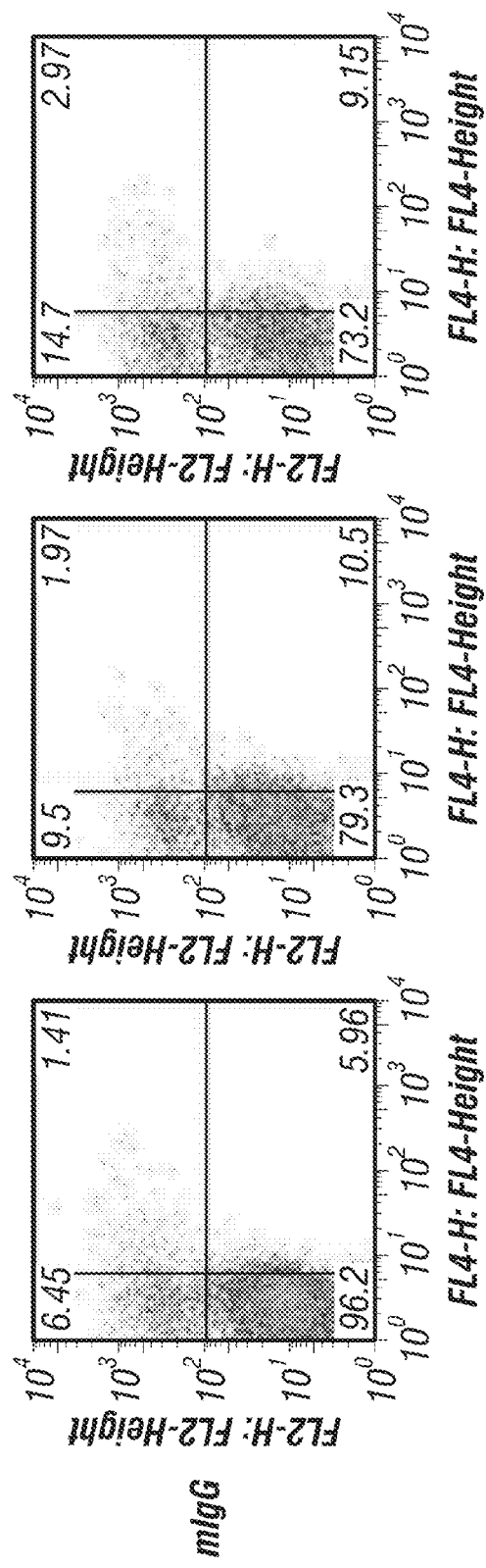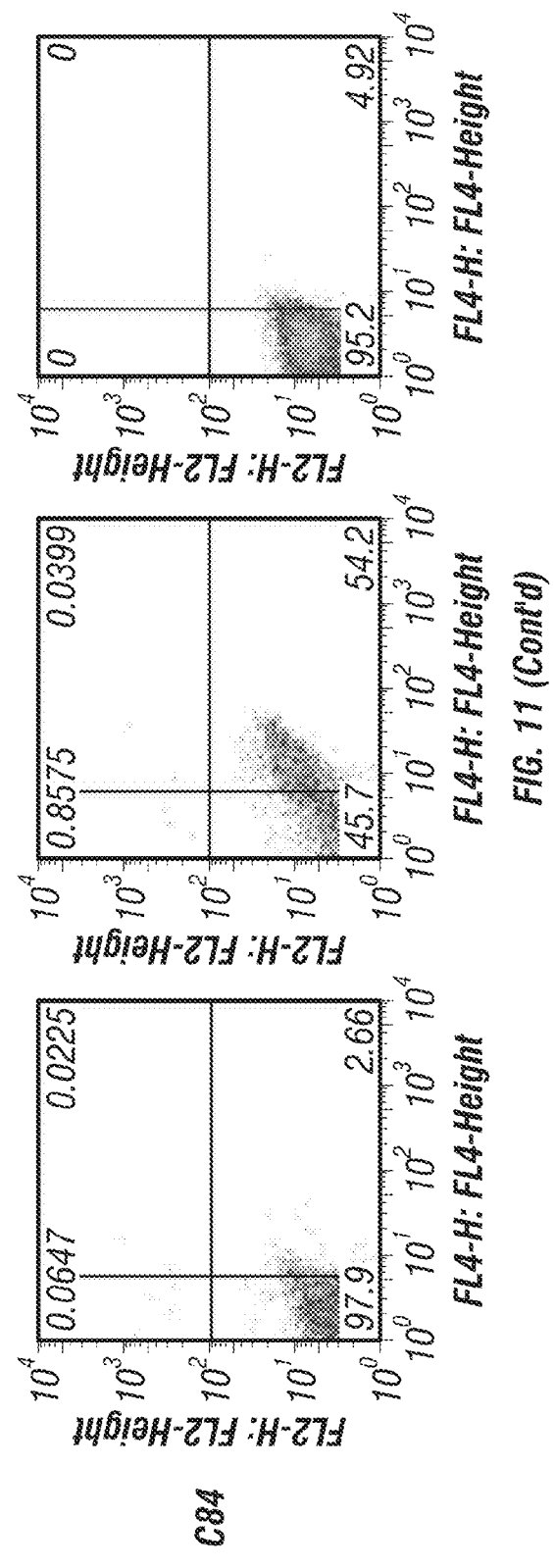
FIG. 11 (Cont'd)

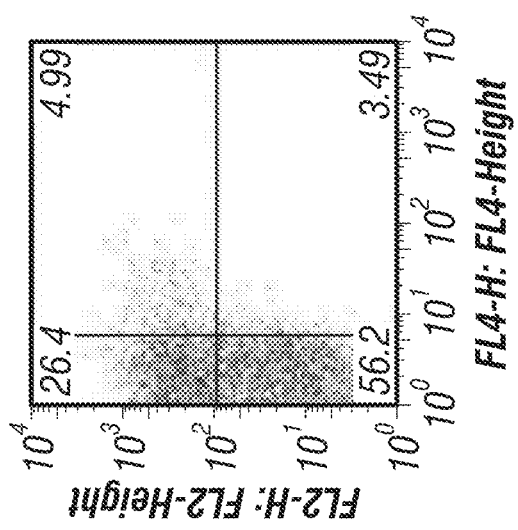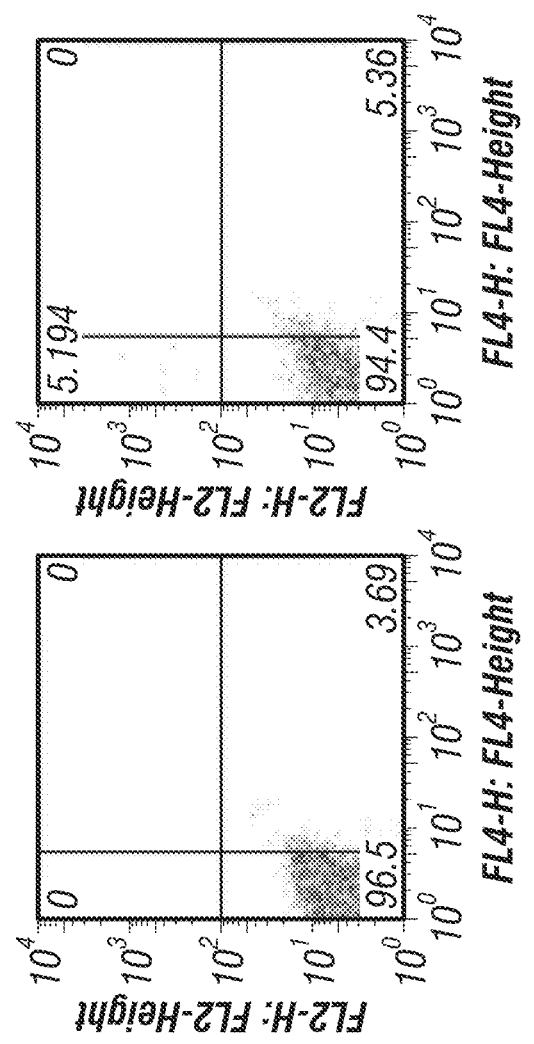
FIG. 11 (Cont'd)

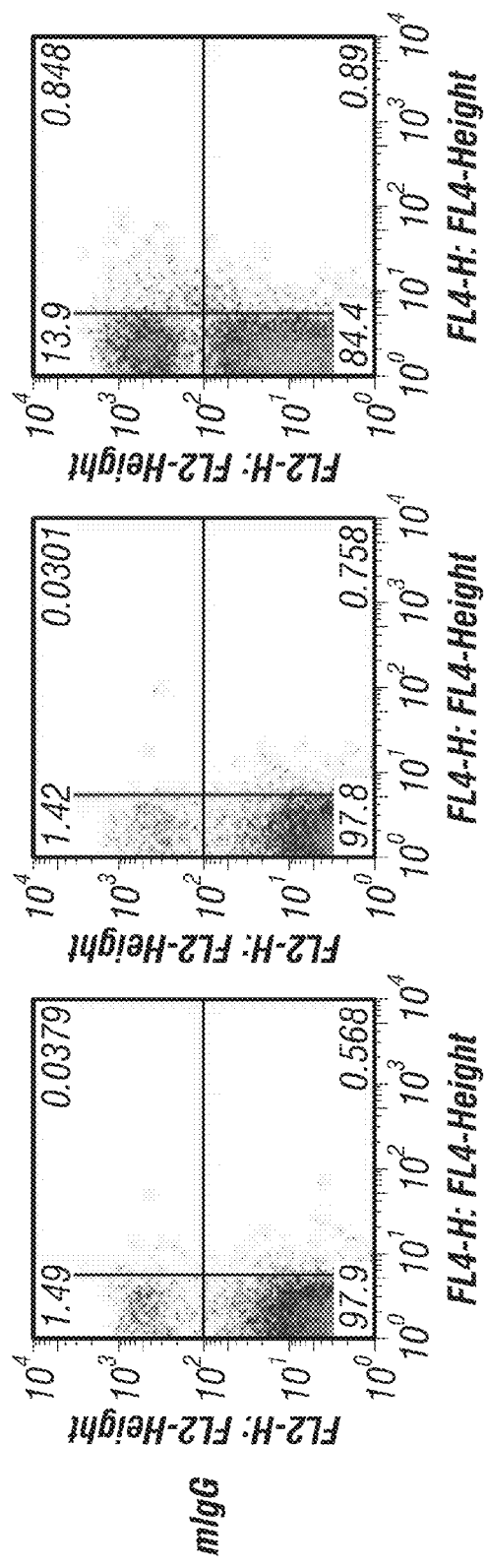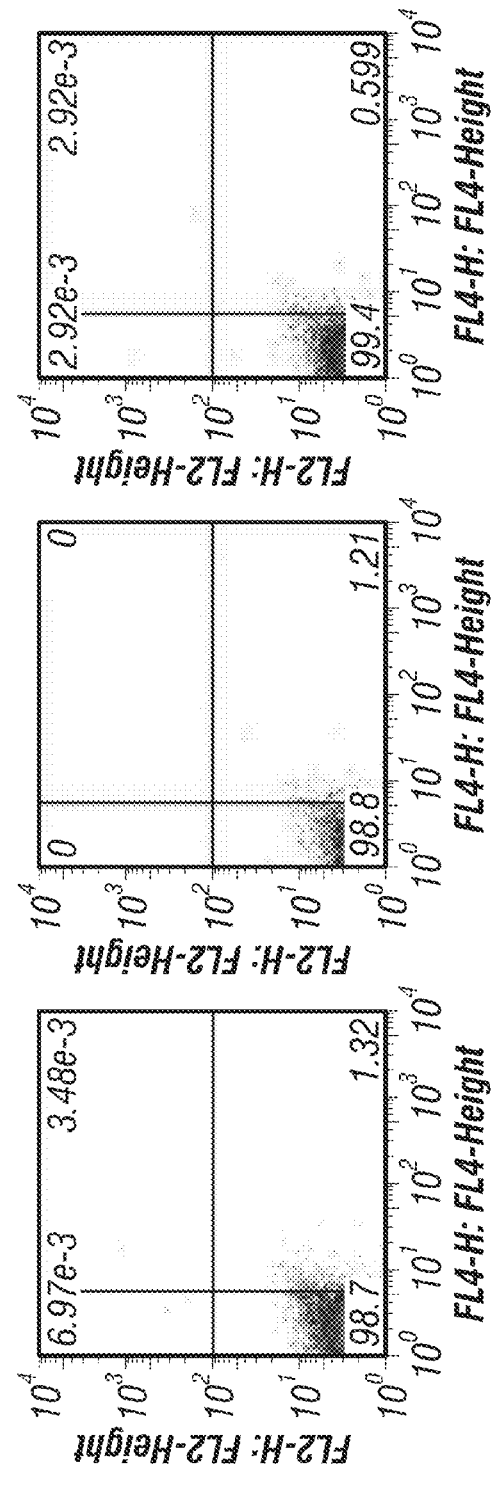
FIG. 12 (Cont'd)

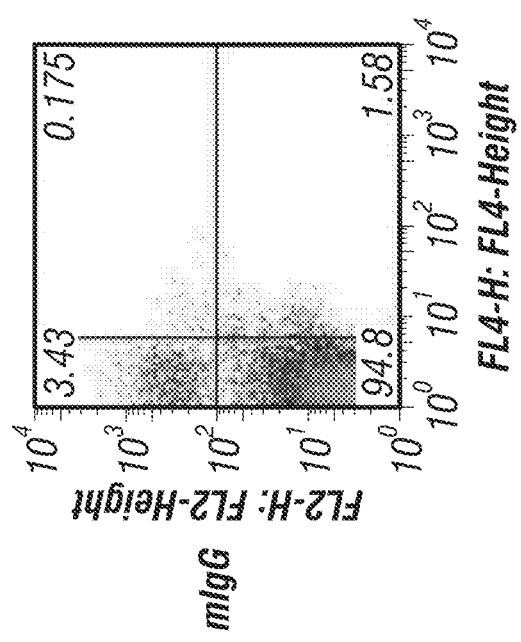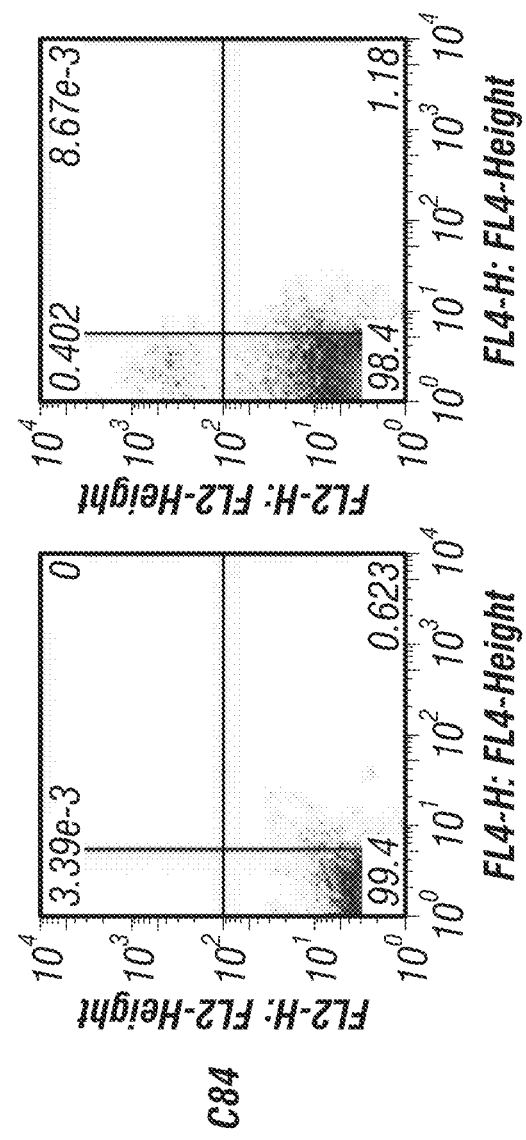
FIG. 12 (Cont'd)

>#192 Heavy (SEQ ID NO: 1)

EQSLEESGGGLVTPGGTLTLTCTVSGFSLSNNAMSWVRQAPGKGLEWIGVILLAGPTYYASWAKGRFTISKTSTTVDLKITSPTTEDTATYFCAIAIGSRPFALWGQGTLV
TISS

>#192 Light (SEQ ID NO: 2)

ELVLTQTPSSTSAAVGGTVTINCQSSQSVYSNWLSWFQQKPGQPPKPLIYLASTLASGVPSRFSGSGSGTQFTLTISDVQCDDAATYYCQGGYNGNIYTFGGGTEVVVK

>#161-1 Heavy (SEQ ID NO: 3)

QSVKESGGRLVTPGTPLTLTCTVSGIDLSVYLMSWVRHSPGKGLEYIGFINSAGITAYATWAKGRFIISKTSTTVDLKVTSPTTEDTATYFCARNWIRDLWGQGTLVTISS

>#161-1 Light (SEQ ID NO: 4)

ELDLTQTPASVSAAVGGTVTISCQSSETIYKNYLSWFQQKPGQPPKLLIYESSKLASGVPSRFSGSGSGTQFTLTISDVQCDDAATYYCLGGYTDGRDTIFGGGTELEIK

>#161-2 Heavy (SEQ ID NO: 5)

QSVKESGGRLVTPGTPLTLTCTVSGIDLSVYLMSWVRHSPGKGLEYIGFINSAGITAYATWAKGRFIISKTSTTVDLKVTSPTTEDTATYFCARNWIRDLWGQGTLVTISS

>#161-2 Light (SEQ ID NO: 6)

TQTPASVSAAVGGTVTISCQSSETIYKNYLSWFQQKPGQPPKLLIYESSKLASGVPSRFSGSGSGTQFTLTISDVQCDDAATYYCLGGYTDGRDTIFGGGTEVEIK

>#208 Heavy (SEQ ID NO: 7)

EQSVEESGGGLVTPGGTLTLTCTVSGFSLSNNAMSWVRQAPGKGLEWIGVILLSGTTYYASWAKGRFTISKTSTTVDLKITSPTTEDTATYFCAIAIGSRPFALWGQGTLV
TISS

FIG. 16

>#208 Light (SEQ ID NO: 8)

ELVMTQTPSSTSAAVGGTVTINCQSSQSVYSNWLSWFQQKPGQPPKPLIYLASTLASGVPSRFSGSGSGTQFTLTISDVQCDDAATYYCQGGYNGNIYTFGGGTEVVK

>#120 Heavy (SEQ ID NO: 9)

QSLEESGGRLVTPGTPLTLTCTVSGIDLNKYAMTWVRQAPGKGLEYIGFINIVGIAGYATWAKGRFTISKTSTTVDLKVTSPTTEDTATYFCARNWIRLDLWGQGTLVTVSS

>#120 Light (SEQ ID NO: 10)

ELDLTQTPASVSAAVGGTVTISCQSSESLYKKNYLSWFQQKPGQPPKLLIFEASKLASGVPSRFSGSGSGTQFTLTISDVQCDDAASYYCLGDYTNGRDTFGGGTEVVK

>#78 Heavy (SEQ ID NO: 11)

QSLQESGGRLVTPGTPLTLTCTVSGIDLSVYLMSWVRQSPGKGLEYIGFINSAGITAYATWAKGRFHSKTSTTVDLKVTSPTTEDTATYFCARNWIRLDLWGQGTLVTISS

>#78 Light (SEQ ID NO: 12)

ELVLTQTPASVSAAVGGTVTISCQSSESIYKNYLSWFQQKPGQPPKLLIYETSKLASGVPSRFSGSGSGTQFTLTISDVQCDDAATYYCLGGYTNGRDTIFGGGTELEIK

>#8 Heavy (SEQ ID NO: 13)

QSVKESGGGLVTPGGTLTLTCTASGFSLISYDMYWVRQAPGKGLEYIGIIYSDGYTFYATGAKGRITISRTSTTVDLKITSPTTEDTATYFCATNAFALWGQGTLVTISS

>#8 Light (SEQ ID NO: 14)

ELDLTQTPSSVSAAVGGTVTISCQSSQNVYNNNWLVWLQQKPGQPPKRLIYTASSLASGVPSRFAGSGSATQFTLTISDLECGDAATYYCAGGYSGPIYTFGGGTEVEIK

FIG. 16 (cont.)

>#128-1 Heavy (SEQ ID NO: 15)

EQSVEESEGRLVTPGGSLTLTCTVSGFGLSSWAMAWVRQAPGKGLEWIGIIGVSGKIYYPTWAKGRFTISRTSTTVDLKIASPTTEDTATYFCAREPYGDSLWGQGTLVTI
SS

>#128-1 Light (SEQ ID NO: 16)

ELVMTQTPSPVSAAVGGTVTISCQSSQNISTYLSWYQQKPGQPPKFLIYQASKLASGVSSRFKGSGSGTQFTLTISDVQCDDAASYYCAGWKSYSNDDNDFGGGTEVVV
K

>#128-3 Heavy (SEQ ID NO: 17)

EQSLEESGGDLVTPGASLTLTCKASGIDFSNHYYIYWVRQAPGKGLEWIGCIFSGDSASTYYASWAKGRFTISKSSSPTVTLQMTSLTAADTATYFCARGMSTNDWASDL
WGPGTMVTVSS

>#128-3 Light (SEQ ID NO: 18)

ELVMTQTPASVSAAVGGTVTINCQASESINSIYLAWYQQKPGQRPKLLIYRASTLASGVSSRFKGSASGTGFTLTISDLECADAATYCCQQSYDWGDVENTFGGGTEVEIK

>#140 Heavy (SEQ ID NO: 19)

EQSLKESGGGRLVTPGTPLTLTCTASGFSLSTYDMSWVRQAPGKGLEWIGIISTSYSIYYTYYASWAKGRFTISRTSSTTVDLKMTSLTTEDTATYFCVGGGGKLNSVVYIRG
LRFWGQGTLVTISS

>#140 Light (SEQ ID NO: 20)

ELVMTQTPSSTSAAVGGTVTINCQASQSVYDDNWCSWYQQKPGQPPKLLIYDASTLPSGVPSRFKGSGSGTQFLTLTISDLECDDAATYCAGAYSDNIYVFGGGTEVEIK

FIG. 16 (cont.)

>#216-1 Heavy (SEQ ID NO: 21)

EQSVEESGGGLVKPGASLTLTCIASGFSFSSSYVMCWVRQAPGKGLELIACIHAGGSGSTYYASWAKGRFTISKTSSTTVTLQMTSLTAADTATYFCARYNYHFYYIGDYS
DLWGPGTLVTVSS

>#216-1 Light (SEQ ID NO: 22)

ELVMTQTPSSVSAAVGGTVTIKCQASEDIDSYLAWYQQKPGQRPKVLIYRASTLASGVPSRFKGSGSGTEFTLTISGLECDDAATYYCQQGWSNDVGSNAFGGGTKVEI
K

>#216-2 Heavy (SEQ ID NO: 23)

EQSLKESGGRLVTPGTPLTLTCTVSGIDLSSYAMTWVRQVPGKGLEYIGFINIVGIAGYATWAKGRFTISKTSTTVDLKVTSPTTEDTATYFCARNWIRLDLWGQGTLVTV
SS

>#216-2 Light (SEQ ID NO: 24)

EQSLKESGGGLVTPGTPLTLTCTVTISCQSSESLYKKNYLSWFQQKPGQPPKLLIYEASKLASGVPSRFSGSGSGTQFLTISDVQCDDAASYYCLGDYTNGRDTTFGGGTEVEIK

>#101 Heavy (SEQ ID NO: 25)

ELVMTQTPASVSAAVGGTVTIISCQSSESLYKNYLSWFQQKPGQPPKLLIYEASKLASGVPSRFSGSGSGTQFLTISDVQCDDAASYYCLGDYTNGRDTTFGGGTEVEIK

HSVKESGGGLVTPGESLKLTCKASGMDFSKYWICWVRQAPGKGLEWIACIDTGRSAITVYAKWAKGRFTISKTSSTTVTLQMTTLTAADTATYFCETSVDLWGPGTLVTI
SS

>#101 Light (SEQ ID NO: 26)

ELDLTQTPASVEAAVGGTVTIKCQASESIYSGLAWYKQKPGQPPKFLILSASTQASGVPSRFKGSGSGTEFTLTISDLECADAATYYCQSRHYGSSRSYGFAFGGGTEVEIK

FIG. 16 (cont.)

>#223 Heavy

EQSVKESGGRLVTPGTPLTLTCIVSGFSLNNYAISWVRQAPEKGLEWIGMIRSDGHVDYATWAKGRFTISKTSTTVDLKMTSLTTEDTATYFCARGGHFFNPWGPGTLV
TISS (SEQ ID NO: 27)

>#223 Light

ELVMTQTPSPVSAAVGGTVTISCQSSQTVVNYNELAWYQQKPGQPPKLLIDAASTLASGVPSRFSGSGSGTQFTLKISEVQCDDAATYYCQGTYYISGWYTFGGGTEV
VVK (SEQ ID NO: 28)

>#139 Heavy

EQSLEESGGRLVTPGTPLTLTCTVSGFSLNSYAMAWVRQAPGKGLEWIGIIGLSTMTYYASWVNGRFTISKTSTTVDLKMTSLTTEDTATYFCVRNDVYWAFNLWGQG
TLVTVSS (SEQ ID NO: 29)

>#139 Light

ELDLTQPSSVSAGVGGTVSISCQSSESVVNNHALSWYQQKPGQPPKLLIYKASTLASGVPSRFSGSGSGAQFTLTISGVQCDDAATYYCQGGFYSGISDYPFGGGTEVEI
K (SEQ ID NO: 30)

>#156-1 Heavy

QSVKESEGDLVKPGASLTLTCRASGFSFSSDYNMCWVRQAAGKGLEWIACIGVGTSGKTAYATWAKGRFTISRSSSTTVALQMTSLTVADTATYFCARPSYGSGGEGG
GSGLWGPGTLVTISS (SEQ ID NO: 31)

>#156-1 Light

ELDLTQTPASVSEPVGGTVTIKCQASQSIHSDLAWYQQKPGQRPKLLIYVASYLASGVPSRFSGSGSGTEYTLTISDLECADAATYYCQSTYYGSDYVGGAFGGGTEVVK
(SEQ ID NO: 32)

FIG. 16 (cont.)

>#129 Heavy

EQSVKESGGGLVKPGASLTLTCTASGFSFSSSYHMCWVRQAPGKGLEWIGCIATGYGSTYYASWAKGRFTISKTSSTTVTLQVPSLTAADTATCFCARGYYRYTSDSYGYF
DLWGPGTLVTISS (SEQ ID NO: 33)

>#129 Light

ELVLTQTASPVSAAVGGTVTVNCQASQSISSGYLSWYQQKPGQPPKLLIYYASRLASGVPSRFSGSGSGTEYTLTISGVQCDDAATYYCLYVSYDGTTTDNAFGGGTEVEI
K (SEQ ID NO: 34)

>#214 Heavy

QSVKESGGRLVTPGTPLTLTCTVSGFSLSSYWMHWVRQAPGKGLEWVGVVSVSGNFYYATWAKGRFTISKTSTTVDLKITSPTIEDTAFYFCTMSFALWGQGTLVTISS
(SEQ ID NO: 35)

>#214 Light

ELVMTQTASPVSAAVGGTVTINCQSSQSVYSNNNLGWLKQKPGQPPKELIYYASTLASGVPSRFKGSGSGTQFTLTISDLECDDAATYYCVGGYGCSSADCSVFGGGTE
VEIK (SEQ ID NO: 36)

>#210 Heavy

EQSVEESGGRLVTPGTPLTLTCTVSGFSLSSYIMGWVRQARGKGLEYIGAINTDGATYYATWAKGRFTISRTSTTVHLKVTSPTTEDTATYFCARSLAPGDSNINLWGQGT
LVTISS (SEQ ID NO: 37)

>#210 Light

ELVLTQTPSPVSAAVGGTVTISCQSSESVYRNNRLAWYQQKPGQPPKRLIYLASTLASGVPSRFKGSGSGTQFTLTISDVQCDDAAAYYCAGDSGVGIIAFGGGTEVEIK
(SEQ ID NO: 38)

FIG. 16 (cont.)

>#6 Heavy

QSVKESGGRLVTPGTPLTLTCTASGFSLSTYYIDWVRQAPGRGLEYIGVINPGGSAVYATWAKGRFTISRTSTTVDLKMTSLTTEDTATYFCARGWSRGDLWGQGTLVTISS (SEQ ID NO: 39)

>#6 Light

ELDMTQTPSPVSAAVGGTVTIKCQSSQNVYDDDTLSWYQQKPGQPPKLLIYDASKLASGVPSRFKGSGSGTQFTLTISGVQCDDAATYYCLGVFHDAADNAFGGGTELEIK (SEQ ID NO: 40)

>#71-1 Heavy

QSVEESGGGLVKPGASLTLTCTASGFSFSSSYHMCWVRQAPGKGLEWIGCIATGYGSTYYASWAKGRFTISKTSSTTVTLQVPSLTAADTATCFCARGYYRYTSDSYGYFDLWGPGTLVTISS (SEQ ID NO: 41)

>#71-1 Light

ELDLTQTASPVSAAVGGTVTVNCQASQSISSGYLSWYQQKPGQPPKLLIYYASRLASGVPSRFSGSGSGTEYTLTISGVQCDDAATYYCLYVSYSGTTTDNAFGGGTDVEIK (SEQ ID NO: 42)

FIG. 16 (cont.)

| mAbs | Heavy Chain | | | Light Chain | | |
|---|---|---|---|---|---|---|
| | CDR1 | CDR2 | CDR3 | CDR1 | CDR2 | CDR3 |
| #192 | GFSL...SNNA (SEQ ID NO: 43) | ILLA...GPT (SEQ ID NO: 44) | AIAIGSRPFAL (SEQ ID NO: 45) | QSVY.....SNW (SEQ ID NO: 46) | LA.......S | QGGYNGNIYT (SEQ ID NO: 47) |
| #161-1 | GIDL...SVYL (SEQ ID NO: 48) | INSA...GIT (SEQ ID NO: 49) | ARNWIRLDL (SEQ ID NO: 50) | ETIY.....KNY (SEQ ID NO: 51) | ES.......S | LGGYTDGRDTI (SEQ ID NO: 52) |
| #161-2 | GIDL...SVYL (SEQ ID NO: 53) | INSA...GIT (SEQ ID NO: 54) | ARNWIRLDL (SEQ ID NO: 55) | ETIY.....KNY (SEQ ID NO: 56) | ES.......S | LGGYTDGRDTI (SEQ ID NO: 57) |
| #208 | GFSL...SNNA (SEQ ID NO: 58) | ILLS...GTT (SEQ ID NO: 59) | AIAIGSRPFAL (SEQ ID NO: 60) | QSVY.....SNW (SEQ ID NO: 61) | LA.......S | QGGYNGNIYT (SEQ ID NO: 62) |
| #120 | GIDL...NKYA (SEQ ID NO: 63) | INIV..GIA (SEQ ID NO: 64) | ARNWIRLDL (SEQ ID NO: 65) | ESLY...KKNY (SEQ ID NO: 66) | EA.......S | LGDYTNGRDTT (SEQ ID NO: 67) |
| #78 | GIDL...SVYL (SEQ ID NO: 68) | INSA...GIT (SEQ ID NO: 69) | ARNWIRLDL (SEQ ID NO: 70) | ESIY.....KNY (SEQ ID NO: 71) | ET.......S | LGGYTNGRDTI (SEQ ID NO: 72) |
| #8 | GFSL...ISYD (SEQ ID NO: 73) | IYSD...GYT (SEQ ID NO: 74) | ATNAFAL (SEQ ID NO: 75) | QNVY...NNNW (SEQ ID NO: 76) | TA.......S | AGGYSGPIYT (SEQ ID NO: 77) |
| #128-1 | GFGL...SSWA (SEQ ID NO: 78) | IGVS...GKI (SEQ ID NO: 79) | AREPYGDSL (SEQ ID NO: 80) | QNI.......STY (SEQ ID NO: 81) | QA.......S | AGWKSYSNDDND (SEQ ID NO: 82) |
| #128-3 | GIDFS..NHYY (SEQ ID NO: 83) | IFSGD.SAST (SEQ ID NO: 84) | ARGMSTNDWASDL (SEQ ID NO: 85) | ESIN......SIY (SEQ ID NO: 86) | RA.......S | QQSYDWGDVENT (SEQ ID NO: 87) |
| #140 | GFSLS..TYDM (SEQ ID NO: 88) | STSYS.IYYT (SEQ ID NO: 89) | VGGGGKLNSVVYYIRGLRF (SEQ ID NO: 90) | QSVY...DDNW (SEQ ID NO: 91) | DA.......S | AGAYSDNIYV (SEQ ID NO: 92) |
| #216-1 | GFSFS..SSYV (SEQ ID NO: 93) | IHAGG.SGST (SEQ ID NO: 94) | ARYNYHFYYIGDYSDL (SEQ ID NO: 95) | EDI.......DSY (SEQ ID NO: 96) | RA.......S | QQGWSNDVGSNA (SEQ ID NO: 97) |
| #216-2 | GIDL...SSYA (SEQ ID NO: 98) | INIV...GIA (SEQ ID NO: 99) | ARNWIRLDL (SEQ ID NO: 100) | ESLY...KKNY (SEQ ID NO: 101) | EA.......S | LGDYTNGRDTT (SEQ ID NO: 102) |
| #101 | GMDF...SKYW (SEQ ID NO: 103) | IDTG..RSAI (SEQ ID NO: 104) | ETSVDL (SEQ ID NO: 105) | ESI.......YSG (SEQ ID NO: 106) | SA.......S | QSRHYGSSRSYGFA (SEQ ID NO: 107) |
| #223 | GFSL...NNYA (SEQ ID NO: 108) | IRSD...GHV (SEQ ID NO: 109) | ARGGHFFNP (SEQ ID NO: 110) | QTVY....NYNE (SEQ ID NO: 111) | AA.......S | QGTYYISGWYYT (SEQ ID NO: 112) |
| #139 | GFSL...NSYA (SEQ ID NO: 113) | IGLS...TMT (SEQ ID NO: 114) | VRNDVYWAFNL (SEQ ID NO: 115) | ESVV....NNHA (SEQ ID NO: 116) | KA.......S | QGGFYSGISDYP (SEQ ID NO: 117) |
| #156-1 | GFSFS..SDYN (SEQ ID NO: 118) | IGVGT.SGKT (SEQ ID NO: 119) | ARPSYGSGGEGGGSGL (SEQ ID NO: 120) | QSI.......HSD (SEQ ID NO: 121) | VA.......S | QSTYYGSDYVGGA (SEQ ID NO: 122) |
| #129 | GFSFS..SSYH (SEQ ID NO: 123) | IATG...YGS (SEQ ID NO: 124) | ARGYYRYTSDSYGYFDL (SEQ ID NO: 125) | QSIS.....SGY (SEQ ID NO: 126) | YA.......S | LYVSYDGTTTDNA (SEQ ID NO: 127) |
| #214 | GFSL...SSYW (SEQ ID NO: 128) | VSVS...GNF (SEQ ID NO: 129) | TMSFAL (SEQ ID NO: 130) | QSVY....SNNN (SEQ ID NO: 131) | YA.......S | VGGYGCSSADCSV (SEQ ID NO: 132) |
| #210 | GFSL...SSYI (SEQ ID NO: 133) | INTD...GAT (SEQ ID NO: 134) | ARSLAPGDSNINL (SEQ ID NO: 135) | ESVY....RNNR (SEQ ID NO: 136) | LA.......S | AGDSGVGIIA (SEQ ID NO: 137) |
| #6 | GFSL...STYY (SEQ ID NO: 138) | INPG...GSA (SEQ ID NO: 139) | ARGWSRGDL (SEQ ID NO: 140) | QNVY....DDDT (SEQ ID NO: 141) | DA.......S | LGVFHDAADNA (SEQ ID NO: 142) |
| #71-1 | GFSFS..SSYH (SEQ ID NO: 143) | IATG...YGS (SEQ ID NO: 144) | ARGYYRYTSDSYGYFDL (SEQ ID NO: 145) | QSIS.....SGY (SEQ ID NO: 146) | YA.......S | LYVSYGTTTDNA (SEQ ID NO: 147) |

FIG. 17

192
(1)
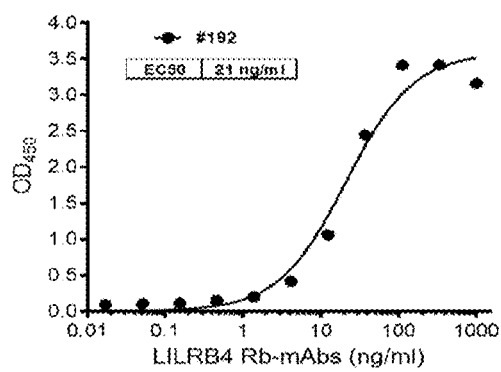
(2)
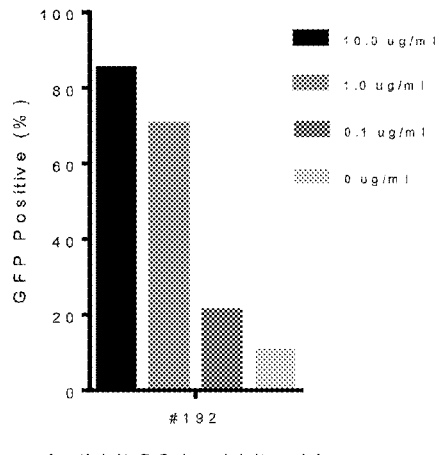
FIG. 18A
161-1
(1)
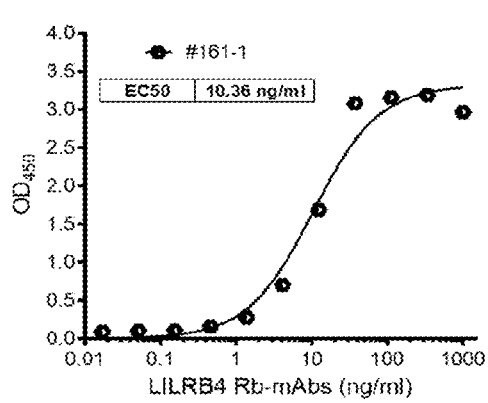
(2)
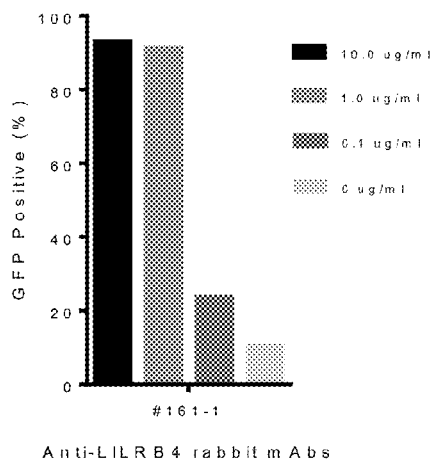
FIG. 18B

161-2
(1)
(2)
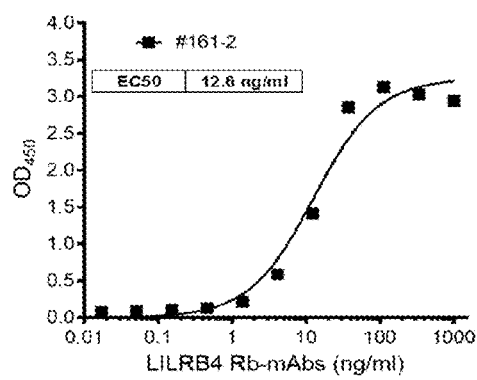
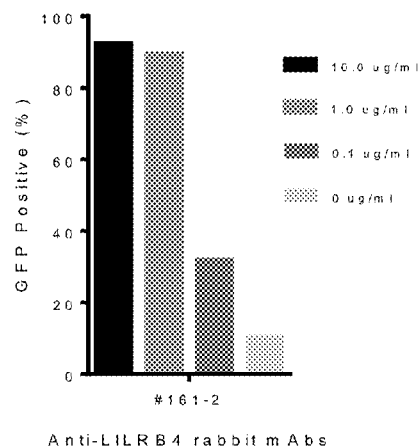
FIG. 18C
208
(1)
(2)
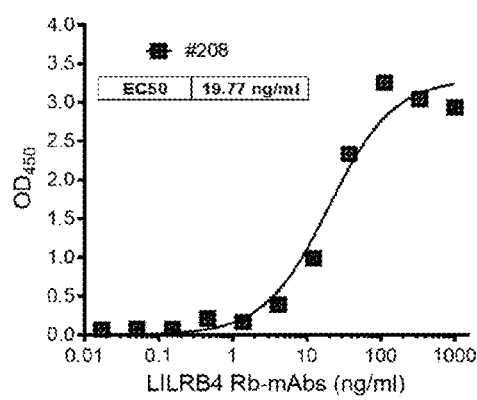
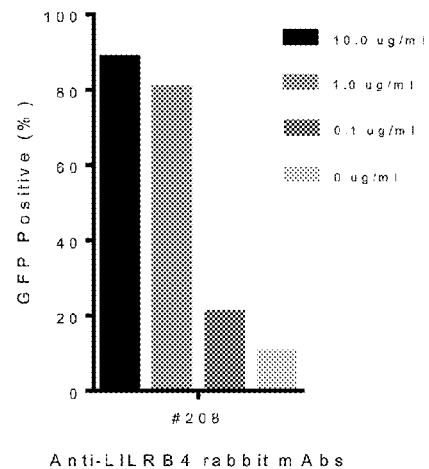
FIG. 18D

120

78

8
(1)
(2)
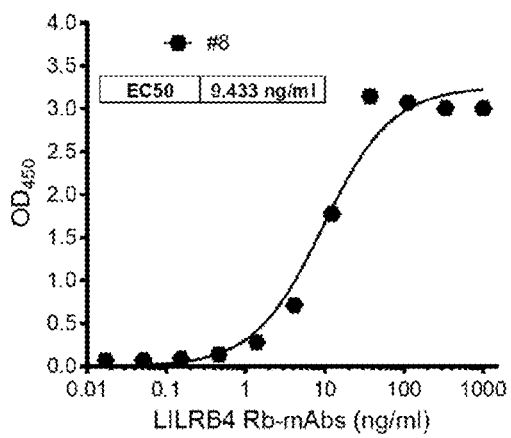
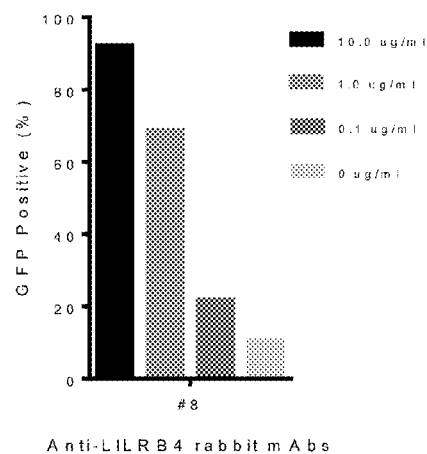
FIG. 18G
128-1
(1)
(2)
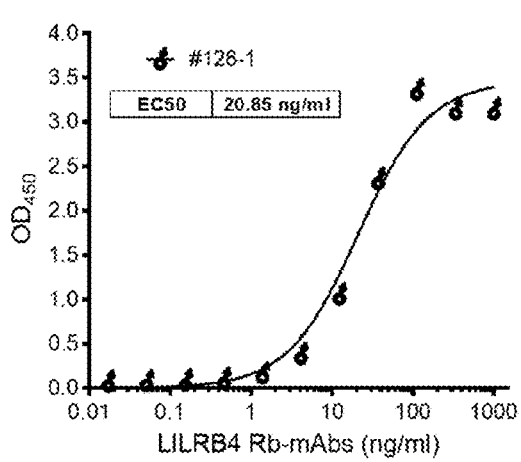
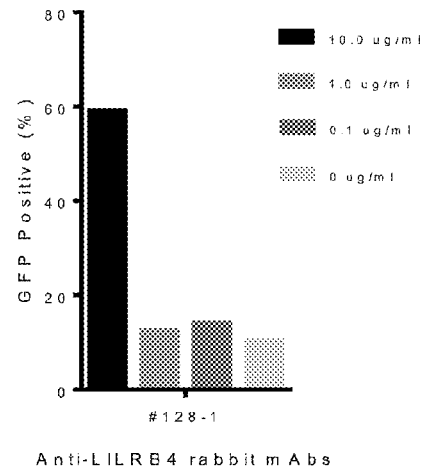
FIG. 18H

128-3
(1)
(2)
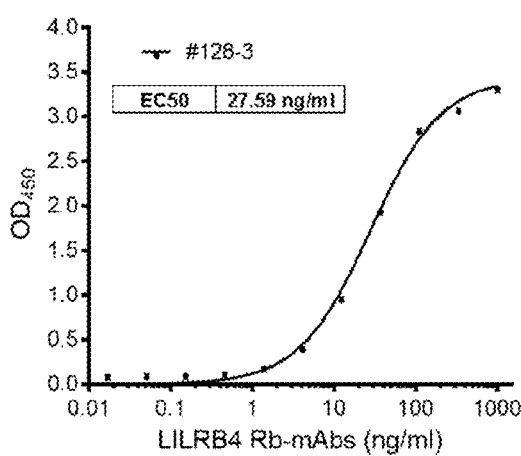
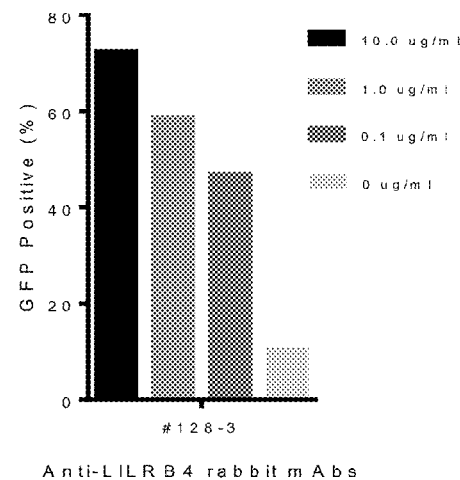
FIG. 18I
140
(1)
(2)
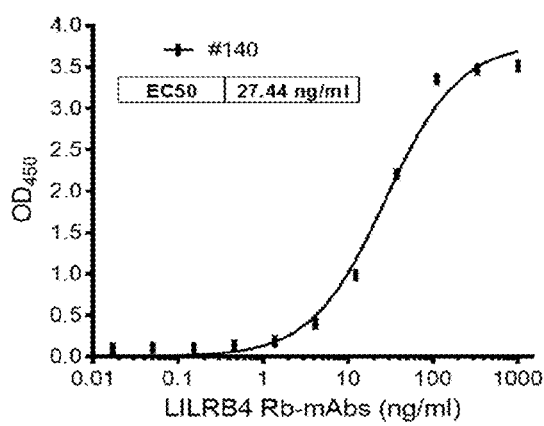
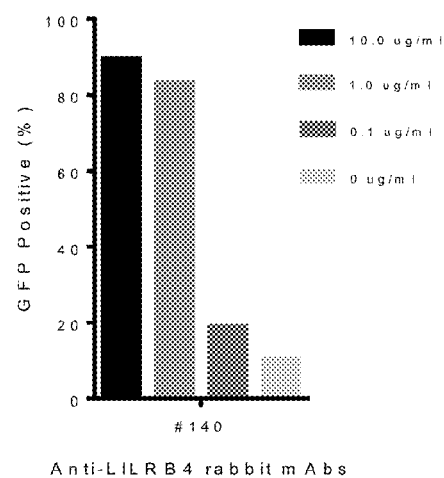
FIG. 18J

216-1
(1)
(2)
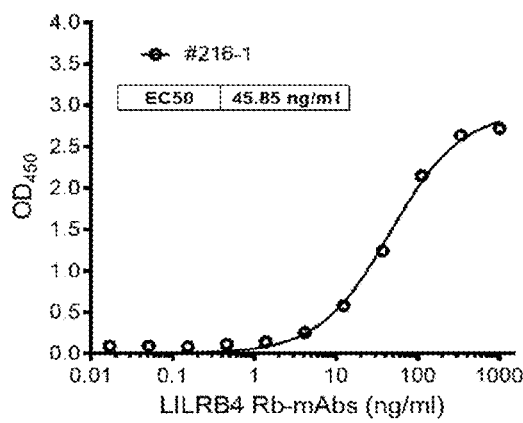
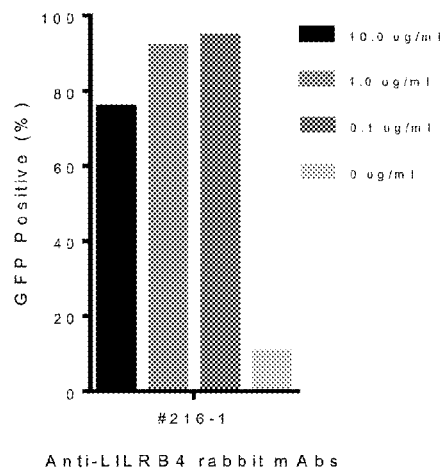
FIG. 18K
216-2
(1)
(2)
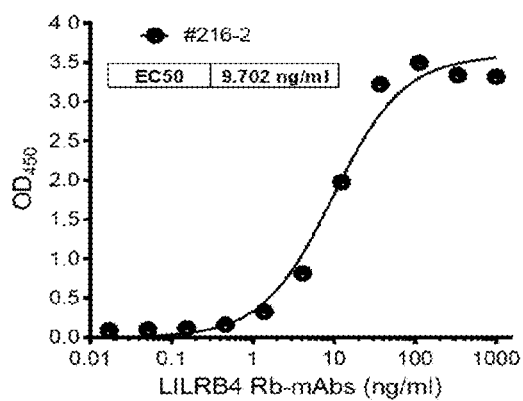
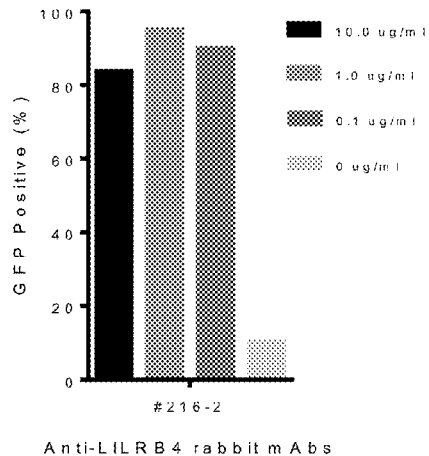
FIG. 18L

101
(1)
(2)
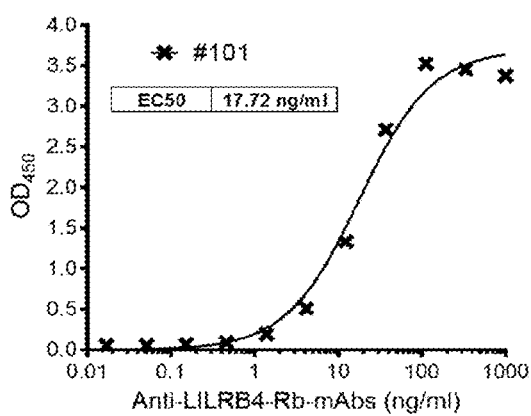
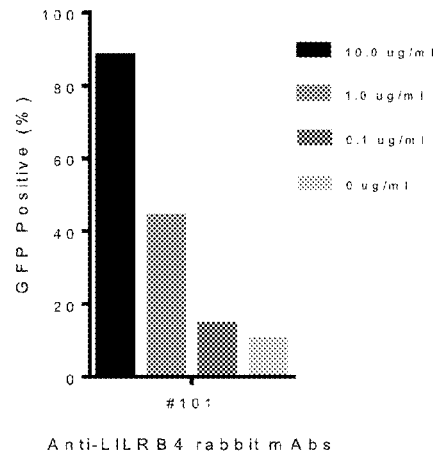
FIG. 18M
223
(1)
(2)
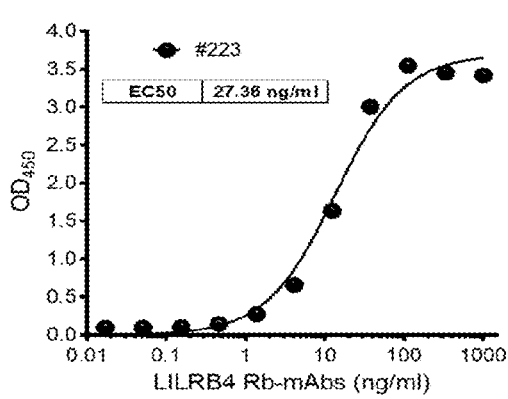
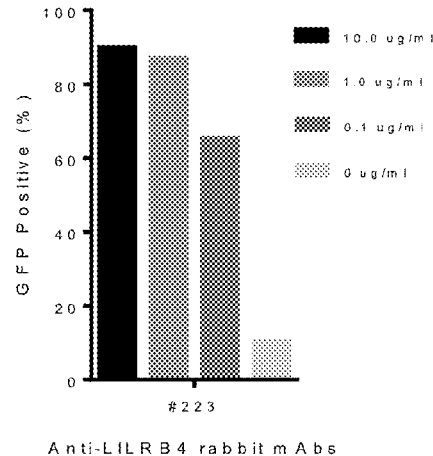
FIG. 18N

139
(1)
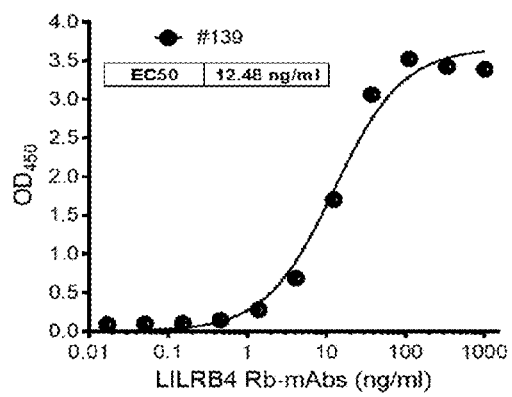
(2)
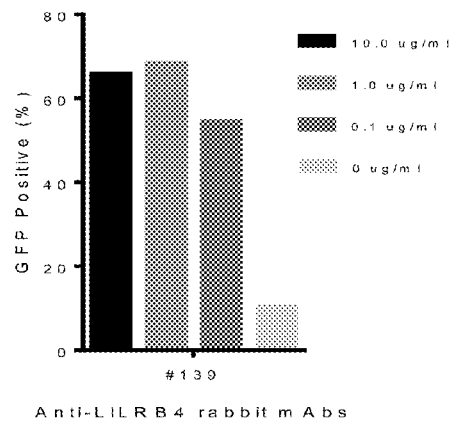
FIG. 18O
156-1
(1)
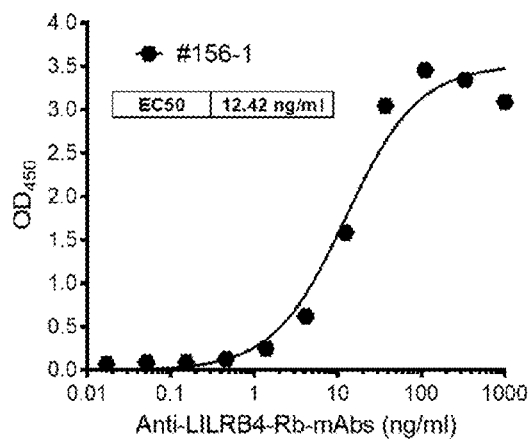
(2)
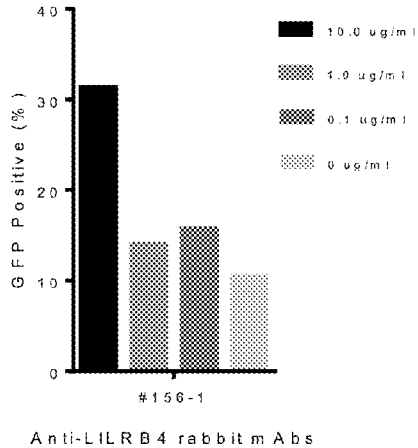
FIG. 18P

129
(1)
(2)
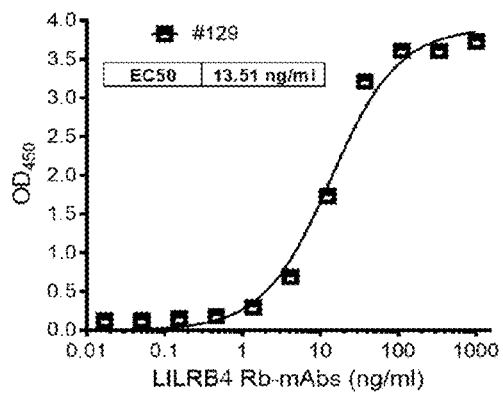
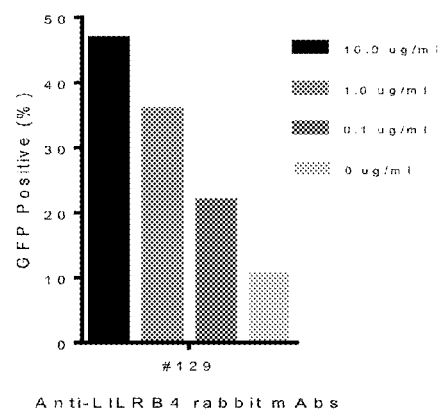
FIG. 18Q
214
(1)
(2)
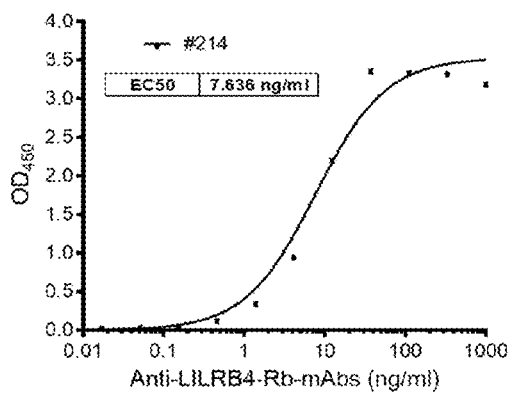
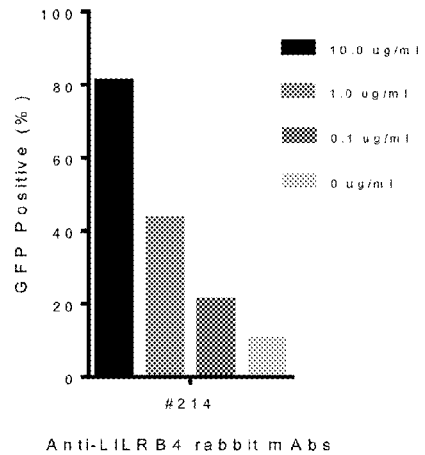
FIG. 18R

210
(1)
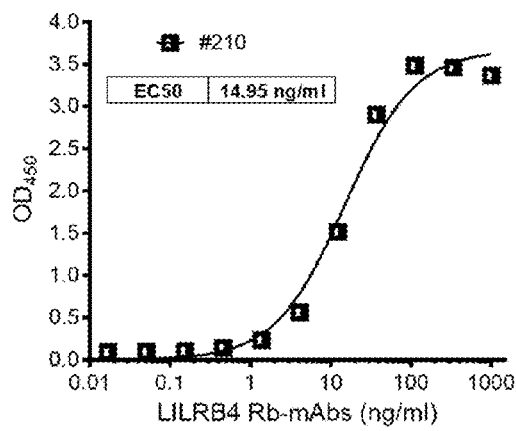
(2)
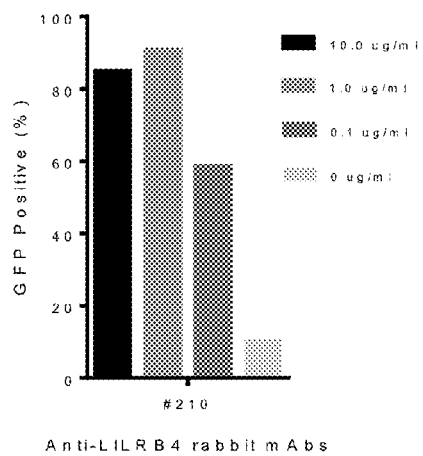
FIG. 18S
6
(1)
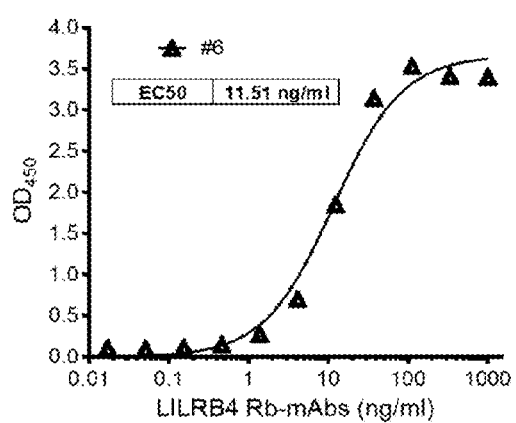
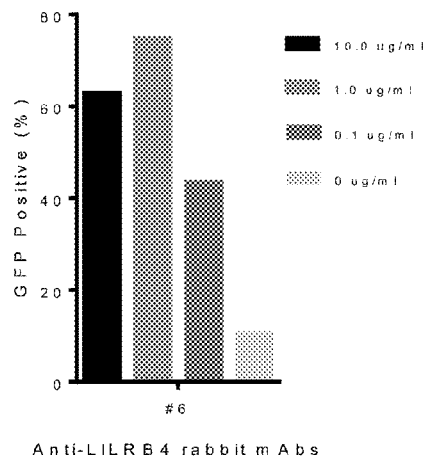
FIG. 18T

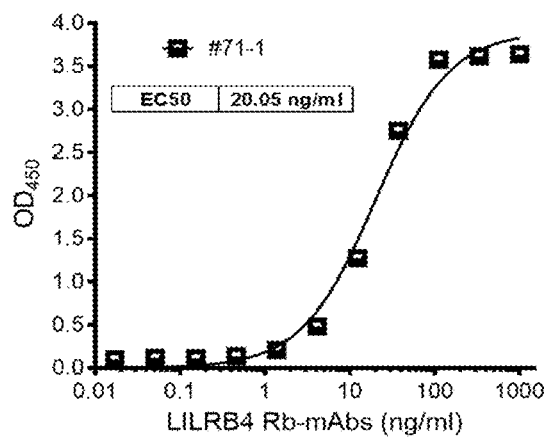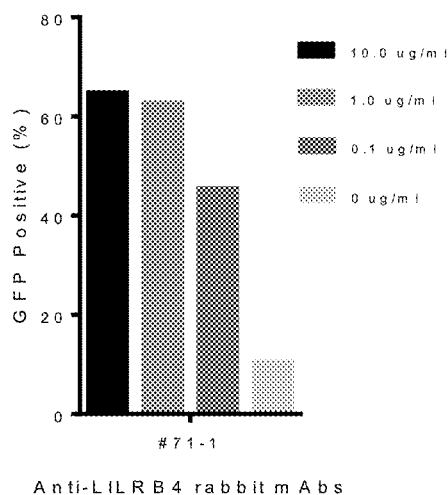
FIG. 18U

| Antibody | Reactivity to individual LILRBs | | | | | AML inhibition |
|---|---|---|---|---|---|---|
| | LILRB1 | LILRB2 | LILRB3 | LILRB4 | LILRB5 | |
| C193 | | + | | | | ++ |
| C102 | | + | | | | + |
| C41 | | | | | | |
| C39 | | ++ | ++ | + | + | +++ |
| C143 | | | | | | |
| C290 | | + | ++ | + | + | ++ |
| C287 | | ++ | | | | + |
| C3 | | | | + | | +++ |
| C1 | | | | | | |
| C84 | | + | | ++ | | ++++ |
| C53 | | | | ++ | | ++++ |
| C201 | | ++ | | ++ | + | ++++ |
| C92 | | | | ++ | | ++++ |

FIG. 19

C53 Heavy: EVNLEESGGGLVQPGGSMKLSCIASGFTFSNYWMNWVRQSPEKGLEWVAEIRLKYNNYATHYAESVK
GRFTISRDDSKSTVYLQMNNLRAEDTGIYYCTGTRYGSSLDYWGQGTSVTVSS (SEQ ID NO: 220)

C53 Light: DIVMSQSPSSLAVSVGEKVTMSCKSSQNLFYSTNQKNYLAWYQQKPGQSPKLLIYWASTRESGVPDR
FTGSGSGTAFTLTISSVKAEDLAVYYCQQYYNYPLTFGAGTKLELK (SEQ ID NO: 221)

C84 Heavy: QIQLVQSGPELKKPGETVKISCKASGYTFTNYGMNWVKQAPGKGLKWMGWINTYTGEPTYADDFKG
RFAFSLETSASTAYLQINNLKNEDMATYFCASIYYHTSLWYFDVWGAGTTVTVSS (SEQ ID NO: 222)

C84 Light: DVLMTQTPLSLPVSLGDQASISCRSSQNIVHSNGNTYLEWYLQKPGQSPKLLIYRVSNRFSGVPVRFSG
SGSGTDFTLKISRVEAEDLGVYYCFQGSHVPLTFGAGTKLELK (SEQ ID NO: 223)

C92 Heavy: QIQLVQSGPELKKPGETVKISCKASGYTFTNYGMNWVKQAPGKGLKWMGWINTYTGEPTYADDFKG
RFAFSLETSASTAYLQINNLKNEDMATYFCASIYYHTSLWYFDVWGAGTTVTVSS (SEQ ID NO: 224)

C92 Light: DVVMTQTPLSLPVSLGDQASISCRSSQSLVHSNGNTYLHWYLQKPGQSPKLLIYKVSNRFSGVPDRFSG
SGSGTDFTLKISRVEAEDLGVYFCSQSTHVPYTFGGGTKLEIK (SEQ ID NO: 225)

C201 Heavy: DVQLQESGPGLVKPSQSLSLTCTVTGYSITSDYAWNWIRQFPGNKLEWMGYISYSGGTSYNPSLKSRIS
ITRDTSKNQFFLQLNSVTTEDTATYYCARLHYGYDYWGLGTTLTVSS (SEQ ID NO: 226)

C201 Light: DVLMTQTPLSLPVSLGDQASISCRSSQSIVHSNGNTYLEWYLQKPGQSPKLLIYKVSNRFSGVPDRFSGS
GSGTDFTLKISRVEAEDLGVYYCFQGLHVPPTFGGGTKLEIK (SEQ ID NO: 227)

C3 Heavy: EVQLVESGGGLVQPKGSLKLSCAASGFTFNNYAMNWGRQAPGKGLEWVARIRSKRNNYATHYDDSVK
DRFTISRDDSQNMLYLQLNNLKTEDTAMYYCVRDGPYAMDYWGQGTSVTVSS (SEQ ID NO: 148)

C3 Light: DIVMSQSPSSLAVSVGEKVTMSCKSSQSLLYSSNQKNYLAWYQQKPGQSPKLLIYWASTRESGVPDRFT
GSGSGTDFTLTISSVKAEDLAVYYCQQYYSYPYTFGGGTKLEIK (SEQ ID NO: 149)

C39 Heavy: EVQLVESGGGLVQPGGSLKLSCAASGFTFSSYGMSWVRQTPDKRLELVATIDSNGGGTYYPDSVKGRFT
ISRDNAKNTLYLQMSSLKSEDTAMHYCARDGGGSYGYYYAMDYWGQGTSVTVSS (SEQ ID NO: 150)

FIG. 21

C39 Light:    DIVMSQSPSSLAVSAGEKVTMRCKSSQSLLNSRTRKSYLAWYQQKSGQSPKLLIYWASTRESGVPDRFT

GSGSGTDFTLTISSVQAEDLAVYYCKQSYNLPWTFGGGTKLEIK          (SEQ ID NO: 151)

C102 Heavy:   EVQLQQSGPELVKPGASVKISCKTSGYTFTEYTMHWVKQSHGKSLEWIGGINPNNGGTSYNQKFKGKA

TLTVDKSSSTAYMDLRSLTSEDSAVYYCARYWDYFDYWGQGTTLTVSS      (SEQ ID NO: 152)

C102 Light:   DVLMTQTPLSLPVSLGDQASISCRSSQSIVHSNGNTYLEWFLQKPGQSPK LLIYKVSNRFSGVPDRFSGS

GSGTDFTLKISRVEAEDLGVYYCFQGSQIPPTFGGGTKLE IK           ((SEQ ID NO: 153)

C193 Heavy:   EVQLVESGGGLVQPKGSLRLSCAASGFIFNTYAMNWVRQAPGKGLEWVARIRSKSNKYATYYVDSVKD

RFTISRDDSQSMLYLQMNNLKTEDTAMYYCVRDGIWGQGTLVTVSA        (SEQ ID NO: 154)

C193 Light:   DIVMTQSPSSLTVTAGEKVTMSCKSSQSLLNSGNQKNYLTWYHQKPGQPPKLLIYWAFTRESGVPDRF

TGSGSGTDFTLTISSVQAEDLAVYYCQNDYSYPLTFGSGTKLEIK         (SEQ ID NO: 155)

C287 Heavy:   QIQLVQSGPELKKPGETVKISCKASGYTFTNYGINWVKQAPGKGLKWMGWINTNTGEPTYAEDFKGR

FAFSLETSASTAYLQINNLKNEDTATYFCTRGSAKGGFFYWGQG TLVTVSA  (SEQ ID NO: 156)

C287 Light:   DVVMTQTPLTLSVTIGQPASISCKSSQSLLYSNGRTYLNWLLQRPGQSPKRLIYLVSKLDSGVPDRFTGS

GSGTDFTLKISRVEAEDLGVYYCVQGTHFPYTFGGGTKLEIK            (SEQ ID NO: 157)

C290 Heavy:   EVQLLQSGPELVKPGASVKISCRTSGYTFTEYTMHWVKQSHGKSLEWIGGINTNNGGTSYNQKFKGKA

TLTVDKSSSTAYMELRSLTSEDSAVYYCARDKRSRGELDSTMDYWGQGTSVTVSS (SEQ ID NO: 158)

C290 Light:   DIVMTQAAPSVPVTPGESVSISCRSSKSLLHSNGNTYLYWFLQRPGQSPQLLIYRMSNLASGVPDRFSGS

GSGTAFTLRISRVEAEDVGVYYCMQHLEYPFTFGSGTMLEIK            (SEQ ID NO: 159)

FIG. 21 (Cont'd)

| | | Heavy Chain | | | Light Chain | | |
|---|---|---|---|---|---|---|---|
| | ISOTYPE | CDR1 | CDR2 | CDR3 | CDR1 | CDR2 | CDR3 |
| C53 | IgG2a,k | GFTFSNYWMN (SEQ ID NO: 160) | EIRLKYNNYATHYAE SVKG (SEQ ID NO: 161) | TRYGSSLDY (SEQ ID NO: 162) | KSSQNLFYSTNQKNYL A (SEQ ID NO: 163) | WASTRES (SEQ ID NO: 164) | QQYYNYPLT (SEQ ID NO: 165) |
| C84 | IgG2b,k | GYTFTNYGMN (SEQ ID NO: 166) | WINTYTGEPTYADD FKG (SEQ ID NO: 167) | IYYHTSLWYF DV (SEQ ID NO: 168) | RSSQNIVHSNGNTYLE (SEQ ID NO: 169) | RVSNRFS (SEQ ID NO: 170) | FQGSHVPLT (SEQ ID NO: 171) |
| C92 | IgG1,k | GYTFTNYGMN (SEQ ID NO: 172) | WINTYTGEPTYADD FKG (SEQ ID NO: 173) | IYYHTSLWYF DV (SEQ ID NO: 174) | RSSQSLVHSNGNTYLH (SEQ ID NO: 175) | KVSNRFS (SEQ ID NO: 176) | SQSTHVPYT (SEQ ID NO: 177) |
| C201 | IgG3,k | GYSITSDYAWN (SEQ ID NO: 178) | YISYSGGTSYNPSLK S (SEQ ID NO: 179) | LHYGYDY (SEQ ID NO: 180) | RSSQSIVHSNGNTYLE (SEQ ID NO: 181) | KVSNRFS (SEQ ID NO: 182) | FQGLHVPPT (SEQ ID NO: 183) |
| C3 | IgG2b,k | GFTFNNYAMN (SEQ ID NO: 184) | RIRSKRNNYATHYD DSVKD (SEQ ID NO: 185) | DGPYAMDY (SEQ ID NO: 186) | KSSQSLLYSSNQKNYLA (SEQ ID NO: 187) | WASTRES (SEQ ID NO: 188) | QQYYSYPYT (SEQ ID NO: 189) |
| C193 | IgG2a,k | GFIFNIYAMN (SEQ ID NO: 190) | RIRSKSNKYATYYVD SVKD (SEQ ID NO: 191) | DGI (SEQ ID NO: 192) | KSSQSLLNSGNQKNYL T (SEQ ID NO: 193) | WAFTRES (SEQ ID NO: 194) | QNDYSYPLT (SEQ ID NO: 195) |
| C287 | IgG1,k | GYTFTNYGIN (SEQ ID NO: 196) | WVKQAPGKGLKW MG (SEQ ID NO: 197) | GSAKGGFFY (SEQ ID NO: 198) | KSSQSLLYSNGRTYLN (SEQ ID NO: 199) | LVSKLDS (SEQ ID NO: 200) | VQGTHFPYT (SEQ ID NO: 201) |
| C39 | IgG3,k | GFTFSSYGMS (SEQ ID NO: 202) | TIDSNGGGTYYPDS VKG (SEQ ID NO: 203) | DGGGSYGYY YAMDY (SEQ ID NO: 204) | KSSQSLLNSRTRKSYLA (SEQ ID NO: 205) | WASTRES (SEQ ID NO: 206) | KQSYNLPWT (SEQ ID NO: 207) |
| C102 | IgG3,k | GYTFTEYTMH (SEQ ID NO: 208) | GINPNNGGTSYNQ KFKG (SEQ ID NO: 209) | YWDYFDY (SEQ ID NO: 210) | RSSQSIVHSNGNTYLE (SEQ ID NO: 211) | KVSNRFS (SEQ ID NO: 212) | FQGSQIPPT (SEQ ID NO: 213) |
| C298 | IgG3,k | GYTFTEYTMH (SEQ ID NO: 214) | GINPNNGGTSYNQ KFKG (SEQ ID NO: 215) | DKRSRGLLDS TMDV (SEQ ID NO: 216) | RSSKSLLHSNGNTYIY (SEQ ID NO: 217) | RMSNLAS (SEQ ID NO: 218) | MQHLLYPFT (SEQ ID NO: 219) |

FIG. 22

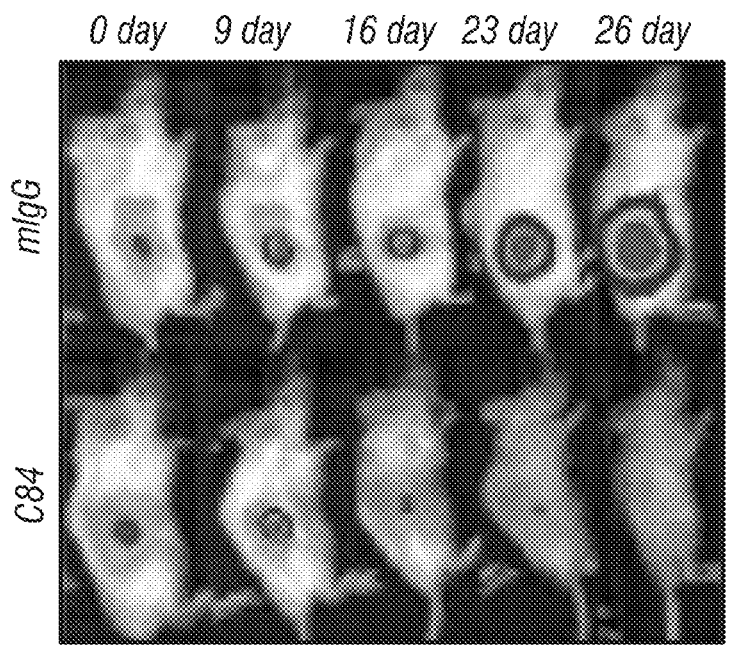
FIG. 30F
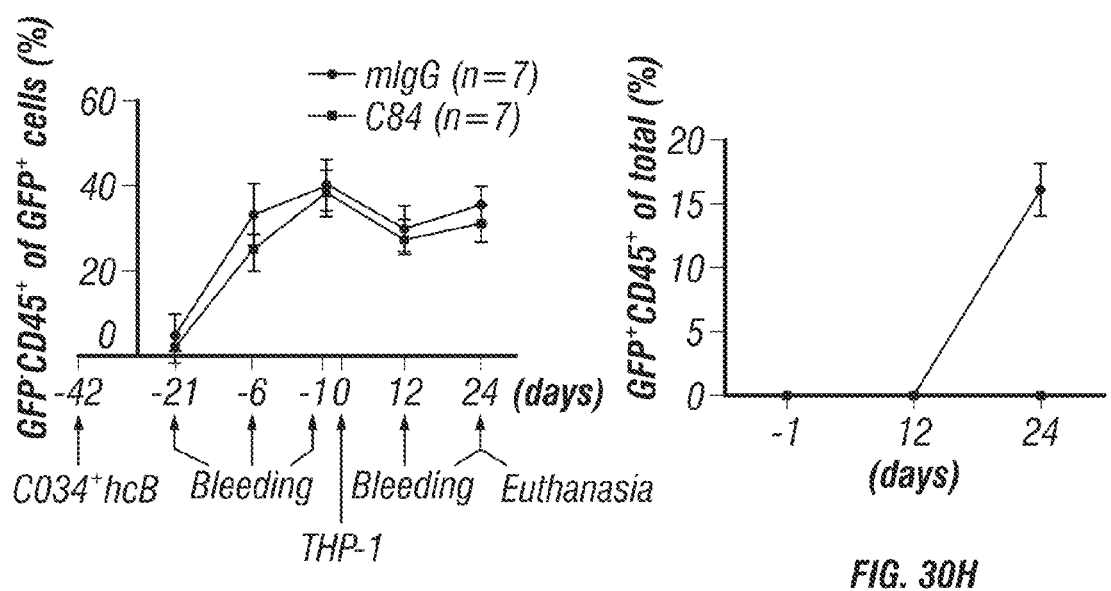
FIG. 30G
FIG. 30H

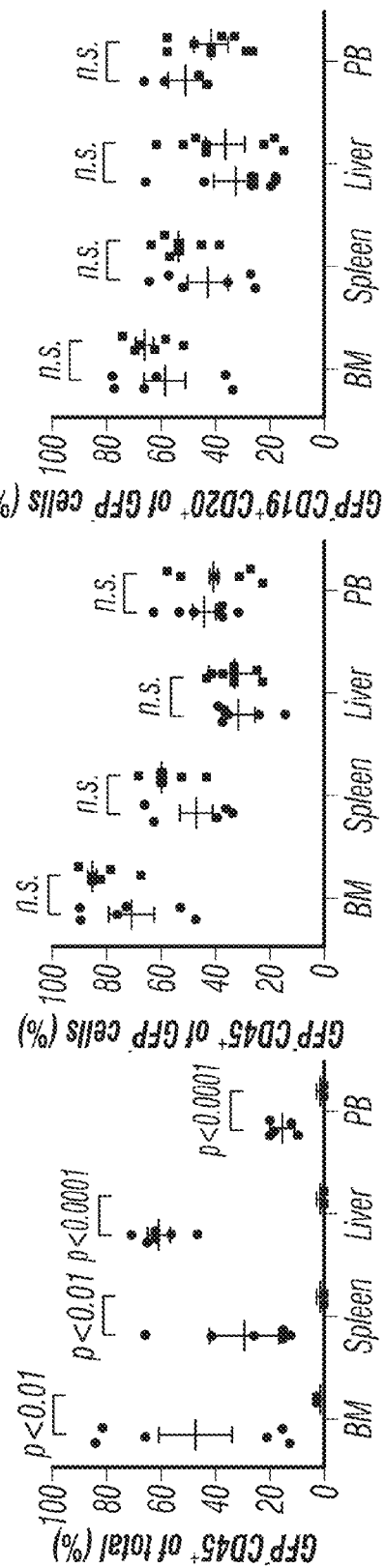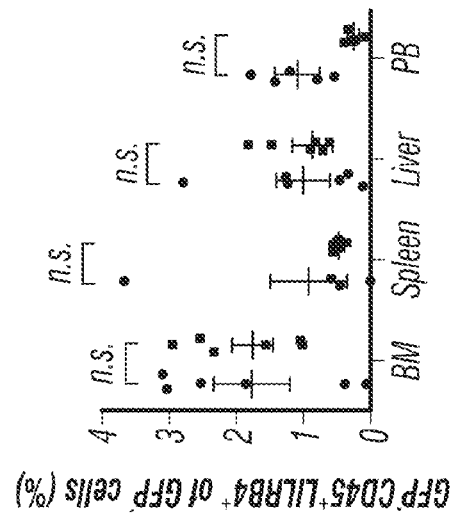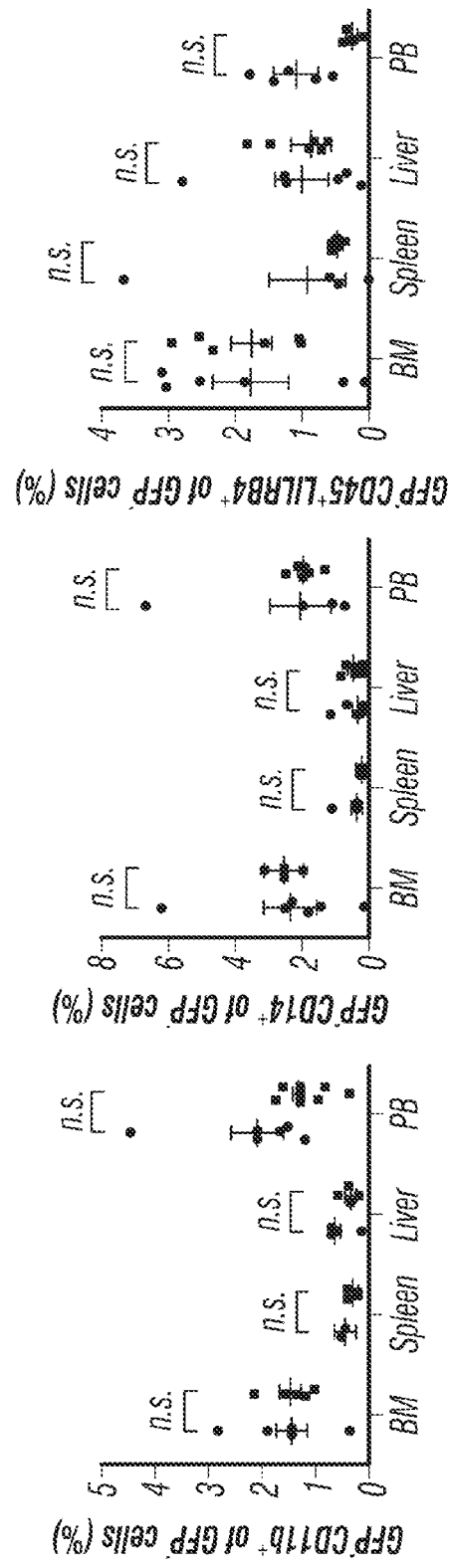

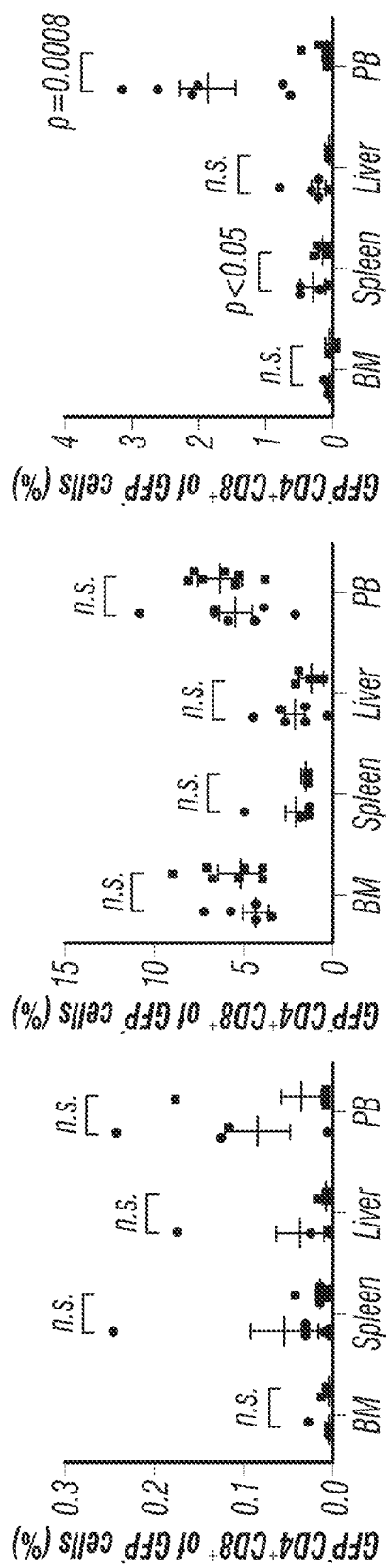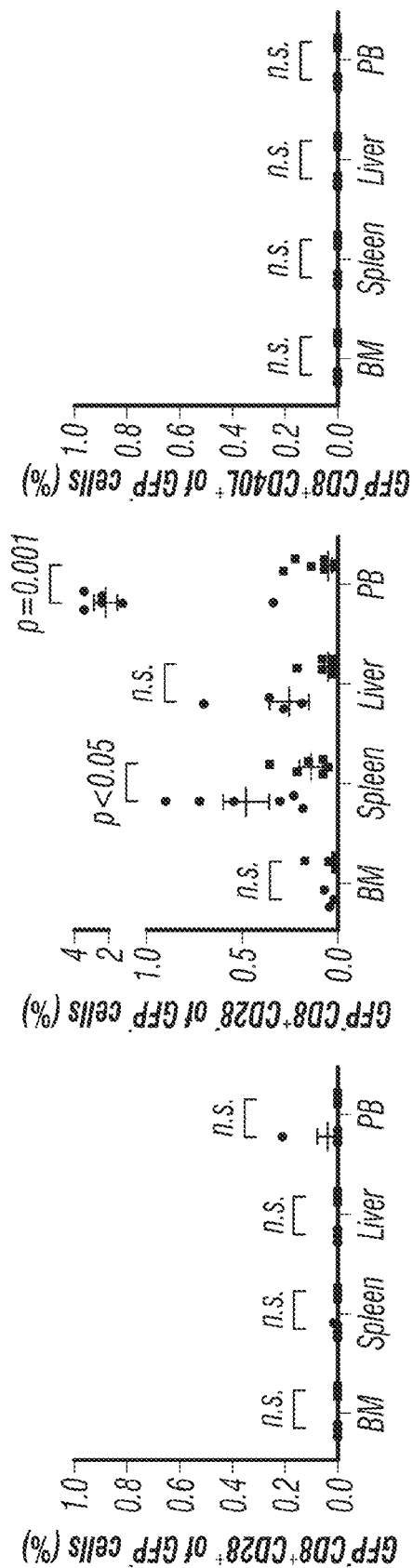

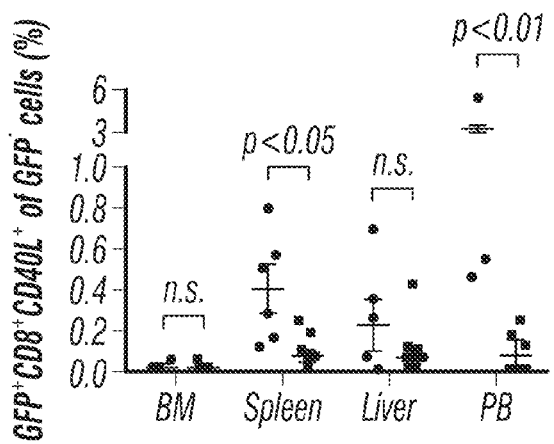
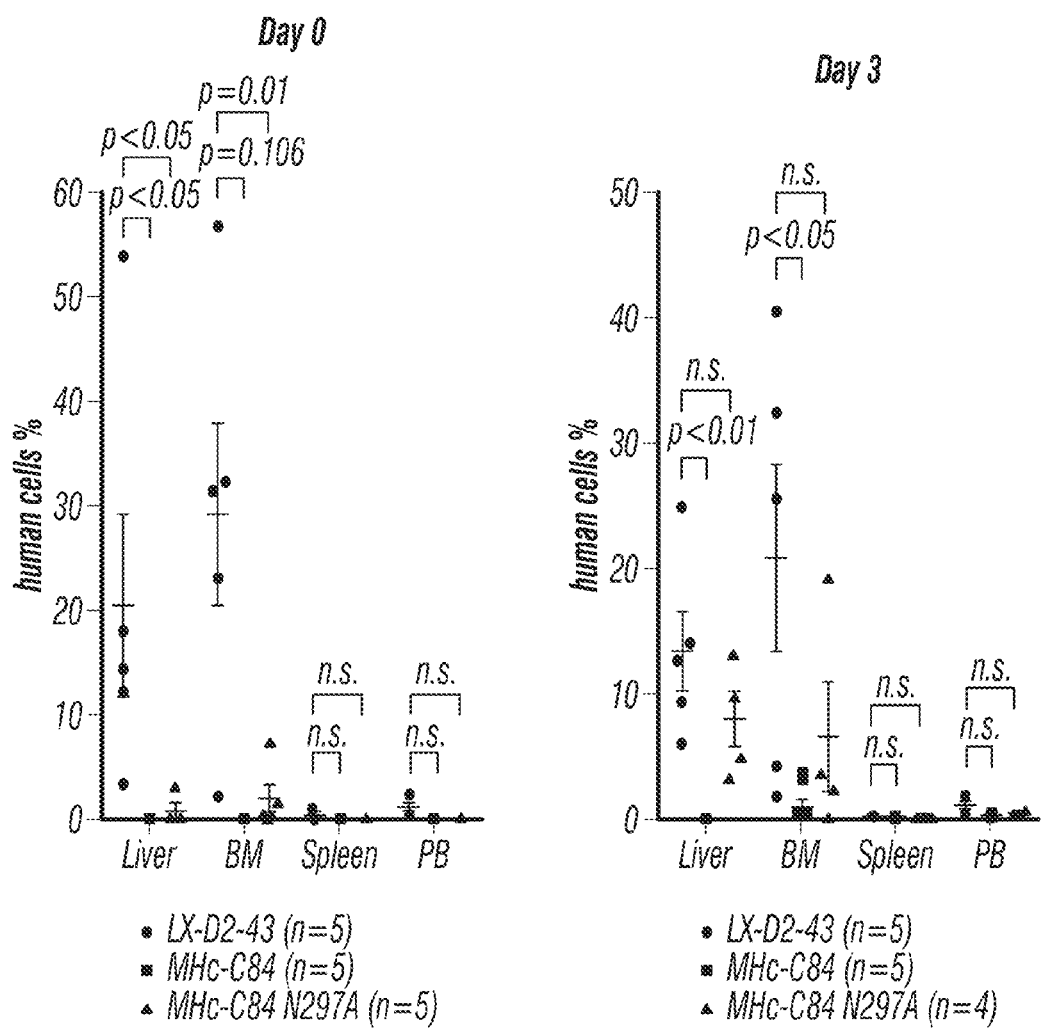
FIG. 31 a
b
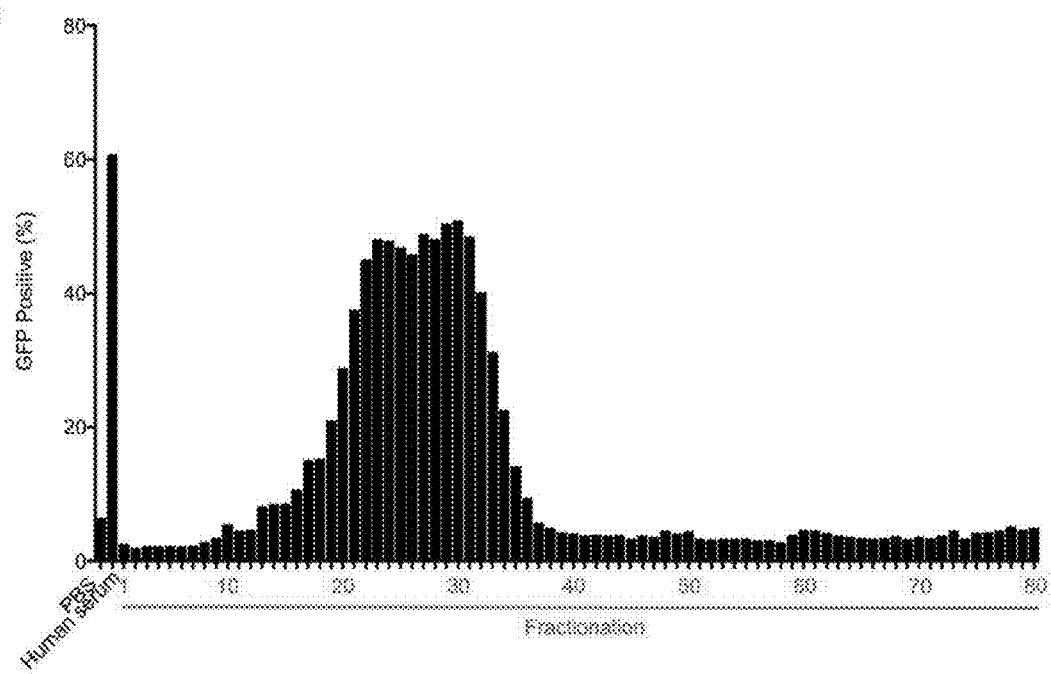
c
FIGS. 36a-36c

ANTI-LILRB ANTIBODIES AND THEIR USE IN DETECTING AND TREATING CANCER

This application is a continuation-in-part of PCT/US2016/020838, filed Mar. 4, 2016, which claims benefit of priority to U.S. Provisional Application Ser. No. 62/129,572, filed Mar. 6, 2015, the entire contents of both applications being hereby incorporated by reference.

The invention was made with government support under Grant No. 1R01 CA172268 awarded by the National Institutes of Health. The government has certain rights in the invention.

INCORPORATION OF SEQUENCE LISTING

The sequence listing that is contained in the file named "UTSHP2882USCP1_ST25.txt", which is 259 KB (as measured in Microsoft Windows®) and was created on Sep. 6, 2017, is filed herewith by electronic submission and is incorporated by reference herein.

BACKGROUND

1. Field of the Disclosure

The present disclosure relates generally to the fields of medicine, oncology, and immunology. More particular, the disclosure relates to antibodies that bind to LILRBs and can treat cancers, including leukemia.

2. Background

Acute myeloid leukemia (AML) is the most common acute leukemia of adults. Despite continuous treatment, most patients relapse within 5 years. To effectively treat acute leukemia, new molecular targets and therapeutic approaches must be identified. Recently, the inventors cloned the human leukocyte immunoglobulin-like receptor B2 (LILRB2) as a receptor for several angiopoietin-like proteins (Angptls) (Zheng et al., 2012). The LILRB family receptors are type I transmembrane glycoprotein containing extracellular Ig-like domains that bind ligands and intracellular immunoreceptor tyrosine-based inhibitory motifs (ITIMs) and are classified as inhibitory receptors because ITIM motifs can recruit phosphatases SHP-1, SHP-2, or SHIP to negatively regulate immune cell activation (Takai et al., 2011; Daeron et al., 2008; Katz et al., 2006). It is known that LILRBs are expressed on myeloid cells and certain other hematopoietic cells (Mori et al., 2008). Surprisingly, the inventors have shown that PirB, the mouse ortholog of LILRB2, and LAIR1, a close related ITIM-receptor, are expressed by AML stem cells (AML-SCs) and support AML development (Zheng et al., 2012; Kang et al., 2015). Although counterintuitive, this result is consistent with the generally immune-suppressive and thus tumor-promoting roles of the inhibitory receptors in the immune system (Ma et al., 2011).

In recent work, the inventors found that several members of the LILRB family are highly expressed on AML cells, and their expression negatively correlates with the overall survival of human AML patients. LILRBs are expressed by both AML-SCs and some differentiated acute leukemia cells (including AML and acute lymphoblastic leukemia or ALL). There is no defect in the normal hematopoietic development in mice that do not express any individual LILRB tested. Interestingly, however, knockout of individual LILRBs reversed leukemia development in a number of AML and acute lymphoblastic leukemia (ALL) mouse models and abolished AML-SCs (Zheng et al., 2012; Kang et al., 2015; also see PCT/US13/43431). In addition, inhibition of expression of several LILRBs individually in different human leukemia cell lines in culture and blocked leukemia development in xenografted mice (Kang et al., 2015; also see PCT/US13/43431).

The inventors have determined that some leukemia stem cells express high levels of ITIM-inhibitory receptors including LILRBs. The current treatment options for patients with acute leukemia, including chemotherapy, do not efficiently target cancer stem cells because these inhibitory receptors enable the leukemia stem cells to survive the conventional therapies eventually resulting in tumor relapse. The inventors theorize that LILRB signaling represents an ideal target for treating AML for several reasons: 1) several LILRBs are essential to the survival of AML cells including AML-SCs; 2) knockout of an individual LILRB does not result in overt defects in normal hematopoiesis; and 3) inhibition of LILRB activity stimulates immunity and indirectly boosts antitumor effects.

SUMMARY

Thus, in one aspect, the present disclosure provides an isolated monoclonal antibody or an antigen-binding fragment thereof that binds specifically to LILRB. In certain embodiments, the LILRB is LILRB1, LILRB2, LIRB3, LILRB4, LILRB5 or LAIR1. In certain embodiments, the LILRB is LILRB4. In certain embodiments, the antibody or antigen-binding fragment, when bound to LILRB4, modulates the activation of LILRB4. In certain embodiments, the antibody or antigen-binding fragment, when bound to LILRB4, activates LILRB4. In certain embodiments, the antibody or antigen-binding fragment, when bound to LILRB4, suppresses activation of LILRB4. In certain embodiments, the antibody or antigen-binding fragment, when bound to LILRB4, specifically blocks binding of ApoE to LILRB4.

In certain embodiments, the antibody or antigen-binding fragment binds to a fragment of LILRB4 comprising amino acid residues 27-118 of SEQ ID NO: 238. In certain embodiments, the antibody or antigen-binding fragment binds to a fragment of LILRB4 comprising amino acid residues 119-218 of SEQ ID NO: 238. In certain embodiments, the antibody or antigen-binding fragment binds to a fragment of LILRB4 comprising amino acid residues 219-259 of SEQ ID NO: 238. In certain embodiments, the antibody or antigen-binding fragment binds to an epitope of LILRB4 comprising amino acid residues 238-244 of SEQ ID NO: 238. In certain embodiments, the antibody or antigen-binding fragment binds to a fragment of LILRB4 comprising amino acid residues 200-211 of SEQ ID NO: 238. In certain embodiments, the antibody or antigen-binding fragment binds to a fragment of LILRB4 comprising amino acid residues 129-140 of SEQ ID NO: 238. In certain embodiments, the antibody or antigen-binding fragment binds to a fragment of LILRB4 comprising amino acid residues 219-230 of SEQ ID NO: 238. In certain embodiments, the antibody or antigen-binding fragment binds to a fragment of LILRB4 comprising amino acid residues 173-184 of SEQ ID NO: 238. In certain embodiments, the antibody or antigen-binding fragment binds to an epitope of LILRB4 comprising amino acid residues 245-250 of SEQ ID NO: 238. In certain embodiments, the antibody or antigen-binding fragment binds to at least one of the following residues: P35, W106 and Y121 of SEQ ID NO: 238. In certain embodiments, the antibody or antigen-binding fragment binds to at least one of the following residues: E54, R56, P103 and W106 of SEQ ID NO: 238. In certain embodiments, the antibody or antigen-binding fragment binds to at least one of the following residues: S220, L221, P224 and P226 of SEQ ID NO: 238. In certain embodiments, the antibody or antigen-binding fragment binds to at least one of the following residues: A67 and Q72 of SEQ ID NO: 238. In certain embodiments, the antibody or antigen-binding fragment binds to at least one of the following residues: R59, A67, Y99, R101 and W106 of SEQ ID NO: 238.

In certain embodiments, the antibody is characterized by clone-paired heavy and light chain CDR sequences contained in FIG. 16 or FIG. 21. In certain embodiments, each CDR is defined in accordance with Kabat definition, the Chothia definition, the combination of Kabat definition and Chothia definition, the AbM definition, or the contact definition of CDR. In certain embodiments, the antibody is characterized by clone-paired heavy and light chain CDR sequences from FIG. 17 or FIG. 22.

In certain embodiments, the antibody is characterized by clone-paired heavy chain and light chain having amino acid sequences at least about 70%, 80%, 90%, or 95% identity to the clone-paired sequences from FIG. 16 or FIG. 21.

In another aspect, the present disclosure provides an isolated monoclonal antibody or an antigen-binding fragment thereof, which competes for the same epitope with an antibody having clone-paired heavy and light chain CDR sequences from FIG. 17 or FIG. 22. In certain embodiments, the antibody competes for the same epitope with an antibody having clone-paired heavy and light chain variable regions from FIG. 16 or FIG. 21.

In certain embodiments, the isolated monoclonal antibody described herein is a chimeric, humanized, or human antibody. In certain embodiments, isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')$_2$ fragment, or Fv fragment.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody, and recovering the antibody.

In another aspect, there is provided a method of treating or ameliorating the effects of a cancer in a subject. The method may comprise administering to the subject a therapeutically effective amount of the antibody or an antigen-binding fragment thereof as provided herein. In certain embodiments, the cancer is acute myeloid leukemia. In certain embodiments, the antibody or an antigen-binding fragment thereof is administered intravenously, intra-arterially, intra-tumorally or subcutaneously.

In yet another aspect, there is provided a method of detecting a cancer cell or cancer stem cell in a sample or subject. In certain embodiments, the method comprises contacting a subject or a sample from the subject with the antibody or an antigen-binding fragment thereof as provided herein, and detecting binding of said antibody to a cancer cell or cancer stem cell in said subject or sample. The sample can be a body fluid or biopsy. The sample can be blood, sputum, tears, saliva, mucous, serum, urine or feces. In certain embodiments, the detection comprises immunohistochemistry, ELISA, RIA or Western blot.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1a-1d—Expression of LILRBs in primary human AML cells. (FIG. 1a) LILRB4 is expressed on ~50% tested human AML cases. (FIGS. 1b-c) LILRB4 is a better marker than CD14 for human monocytic AML cells (M5b, peripheral blood) and LILRBs including LILRB4 can be co-expressed with the leukemia stem cell marker CD34 (FIG. 1d).

LILRBs including LILRB4 can be co-expressed with the leukemia stem cell marker CD34

FIGS. 2a-2d—Expression of individual LILRB1, 2, 3, 4 inversely correlates with overall survival of AML patients. Data were from the TCGA database (tcga-data.nci.nih.gov/tcga/; accessed Nov. 5, 2012). n=92, p<0.05.

FIGS. 3a-3d—The expression of shRNA against LILRB3 or LILRB4 robustly inhibited cell growth. (FIG. 3a) Both THP-1 and MV4-11 human AML cells express LILRB4 on their cell surfaces. (FIG. 3b) shRNAs were designed specifically knockdown individual LILRB expression as determined by real-time RT-PCR. (FIGS. 3C-D) THP-1 (FIG. 3c) and MV4-11 (FIG. 3d) cells were respectively infected with P113.7 lentiviruses that express shRNAs targeted to individual LILRBs or a scrambled control. The expression of shRNA against LILRB3 or LILRB4 robustly inhibited cell growth.

Figure 2A:
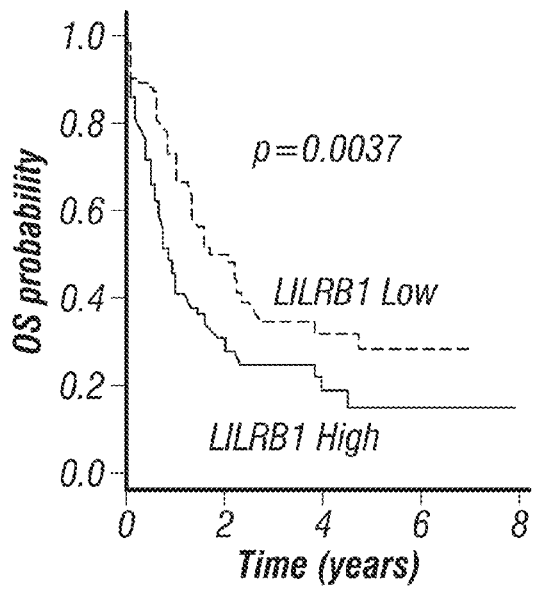
Figure 2B:
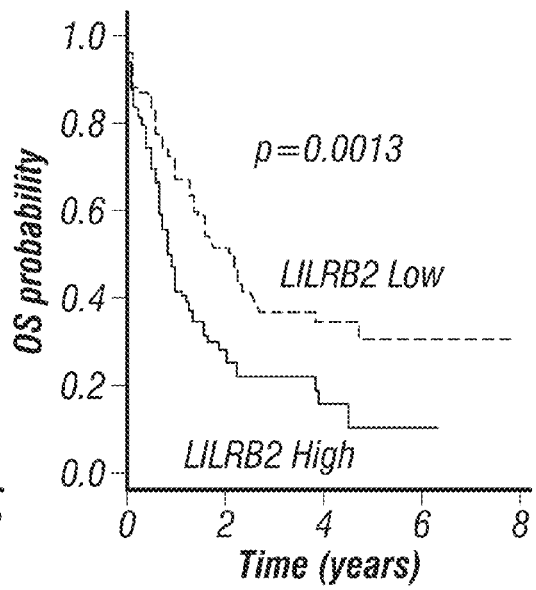
Figure 2C:
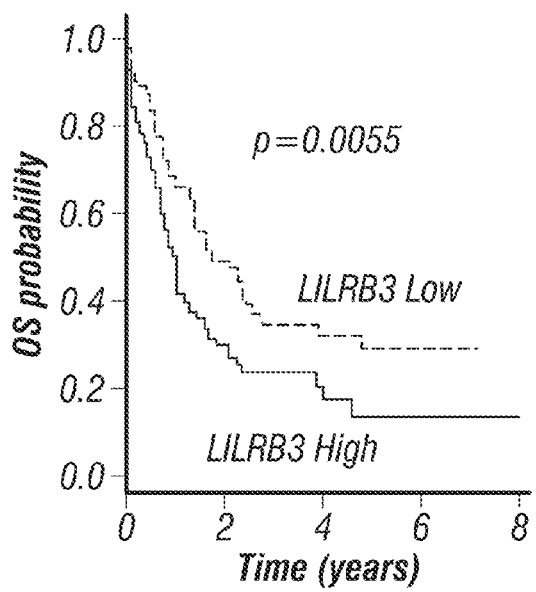
Figure 2D:
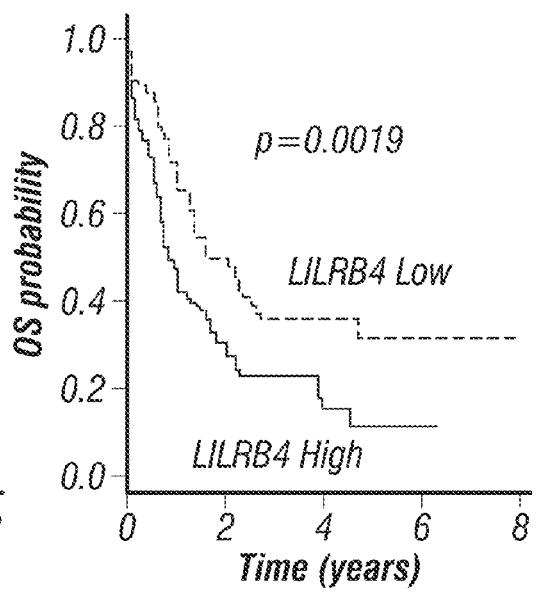
Figure 3A:
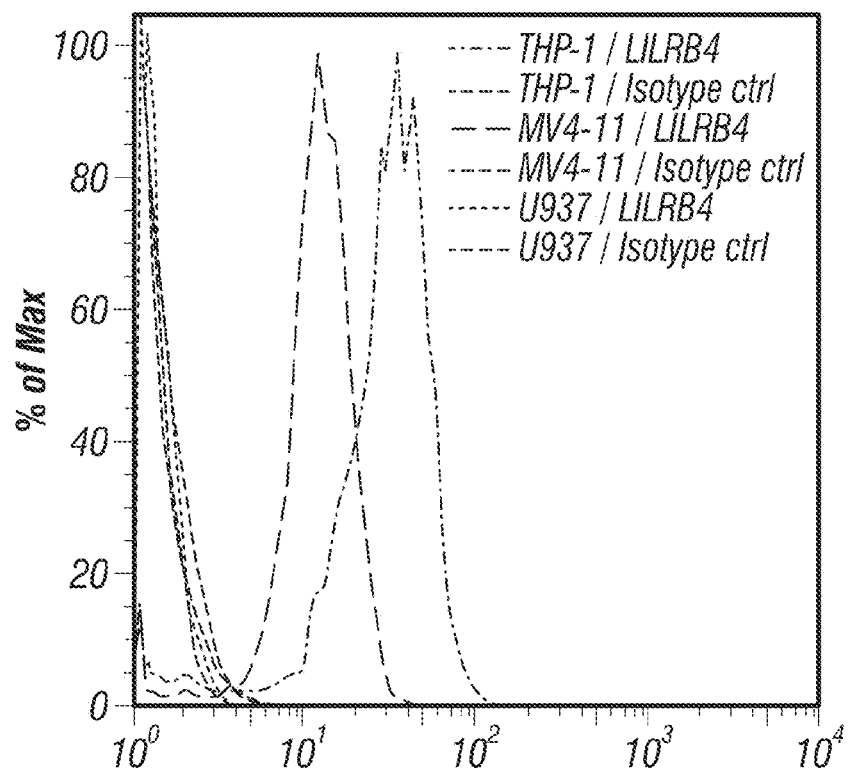
Figure 3B:
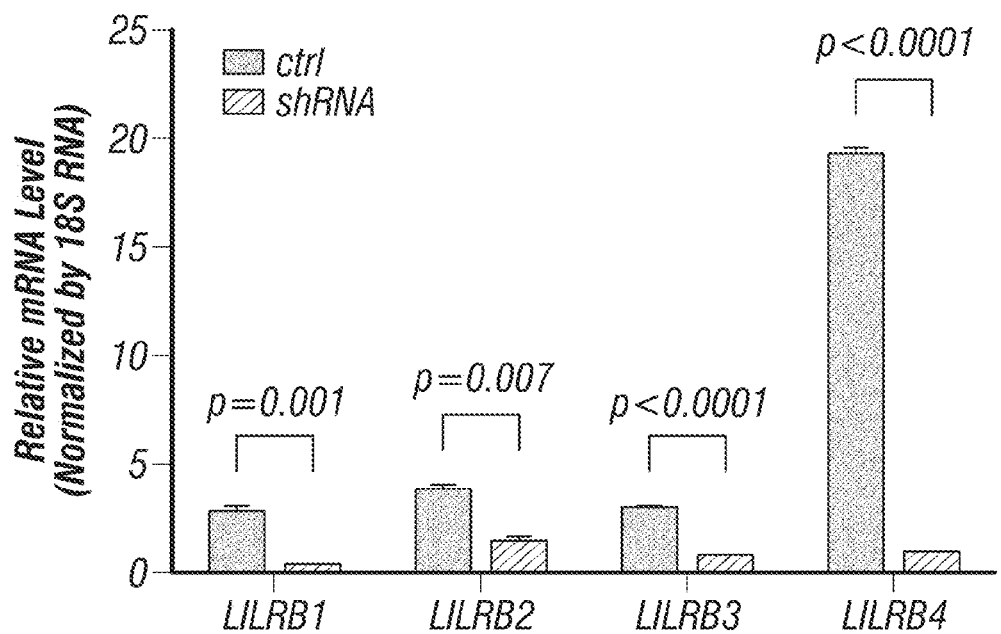
Figure 3C:
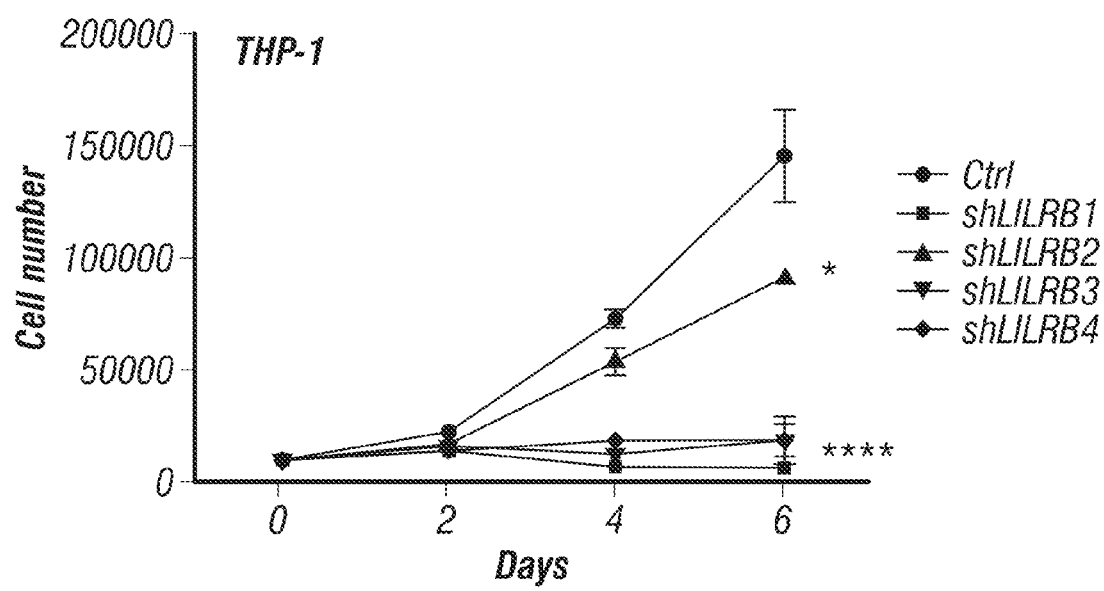
Figure 3D:
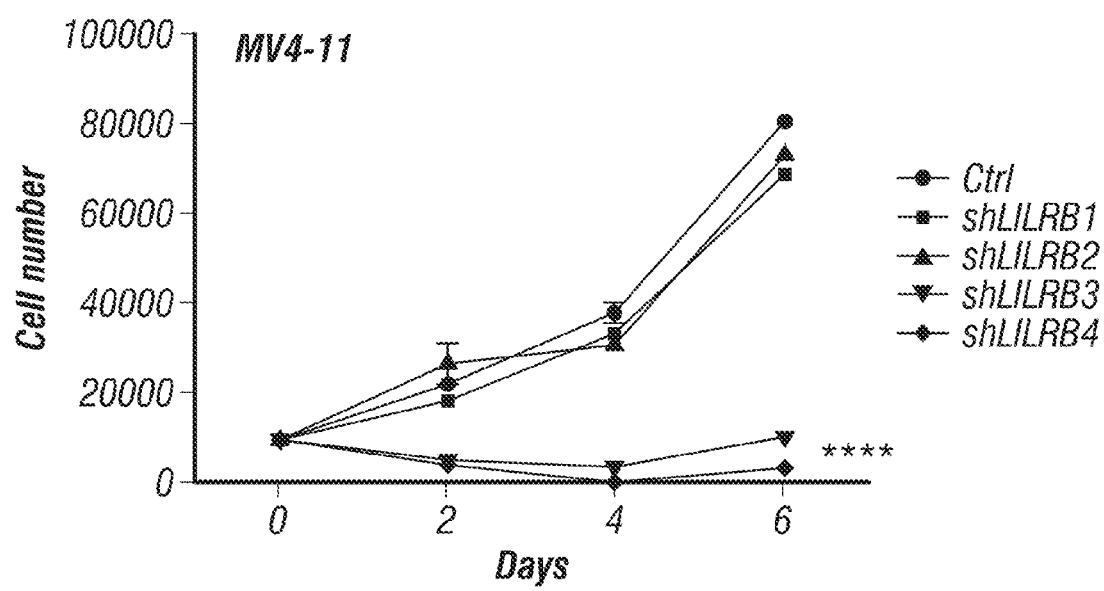
Figure 4:
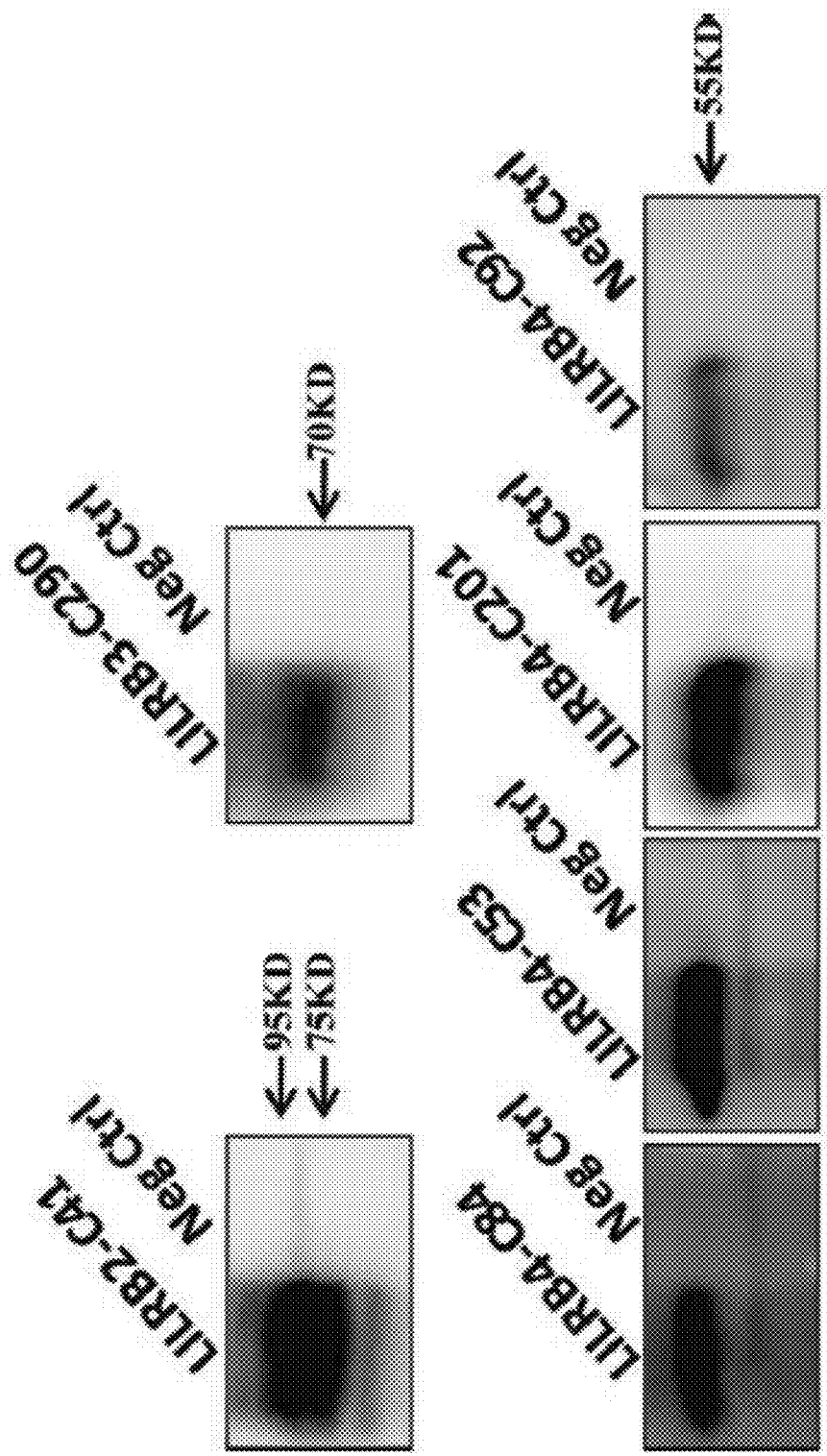

FIG. 4—LILRB Abs for Western blotting. Indicated mAbs bind to human LILRB2, 3, 4 respectively in Western blotting.

Figure 5:
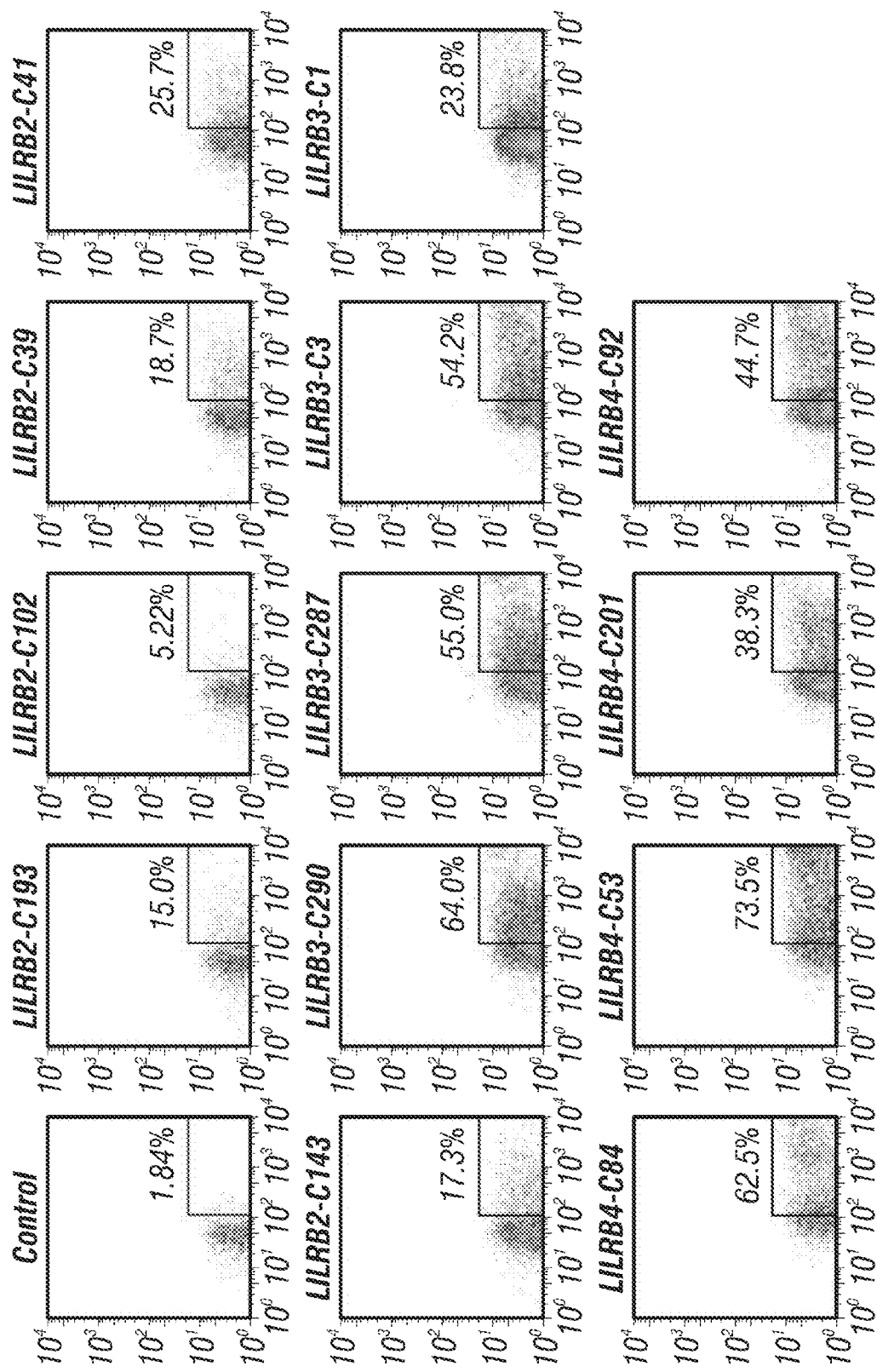

FIG. 5—LILRB Abs' binding on LILRB-overexpressing 293T cells. Indicated 2 μg/ml mAbs bind to human LILRB2, 3, 4 overexpressing 293T cells as determined by flow cytometry.

FIG. 6—Immobilized (coated) LILRB Abs' effects on reporter cells. Indicated immobilized mAbs that were developed to target human LILRB2, 3, 4 induce activation of LILRB2,3,4 respectively. Together with FIG. 7 that shows soluble anti-LILRB4 inhibits activation of the chimeric receptor reporter, the result indicate that these antibodies are blocking antibodies against LILRB2, 3, 4 respectively. Indicated mAbs were immobilized on tissue culture dishes (10 μg/ml). LILRB2, 3, 4 chimeric receptor reporter cells were cultured in these dishes. GFP induction was measured by flow cytometry at 12 hr. The chimeric receptor reporter system that can measure the activity of LILRB agonists and antagonists was described in Deng et al., 2014 *Blood*, 124(6):924-35

FIG. 7—Soluble anti-LILRB4 mAbs inhibit GFP induction in reporter cells. Antibodies including C84, C53, C92, C201 inhibit GFP induction by coated antibody in the chimeric receptor reporter system for LILRB4.

Figure 8:
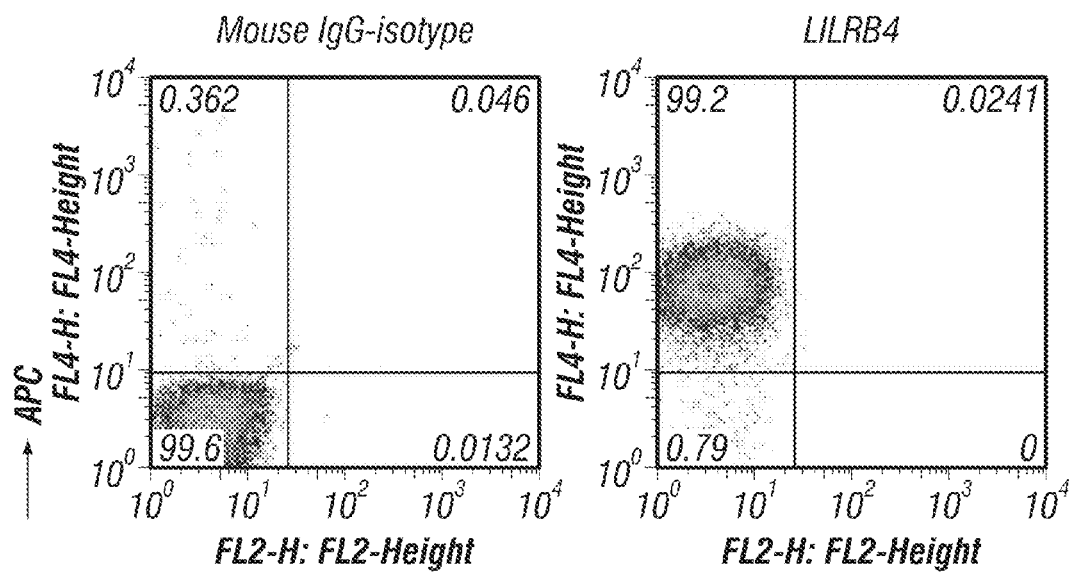
Figure 9:
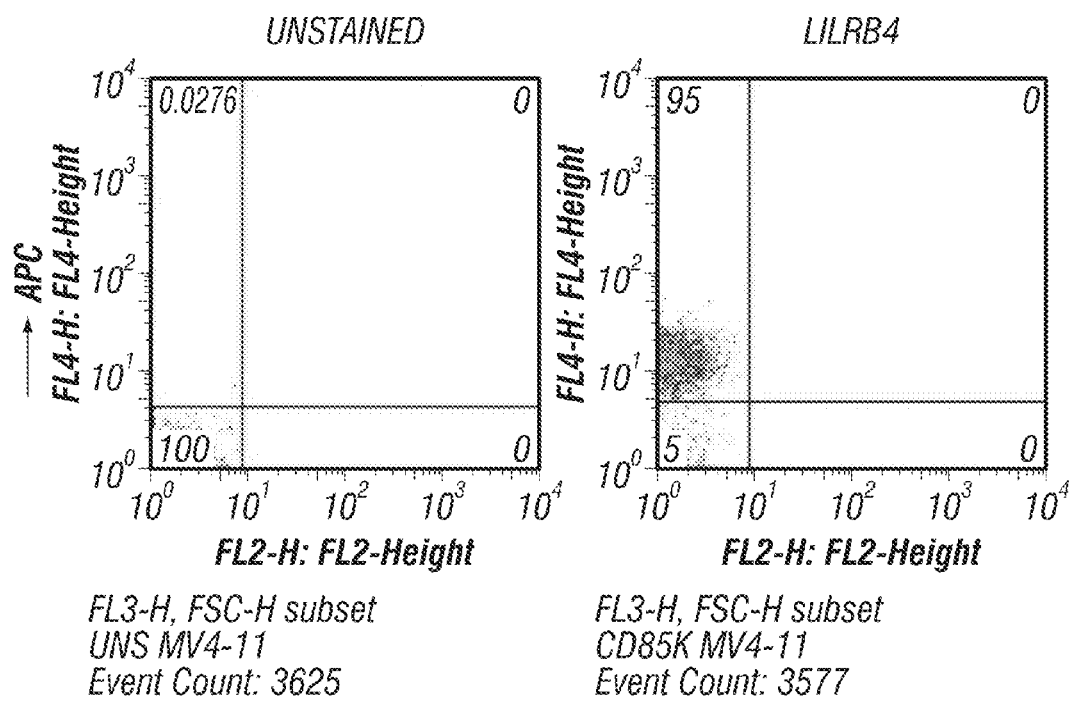

FIGS. 8-9—THP-1 (FIG. 8) and MV4-11 (FIG. 9) cells express LILRB4 on cell surface as determined by flow cytometry.

Figure 10:
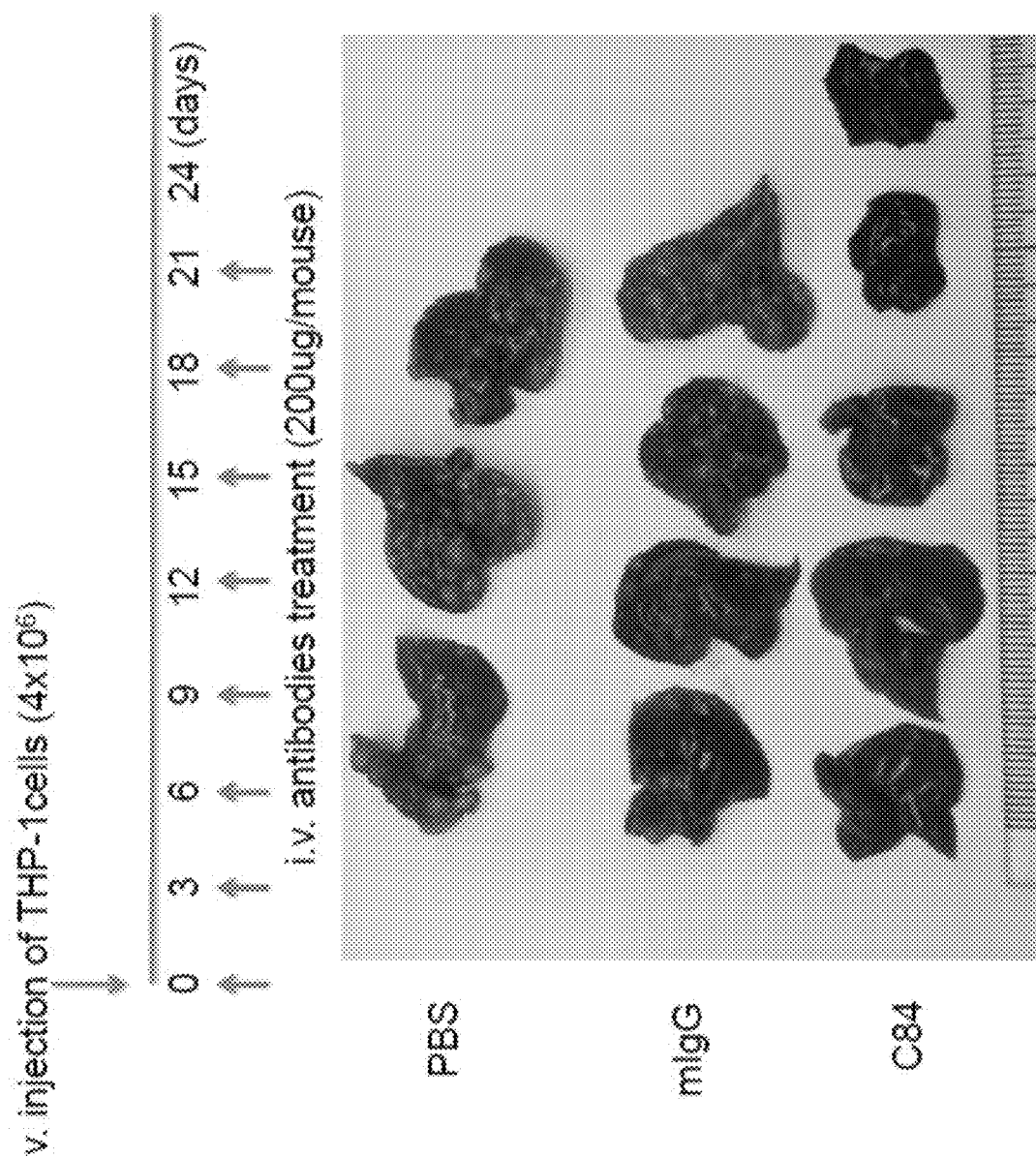
Figure 11:
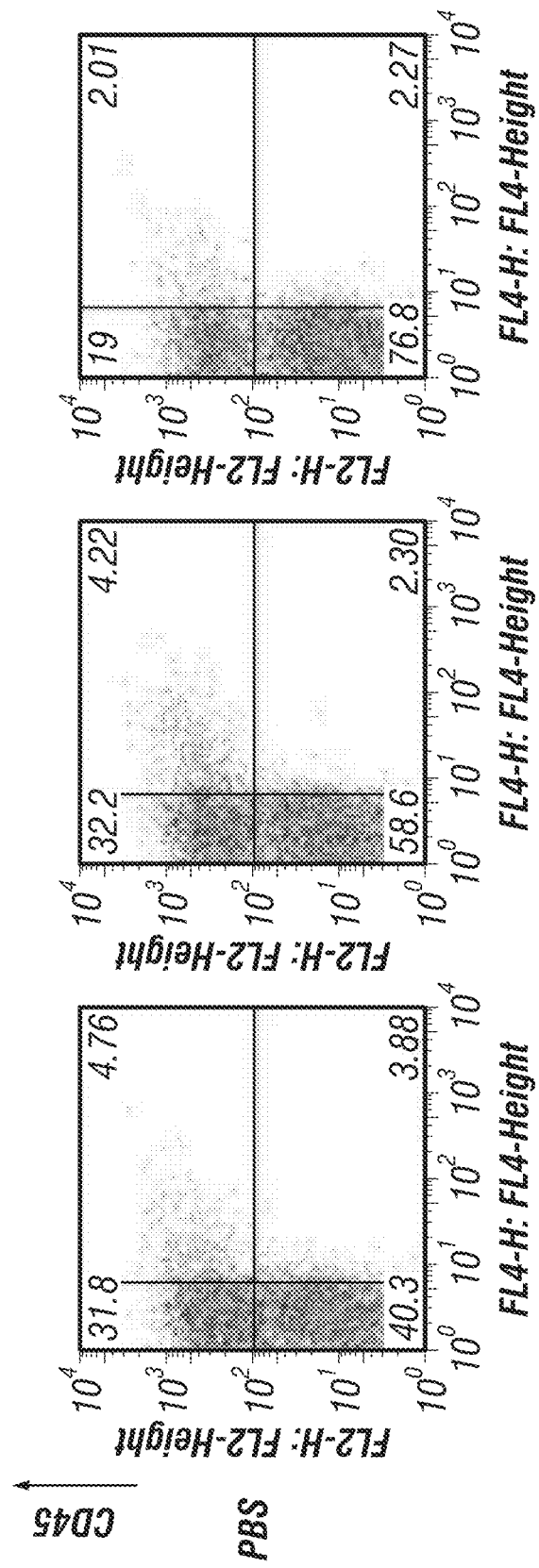
Figure 12:
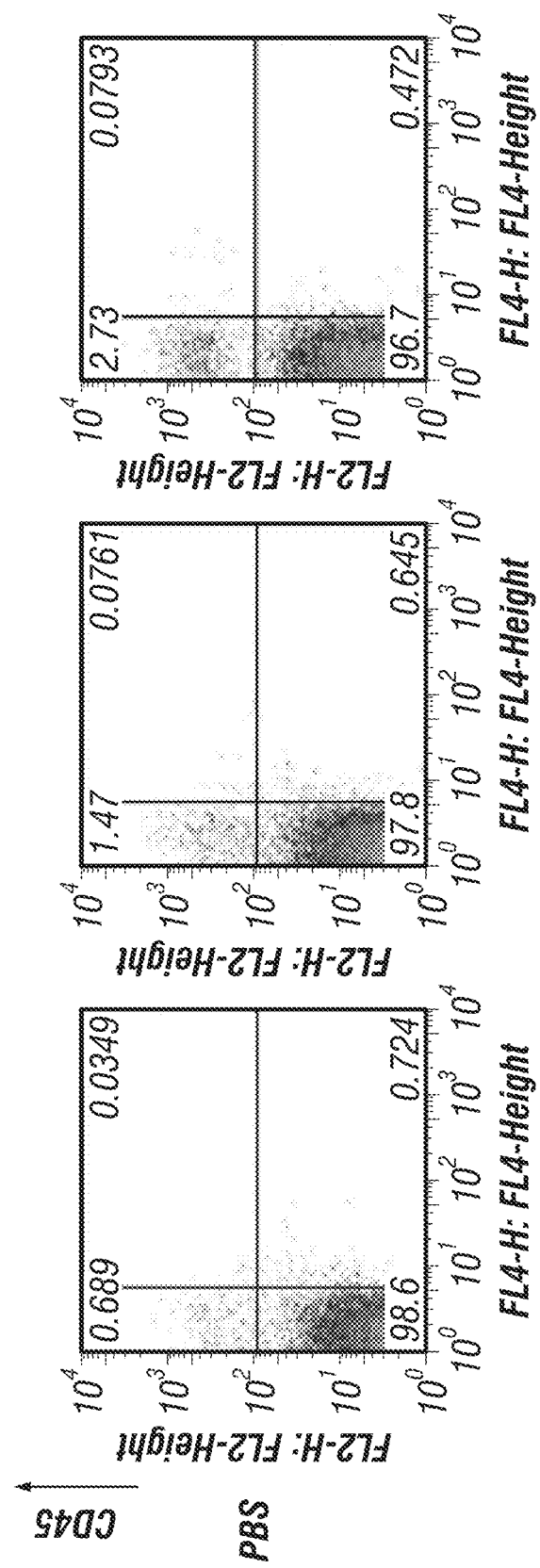

FIGS. 10-12—C84 (anti-hLILRB4) inhibits human AML development in intravenously xenografted NSG mice. $4 \times 10^6$ human AML cell line THP-1 that are LILRB4$^+$ were intravenously implanted into NSG mice. 200 μg C84 was i.v. injected into each mouse every 3 days (for a total of 8 times) starting from the first day when THP-1 cells were implanted. PBS and mouse IgG served as controls. Tumor growth was monitored over time by examining the leukemia infiltration in recipient liver (FIGS. 10-11) and bone marrow (FIG. 12). hCD45 was used to detect human leukemia cells by flow cytometry.

Figure 13:
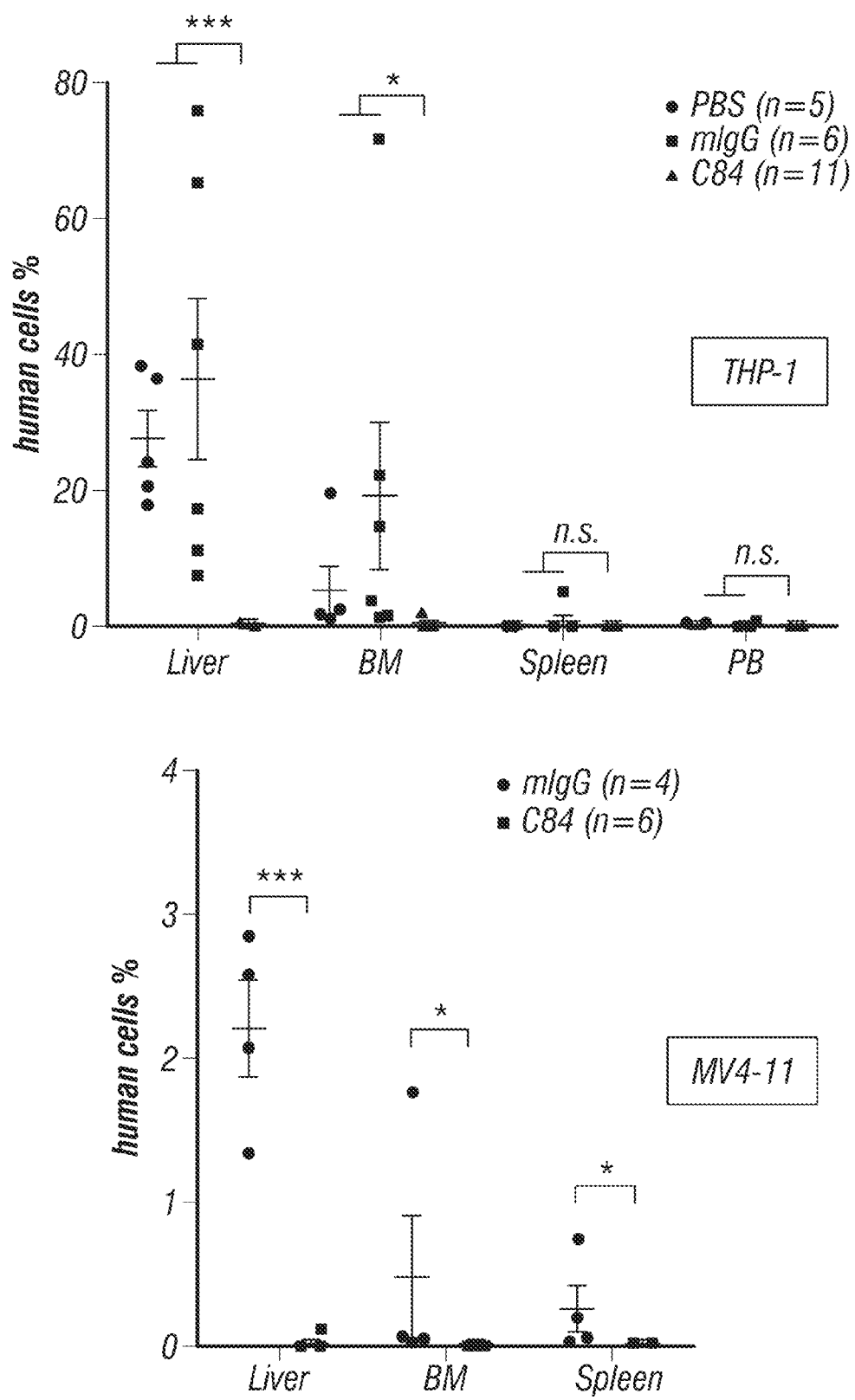
Figure 13:
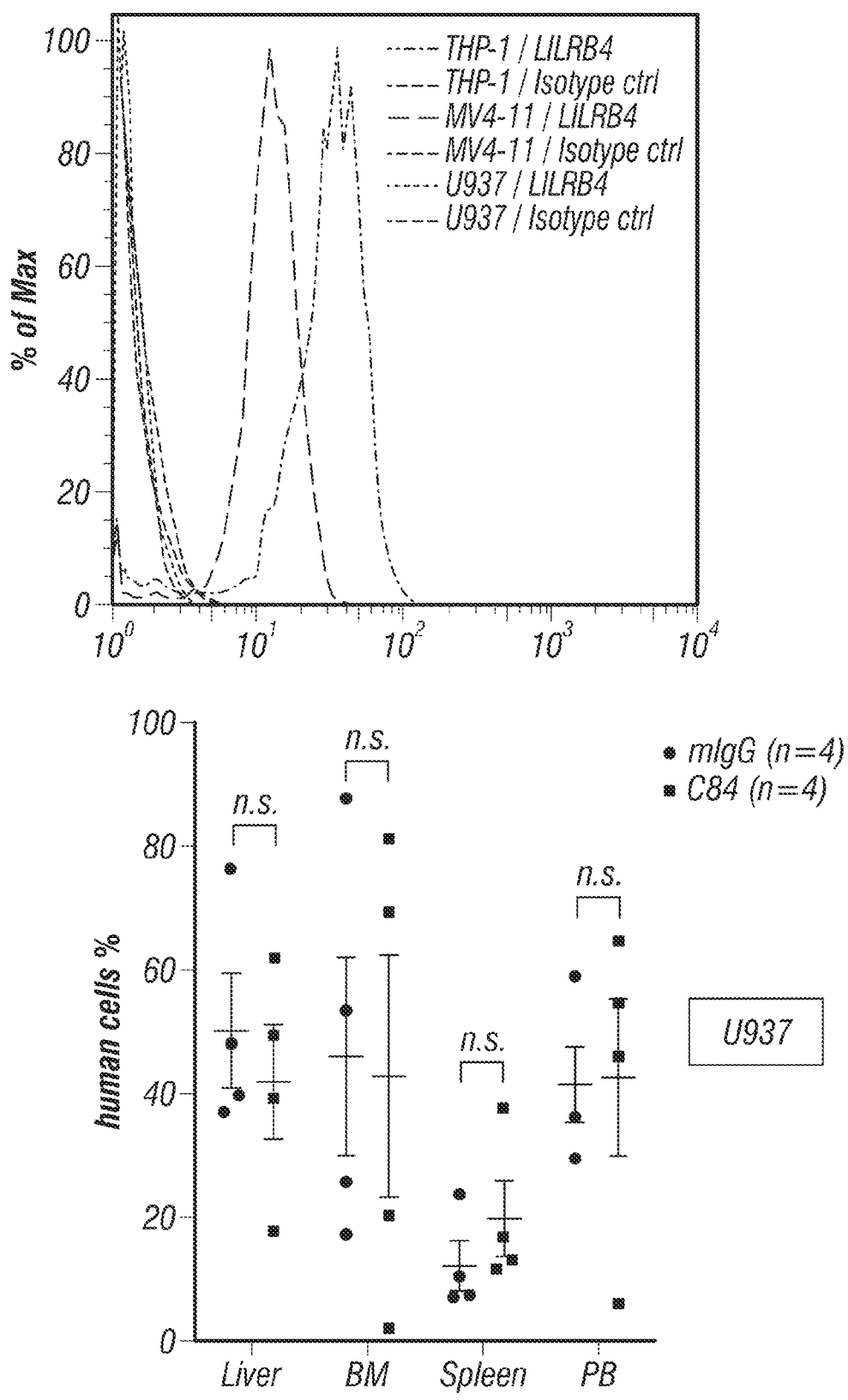

FIG. 13—C84 suppresses tumor engraftment of all tested LILRB4+ human leukemia cells. Only the tumors formed by the LILRB4+ human leukemia cells (THP-1 and MV4-11) can be effectively inhibited by C84. The tumors formed by LILRB4$^-$ cells (U937) cannot be inhibited by C84. Graphs show tumor growth by examining the leukemia infiltration in recipient liver, spleen, bone marrow, and peripheral blood implanted with THP-1, MV4-11, and U937 cells. hCD45 was used to detect human leukemia cells by flow cytometry. LILRB4 was detected on cell surface of THP-1 and MV4-11 cells but not on U937 cells by flow cytometry (lower left panel).

Figure 14:
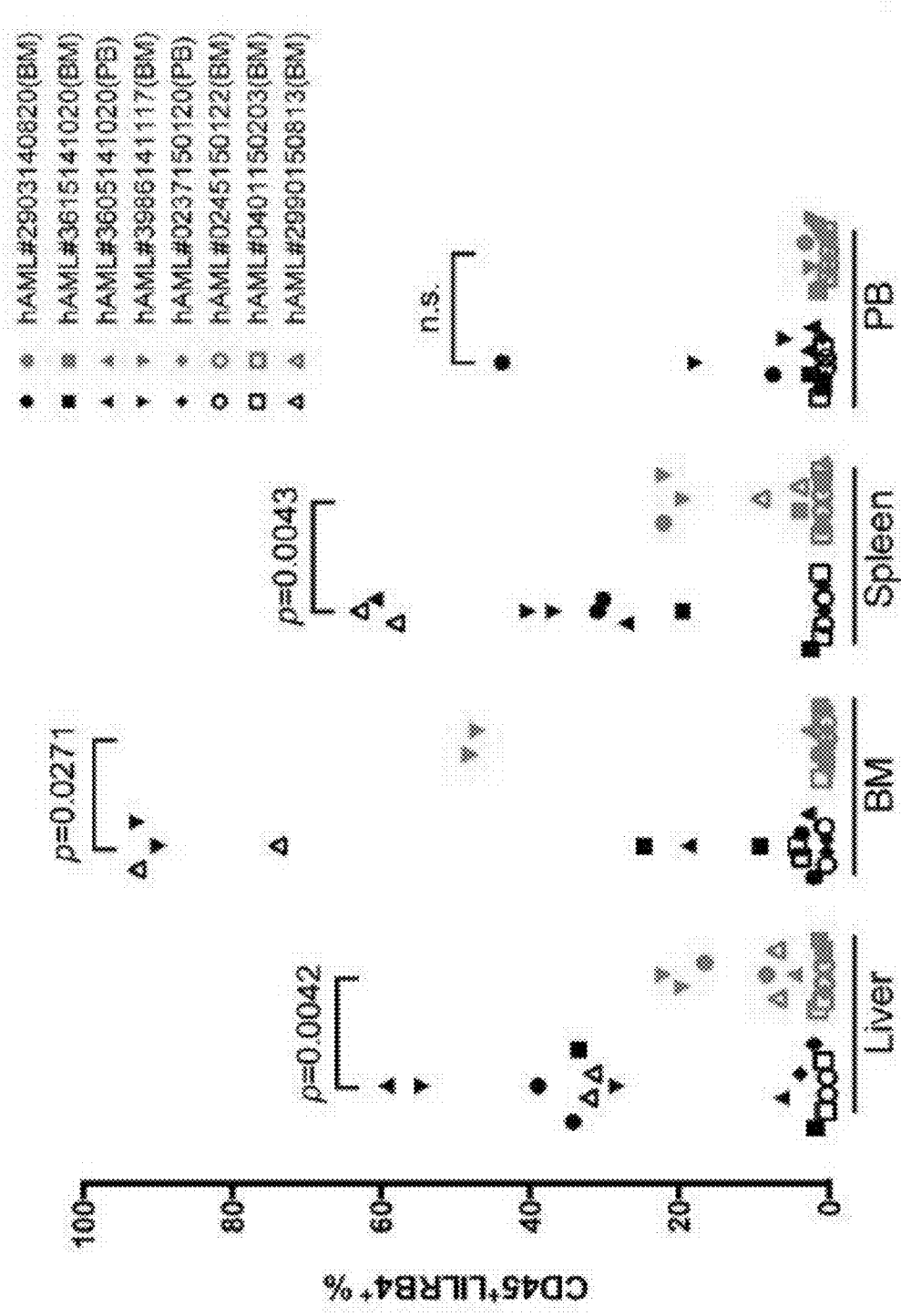

FIG. 14—C84 (anti-hLILRB4) inhibits development of primary patient AML in intravenously xenografted NSG mice (8 different patients). $4$-$10 \times 10^6$ primary human AML cells that are LILRB4$^+$ were intravenously implanted into NSG mice. 200 μg C84 was iv injected into each mouse twice per week starting from the first day when AML cells were implanted. Mouse IgG served as controls. Tumor growth was monitored over time by examining the leukemia infiltration in recipient liver, spleen, bone marrow, and peripheral blood. hCD45 and hLILRB4 were used to detect human leukemia cells by flow cytometry.

Figure 15:
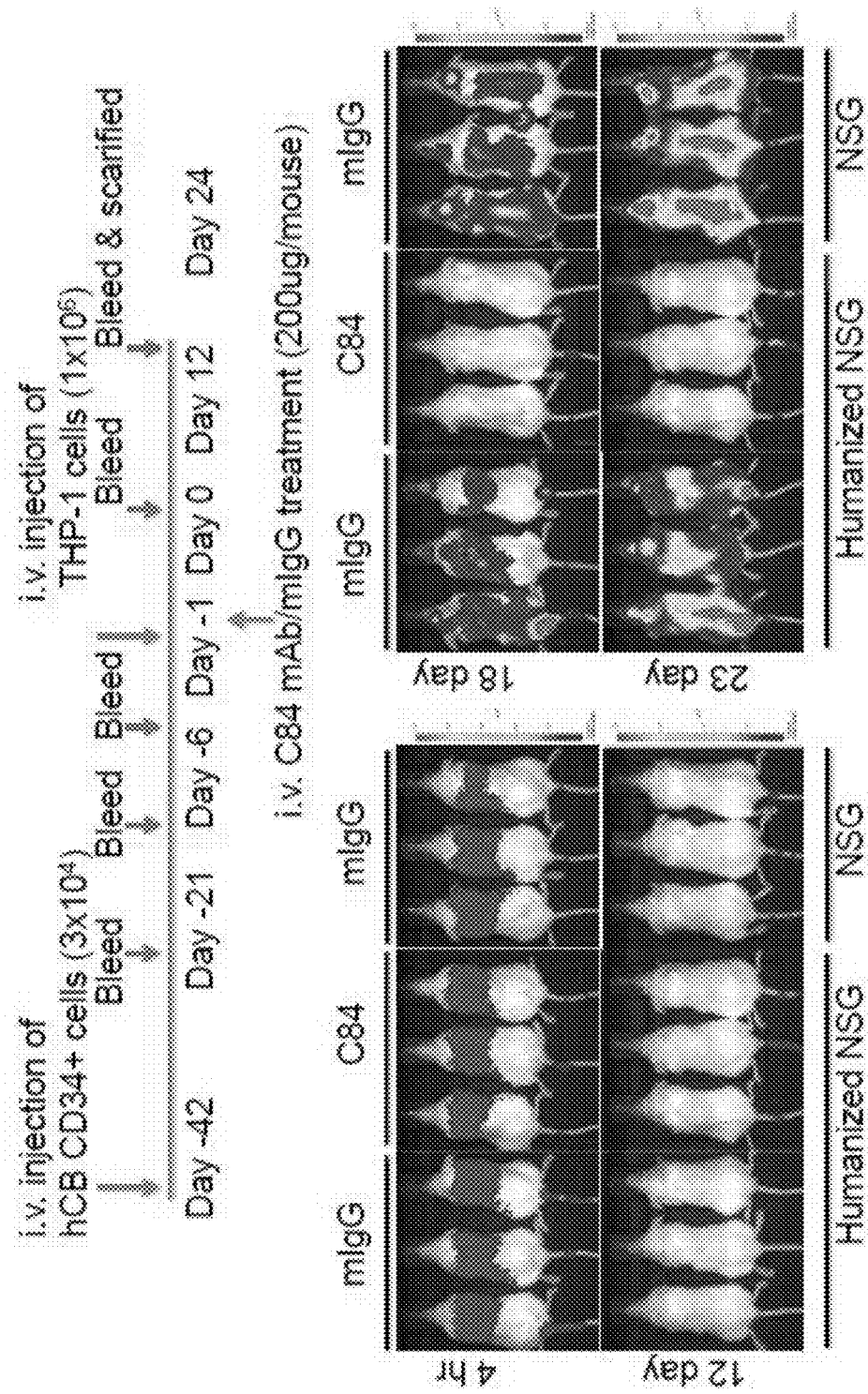

FIG. 15—Testing of anti-hLILRB4 in hCB-HSC-derived humanized NSG mice. $3 \times 10^4$ human cord blood CD34$^+$ cells were transplanted into sub-lethally irradiated (250 rad) NSG mice and multi-lineage human hematopoietic reconstitution was confirmed at various time points at day 21 to day 41 post-transplantation. At day 42, $1 \times 10^6$ human THP-1-Luc-GFP (THP-1 cells that stably express Luciferase and GFP to facilitate real-time in vivo tracking) AML cells were intravenously implanted into NSG mice. 200 μg C84 was i.v. injected into each mouse right after AML cells were implanted. Mouse IgG served as controls. Tumor growth was monitored over time by luminescence imaging.

FIG. 16—The amino acid sequences of variable regions of the heavy chain and light chain of 21 rabbit anti-human LILRB4 mAbs.

FIG. 17—The amino acid sequences of CDRs of the heavy chain and light chain of 21 rabbit anti-human LILRB4 mAbs.

Figure 18E:
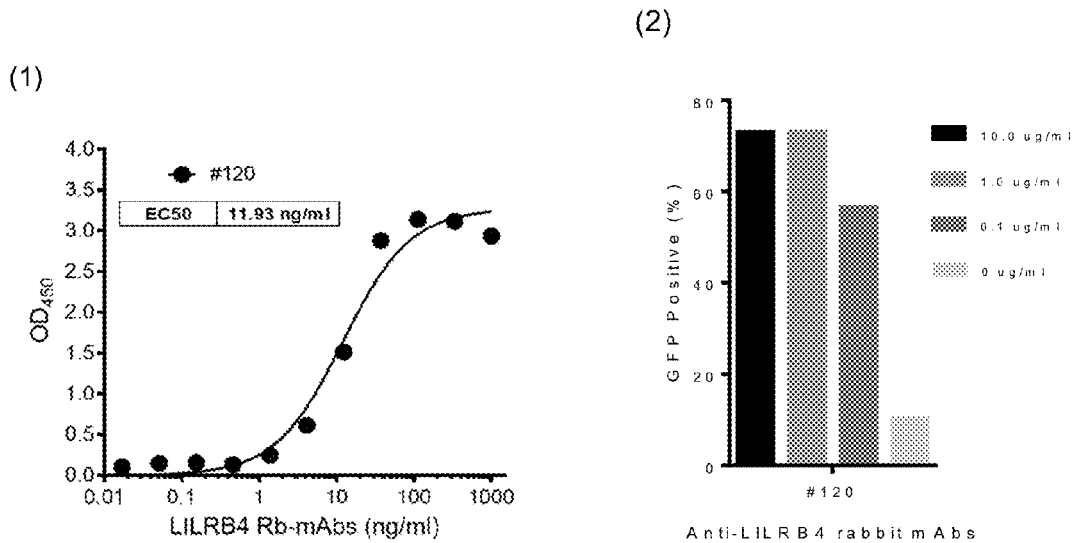

FIGS. 18a-18u—EC50 of these antibodies binding to LILRB4 as determined by ELISA and the activation abilities of the immobilized antibodies (thus the blocking abilities of the soluble antibodies) toward the chimeric LILRB4 reporter system.

FIG. 19—Anti-leukemia potency and cross-reactivity of mAbs against LILRB1-5. The anti-leukemia potency was determined by administration of indicated antibodies into AML xenograft models.

Figure 20:
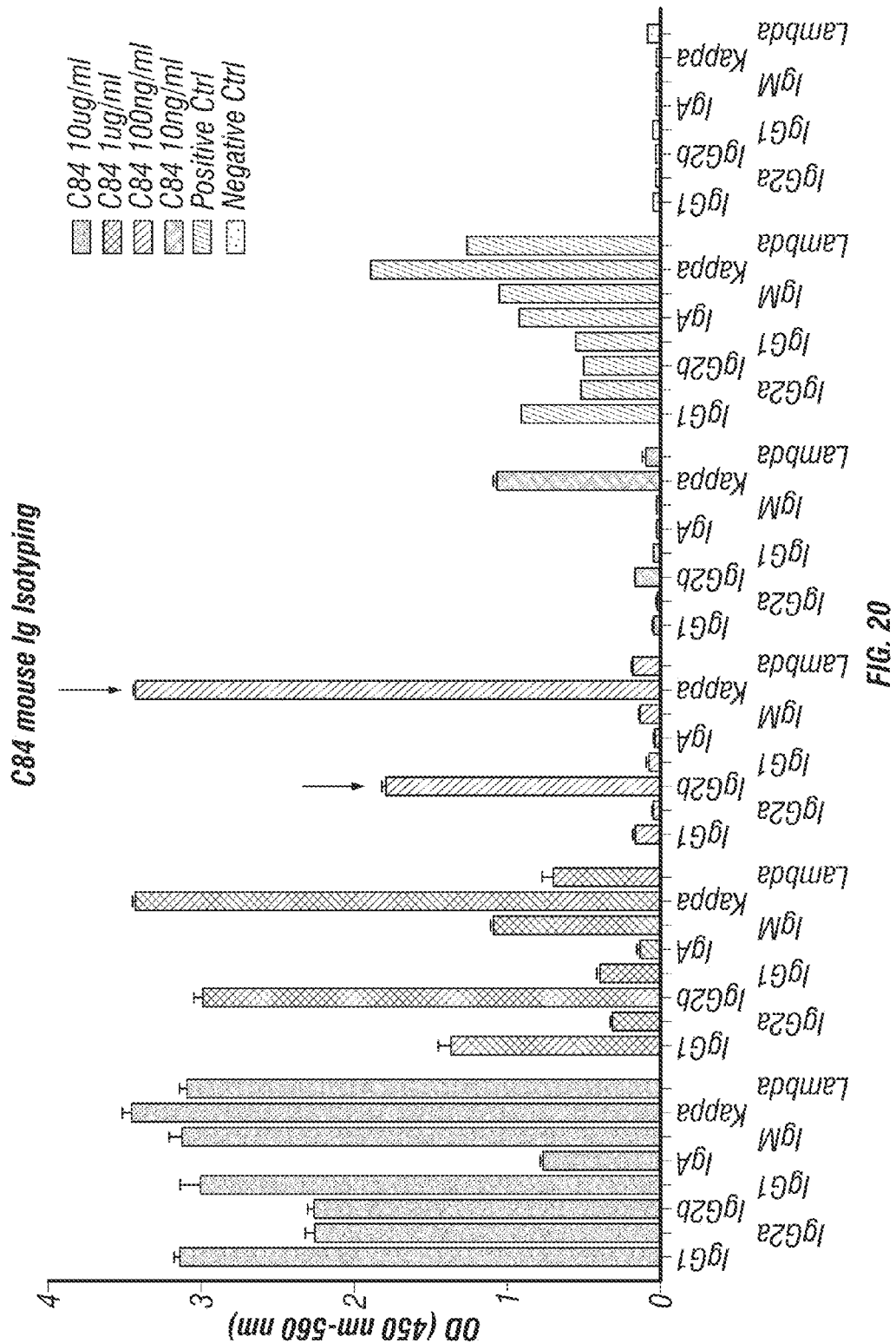
Figure 20:
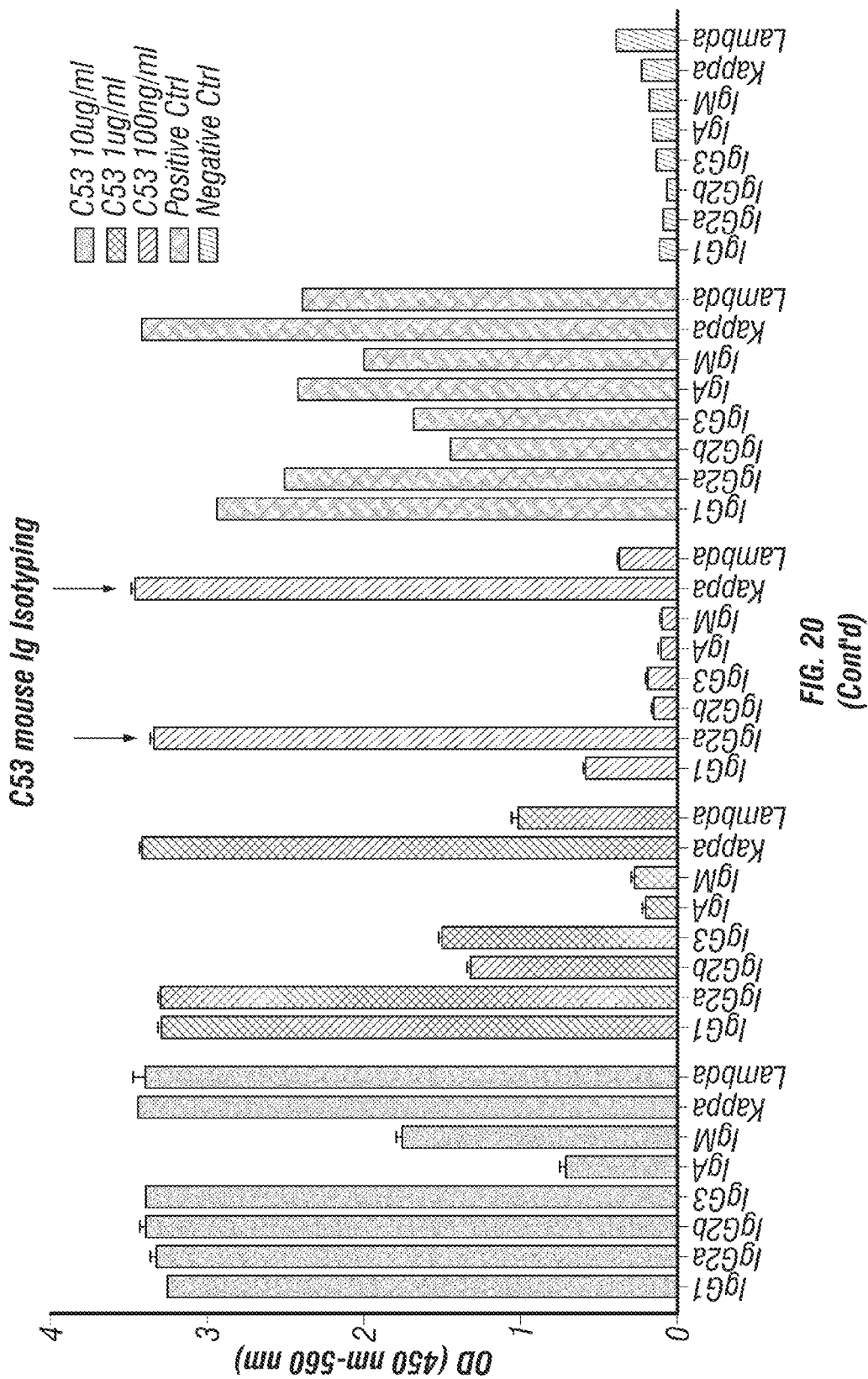
Figure 20:
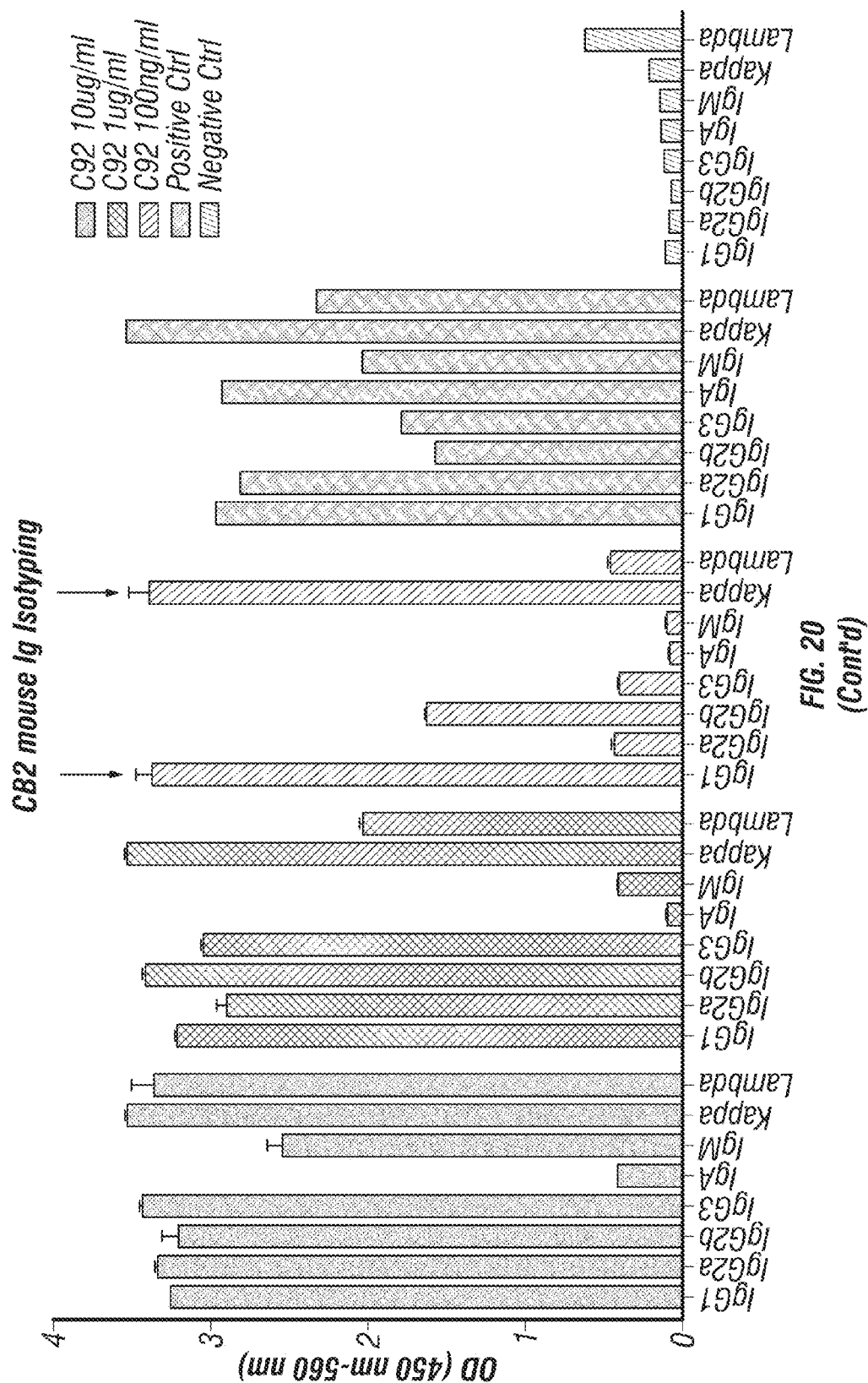
Figure 20:
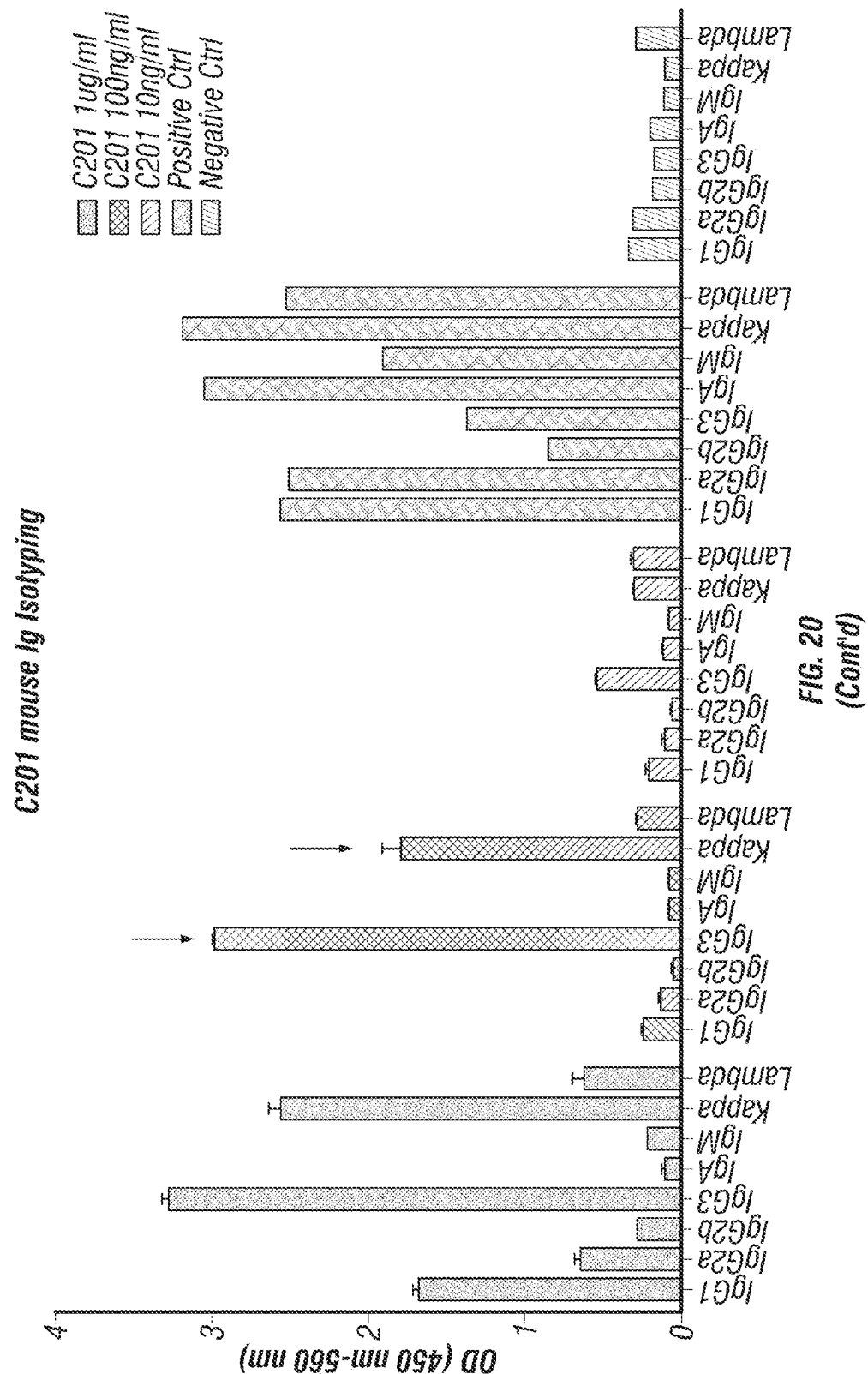

FIG. 20—Ig isotyping of 4 individual anti-LILRB4 mouse antibodies.

FIGS. 21-22—Sequencing and isotyping results of variable regions of individual anti-LILRB antibodies.

Figure 23:
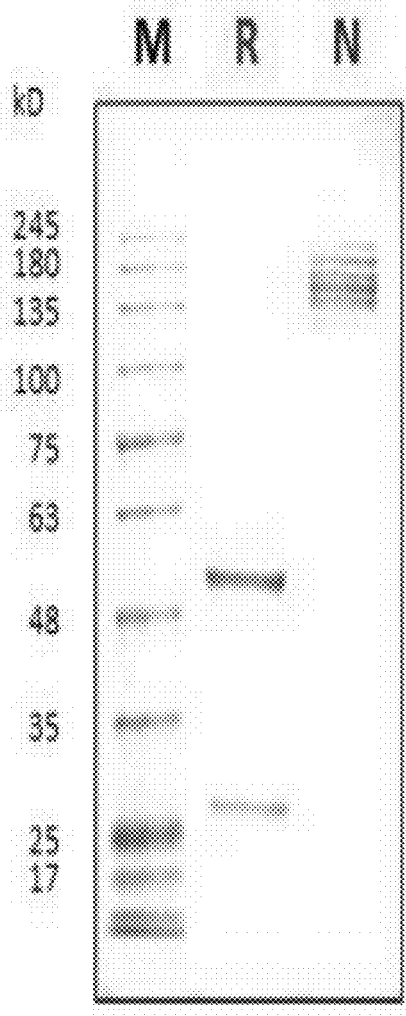

FIG. 23—Expression of chimeric anti-C84 (Mouse/Human Chimeric ab known as MHC-C84) as determined by SDS-PAGE.

Figure 24:
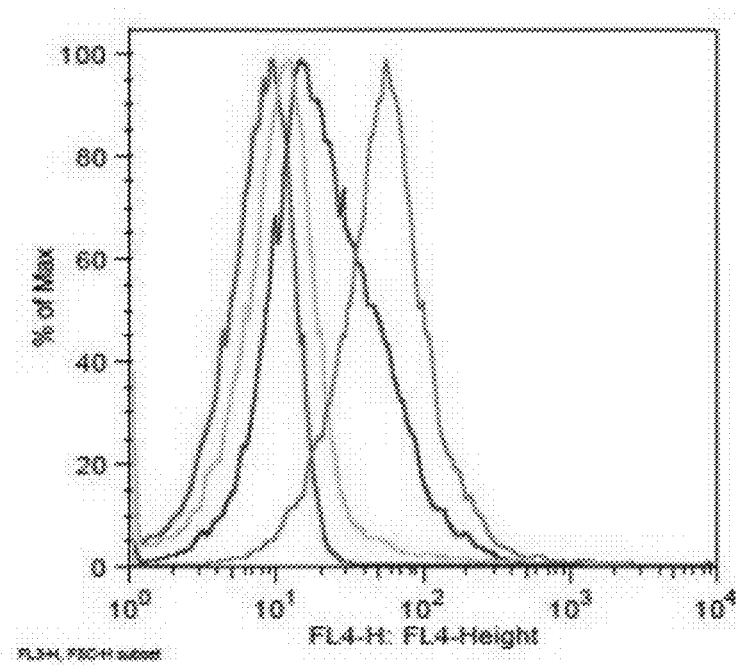

FIG. 24—Chimeric ab MHC-C84 binds LILRB4+THP-1 cells similar to or better than C84, as determined by flow cytometry.

Figure 25:
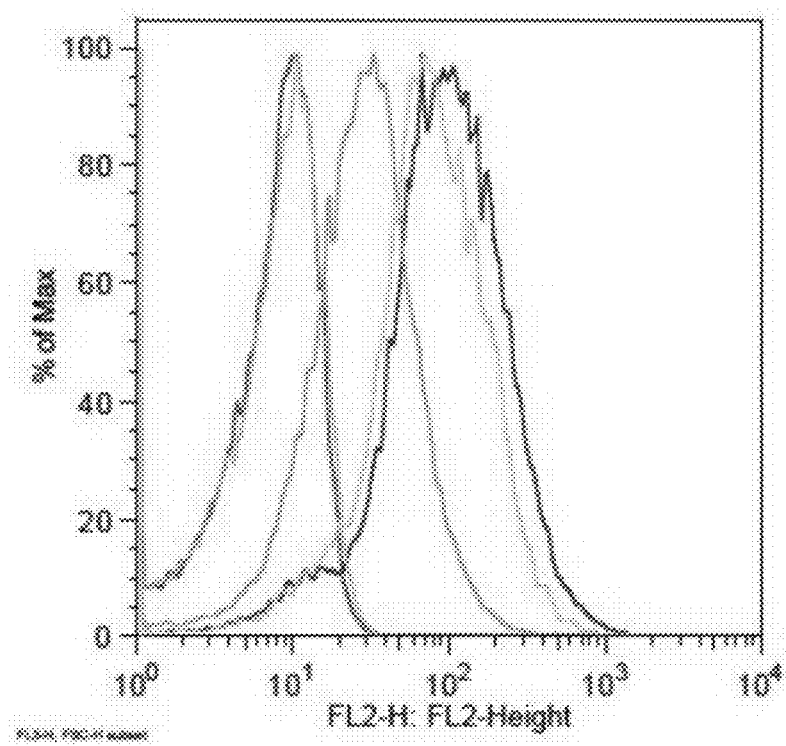

FIG. 25—Chimeric ab MHC-C84 binds LILRB4 chimeric receptor reporter cells as C84 does, as determined by flow cytometry.

Figure 26:
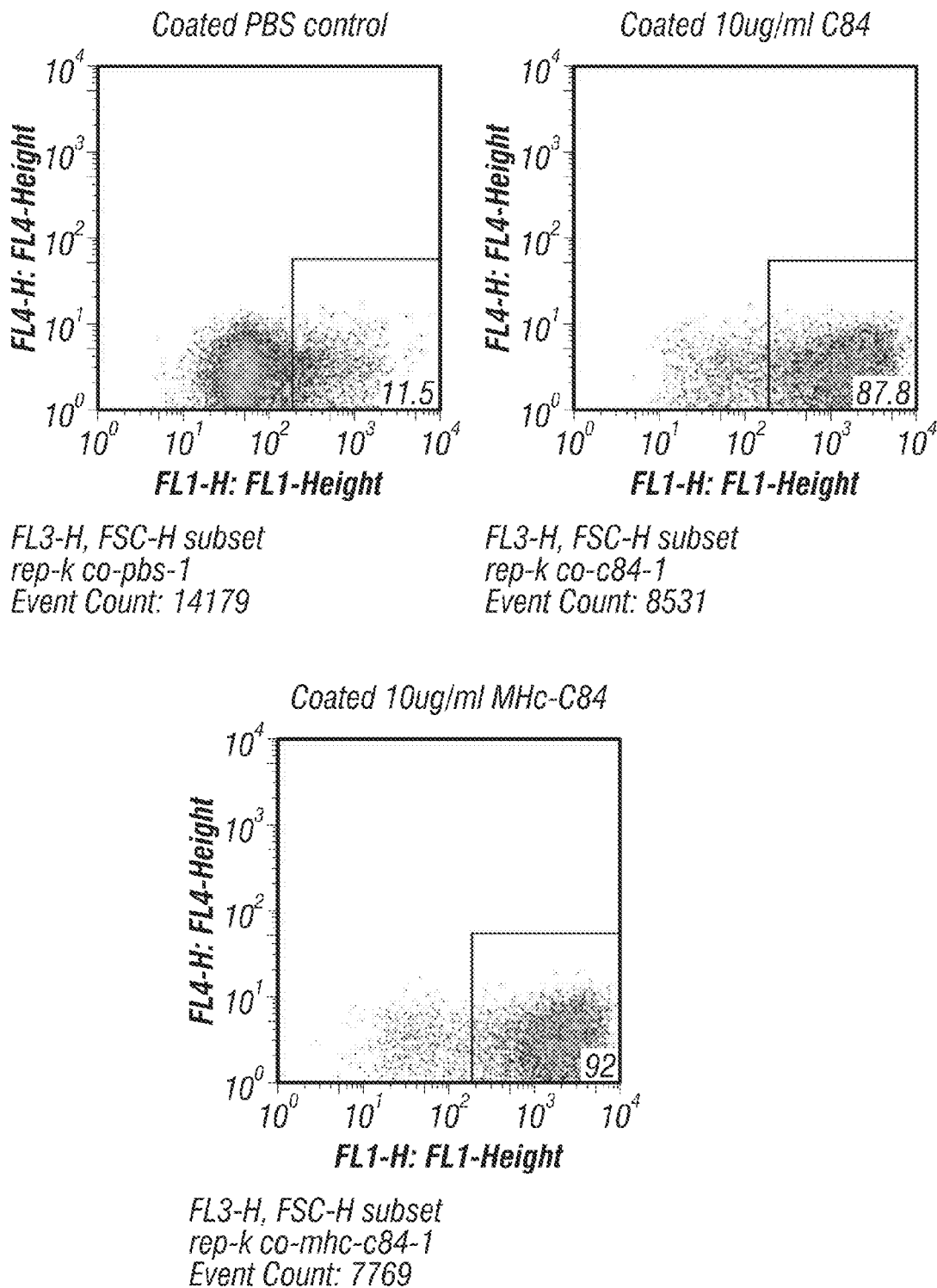

FIG. 26—Chimeric ab MHC-C84 is a blocking antibody for LILRB4 as C84 is, as determined by chimeric receptor reporter assay.

Figure 27:
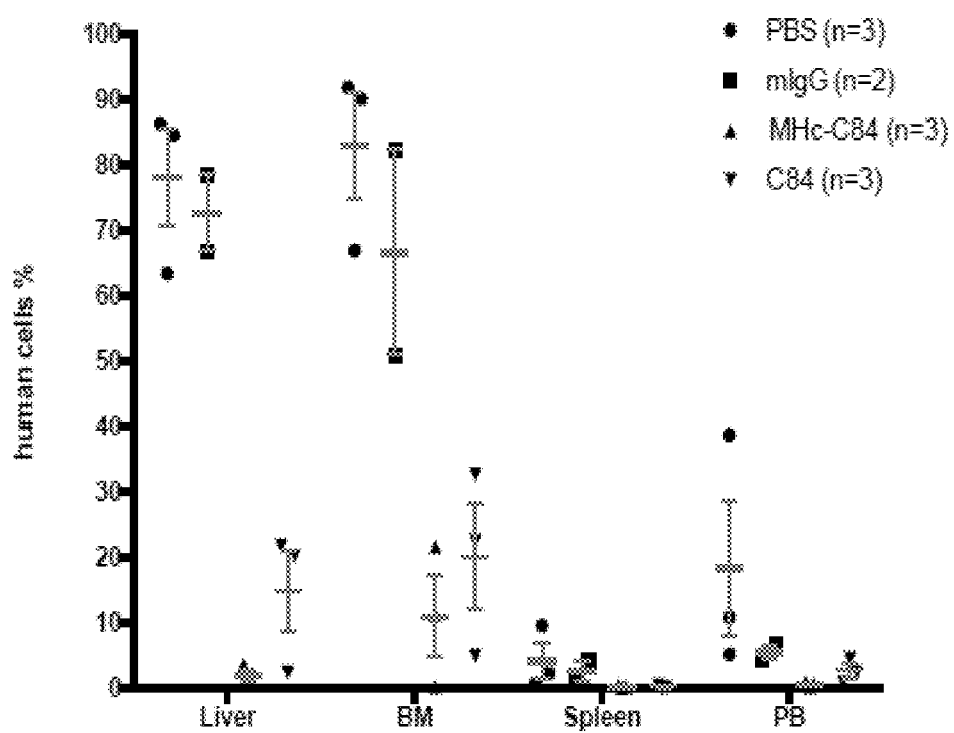

FIG. 27—Chimeric ab MHC-C84 inhibits AML development in xenograft model (same or better than original mAb C84). $3 \times 10^6$ human AML cell line THP-1-Luc-GFP (THP-1 cells that stably express Luciferase and GFP to facilitate real-time in vivo tracking) were intravenously implanted into NSG mice. 200 μg MHC-C84 or C84 was i.v. injected into each mouse only one time 30 min-1 hr right after implantation of $3 \times 10^6$ THP-1-Luc-GFP cells. PBS or mouse IgG served as controls. Tumor growth was monitored after 1 month by examining the leukemia infiltration in recipient liver, spleen, bone marrow, and peripheral blood. hCD45 was used to detect human leukemia cells by flow cytometry.

Figure 28:
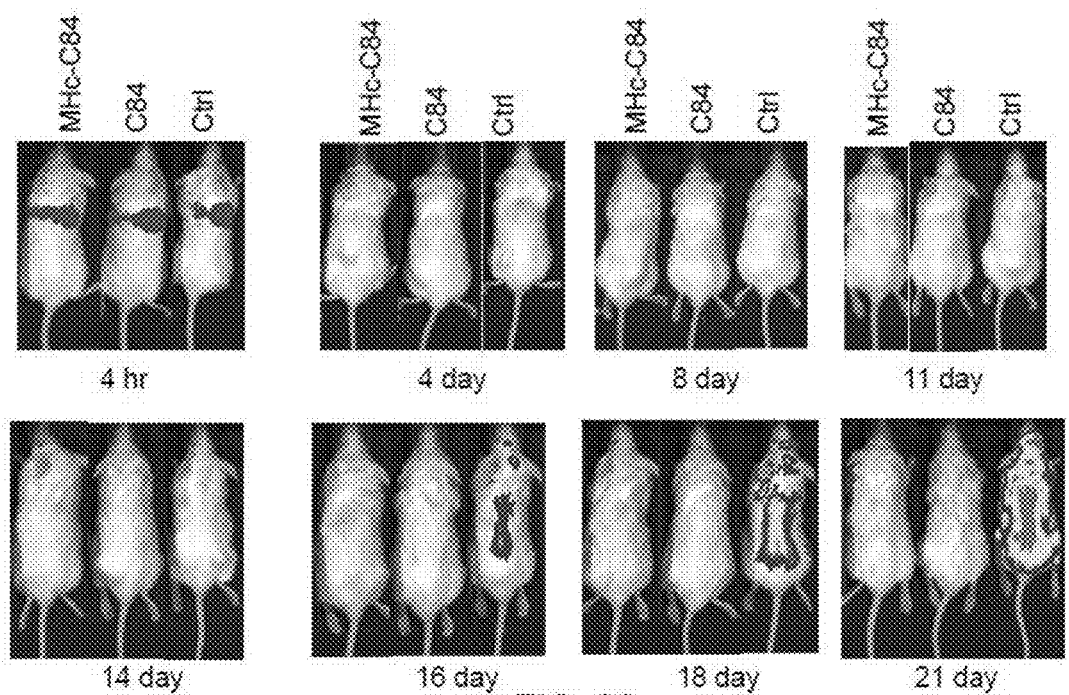
Figures 29A, 29B:
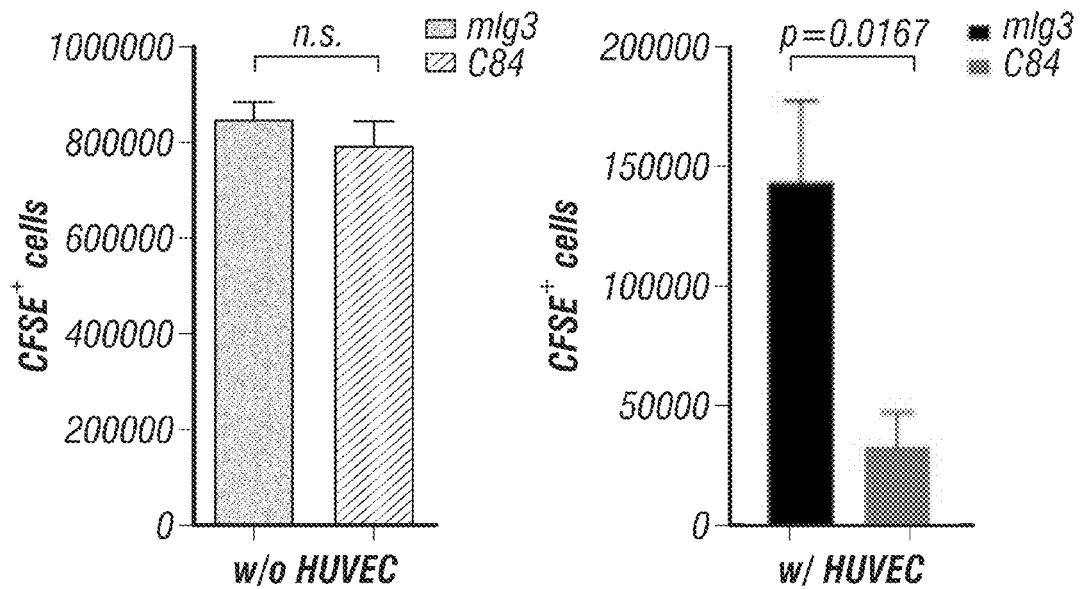
Figure 29C:
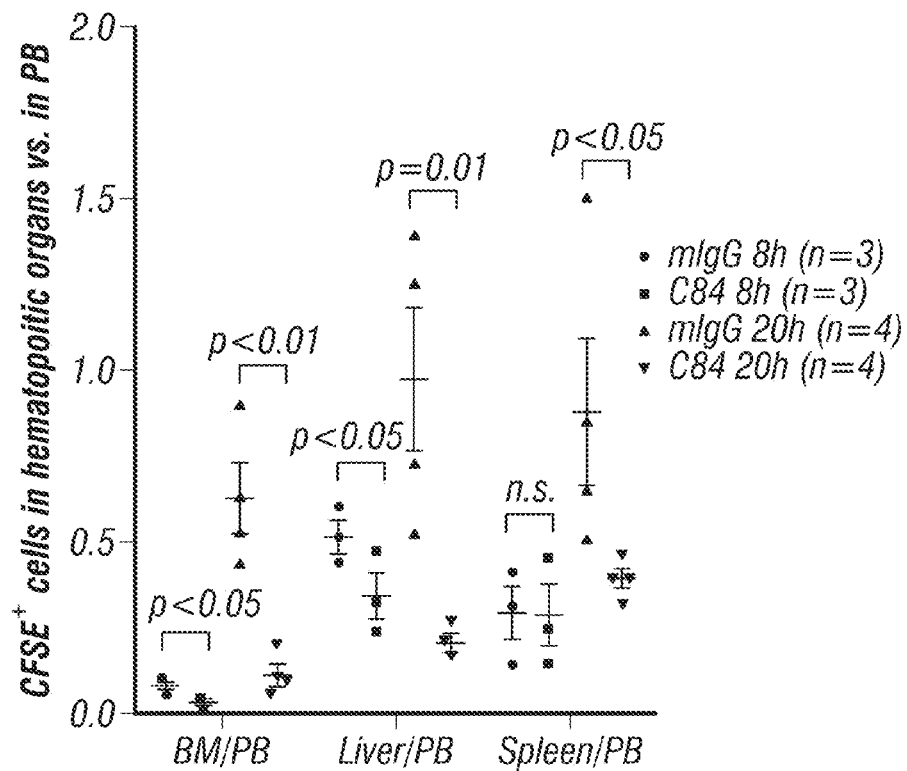
Figure 29D:
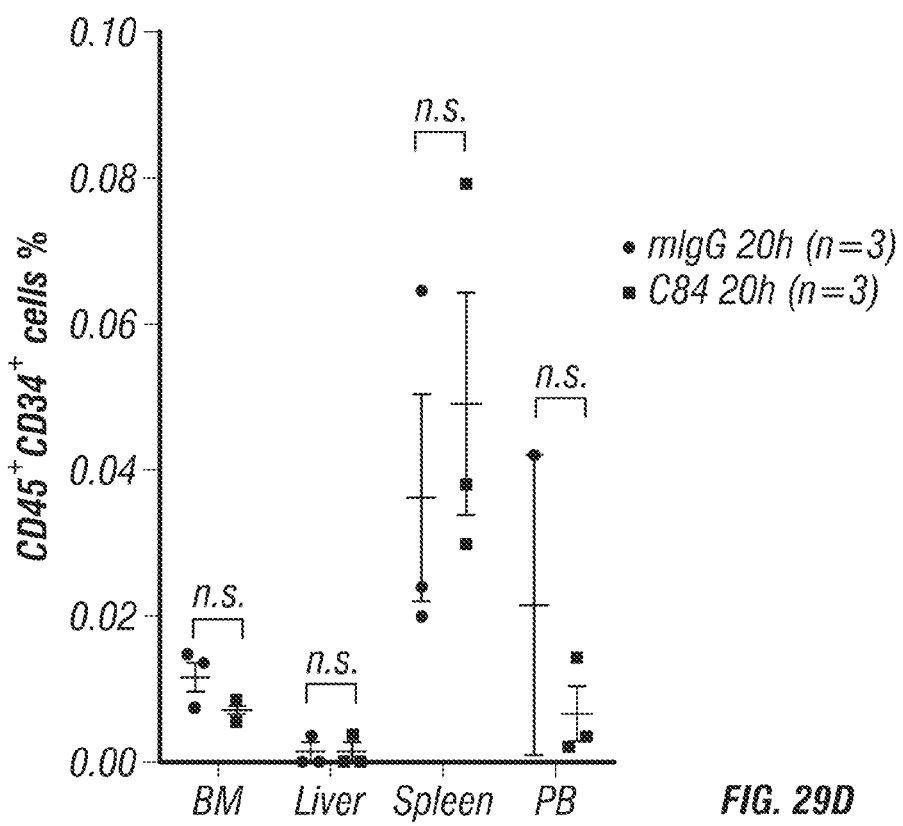
Figure 29E:
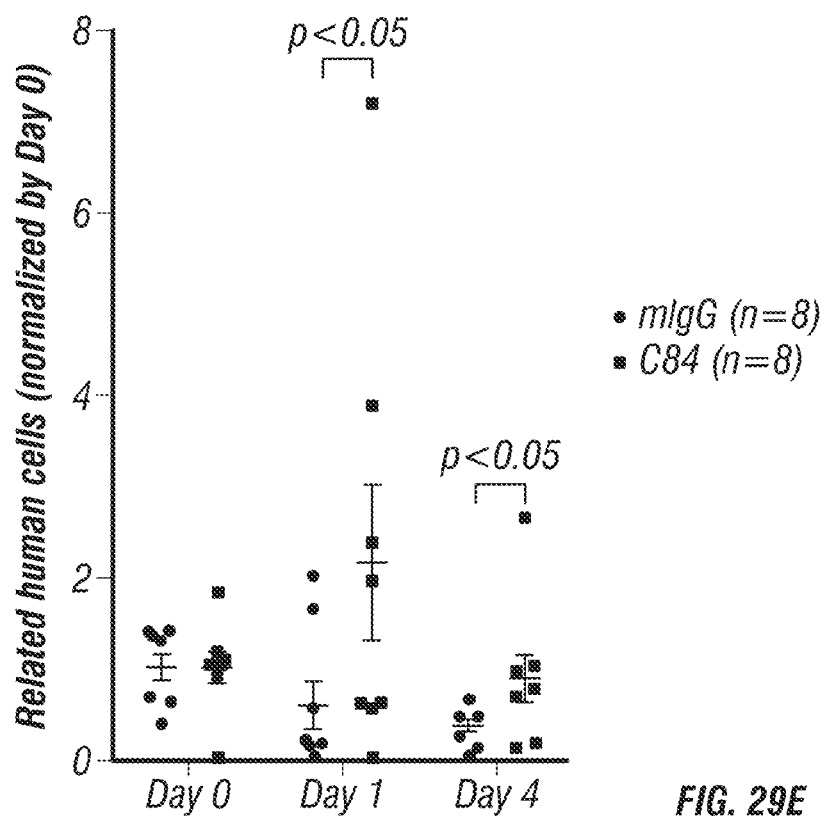
Figure 29F:
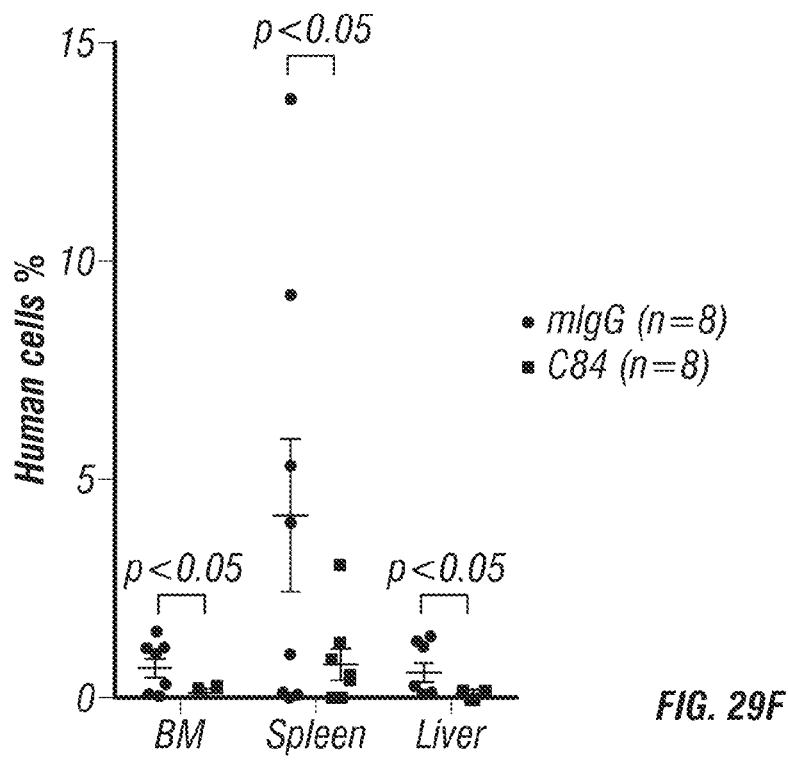
Figure 29G:
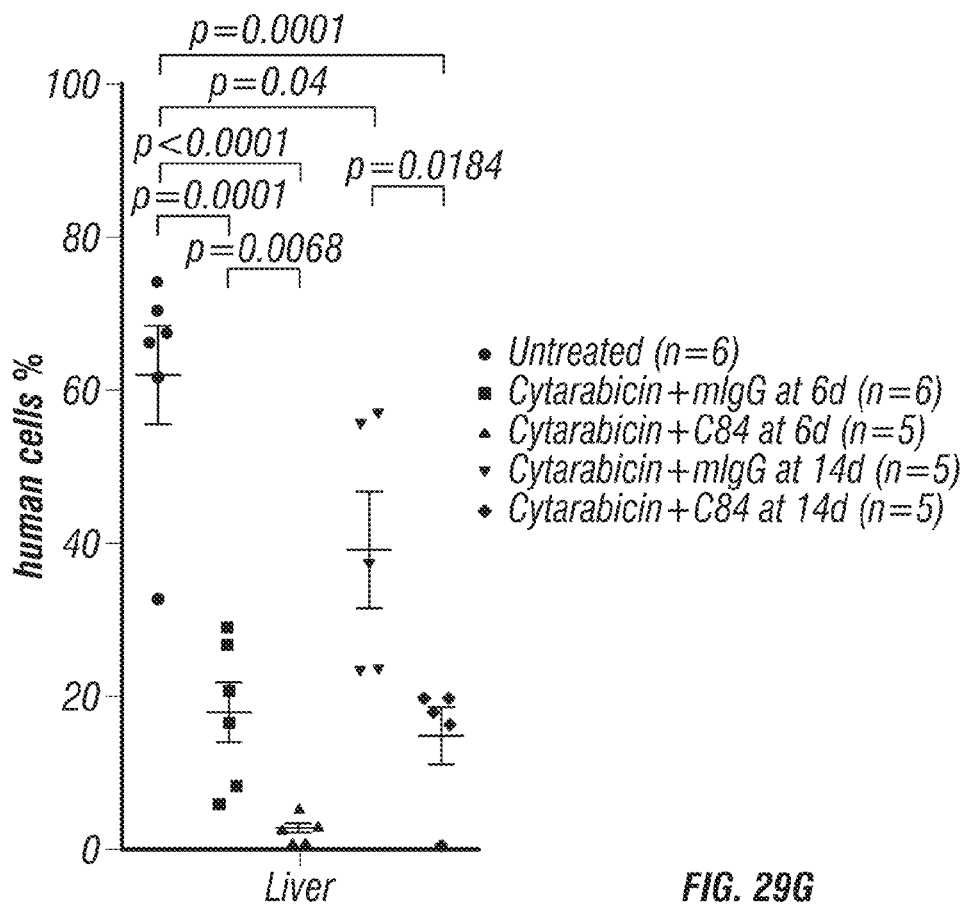

FIG. 28—Chimeric ab MHC-C84 inhibits AML development in xenograft model as determined by luminescence imaging. $3 \times 10^6$ human AML cell line THP-1 that stably express luciferase (as THP-1-Luc-GFP cells) were intravenously implanted into NSG mice. 200 μg MHC-C84 or C84 was i.v. injected into each mouse only one time 30 min~1 hr right after implantation of $3 \times 10^6$ THP-1-Luc-GFP cells. Mouse IgG served as controls. Tumor growth was monitored over time by luminescence imaging. While all conditions had the same luciferase intensity at day 0 (4 hr after tumor implantation), MHC-C84 or C84 treated mice displayed no luciferase signal over time (compare them with control at day 16, 18, and 21).

FIGS. 29a-29g—Anti-LILRB4 inhibits AML cell transmigration and accelerates mobilization. (FIG. 29a) C84 doesn't inhibits MV4-11 cell plasticity. $1 \times 10^5$ MV4-11 cells were cultured in the up chamber of a transwell and treated with 100 μg/ml of C84 or mIgG for 18 hrs. Cells in down chamber were counted. (FIG. 29b) C84 inhibits MV4-11 cell transmigration through endothelial cells. $3 \times 10^5$ HUVEC cells were cultured on the membrane of a transwell for 3 days. 1×10⁵ MV4-11 cells were cultured in the up chamber of a transwell and treated with 100 μg/ml of C84 or mIgG for 18 hrs. Cells in down chamber were counted. (FIG. 29c) C84 inhibits MV4-11 cell homing. 5×10⁶ MV4-11 cells were i.v. injected into each NSG mouse that were scarified after 8 or 20 hrs. hCD45 was used to detect human leukemia cells by flow cytometry. The percentage of leukemia cells in recipient liver, spleen and bone marrow were normalized by that in peripheral blood. (FIG. 29d) C84 doesn't inhibits HSCs homing. 1×10⁷ human cord blood mononuclear cells were i.v. injected into each NSG mouse that were scarified after 20 hrs. hCD45 and hCD34 were used to detect human HSCs by flow cytometry. (FIGS. 29e-29f) C84 accelerates MV4-11 mobilization to PB. 5×10⁶ MV4-11 cells were i.v. injected into each NSG mouse. Leukemia cells in peripheral blood were examined at Day 0 (3 days after MV4-11 cell transplantation), Day 1 and Day 4. 200 μg C84 or mIgG was i.v. injected into each mouse at Day 0 and Day 1. Mice were scarified at Day 4. hCD45 was used to detect human leukemia cells by flow cytometry. (FIG. 29g) synergic C84 treatment with chemodrug cytarabicin inhibits AML development. 1×10⁶ human AML THP-1 cells that stably express luciferase (as THP-1-Luc-GFP cells) were intravenously implanted into NSG mice. 10 mg/kg Cytarabicin was i.p. injected into each mouse every day starting from 6 days or 14 days after implantation of leukemia cells. 200 μg C84 or mIgG was i.v. injected into each mouse twice a week starting from 6 days or 14 days after implantation of leukemia cells. Mice were scarified at 21 days after implantation of leukemia cells. hCD45 was used to detect human leukemia cells by flow cytometry.

Figure 30A:
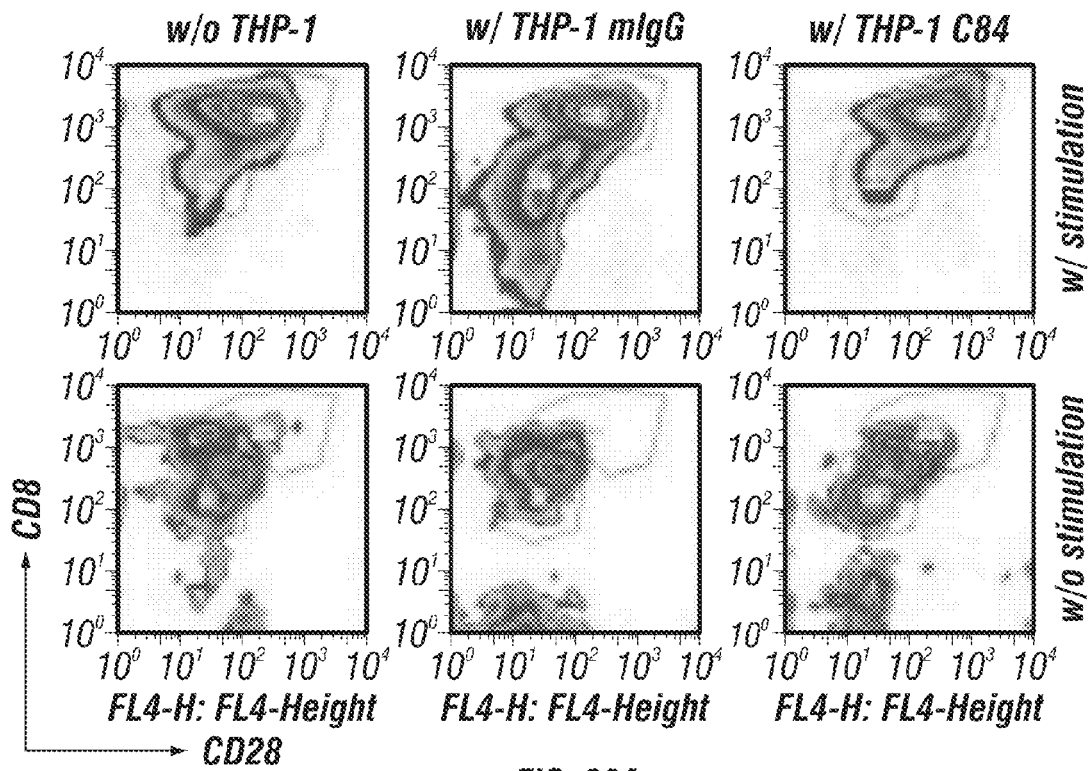
Figure 30B:
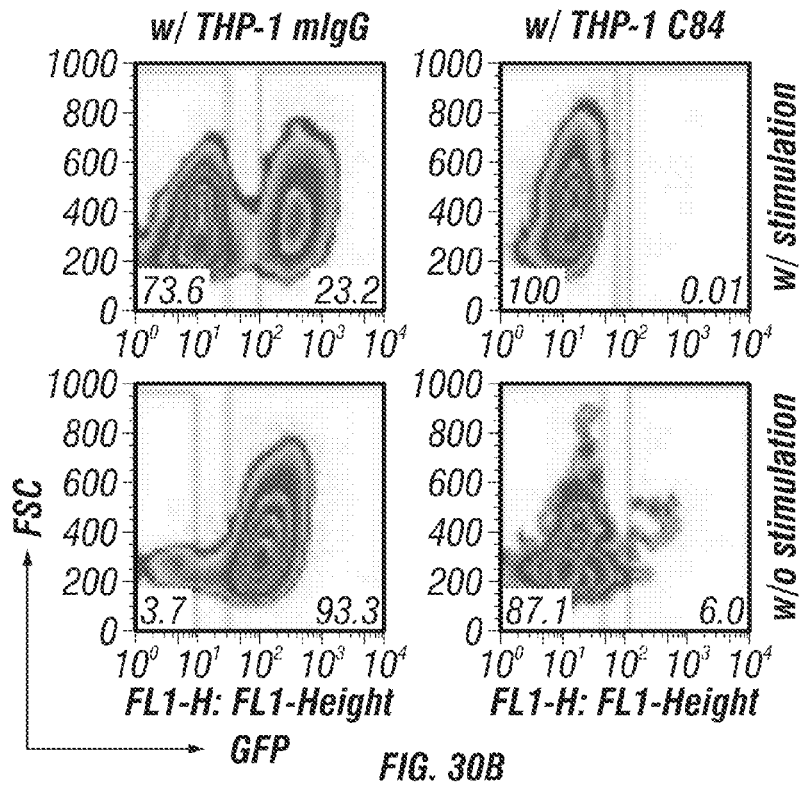
Figure 30C:
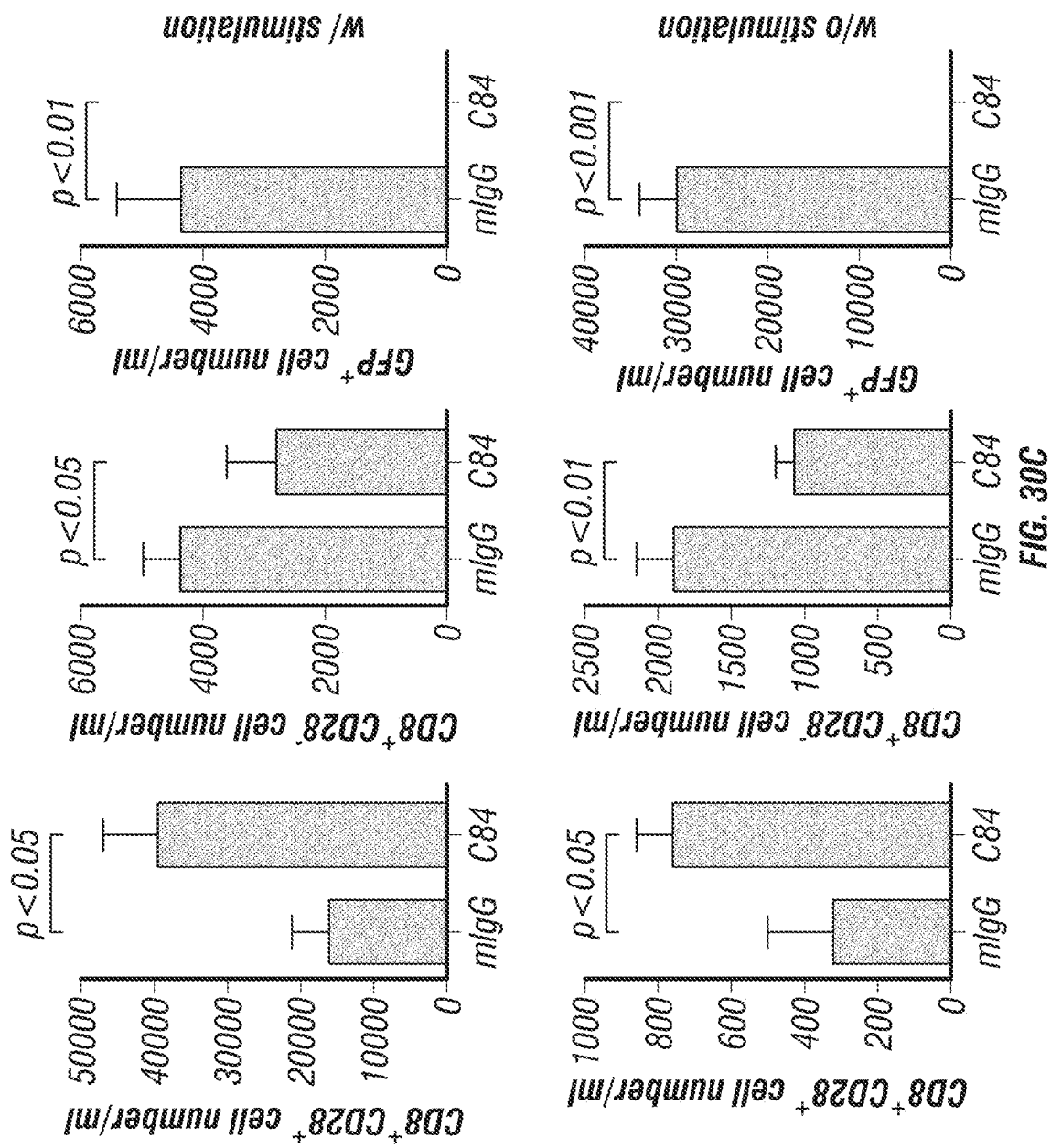
Figure 30D:
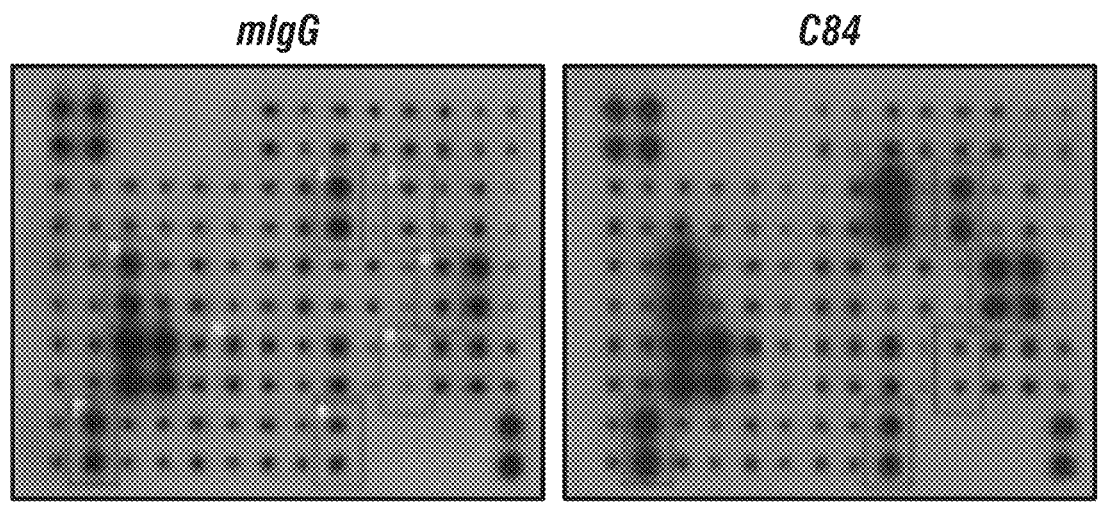
Figure 30E:
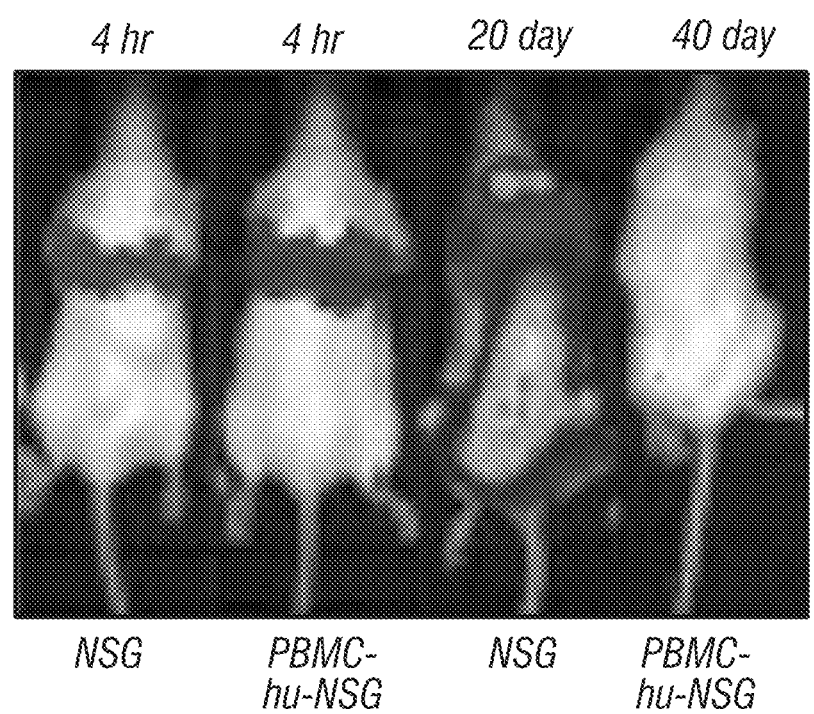
Figure 32A:
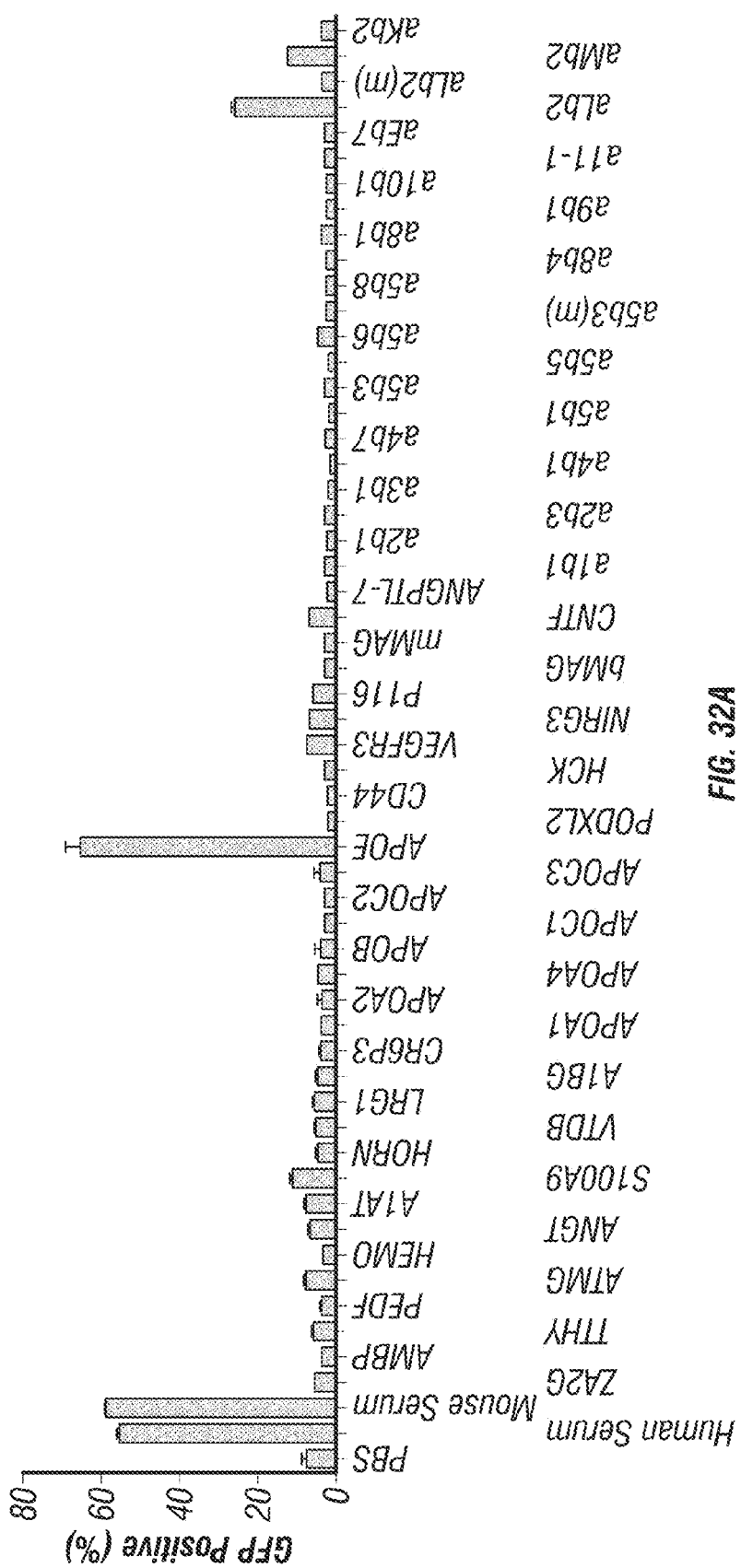
Figure 32B:
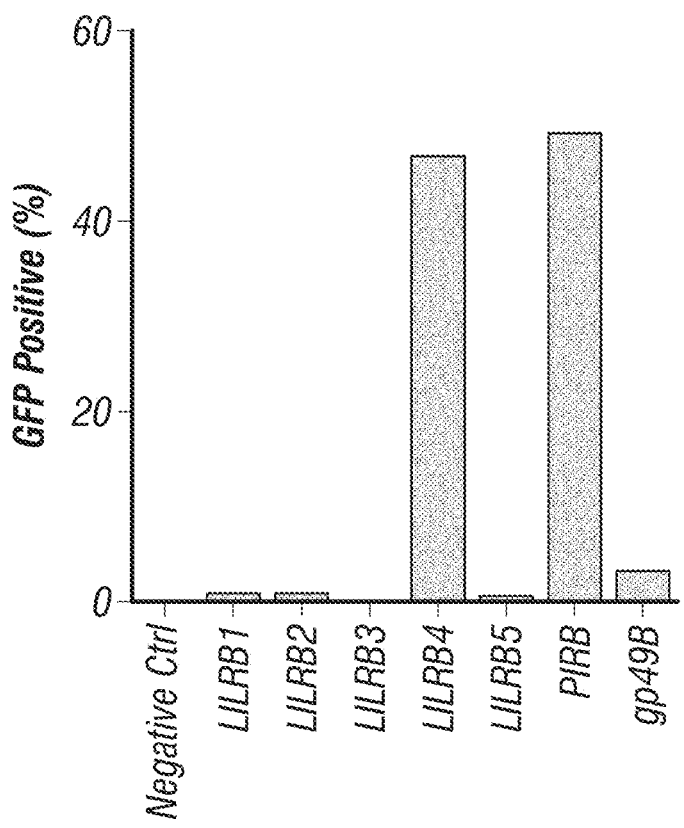
Figure 32C:
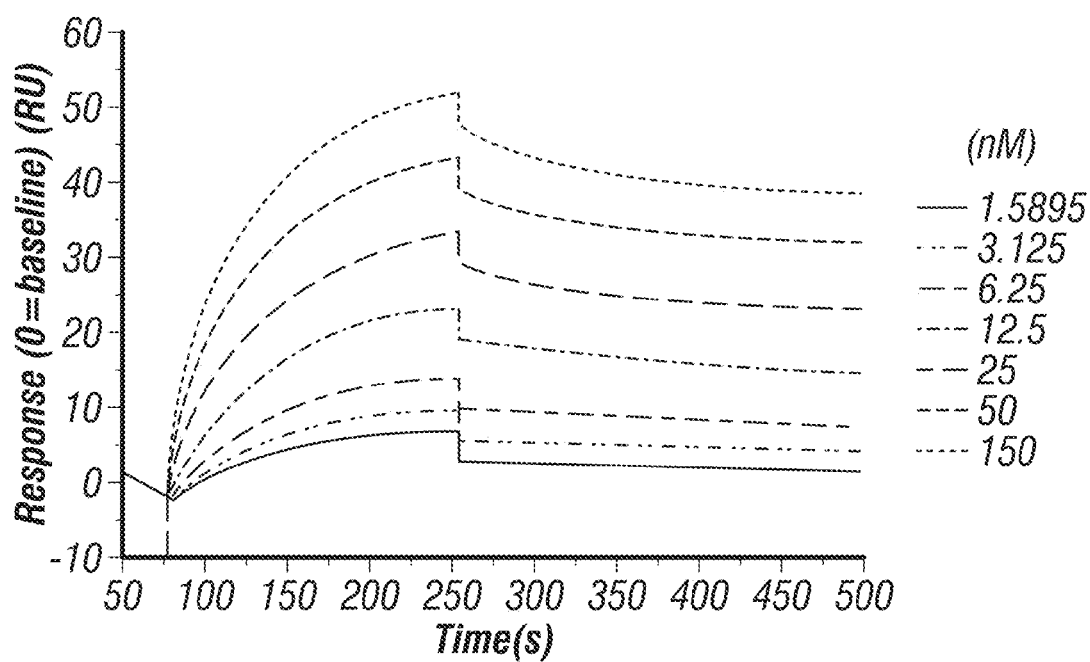
Figure 32D:
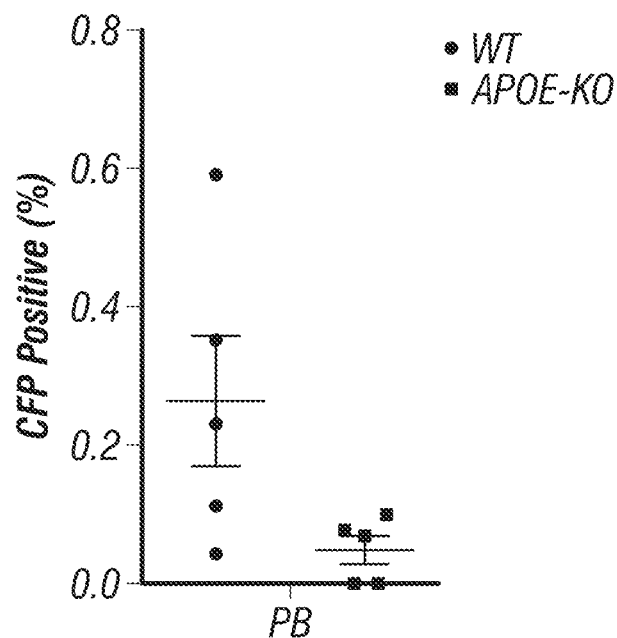
Figure 32E:
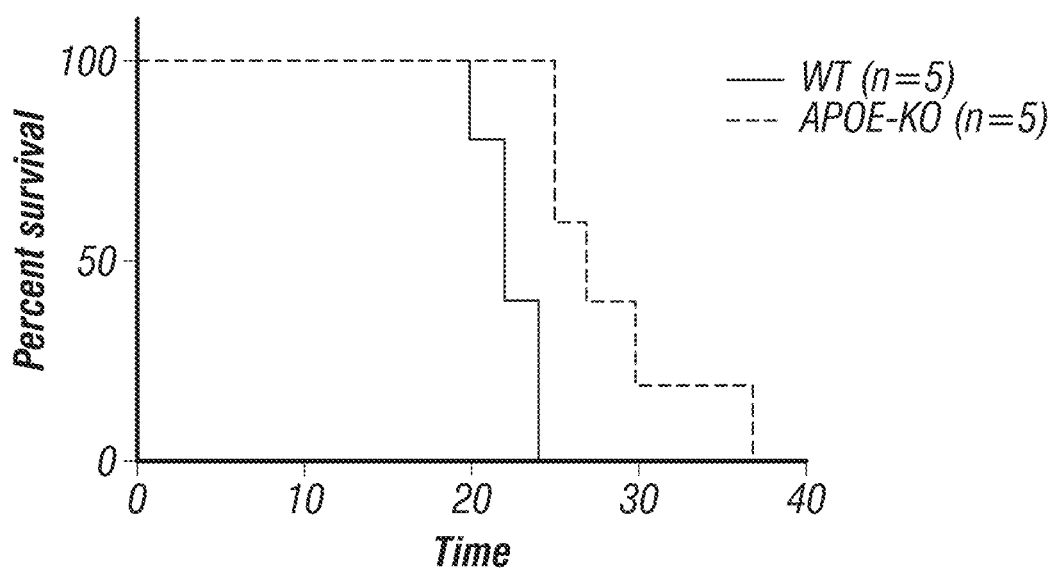

FIGS. 30a-30u—Anti-LILRB4 stimulates T cell immunity for anti-cancer effects. (FIGS. 30a-30c) C84 repress the inhibition of CTL by LILRB4. 5×10⁴ CD8⁺ T cells isolated from hPBMC of a healthy donor were stimulated with anti-CD3/CD28/CD137-coated beads or without stimulation for 2 days. Then, 5×10³ THP-1-Luc-GFP cells were co-cultured with these T cells and treated with 500 μg/ml C84 or mIgG for 5 days. CD8 and CD28 were used to detect human CTL cells by flow cytometry; and GFP was used to detect human leukemia cells. (FIG. 30d) c84 increases CTL cytokine production. Cell supernatants from co-culture of stimulated CTL cells and THP-1 cells that were treated with C84 or mIgG were used to examine the cytokine production by human cytokine arrays. (FIG. 30e) THP-1 cannot engraft into PBMC-driven humanized NSG mice. 1×10⁷ human PBMCs were i.v. injected into each NSG mouse. Three weeks after implantation of hPBMC, these mice had 30~50% human T cells engraftment. Then, 1×10⁶ human AML THP-1 cells that stably express luciferase (as THP-1-Luc-GFP cells) were intravenously implanted into these hPBMC-humanized NSG mice or age-matched regular NSG mice. Tumor growth was monitored over time by luminescence imaging. (FIG. 30f) C84 inhibits subcutaneous implantation of THP-1 cells in PBMC-driven humanized NSG mice. 1×10⁷ human PBMCs were i.v. injected into each NSG mouse. Three weeks after implantation of hPBMC, these mice had 30~50% human T cells engraftment. Then, 1×10⁶ human AML THP-1 cells that stably express luciferase (as THP-1-Luc-GFP cells) were subcutaneously implanted into these hPBMC-humanized NSG mice with 200 μg C84 or mIgG treatment twice a week. Tumor growth was monitored over time by luminescence imaging. (FIGS. 30g-30u) C84 inhibits leukemia development and decreases CD8+ T suppressor cells in human cord blood-humanized NSG mice. The hCB-humanized mice were obtained as same as shown in FIG. 15. GFP was used to detect human leukemia cells, CD19 and CD20 were used to detect CB-derived human B cells, CD11b, CD14 and LILRB4 were used to detect CB-derived human myeloid cells, CD4 and CD8 were used to detect CB-derived human T cells, CD8, CD28 and CD40L were used to detect CB-derived human CTL and T suppressor cells, FIG. 31—Fc-dependent and Fc-independent effect of anti-LILRB4 on AML development. 1×10⁶ human AML THP-1 cells that stably express luciferase (as THP-1-Luc-GFP cells) were intravenously implanted into NSG mice. 200 μg MHC-C84 or MHC-C84-N297A was i.v. injected into each mouse at the same day (as "Day 0") or at 3 days (as "Day 3") after implantation of 1×10⁶ THP-1-Luc-GFP cells. Anti-CMV human IgG antibody (LX-D2-43) served as controls. Tumor growth was monitored over time by luminescence imaging and hCD45 was used to detect human leukemia cells by flow cytometry.

FIGS. 32a-32e—APOE is a potential LILRB4 ligand. (FIG. 32a) human/mouse serum, APOE and LFA-1 induce LILRB4 activation; (FIG. 32B) APOE activates human LILRB4 and mouse PIRB; (FIG. 32c) SPR shows that APOE binds to LILRB4 in a high affinity, Kd=2.485 nM; (FIGS. 32d-32e) APOE-Knockout delays mouse AML cells development and elongate overall survival. 1×10⁶ mouse AML C1498 cells that stably express GFP were intravenously implanted into C57BL/6 mice or APOE-knockout mice. GFP was used to detect mouse leukemia cells by flow cytometry in peripheral blood at 20 days after implantation of C1498 cells.

Figures 33A, 33B, 33C:
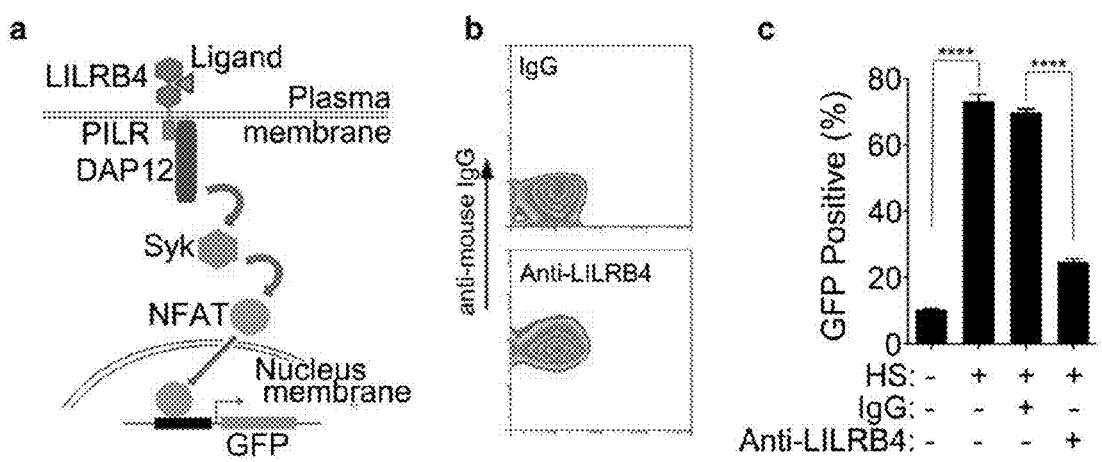

FIGS. 33a-33c—Anti-LILRB4 antibodies block human serum induced LILRB4 activation. FIG. 33a: Schematic of the LILRB4 reporter system. FIG. 33b: Flow cytometry demonstrates anti-LILRB4 antibody binds to human LILRB4 reporter cells. FIG. 33c: The LILRB4 activation induced by 10% human serum (HS) was inhibited by anti-LILRB4 antibody. IgG was used as control. ****, $p<0.0001$.

Figure 34:
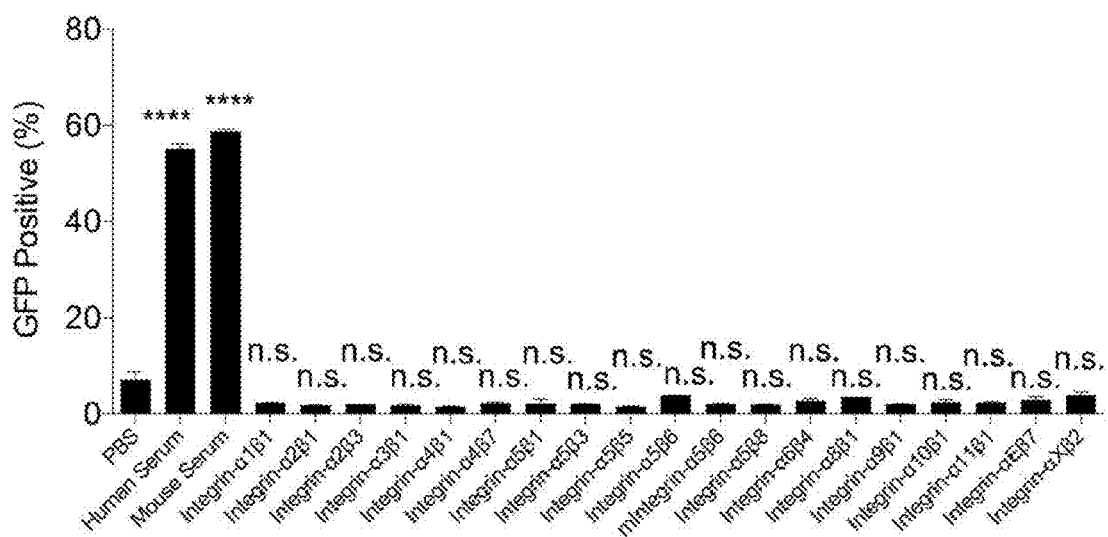

FIG. 34—Human and mouse integrin heterodimer proteins cannot activate LILRB4 reporter. Human and mouse serum were used as positive controls. n.s., not significant. **** $p<0.0001$.

Figures 35A, 35B, 35C, 35D, 35E, 35F:
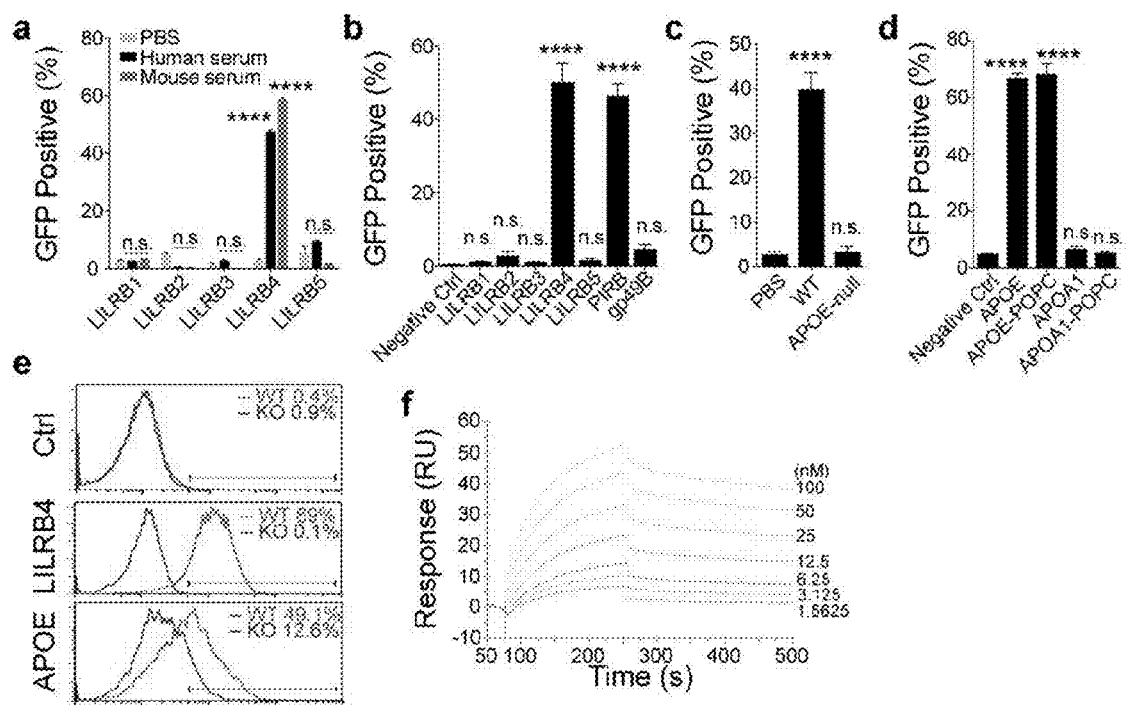

FIGS. 35a-35l—APOE binds LILRB4 and supports AML migration. FIG. 35a: As shown by analysis of the percentage of cells in the LILRB4 reporter system that are GFP⁺, human serum and mouse serum specifically activate LILRB4. FIG. 35b: Recombinant APOE activates human LILRB4 and mouse PIRB in reporter systems.

Figures 35G, 35H, 35I, 35J, 35K, 35L:
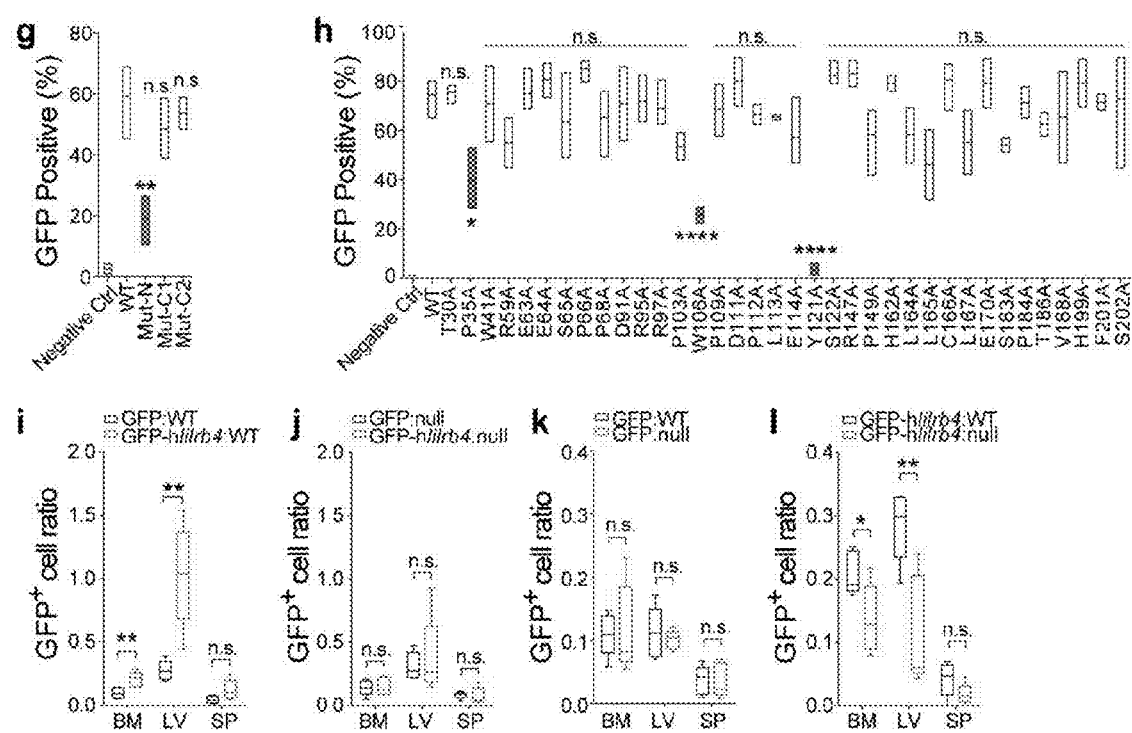

FIG. 35c: Serum from APOE-null mouse was unable to activate LILRB4. FIG. 35d: Lipid-reconstituted APOE (APOE-POPC) activates human LILRB4 as well as recombinant APOE in reporter systems. FIG. 35e: lilrb4-knockout THP-1 cells showed decreased APOE binding as determined by flow cytometry. Cells stained with anti-His tag-APC served as a negative control. FIG. 35f: Binding kinetics of human APOE-3 to LILRB4-ECD-Fc were measured using surface plasmon resonance (SPR). LILRB4-ECD-Fc was immobilized on Protein A biosensor tips and incubated with APOE-3 concentrations ranging from 1.5625 nM to 100 nM. FIG. 35g: The activation of LILRB4 by APOE was reduced by mutation at N-terminal of APOE. FIG. 35h: The activation of LILRB4 by APOE was reduced by the indicated single amino acid mutation of LILRB4. FIGS. 35i-l: APOE is necessary for LILRB4-mediated homing. Forced expression of human lilrb4 on mouse leukemia C1498 cells increases leukemia cell homing in wildtype (WT) recipient mice (n=5) (shown in FIG. 35i). However, forced lilrb4 expression doesn't increase homing in APOE-null (KO) recipient mice (n=5) (shown in FIG. 35j). Human lilrb4-expressing C1498 cells (FIG. 35l), but not control GFP-expressing C1498 cells (FIG. 35k), were less capable of homing in APOE-null (KO) mice (n=5) than in WT mice (n=5); Mice were sacrificed at 20 hrs after injection of leukemia cells. GFP was used to detect leukemia cells by flow cytometry.

FIGS. 36a-36c—Identification of potential ligands of LILRB4 in human serum. FIG. 36a: Flowchart of ligand screen. FIG. 36b: Fractionation of LILRB4 stimulating activities from human serum by FPLC. 10% human serum was used as a positive control. FIG. 36c: A list of proteins identified from the LILRB4 stimulating fractions by mass spectrometry (MS). PSMs: peptide spectrum matches.

Figure 37:
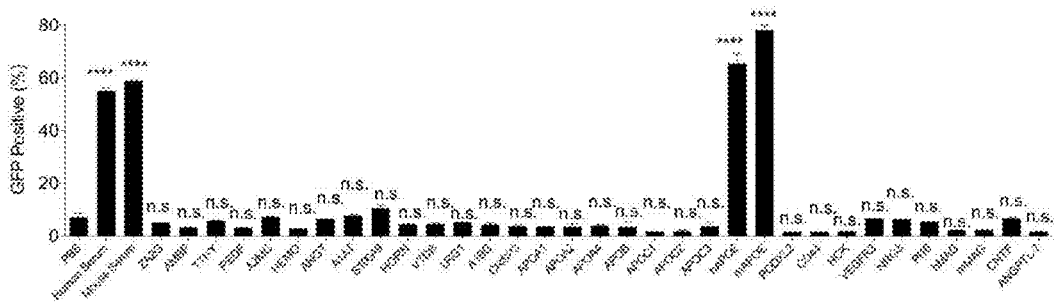

FIG. 37—Both Human and mouse APOE proteins can activate LILRB4 reporter. Human and mouse serum were used as positive controls. n.s., not significant. ****, $p<0.0001$.

Figures 38A, 38B:
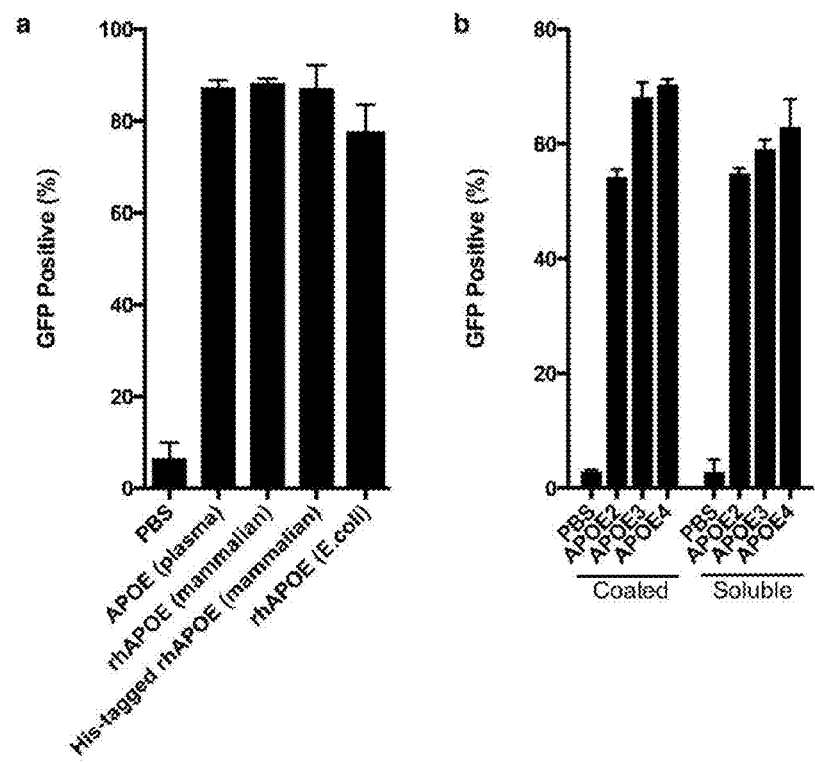

FIGS. 38a-38b—APOE proteins from different sources all activate LILRB4. FIG. 38a: APOE (20 μg/ml) purified from human plasma, His-tagged or tag-free recombinant human APOE (rhAPOE) (20 μg/ml) expressed by 293T mammalian cells, or rhAPOE (20 μg/ml) expressed by bacteria all activate the LILRB4 reporter. These APOE all represent human APOE3. FIG. 38b: APOE2, APOE3 and APOE4 all activate the LILRB4 reporter. 40 μg/ml APOEs were coated on plates or directly added in cell culture media (soluble).

Figures 39A, 39B, 39C, 39D, 39E, 39F, 39G:
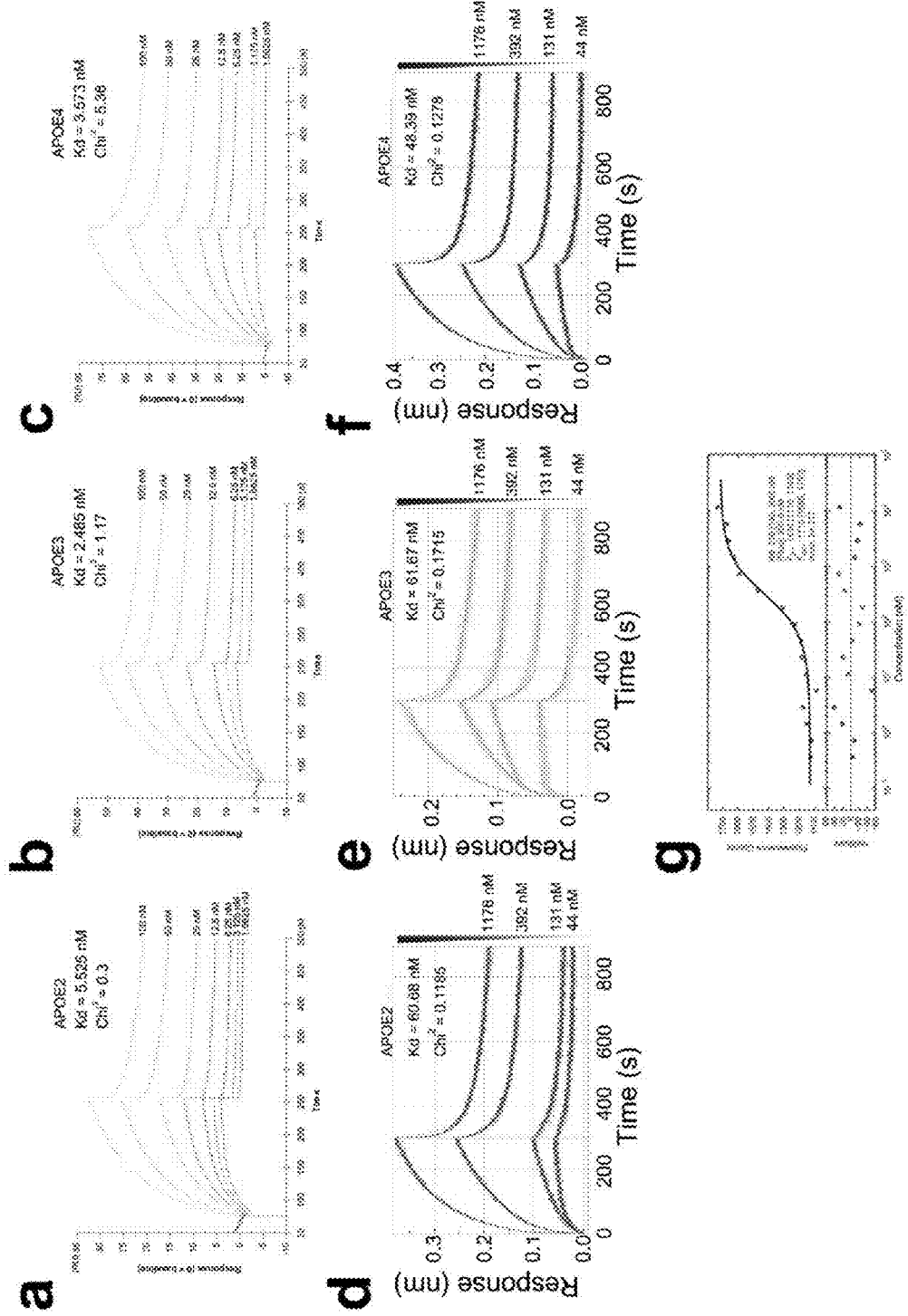

FIGS. 39a-39g—Three APOE isoforms bind to human LILRB4. FIG. 39a-c: Binding kinetics of APOE 2, 3, and 4 to LILRB4-Fc were measured using surface plasmon resonance (SPR). LILRB4-Fc was immobilized on Protein A biosensor tips and incubated with APOE concentrations ranging from 1.5625 nM to 100 nM. The Kd of APOE2, APOE3 and APOE4 binding to LILRB4 are 5.525 nM, 2.485 nM and 3.573 nM, respectively. (FIGS. 39d-f) Binding kinetics of APOE 2, 3, and 4 to LILRB4-Fc were measured using Bio-layer Interferometry (Octet). LILRB4-Fc was immobilized on Protein A biosensor tips and incubated with APOE concentrations ranging from 44 nM to 1176 nM. The Kd of APOE2, APOE3 and APOE4 binding to LILRB4 are 60.68 nM, 61.67 nM and 48.39 nM, respectively. (FIG. 39g) Binding kinetics of APOE 3 to His-LILRB4 was measured using microscale thermophoresis (MST). The Kd of APOE3 binding to LILRB4 is 210 nM.

Figures 40A, 40B:
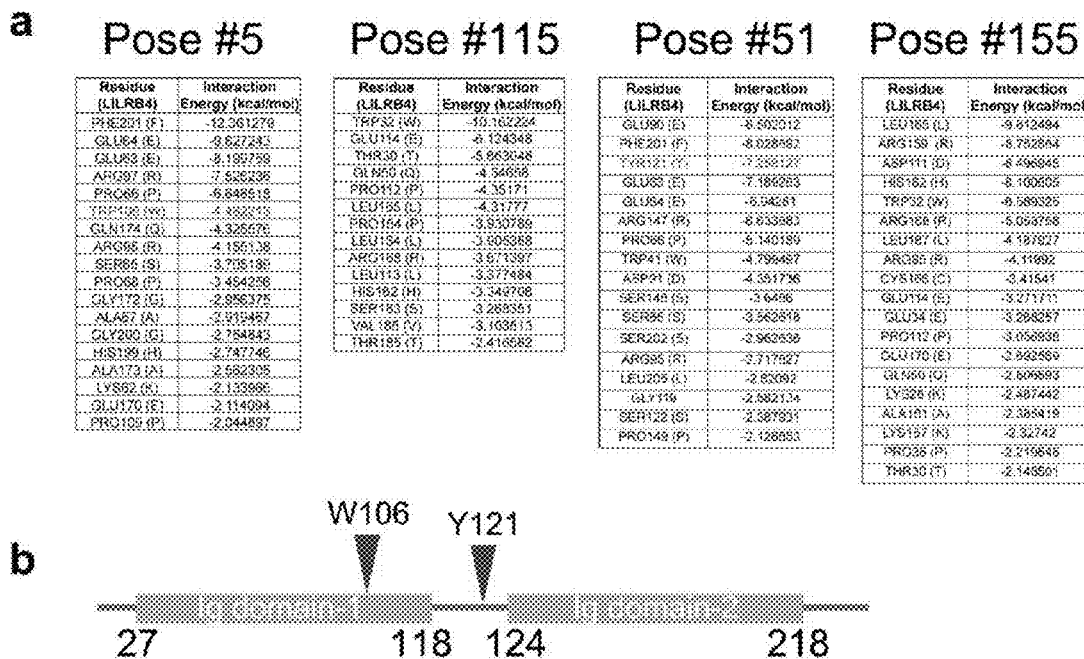

FIGS. 40a-40b—The role of mutated residues of LILRB4 in the possible APOE binding interface based on the known structures of LILRB4 and APOE. FIG. 40a: Based on the PDB structure of LILRB4 (PDBID: 3P2T) and APOE3 (PDBID: 2L7B), residues in four possible ligand binding interfaces (the top 4 APOE-LILRB4 interaction poses based on the scores) are shown. Each of the amino acid residues on the interaction surface of LILRB4 for the 4 poses was mutated and tested in a series of mutant LILRB4 reporter cells. FIG. 40b: Mutation of two residues, W106 and Y121 significantly reduced activation of LILRB4 by APOE, located in the first Ig domain and in the linker between two Ig domains, respectively.

Figure 41A:
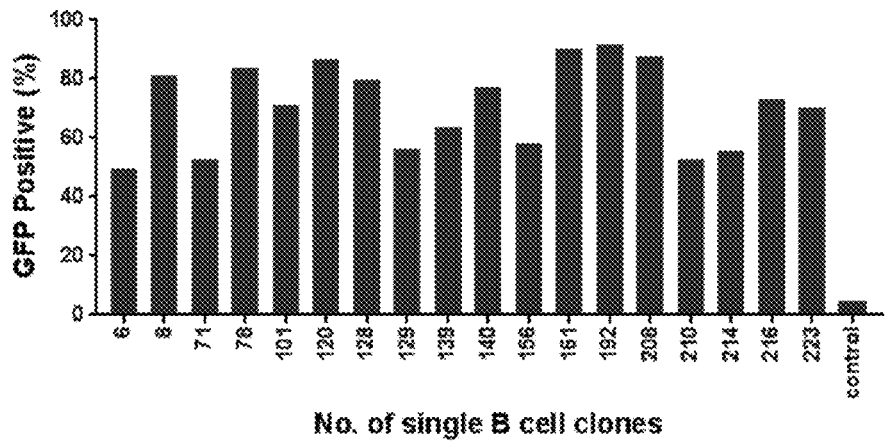
Figure 41B:
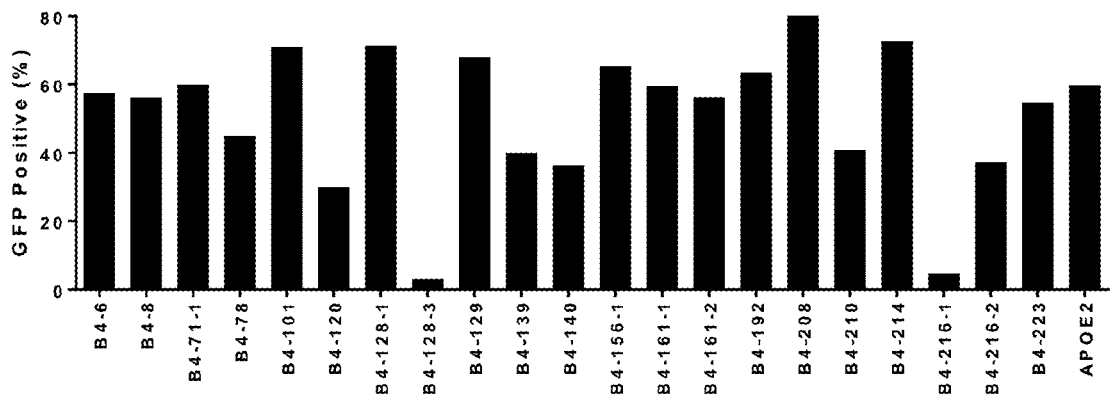

FIGS. 41a-41b—reporter assays of rabbit monoclonal antibodies. FIG. 41a: LILRB4 reporter activation signal of single B cell clones from rabbit to immunization with human LILRB4. The hybridoma supernatant is coated on the plate in the absence of LILRB4 ligand. FIG. 41b: Anti-LILRB4 rabbit mAbs block APOE activation of LILRB4 signal pathway. APOE2 used as functional ligand control.

Figure 42:
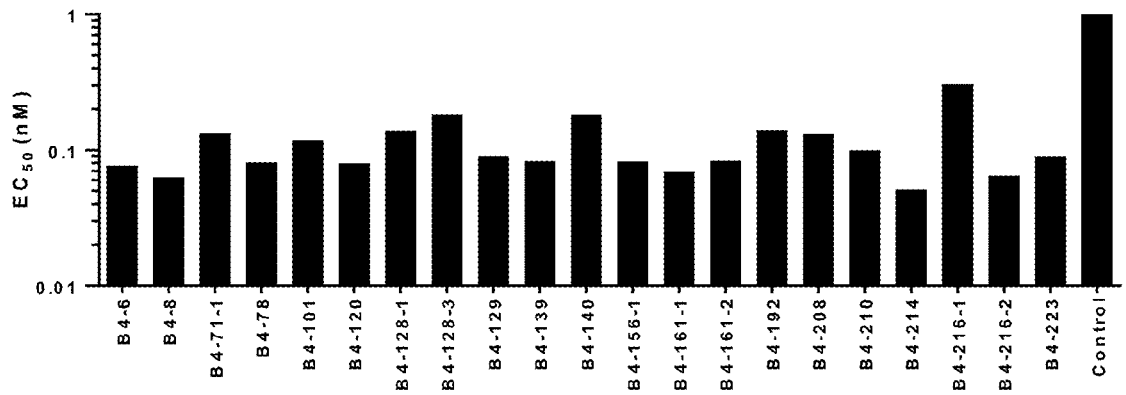

FIG. 42—Binding of 21 anti-LILRB4 rabbit mAbs performed in ELISA.

Figure 43:
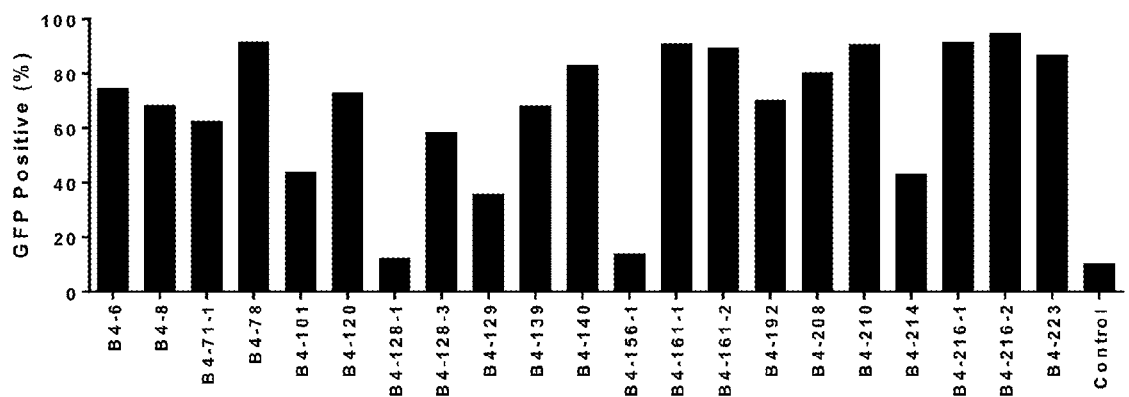

FIG. 43—Reporter activation signal of 21 anti-LILRB4 rabbit mAbs. Purified mAbs were coated on plates at the concentration of 1 μg/ml.

Figure 44:
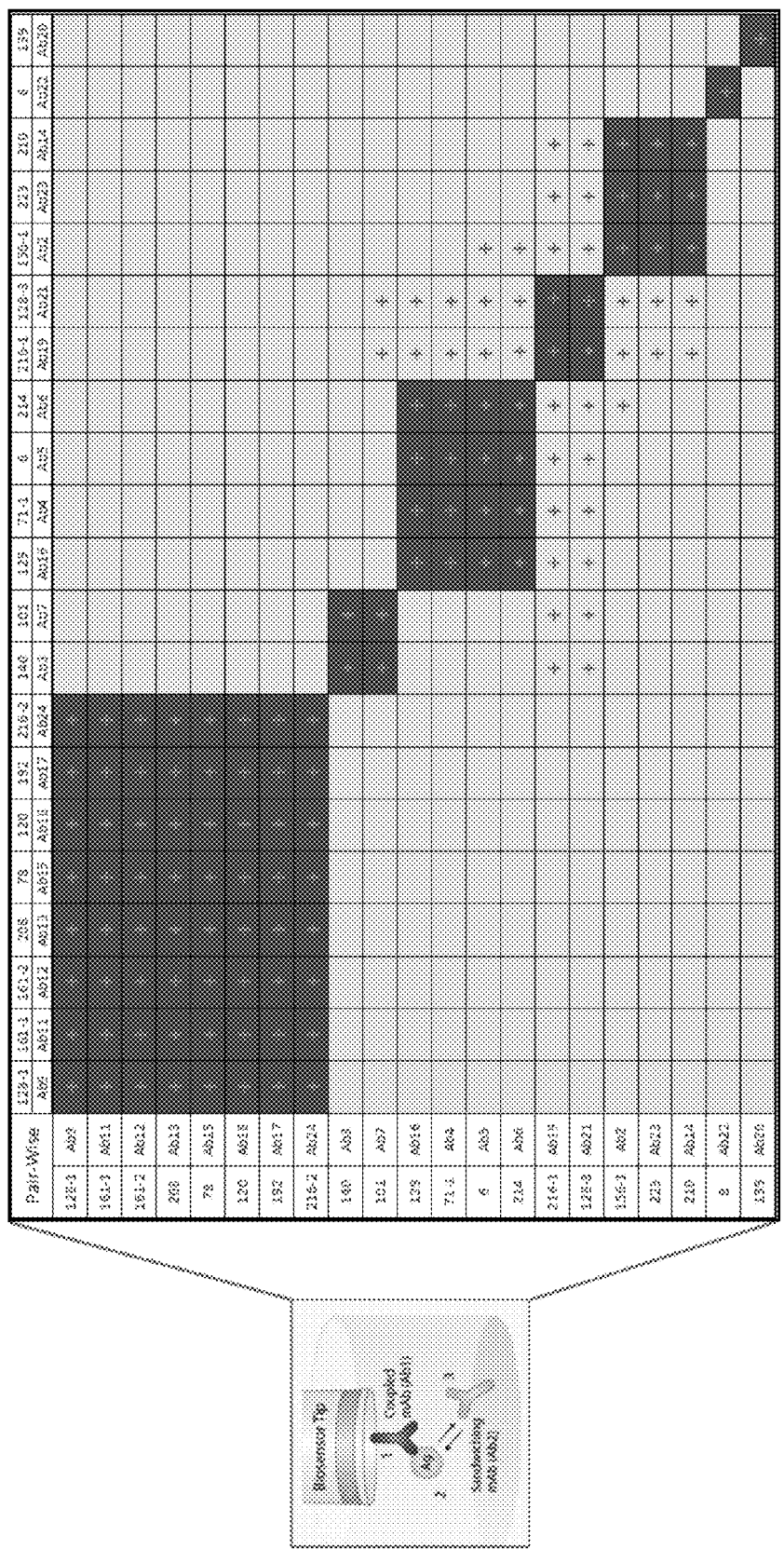

FIG. 44—BLI analysis of 21 anti-LILRB4 rabbit mAbs using classic sandwich epitope binning assay format performed in Octet RED96.

Figure 45:
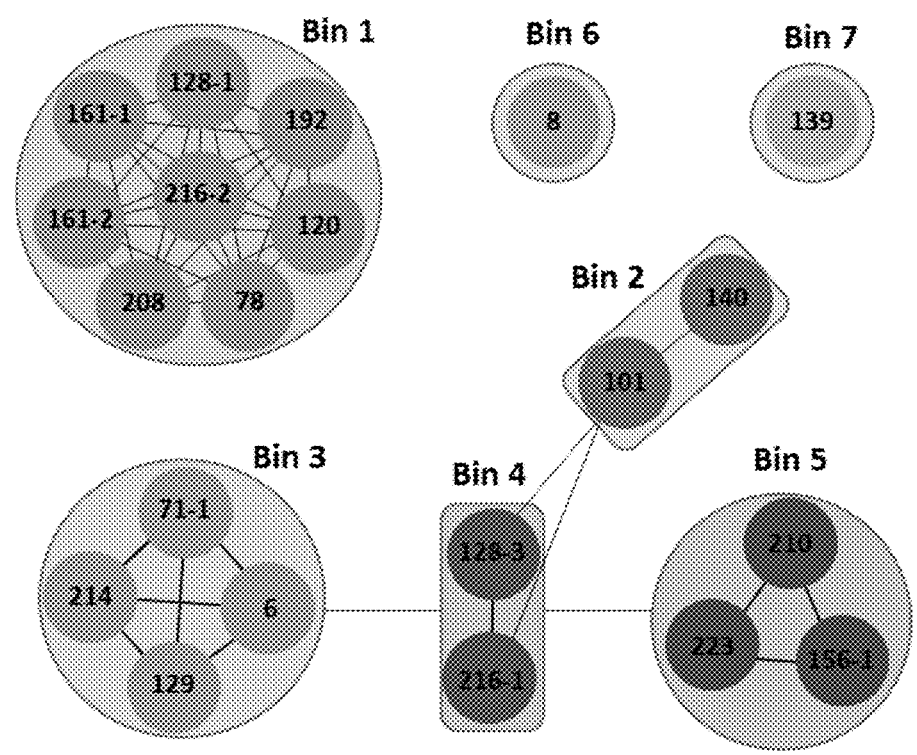

FIG. 45—Node plot of the epitope bins of 21 LILRB4 rabbit mAbs determined from BLI analysis.

Figure 46:
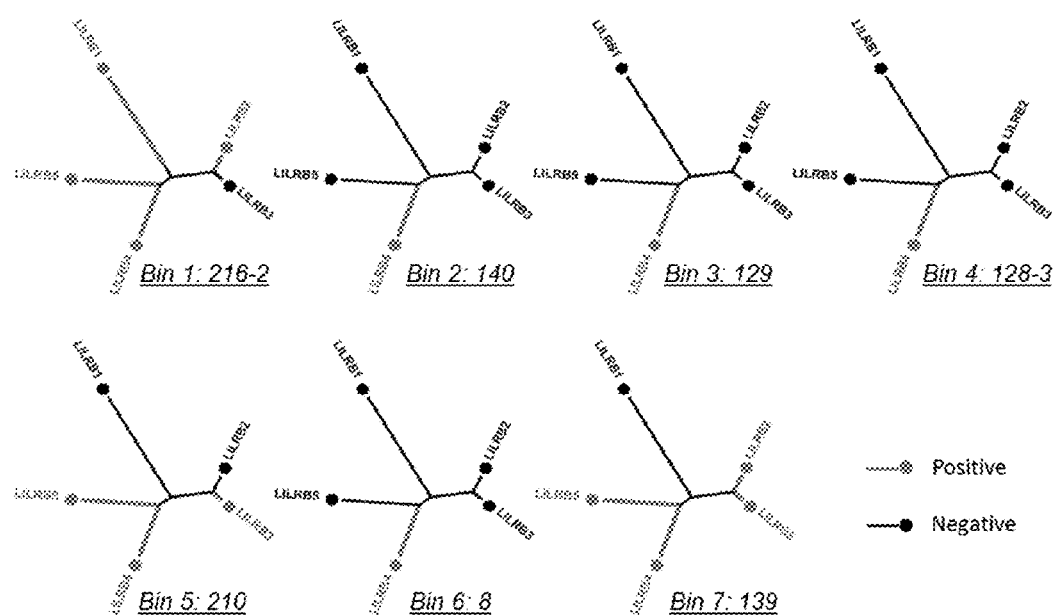

FIG. 46—Cross-reactivity of representative mAbs (216-2, 140, 129, 128-3, 210, 8 and 139) recognize different epitope bins (bin 1-7).

Figure 47:
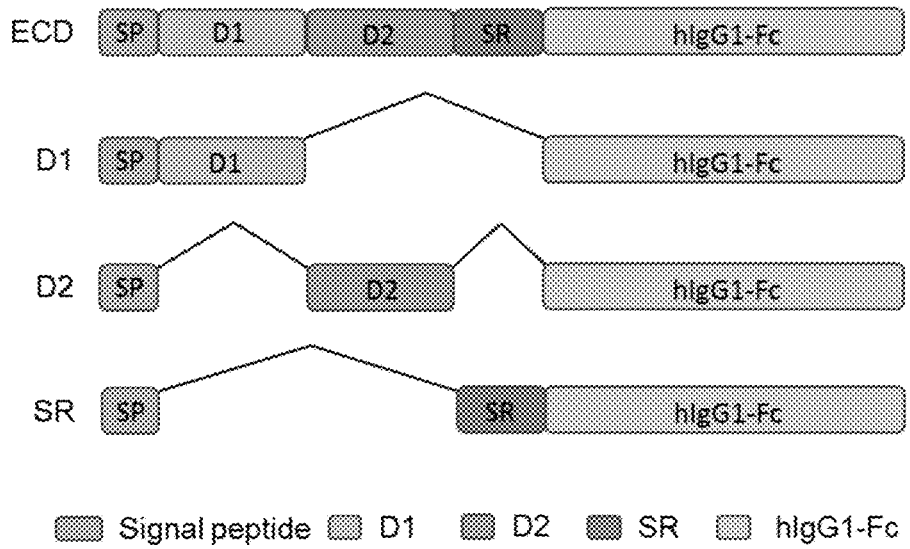

FIG. 47—Mutated forms of LILRB4 ECD-Fc fusion proteins. D1: first Ig-like domain of LILRB4 (27-118 aa). D2: second Ig-like domain of LILRB4 (119-218 aa). SR: stalk region of LILRB4 (219-259 aa). ECD: full-length of LILRB4 ECD (27-259 aa).

Figure 48:
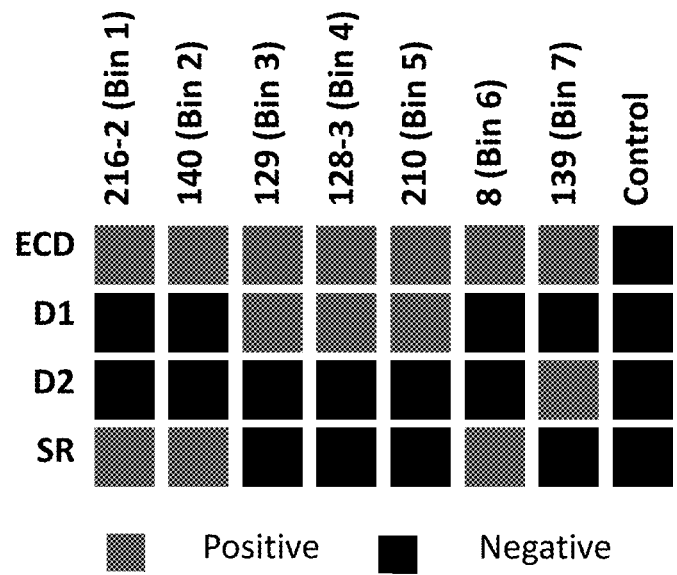

FIG. 48—Binding of anti-LILRB4 representative mAbs which recognizes different epitope bins with LILRB4 mutated proteins.

Figure 49:
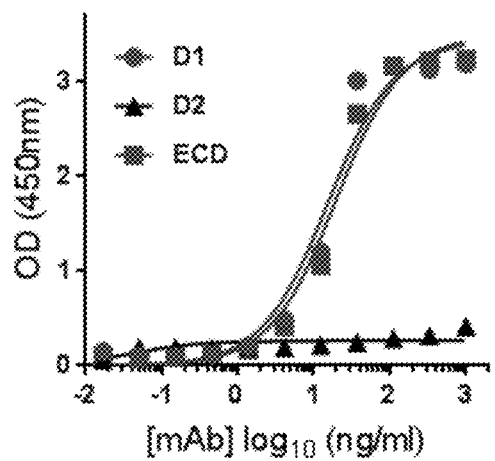

FIG. 49—Binding of mAb 128-3 with D1, D2 and ECD of LILRB4 performed in ELISA.

Figure 50:
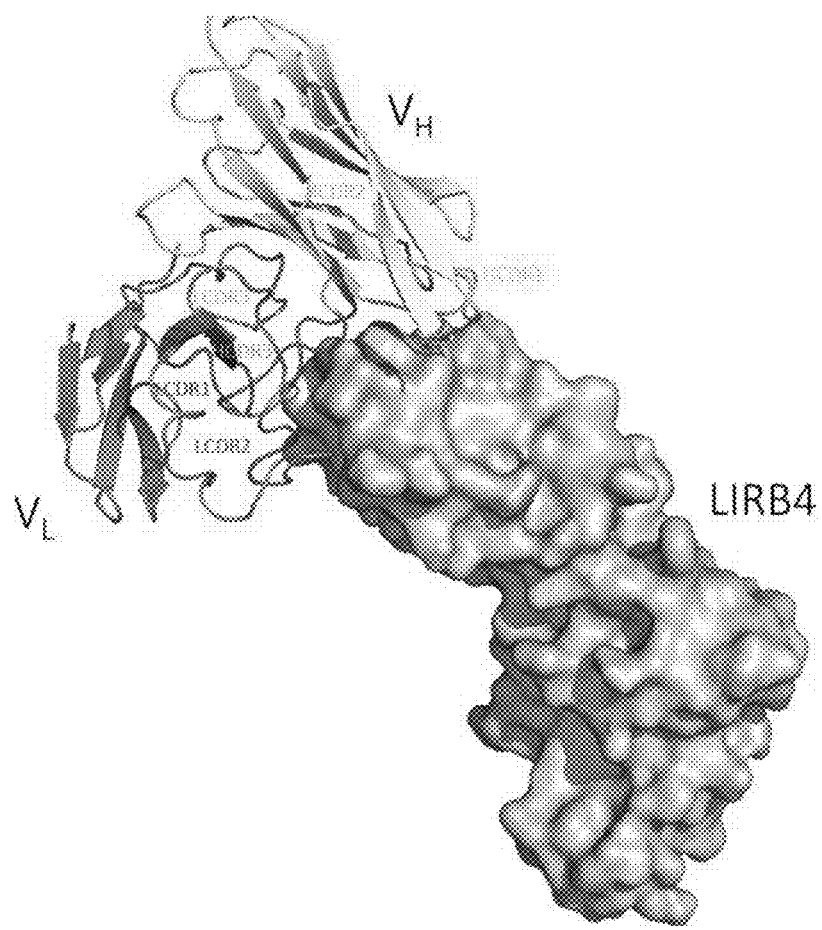

FIG. 50—Docking model of mAb 128-3 Fv with LILRB4 suggests 128-3 binding to the "head region" of D1.

Figure 51:
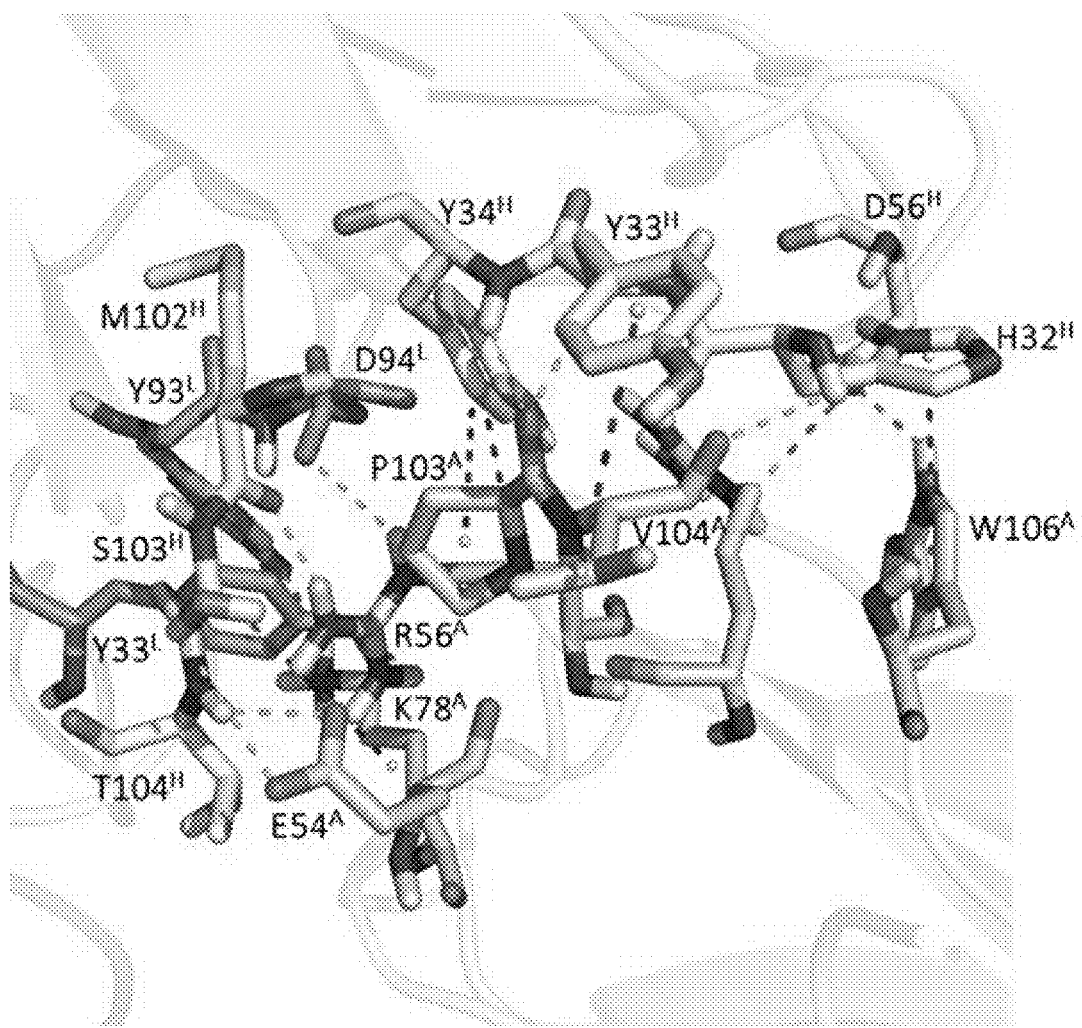

FIG. 51—Detailed interaction of mAb 128-3 with LILRB4 based on molecular docking.

Figure 52:
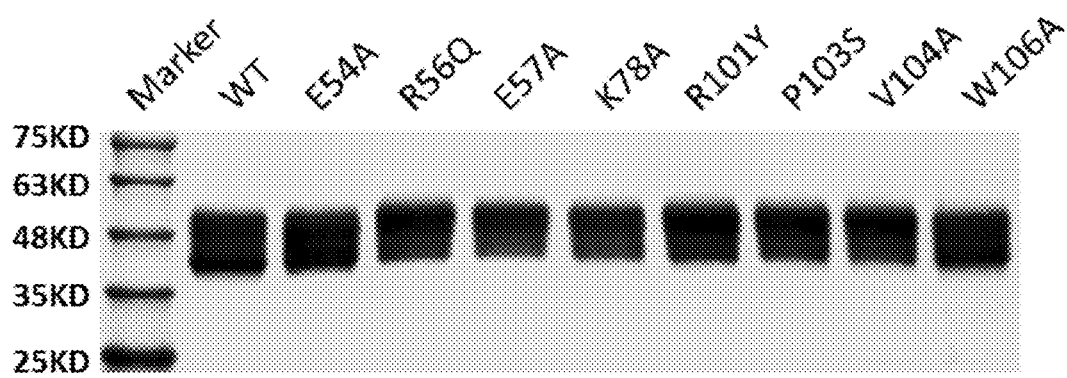

FIG. 52—Generation of LILRB4 mutated proteins.

Figure 53:
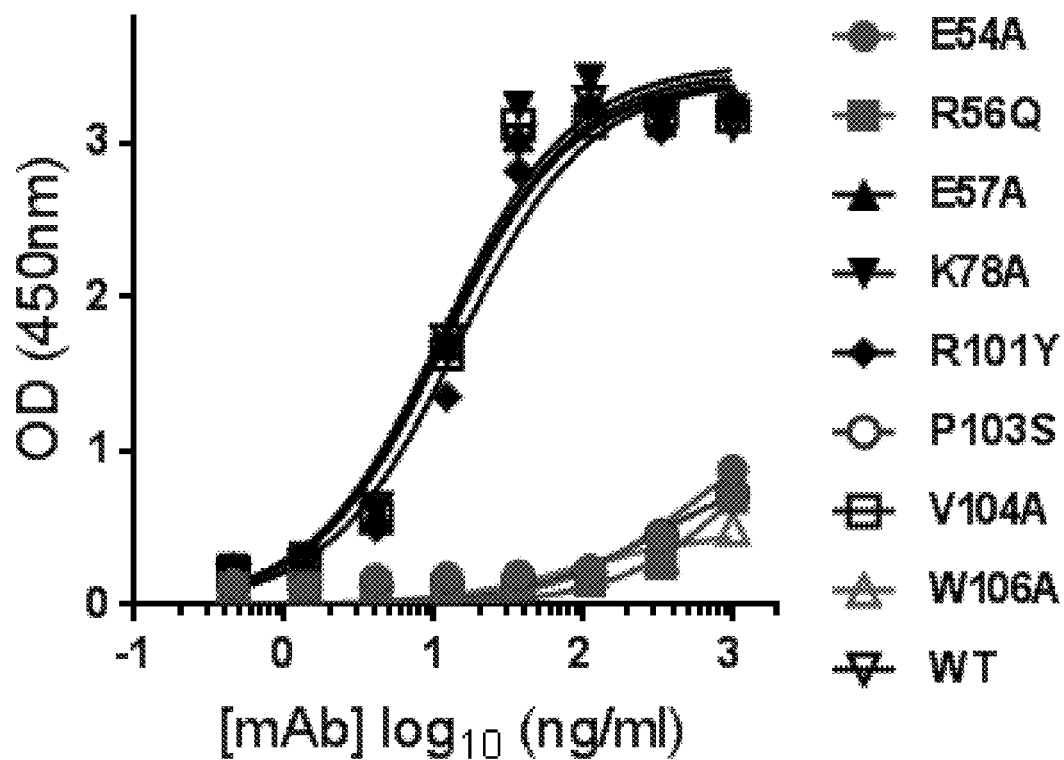

FIG. 53—Binding of mAb 128-3 with LILRB4 mutated proteins. 4 key amino acid residues (E54, R56, P103 and W106) on LILRB4 contribute to 128-3 binding.

Figure 54:
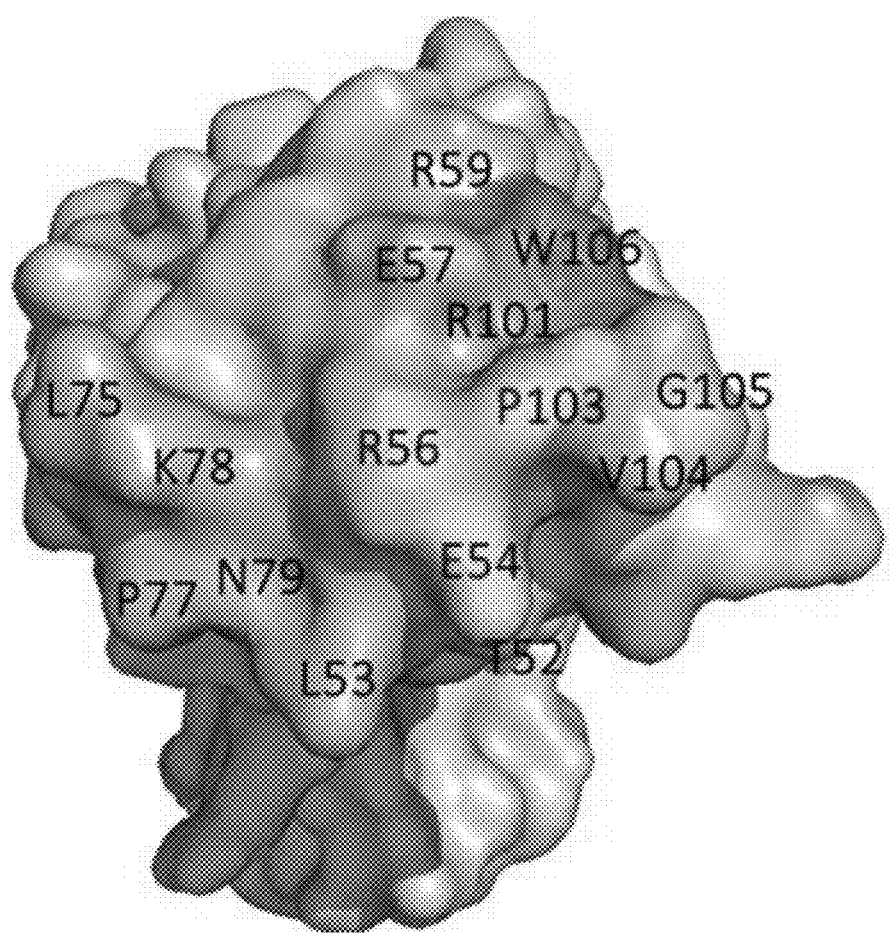

FIG. 54—Binding surface of LILRB4 by mAb 128-3.

Figure 55:
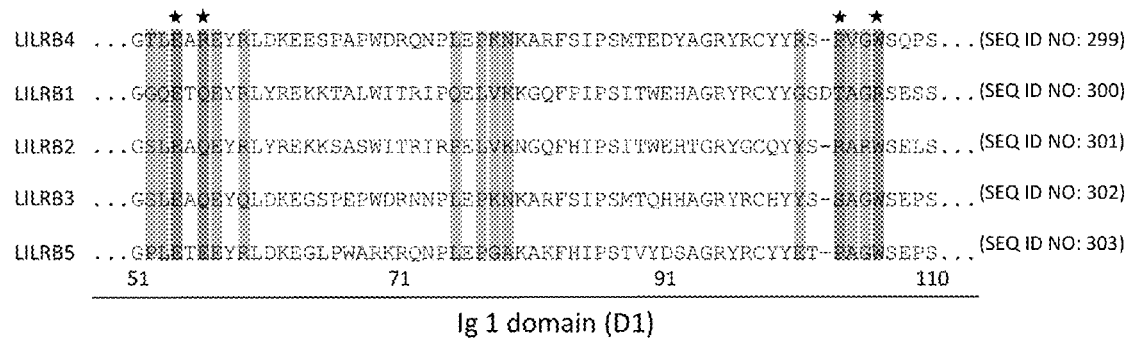

FIG. 55—Amino acid sequences at and around the mAb 128-3 binding epitope (motif). Residues in direct contact are boxed. For comparison, sequences of LILRB1, LILRB2, LILRB3 and LILRB5 are aligned to LILRB4.

Figure 56:
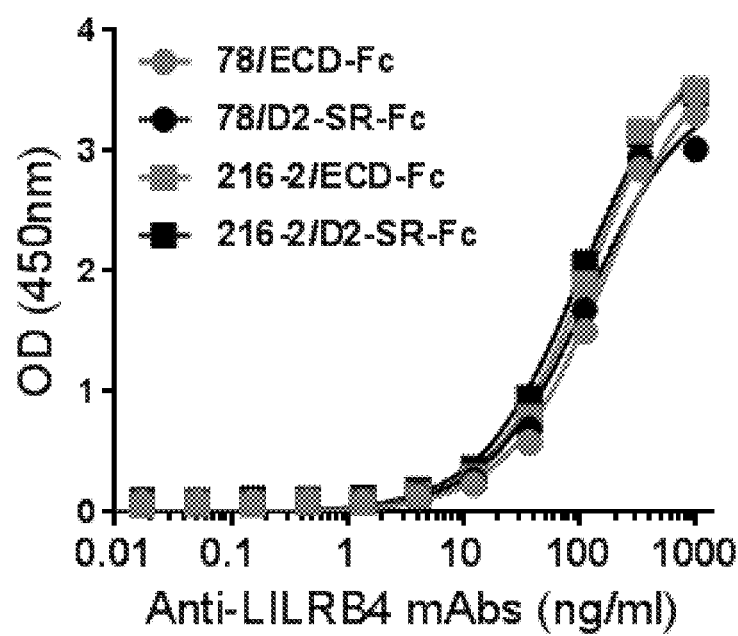

FIG. 56—Binding of mAbs 78 and 216-2 (bin 1) to ECD and D2-SR of LILRB4 in ELISA.

Figure 57:
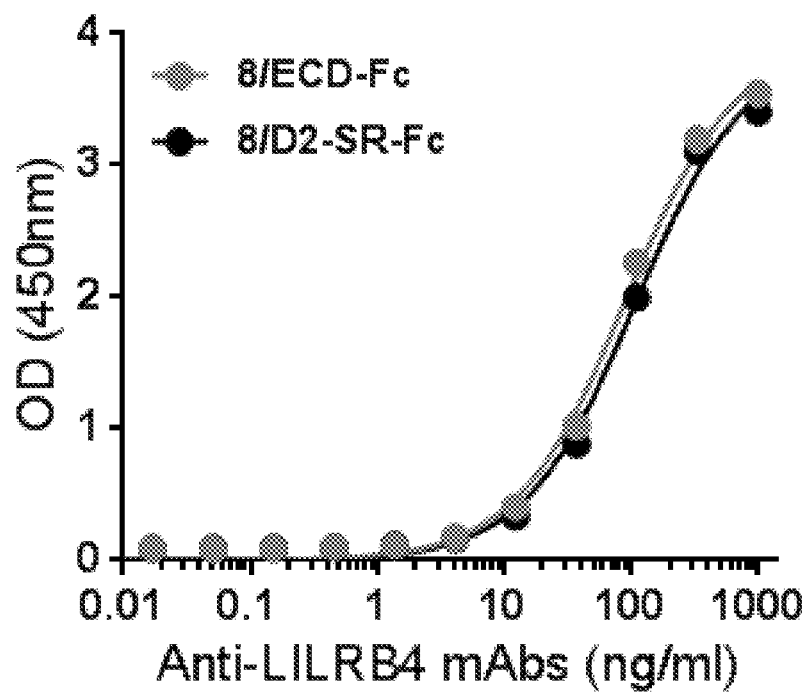

FIG. 57—Binding of mAb 8 (bin 6) to ECD and D2-SR of LILRB4 in ELISA.

Figure 58:
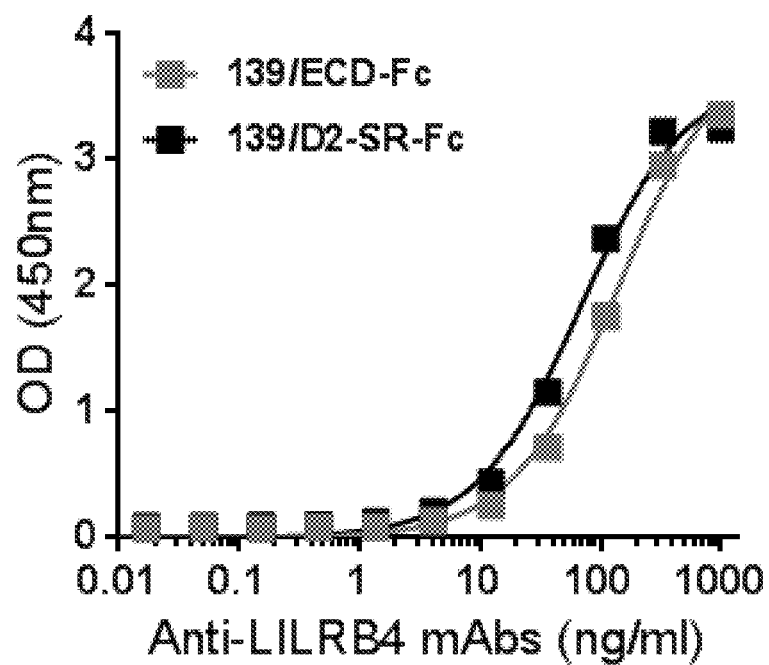

FIG. 58—Binding of mAb 139 (bin 7) to ECD and D2-SR of LILRB4 in ELISA.

Figure 59:
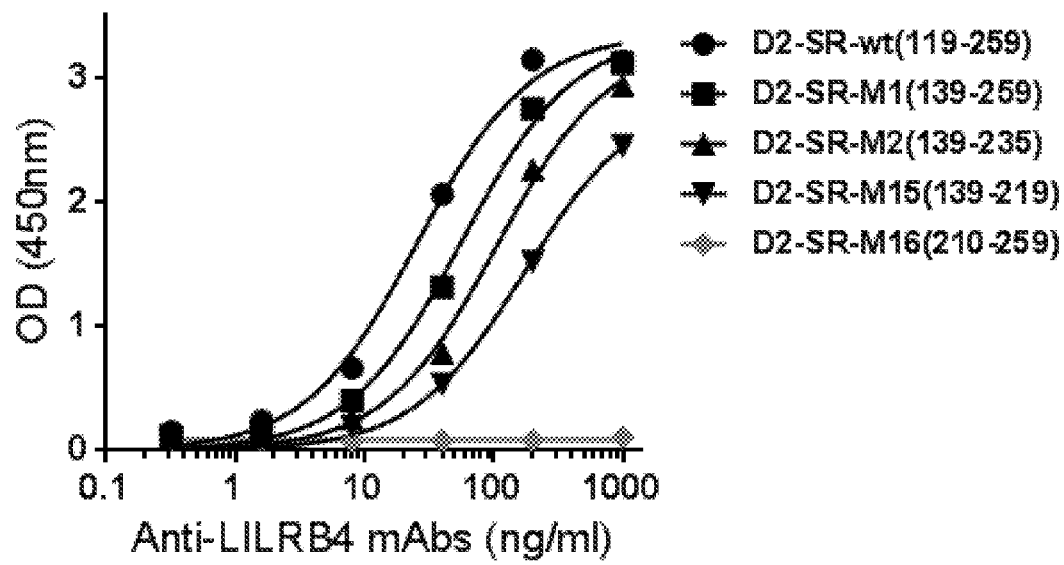

FIG. 59—Binding of mAb 139 (bin 7) to D2-SR mutants of LILRB4 in ELISA.

Figure 60:
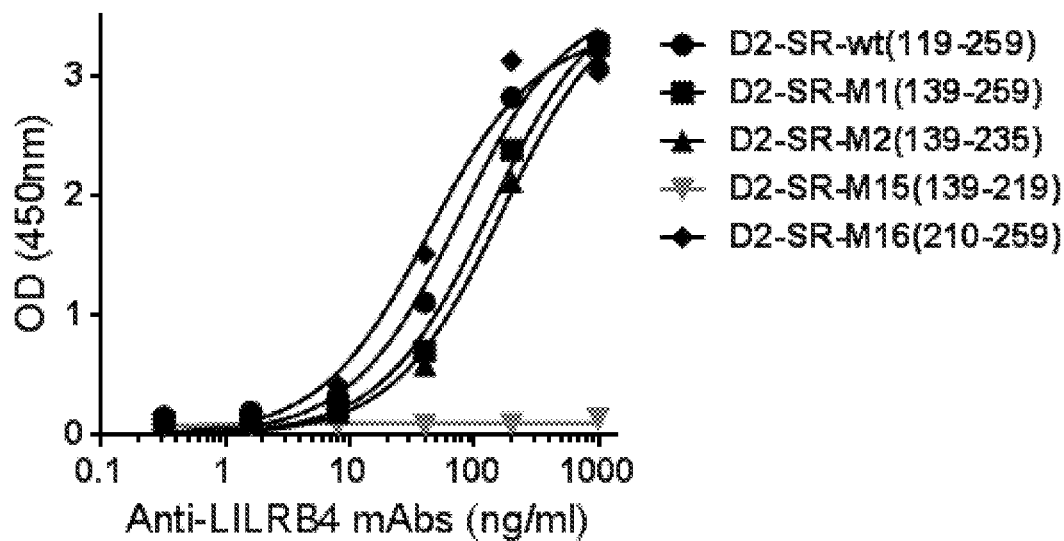

FIG. 60—Binding of mAb 140 (bin 2) to D2-SR mutants of LILRB4 in ELISA.

Figure 61:
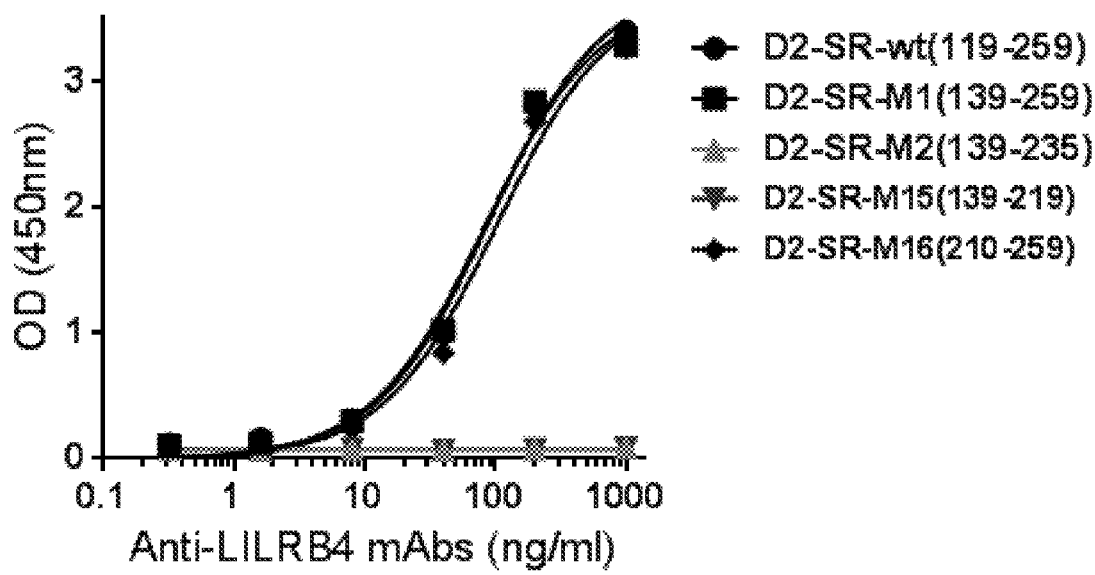

FIG. 61—Binding of mAb 216-2 (bin 1) to D2-SR mutants of LILRB4 in ELISA.

Figure 62:
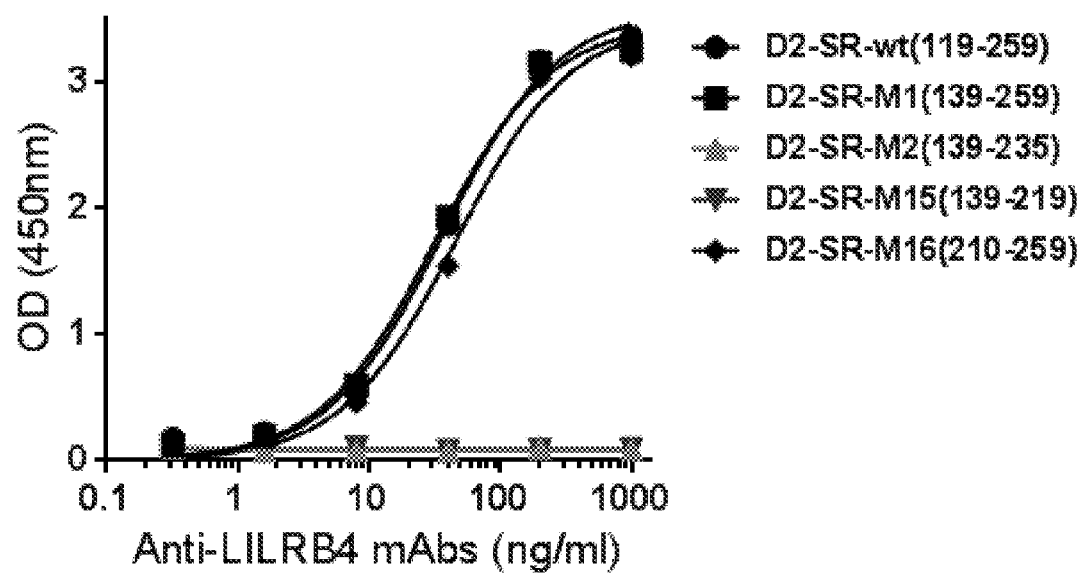

FIG. 62—Binding of mAb 8 (bin 6) to D2-SR mutants of LILRB4 in ELISA.

Figure 63:
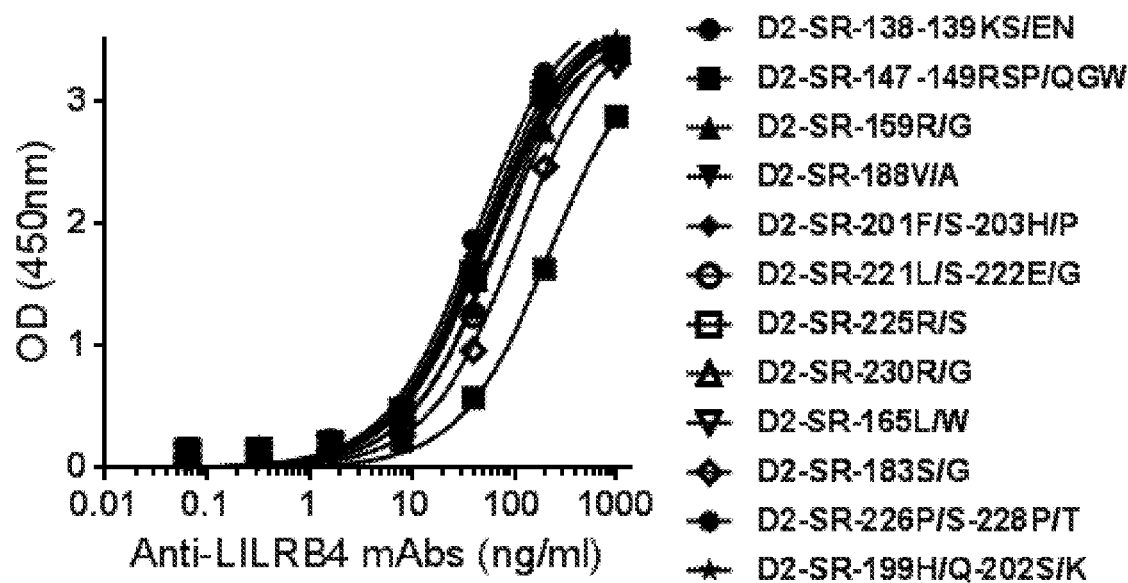

FIG. 63—Binding of mAb 139 (bin 7) to D2-SR mutants of LILRB4 in ELISA.

Figure 64:
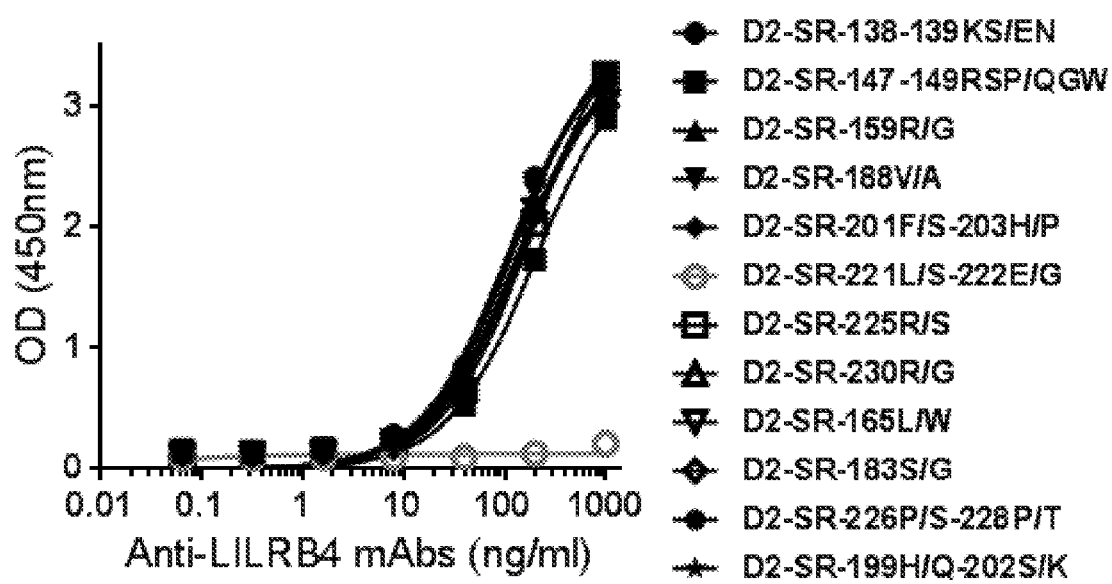

FIG. 64—Binding of mAb 140 (bin 2) to D2-SR mutants of LILRB4 in ELISA.

Figure 65:
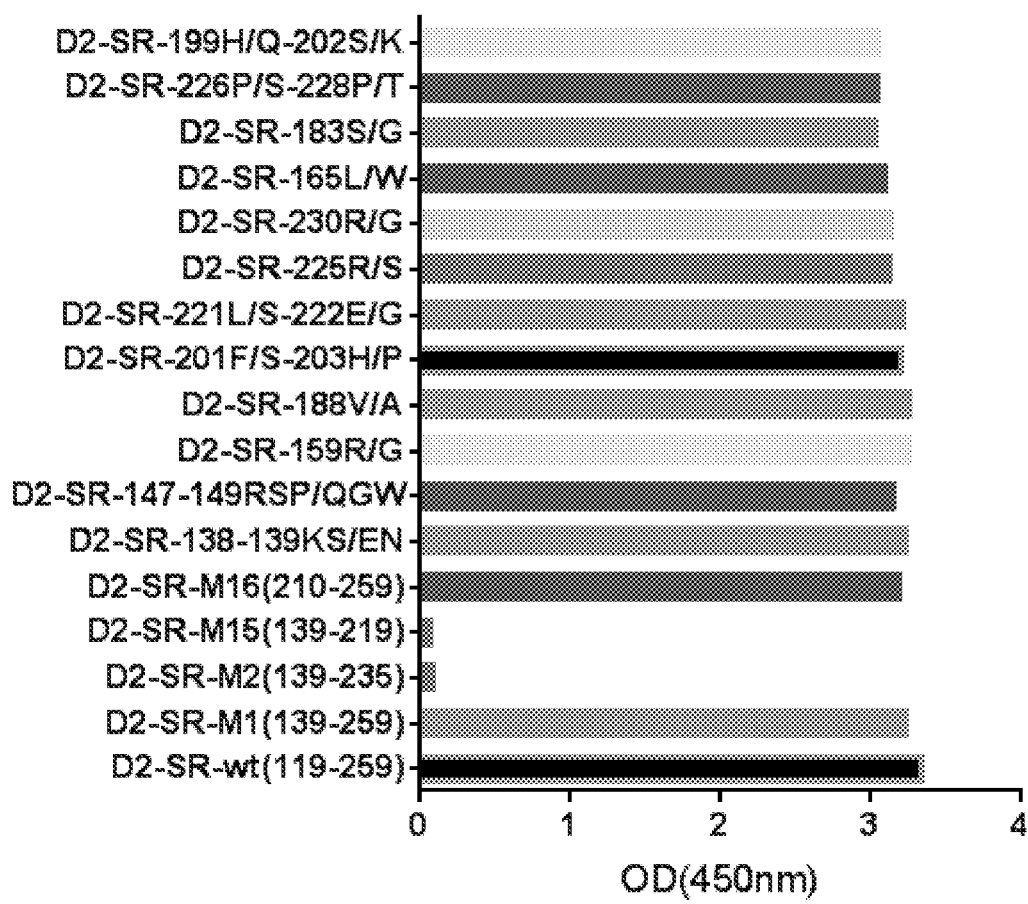

FIG. 65—Binding of mAb 8 (bin 6) to D2-SR mutants of LILRB4 in ELISA.

Figure 66:
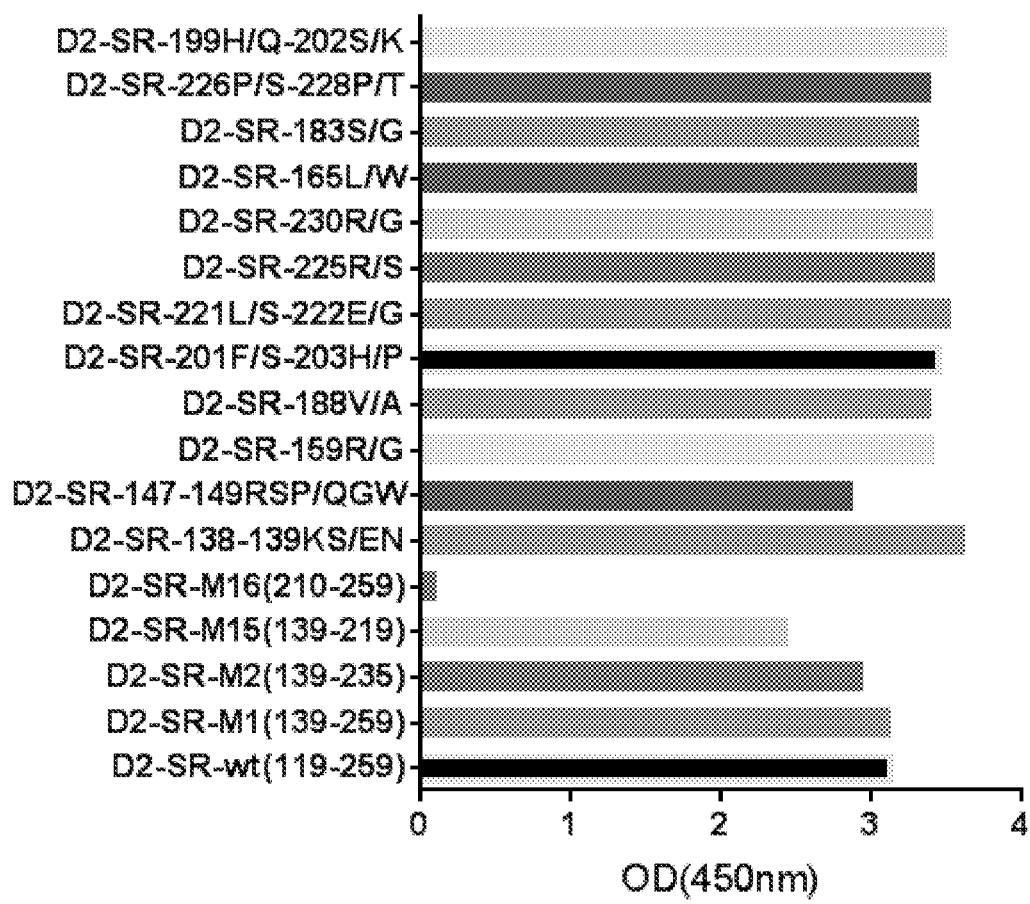

FIG. 66—Binding of mAb 139 (bin 7) to D2-SR mutants of LILRB4 in ELISA.

Figure 67:
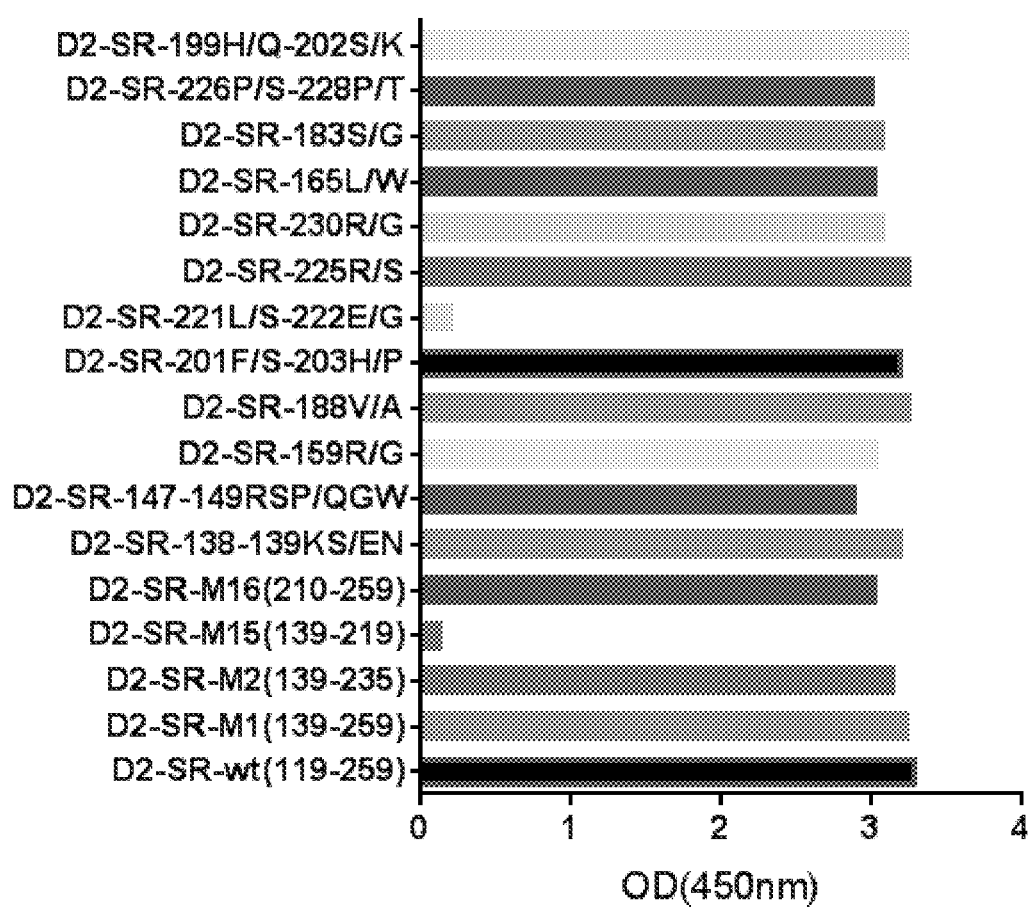

FIG. 67—Binding of mAb 140 (bin 2) to D2-SR mutants of LILRB4 in ELISA.

Figure 68:
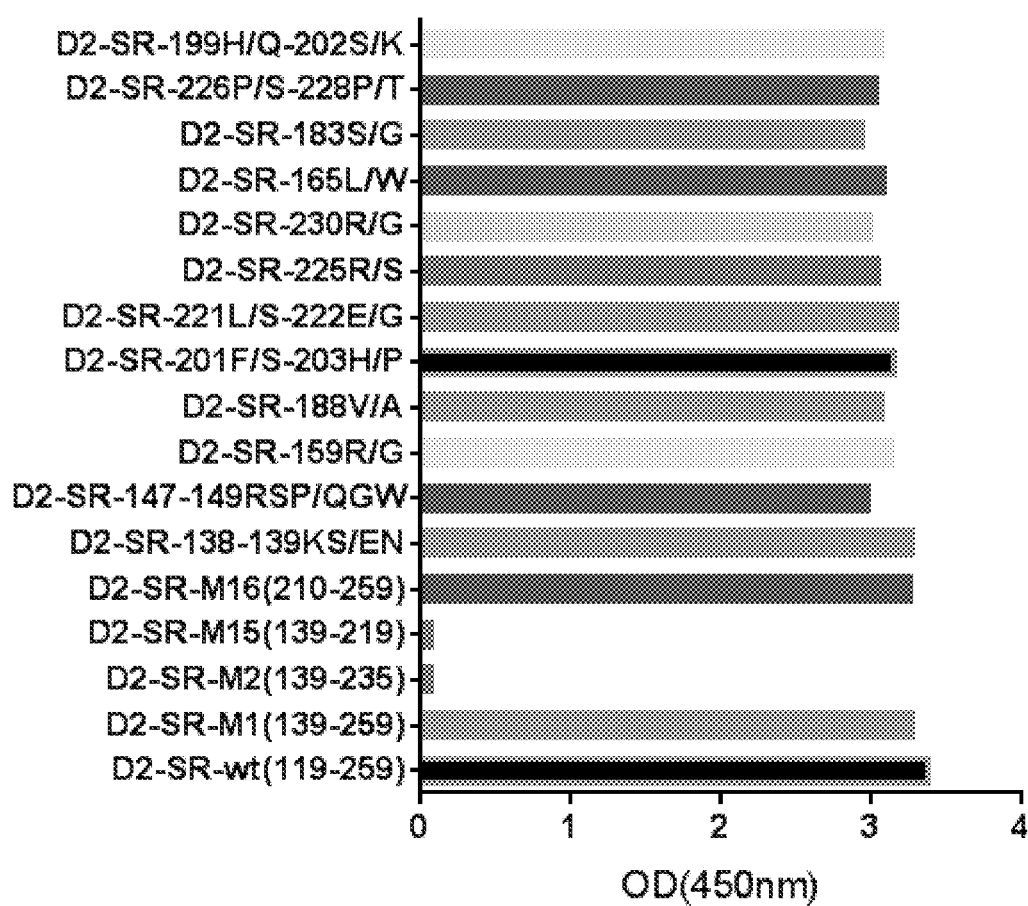

FIG. 68—Binding of mAb 216-2 (bin 1) to D2-SR mutants of LILRB4 in ELISA.

Figure 69:
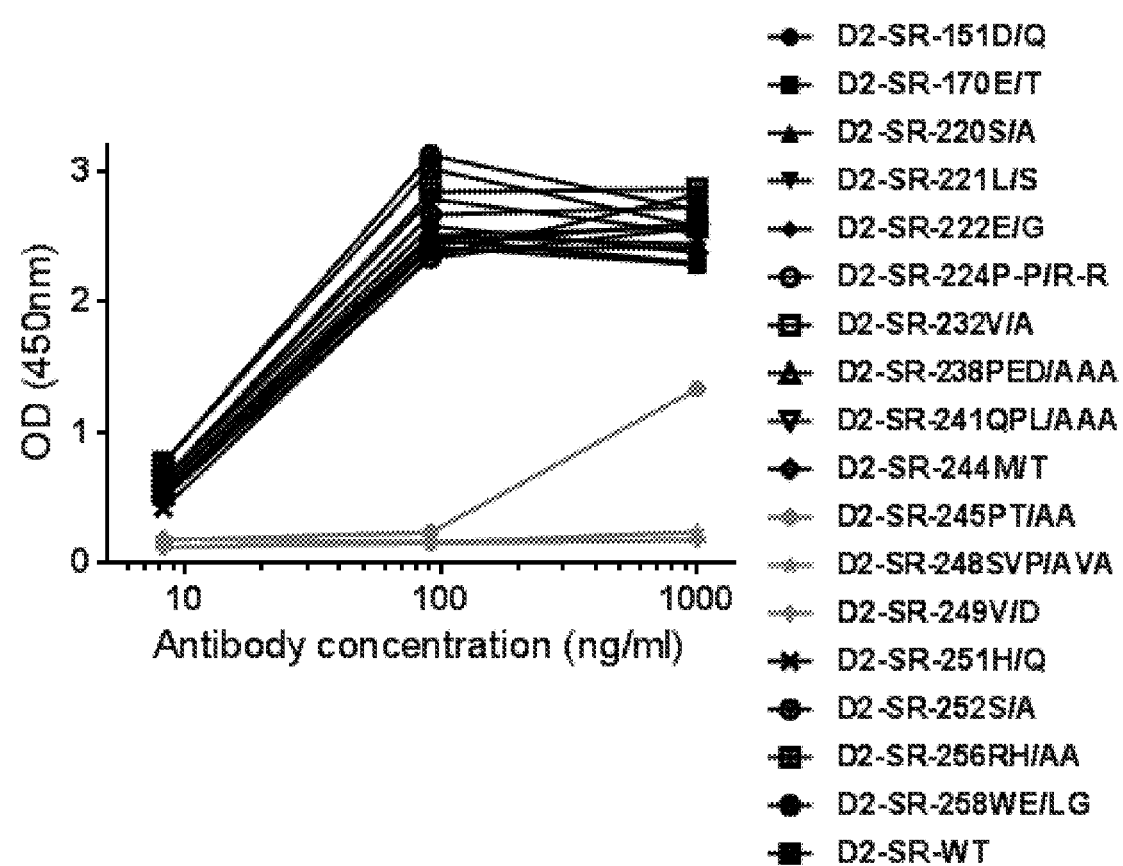

FIG. 69—Binding of mAb 8 (bin 6) to D2-SR mutants of LILRB4 in ELISA.

Figure 70:
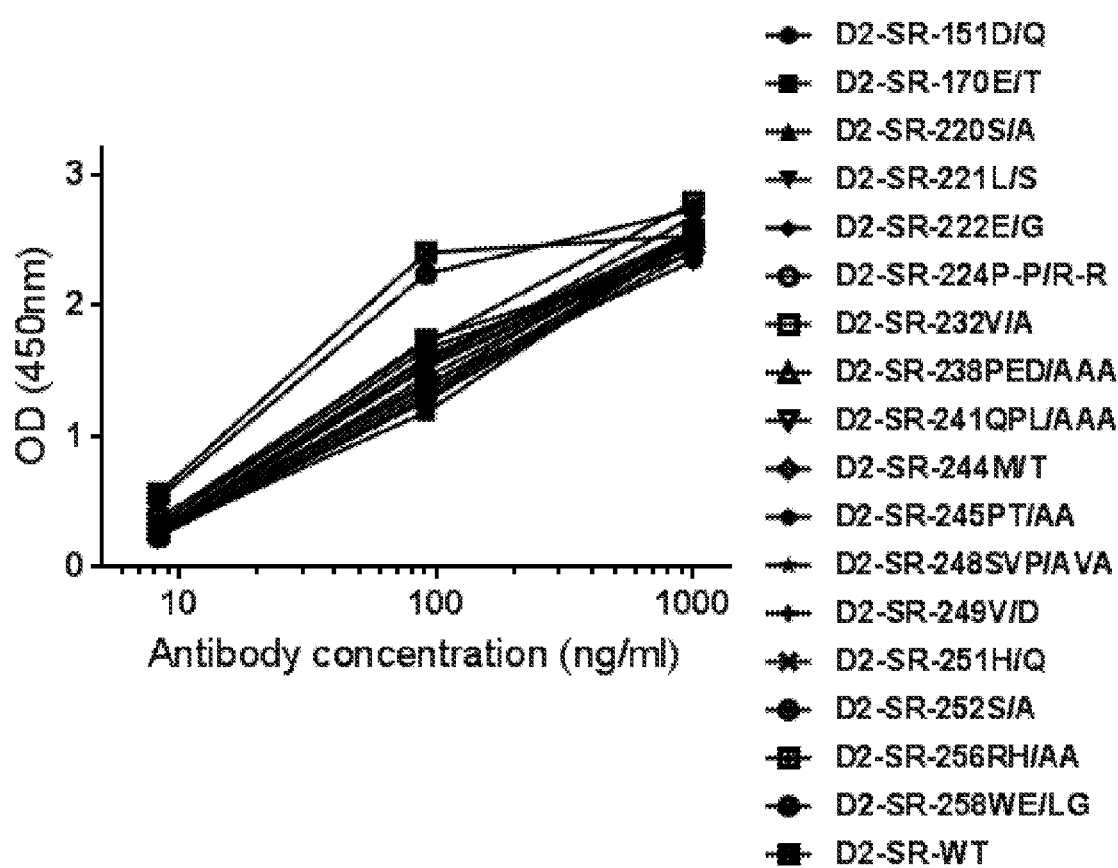

FIG. 70—Binding of mAb 139 (bin 7) to D2-SR mutants of LILRB4 in ELISA.

Figure 71:
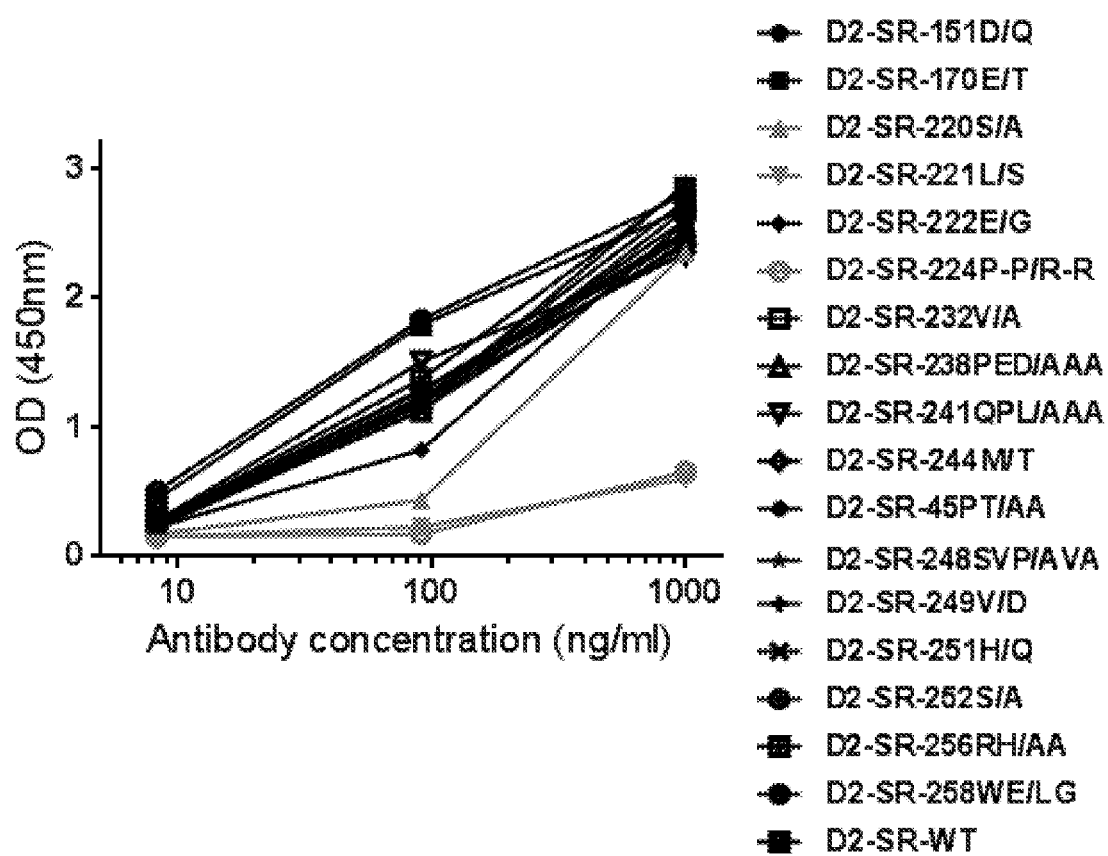

FIG. 71—Binding of mAb 140 (bin 2) to D2-SR mutants of LILRB4 in ELISA.

Figure 72:
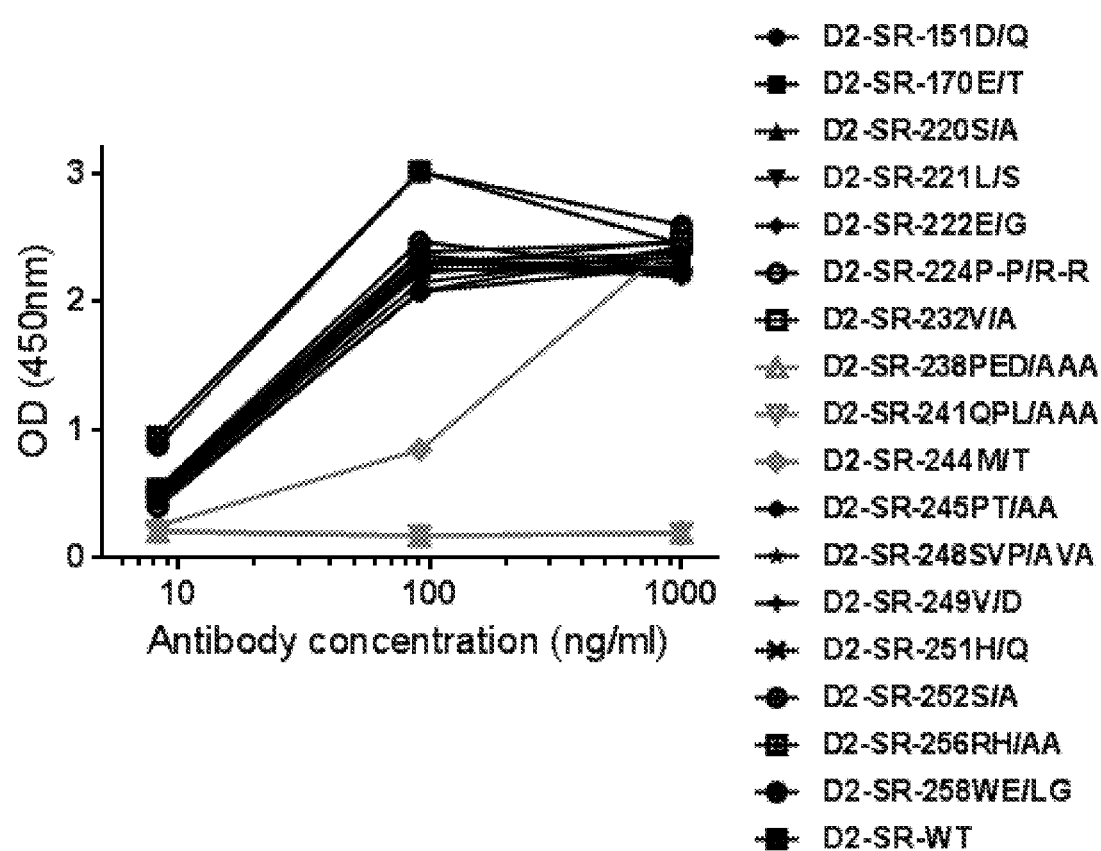

FIG. 72—Binding of mAb 216-2 (bin 1) to D2-SR mutants of LILRB4 in ELISA.

Figure 73:
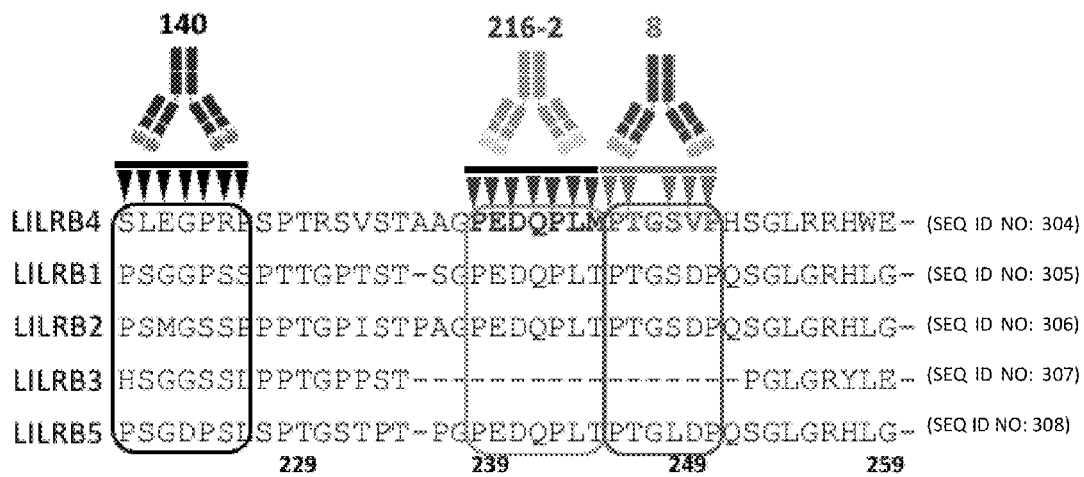

FIG. 73—Epitope mapping data showed that mAbs 140, 216-2 and 8 binding to SR of LILRB4. 216-2 recognizes a conformational epitope on SR, and amino acid sequence (PEDQPLM; SEQ ID NO: 283) is the key region for mAb 216-2 binding. mAb 8 recognizes a linear epitope with amino acid sequence (PTGSVP; SEQ ID NO: 284) on SR.

Figure 74:
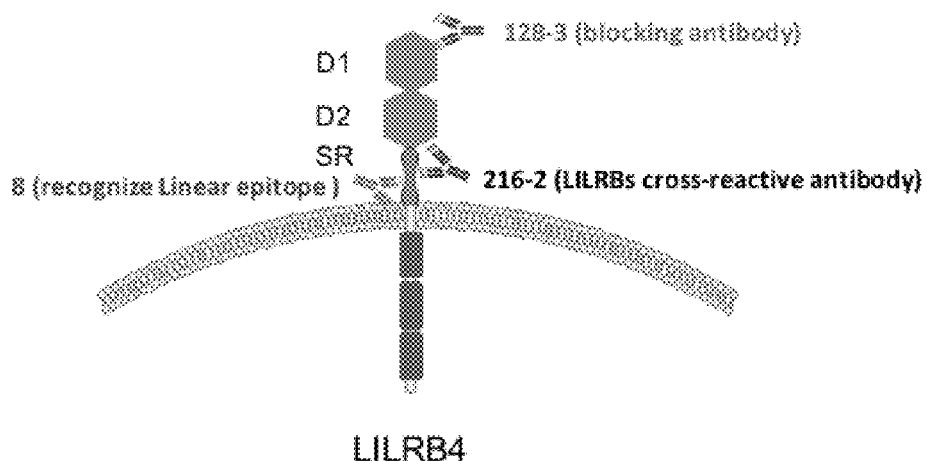

FIG. 74—Binding model of mAbs 128-3, 216-2 and 8 with LILRB4. mAb 128-3 which binds to D1 of LILRB4 can block LILRB4 activation by APOE. mAb 216-2, which has cross-reactivity with LILRB1, LILRB3 and LILRB5 recognizes a conformational epitope on SR of LILRB4. LILRB4 specific mAb 8 recognizes a linear epitope on SR.

Figure 75:
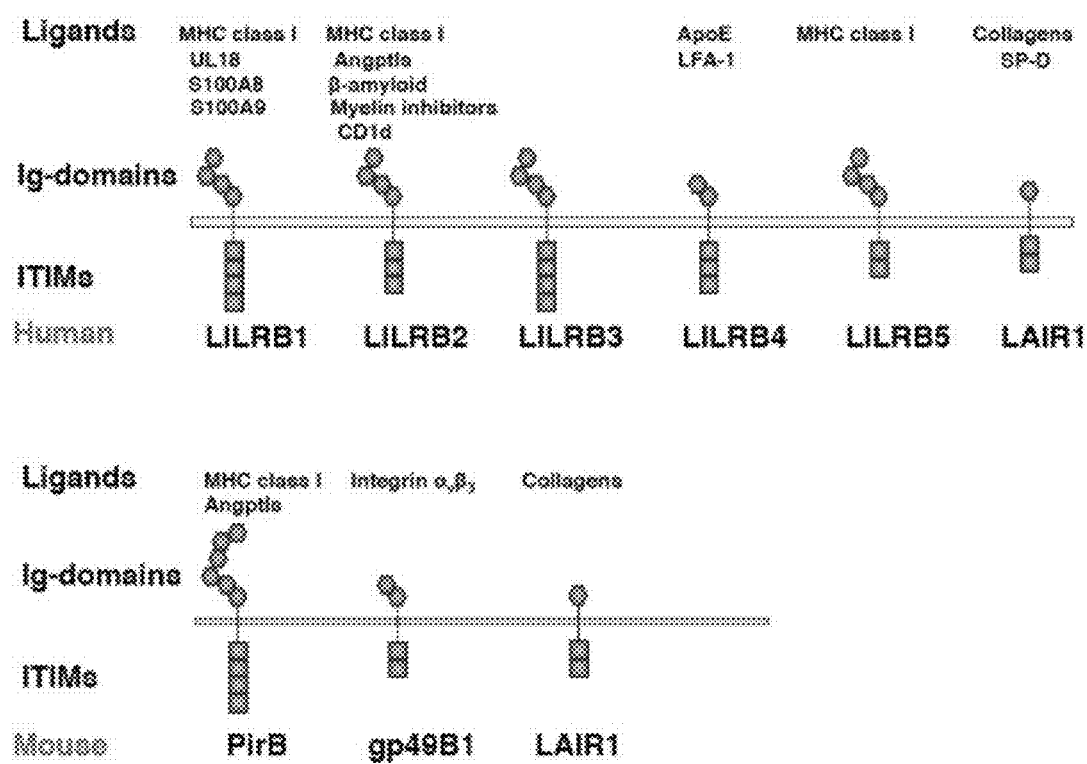

FIG. 75—Diagram of LILRBs, their family members and orthologues, and their ligands.

Figure 76:
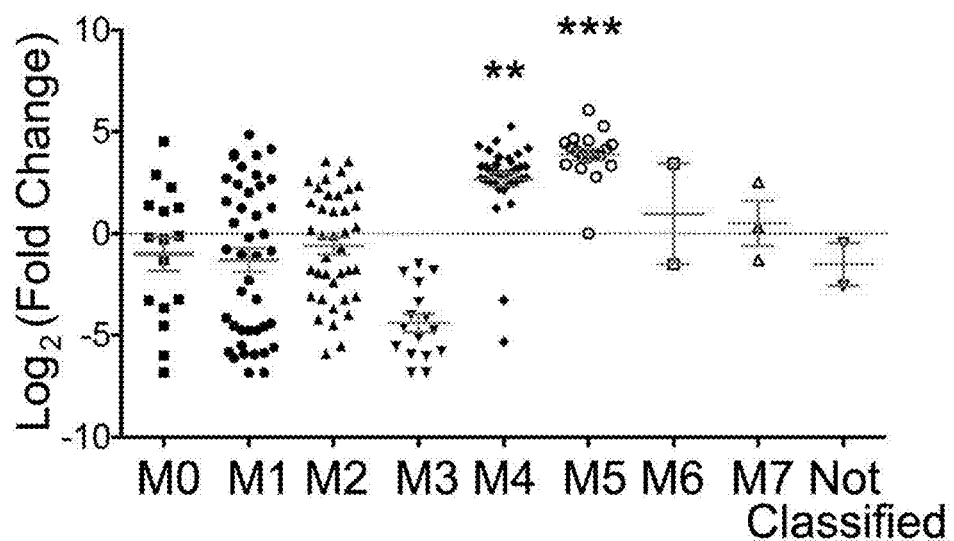

FIG. 76—Analysis of mRNA expression data from the TCGA database shows that LILRB4 mRNA is present at higher concentration in M4 and M5 AML cells than in other subtypes. , $p<0.01$, *, $p<0.001$.

Figures 77A, 77B, 77C:
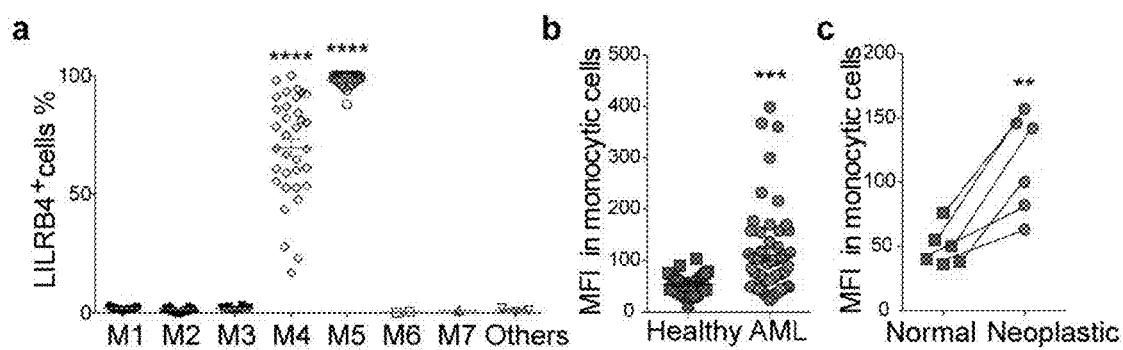
Figure 77D:
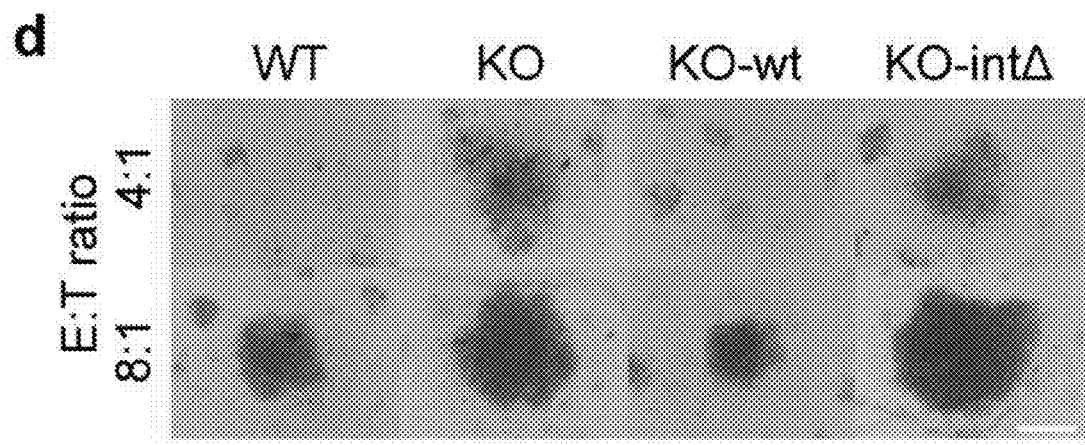
Figures 77E, 77F:
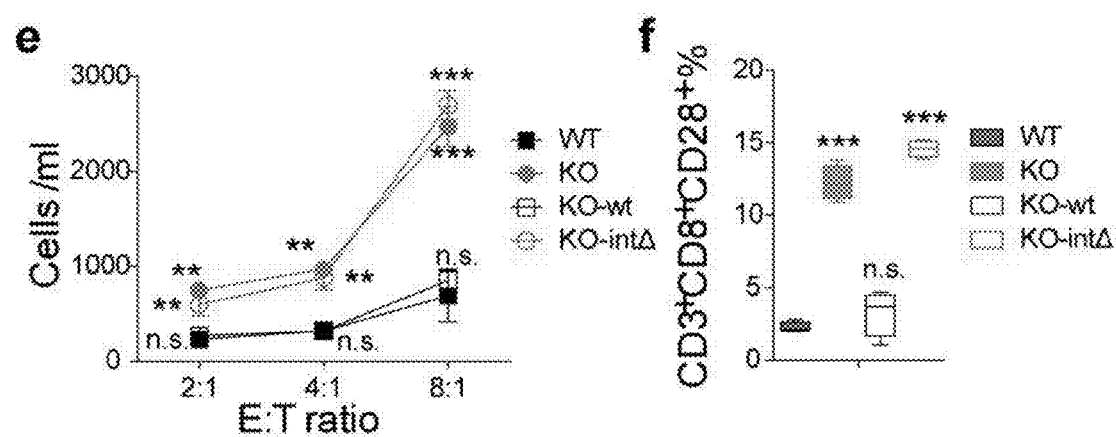
Figure 77G:
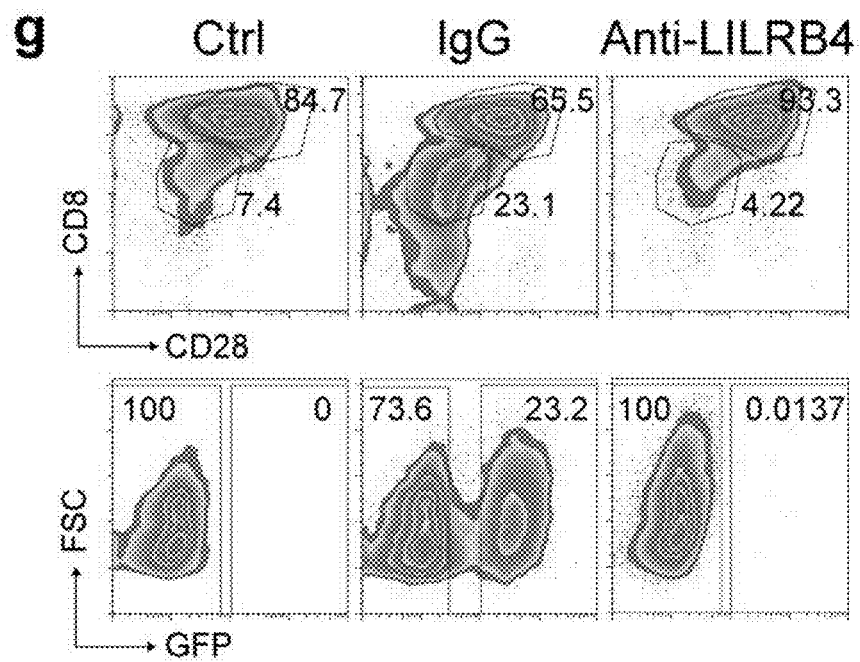
Figures 77H, 77I, 77J, 77K:
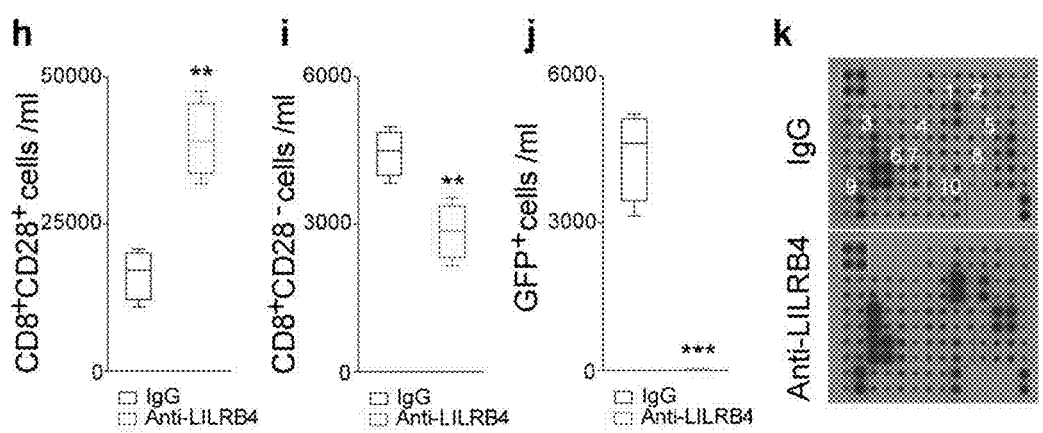

FIGS. 77a-77k—LILRB4 expressed on leukemia cells directly suppresses T cell proliferation in vitro. FIG. 77a: LILRB4 surface expression was quantified by flow cytometric analysis of samples from 105 patients at UT Southwestern. The "Other" category includes cells from patients with acute undifferentiated leukemia (AUL) and tumor-associated macrophages. FIGS. 77b-c: LILRB4 surface expression was compared on normal monocytes and neoplastic monocytes from healthy donors (n=25) and AML patients (n=53) respectively (FIG. 77b), or from the same AML patient (n=6) (shown in FIG. 77c). MFI: mean fluorescence intensity. FIG. 77d: T cells isolated from healthy donors were incubated with irradiated lilrb4-modulated THP-1 cells in indicated E:T ratios. After culture with anti-CD3/CD28/CD137-coated beads and rhIL-2 for 5 days, representative cells were photographed using an inverted microscope. E cells are effect cells; T, THP-1 cells are target cells. FIG. 77e: Total T cells were stained with anti-CD3 antibody and analyzed by flow cytometry. FIG. 77f: The percentage of CTL cells was determined using flow cytometry with staining of anti-CD3, anti-CD8 and anti-CD28 antibodies. FIG. 77g: CD8$^+$ T cells stimulated by anti-CD3/CD28/CD137-coated beads were co-cultured with THP-1 cells that stably express GFP and treated with anti-LILRB4 antibodies or control IgG. GFP$^+$ cells are THP-1 leukemia cells, CD8$^+$CD28$^+$ are activated CTLs, and CD8$^+$CD28$^-$ cells are inactive T cells or T suppressor cells. FIGS. 77h-j: Quantification of the indicated cells shows that anti-LILRB4 antibody reversed LILRB4 mediated inhibition of T cell activation by upregulation of CD8$^+$CD28$^+$ cells and led to killing of LILRB4$^+$ AML cells. FIG. 77k: Anti-LILRB4 antibody increases CTL cytokine production. Numbers 1-10 represent transwell plates to which were added GM-CSF, IFNγ, IL-13, IL-1β, IL-5, MCP-3, MCP-4, MIP-3α, RANTES, and TNFβ, respectively. The red boxes indicate increases as the result of anti-LILRB4 antibody treatment and the green boxes indicate decreases as the result of anti-LILRB4 antibody treatment; blue boxes indicate internal controls in the cytokine array.

Figure 78:
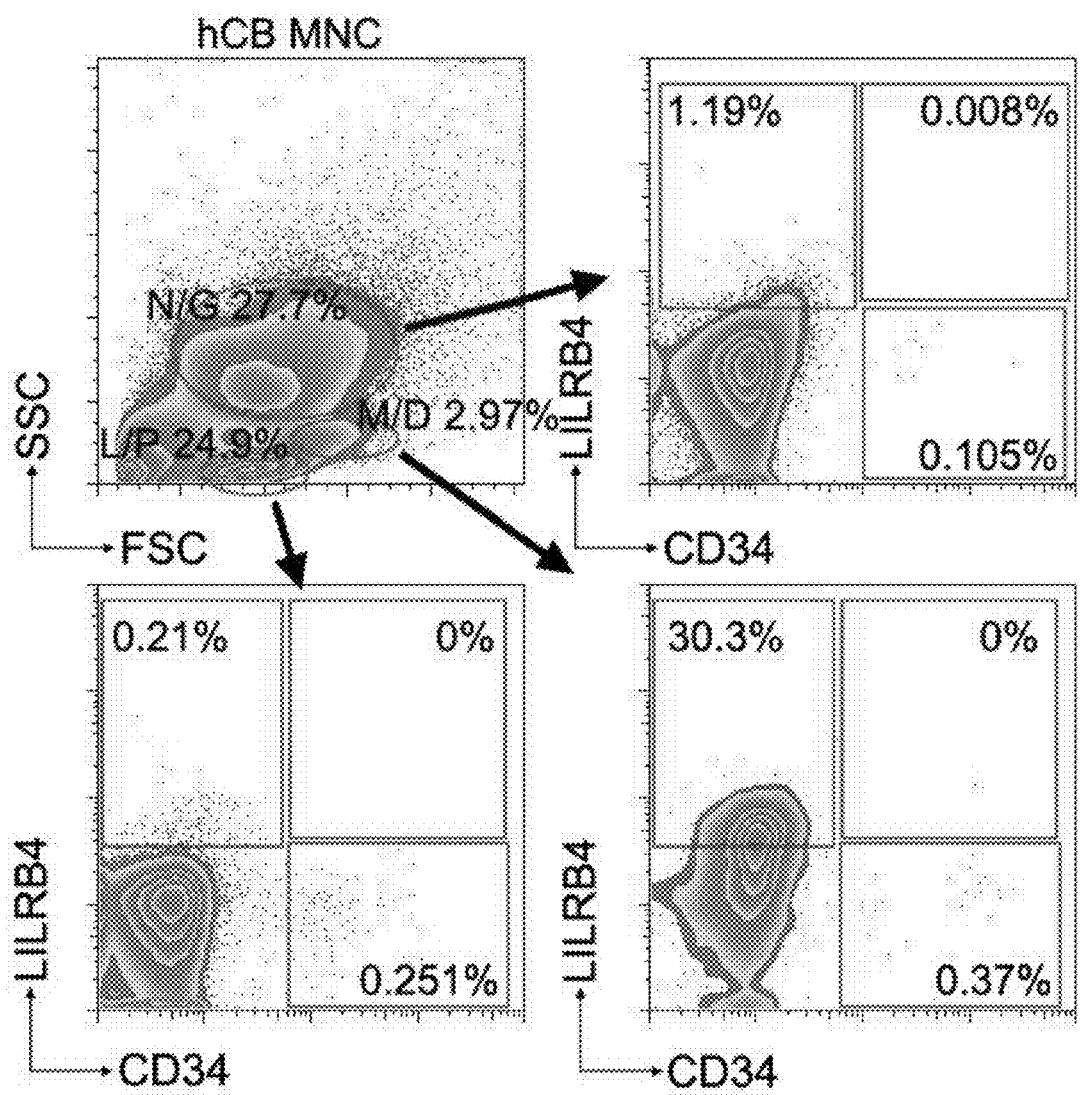

FIG. 78—LILRB4 is not expressed on normal CD34$^+$ HSCs. Shown are LILRB4 and CD34 co-staining patterns of human cord blood mononuclear cells (hCB MNCs). N/G, neutrophils and granulocytes; M/D, monocytes, macrophages and dendritic cells; L/P, lymphocytes, hematopoietic stem and progenitor cells.

Figures 79A, 79B, 79C, 79D, 79E, 79F:
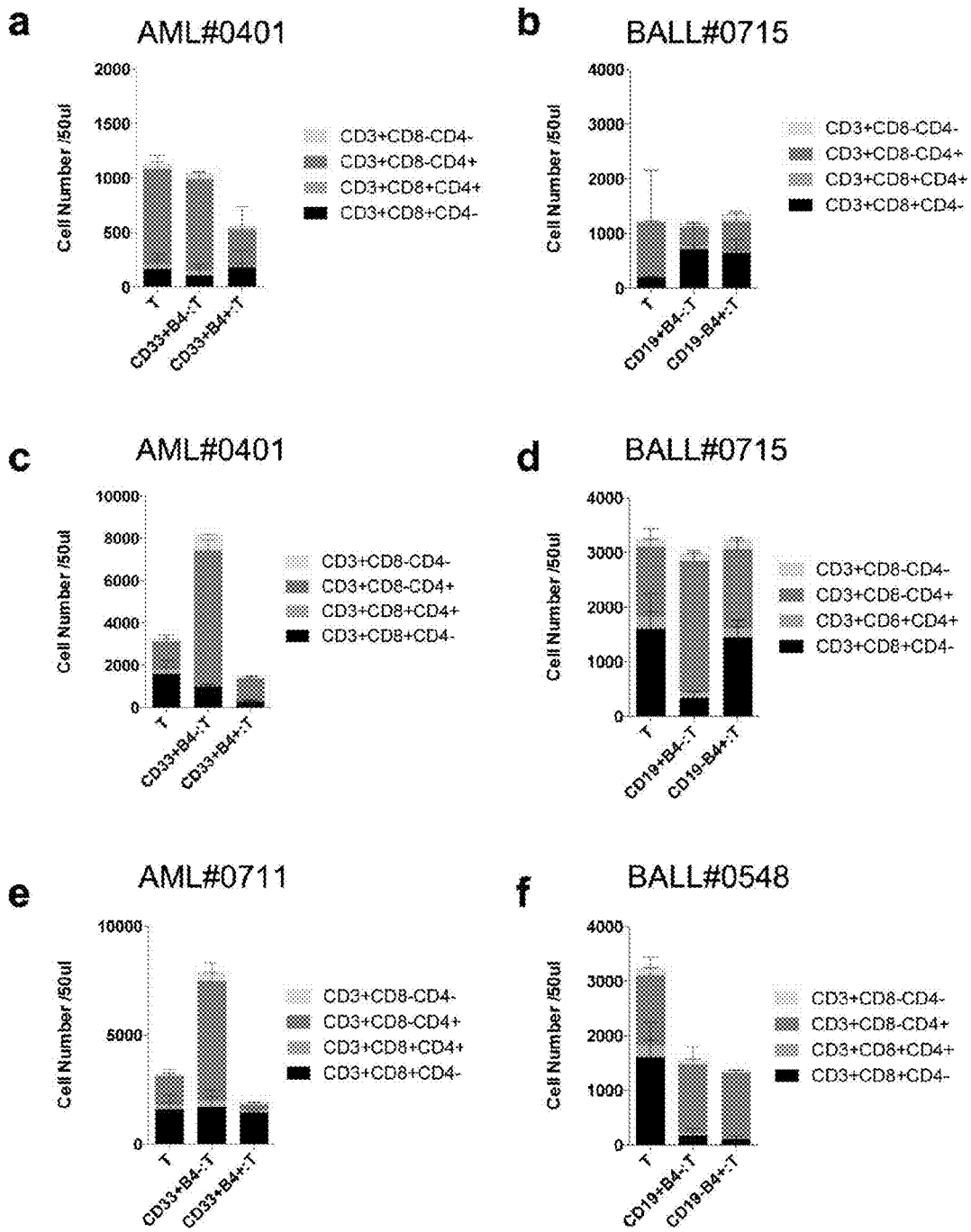

FIGS. 79a-79f—LILRB4-expressing primary AML cells suppress T cell proliferation. FIG. 79a-79b: T cells isolated from individual AML (FIG. 79a) or B-ALL (FIG. 79b) patient were incubated with irradiated lilrb4-positive or negative primary leukemia cells from the same patient. FIGS. 79c-f: T cells isolated from healthy donors were incubated with irradiated lilrb4-positive or negative primary leukemia cells from indicated AML (FIG. 79c, FIG. 79e) or B-ALL (FIG. 79d, FIG. 79f) patients. E:T=10:1. After culture with anti-CD3/CD28/CD137-coated beads and rhIL-2 for 5 days, T cells were stained with anti-CD3, anti-CD4 and anti-CD8 antibodies and analyzed by flow cytometry.

Figures 80A, 80B:
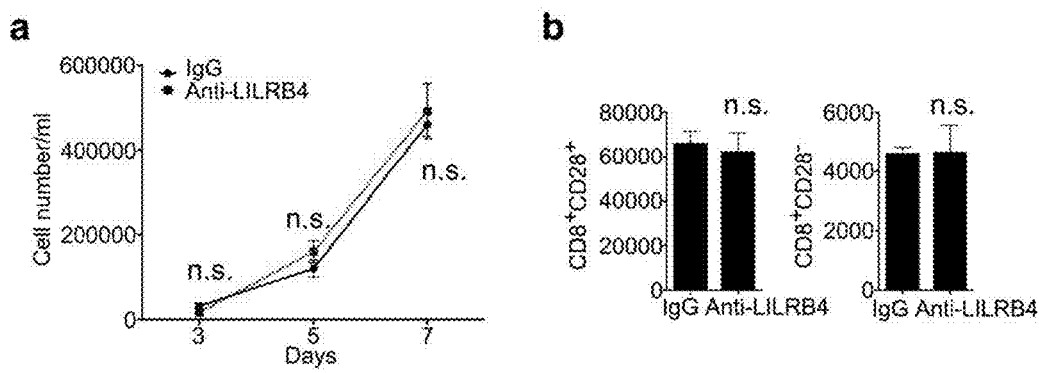

FIGS. 80a-80b—Anti-LILRB4 antibody had no effect on proliferation of THP-1 cells or cell activation or proliferation of T cells. FIG. 80a: The growth of THP-1 cells was not changed after 7 days of treatment of IgG or anti-LILRB4 antibody. FIG. 80b: The activation status of human primary CD8+ cells were not affected after 5 days' treatment of IgG or anti-LILRB4 antibody in vitro. n.s., not significant.

Figures 81A, 81O:
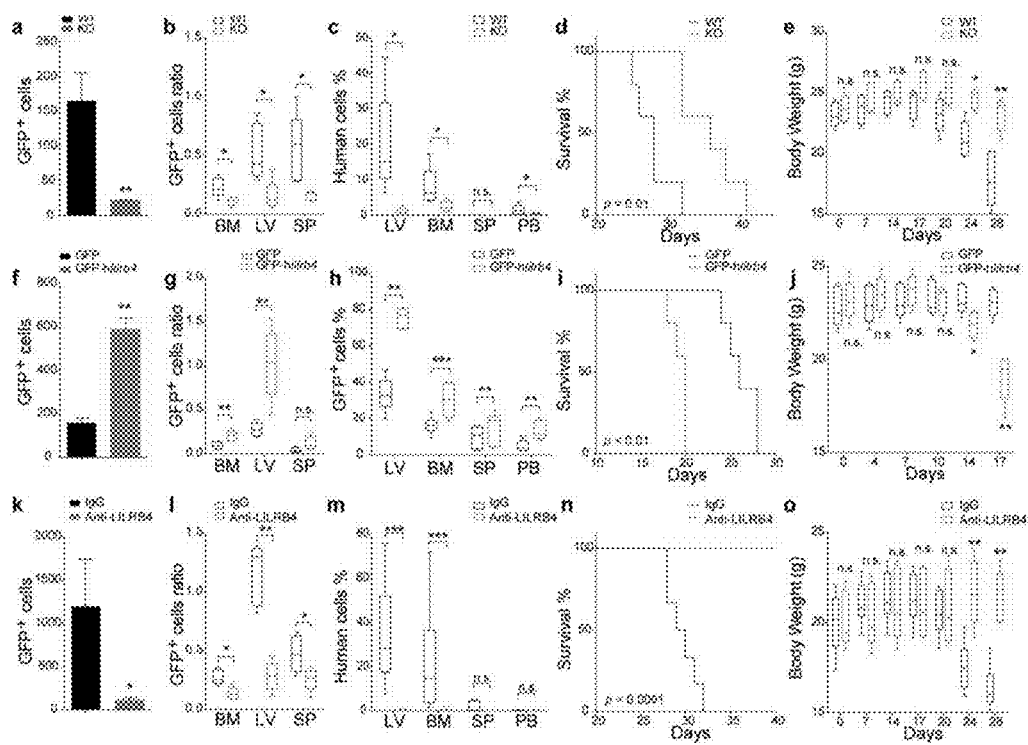
Figures 81P, 81Q, 81R, 81S, 81T, 81U, 81V:
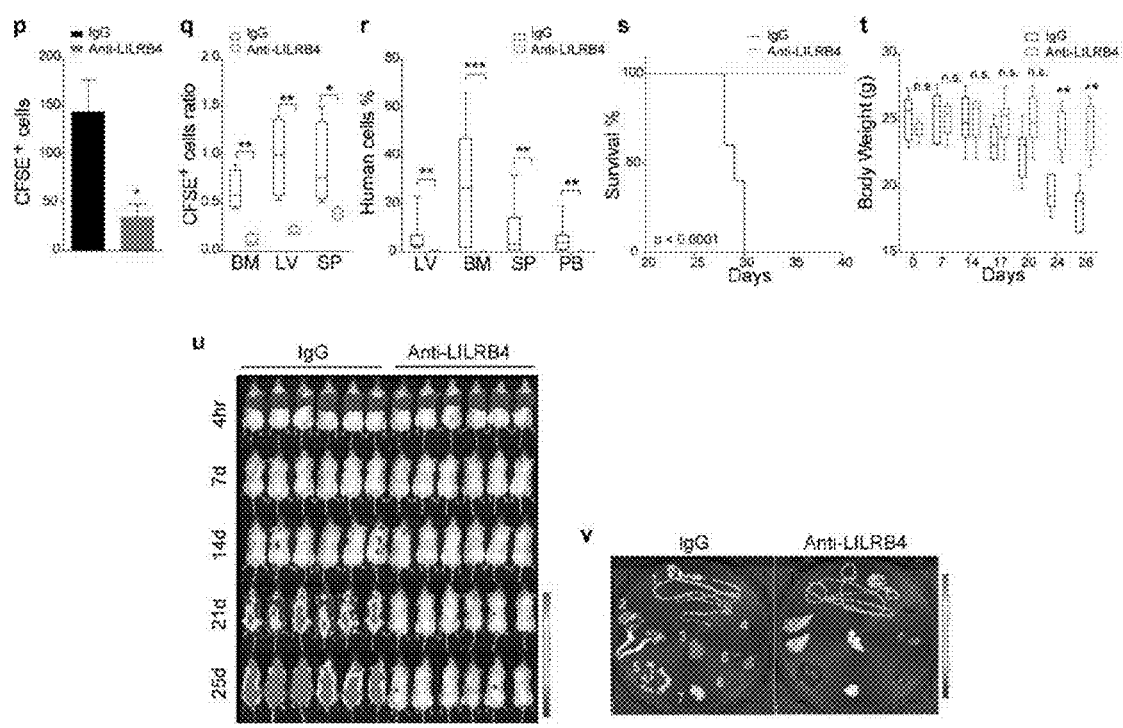

FIGS. 81a-81v—LILRB4 promotes AML cells migration and supports leukemia development. FIG. 81a: Knockout of lilrb4 reduced THP-1 cell transmigration across endothelial cells. FIG. 81b: $2\times10^6$ lilrb4-knockout (KO) or scrambled control (WT) THP-1 cells were injected into NSG mice (n=5), and then mice were sacrificed at 20 hrs after transplant. The number of leukemia cells (GFP positive) in liver, spleen, and bone marrow were normalized to that in peripheral blood as determined by flow cytometry. FIG. 81c: NSG mice (n=5) were injected with $1\times10^6$ lilrb4-knockout (KO) or scramble control (WT) THP-1 cells. Mice were sacrificed at day 21 post-transplant for analysis. Anti-human CD45 was used to detect THP-1 cells by flow cytometry. FIG. 81d: Overall survival and (FIG. 81e) body weight of these mice have been also examined. FIG. 81f: Forced expression of human LILRB4 promotes transmigration of mouse AML C1498 cells. FIG. 81g: $3\times10^6$ human lilrb4-expressing (GFP-hlilrb4) or control (GFP) C1498 cells were injected into NSG mice (n=5), and then mice were sacrificed at 20 hrs after transplant. The number of leukemia cells (GFP positive) in liver, spleen, and bone marrow were normalized to that in peripheral blood as determined by flow cytometry. FIG. 81h: NSG mice (n=5) were injected with $3\times10^6$ human lilrb4-expressing (GFP-hlilrb4) or control (GFP) C1498 cells. Mice were sacrificed at day 16 post-transplant for analysis. FIG. 81i: Overall survival and FIG. 81j: body weight of these mice was determined. FIG. 81k: Anti-LILRB4 antibody inhibits transmigration of THP-1 cells. IgG was used as control. FIG. 81l: $1\times10^6$ THP-1 cells were injected into NSG mice followed immediately by IgG or anti-LILRB4 antibody treatment, and then mice (n=5) were sacrificed at 20 hrs after transplant. The number of leukemia cells (GFP positive) in liver, spleen, and bone marrow were normalized to that in peripheral blood as determined by flow cytometry.

FIG. 81m: NSG mice (n=5) were injected with $1\times10^6$ THP-1 cells followed immediately by IgG or anti-LILRB4 antibody treatment. Mice were sacrificed at day 21 post-transplant for analysis. Anti-human CD45 was used to detect THP-1 cells by flow cytometry. Overall survival (FIG. 81n) and body weight (FIG. 81o) of these mice was also examined. FIG. 81p: Anti-LILRB4 antibody inhibits transmigration of MV4-11 cells. IgG was used as control. FIG. 81q: $5\times10^6$ CFSE-labeled MV4-11 cells were injected into NSG mice (n=5) followed immediately by IgG or anti-LILRB4 antibody treatment, and then mice were sacrificed at 20 hrs after transplant. The number of leukemia cells (CFSE positive) in liver, spleen, and bone marrow were normalized to that in peripheral blood as determined by flow cytometry. FIG. 81r: NSG mice (n=5) were injected with $1\times10^6$ MV4-11 cells followed immediately by IgG or anti-LILRB4 antibody treatment. Mice were sacrificed at day 21 post-transplant for analysis. Anti-human CD45 was used to detect MV4-11 cells by flow cytometry. Overall survival (FIG. 81s) and body weight (FIG. 81t) of these mice was also examined. FIG. 81u: THP-1 leukemia development was monitored by whole animal bioluminescence imaging. Mice were treated with control IgG or anti-LILRB4 antibodies. FIG. 81v: Representative mice were sacrificed at 21 days for ex vivo bioluminescence imaging of internal organs after luciferase-expressed THP-1 transplantation. 1: GI tract; 2: legs; 3: lung; 4: spleen; 5: liver; 6: kidneys; 7: brain; 8: heart. WT, wild-type THP-1 cells with inducible Cas9 and scramble gRNA expression; KO, lilrb4-knockout THP-1 cells selected by inducible Cas9 expression and scramble lilrb4-specific gRNA expression; KO-wt, overexpression of wild-type lilrb4 cDNA lilrb4-knockout in THP-1 cells; KO-int A, overexpression of intracellular domain-deleted lilrb4 cDNA lilrb4-knockout in THP-1 cells.

Figure 82:
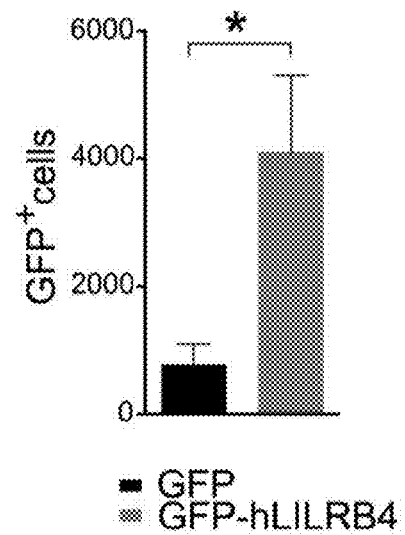

FIG. 82—Forced expression of human LILRB4 promotes transmigration of mouse AML WEHI-3 cells. *, p<0.05.

Figures 83A, 83B:
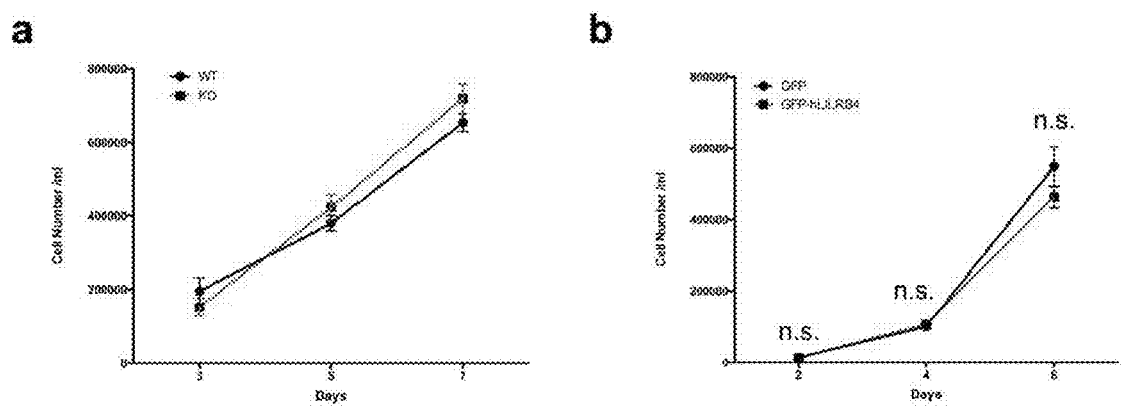

FIGS. 83a-83b—Modulation of LILRB4 expression doesn't affect proliferation of AML cells. (FIG. 83a) The growth of THP-1 cells was not changed by knockout of lilrb4. WT, wild-type THP-1 cells with inducible Cas9 and scramble gRNA expression; KO, lilrb4-knockout THP-1 cells selected by inducible Cas9 expression and scramble lilrb4-specific gRNA expression. (FIG. 83b) The growth of mouse AML C1498 cells was not changed by forced expression of human lilrb4. n.s., not significant.

Figure 84:
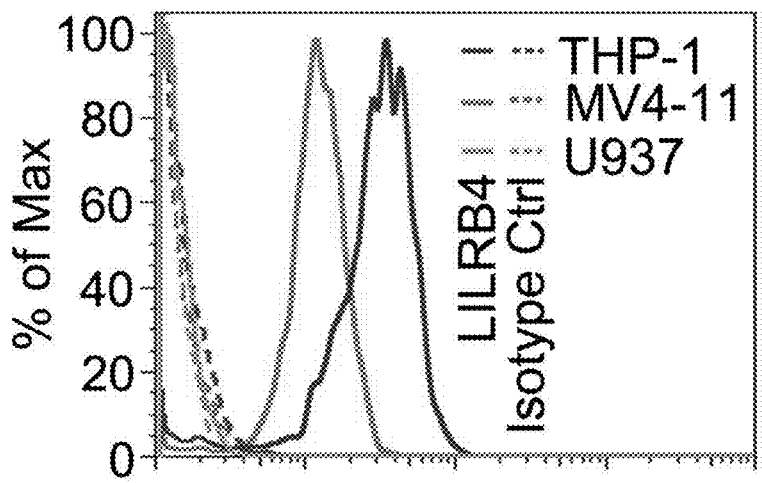

FIG. 84—LILRB4 expression on the indicated immortalized human AML cells as determined by flow cytometry. Isotype IgG was used as control.

Figure 85:
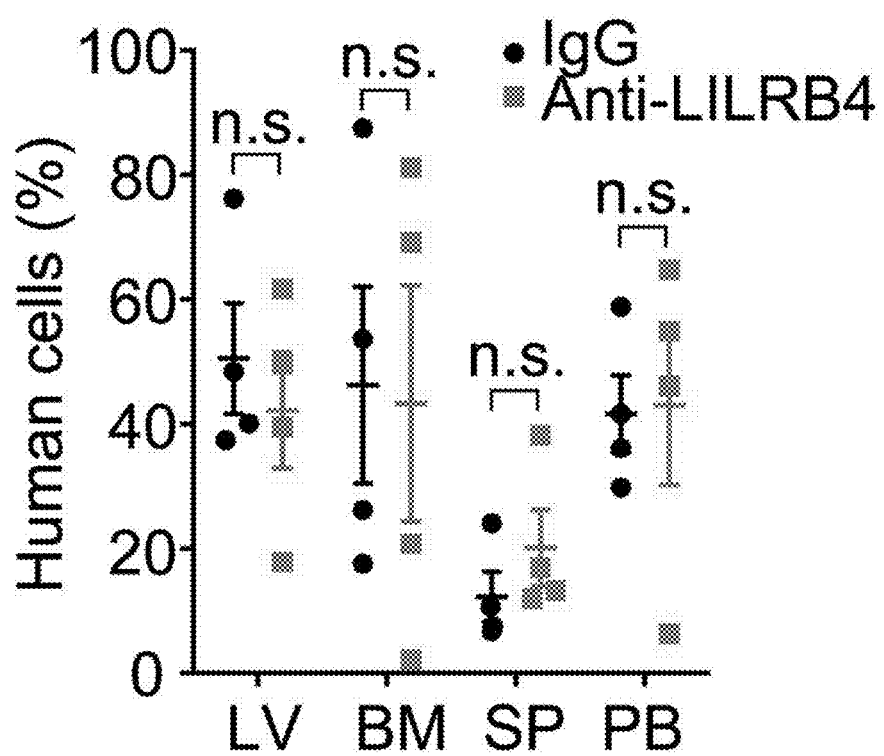

FIG. 85—Anti-LILRB4 antibodies do not act on LILRB4-negative cancer cells. NSG mice were injected with LILRB4-human AML U937 cells and then treated with anti-LILRB4 antibodies. IgG served as a control antibody. Mice were sacrificed at day 25 post-transplant for analysis of liver (LV), bone marrow (BM), spleen (SP), and peripheral blood (PB) by flow cytometry. The presence of human AML cells was detected by anti-human CD45 antibody staining. n.s., not significant.

Figures 86A, 86B, 86C, 86D:
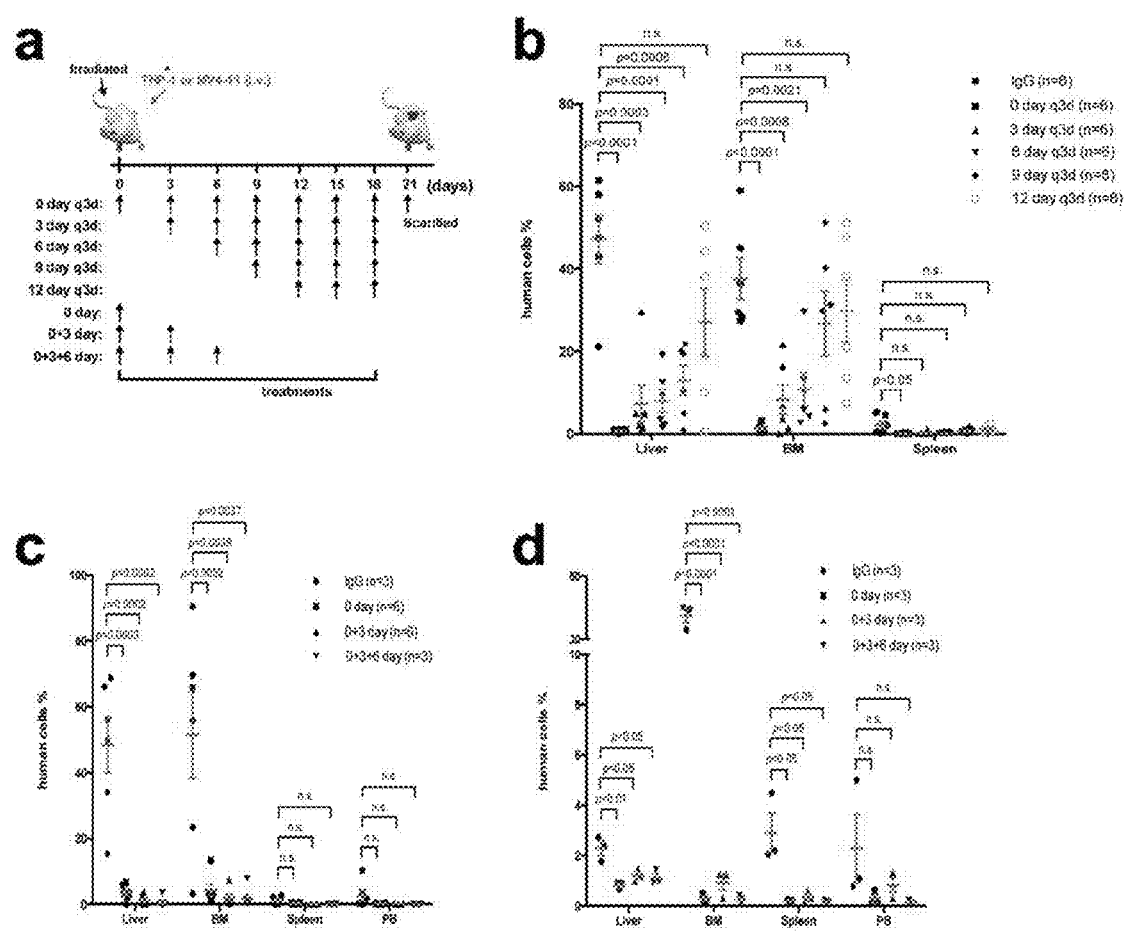

FIGS. 86a-86d—Anti-LILRB4 antibodies suppress human AML xenograft. (FIG. 86a) Schematic of antibody administration in AML xenograft. Antibodies (either control IgG or anti-LILRB4 antibodies) were administered as indicated by arrows. (FIG. 86b) The percentages of human leukemia (THP-1, CD45+) cells in liver (LV), bone marrow (BM), and spleen (SP) of recipient NSG mice (n=6) were determined by flow cytometry for antibody given every three days beginning on the indicated day. (FIGS. 86c-86d) Antibodies were administered at day 0, day 0+day 3, day 0+day 3+day 6, all similarly blocked AML development initiated by transplanted THP-1 cells (FIG. 86c) and MV4-11 cells (FIG. 86d).

Figure 87:
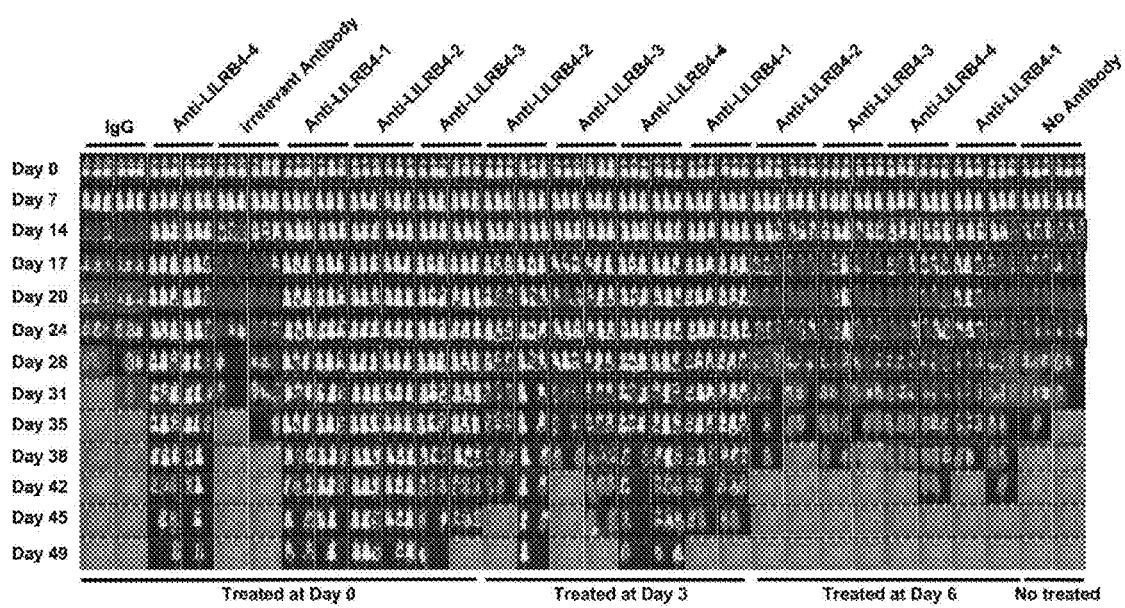

FIG. 87—Anti-LILRB4 antibodies suppress human AML xenograft. 200 µg of each antibody were administered at day 0, day 3 or day 6 as indicated. THP-1 leukemia development monitored by whole animal bioluminescence imaging.

Figures 88A, 88B, 88C:
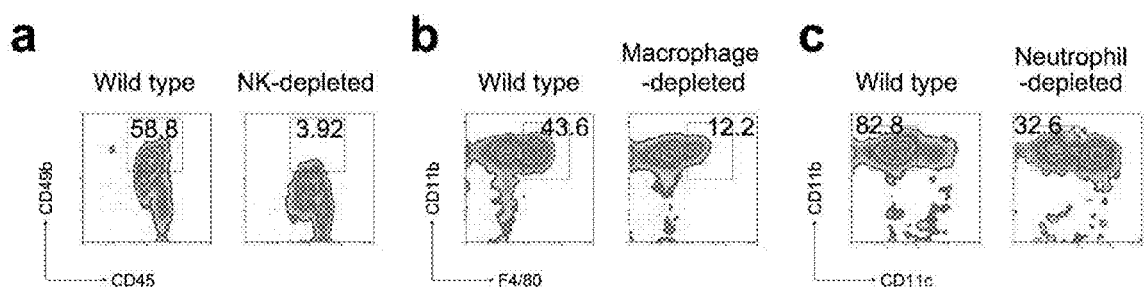

FIGS. 88a-c—Representative flow cytometry plots demonstrating successful reduction in NK cell (CD45+CD49b+; FIG. 88a), macrophage (CD11b+F4/80+; FIG. 88b), and neutrophil (CD11b+CD11c−; FIG. 88c) frequency in NSG mice depleted of the respective immune cell subtype as compared to non-depleted (wild-type) NSG mice.

Figure 89A:
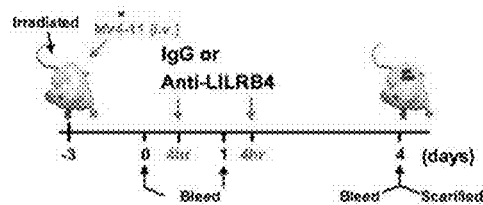
Figure 89B:
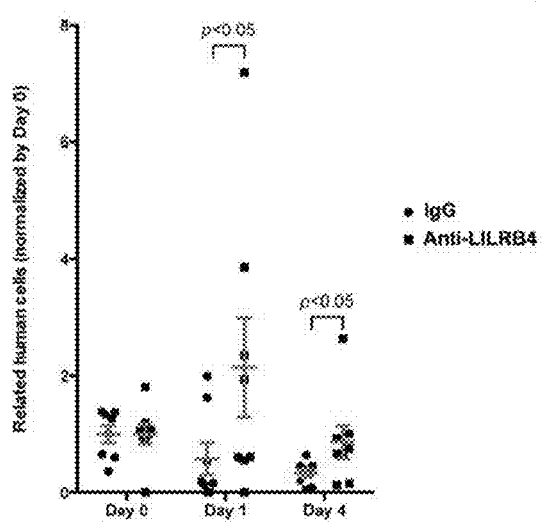
Figure 89C:
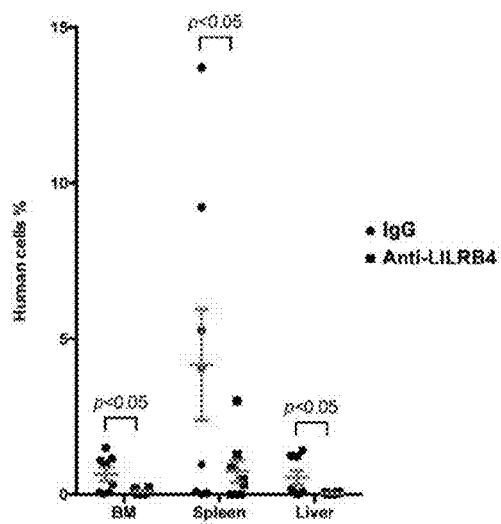

FIGS. 89a-89c—Anti-LILRB4 antibodies accelerate mobilization of MV4-11 cells to peripheral blood. (FIG. 89a) Schematic of antibody administration. (FIG. 89b) The number of leukemia cells in peripheral blood (PB) was normalized to that in peripheral blood as determined by flow cytometry. (FIG. 89c) The number of leukemia cells in liver (LV), spleen (SP), and bone marrow (BM) were normalized to that in peripheral blood as determined by flow cytometry. Anti-human CD45 was used to detect MV4-11 cells.

Figures 90A, 90B, 90C, 90D, 90E:
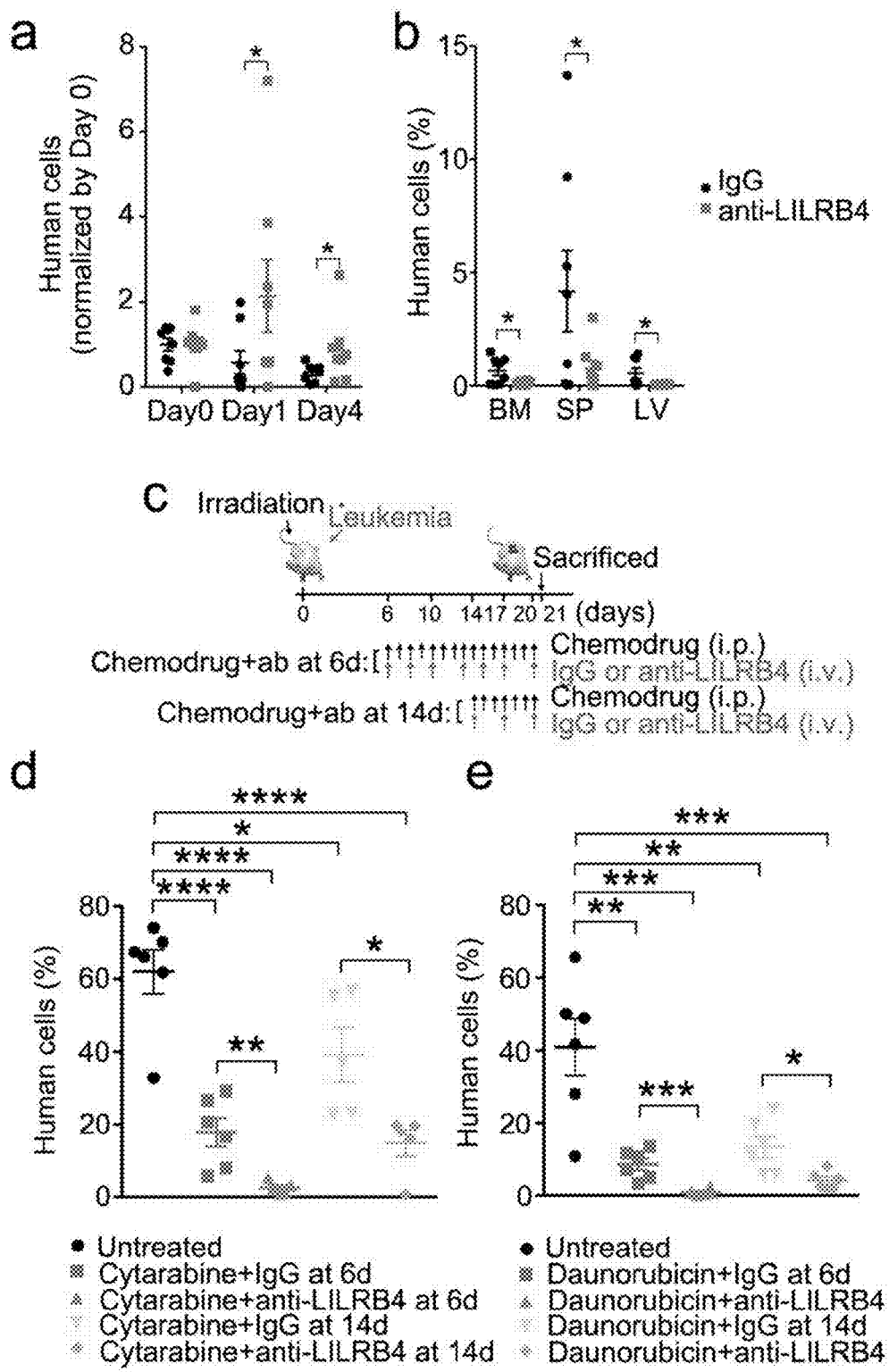

FIGS. 90a-90e—Synergistic effects of anti-LILRB4 and chemotherapy drugs. FIGS. 90a-b: Anti-LILRB4 antibody accelerates the mobilization of MV4-11 cells to peripheral blood (PB) (FIG. 90a) from bone marrow (BM), liver (LV) and spleen (SP) (FIG. 90b). Anti-human CD45 was used to detect MV4-11 cells by flow cytometry. Mice in each group, n=6. FIGS. 90c-e: Synergistic effects of anti-LILRB4 antibody treatment in combination with the chemotherapy drug cytarabine (FIG. 90d) or daunorubicin (FIG. 90e) inhibited AML development. Mice in each group, n=6. The administration of chemotherapy drugs and anti-LILRB4 antibody are shown in the diagram (FIG. 90c). Anti-human CD45 was used to detect human leukemia cells by flow cytometry.

Figure 91:
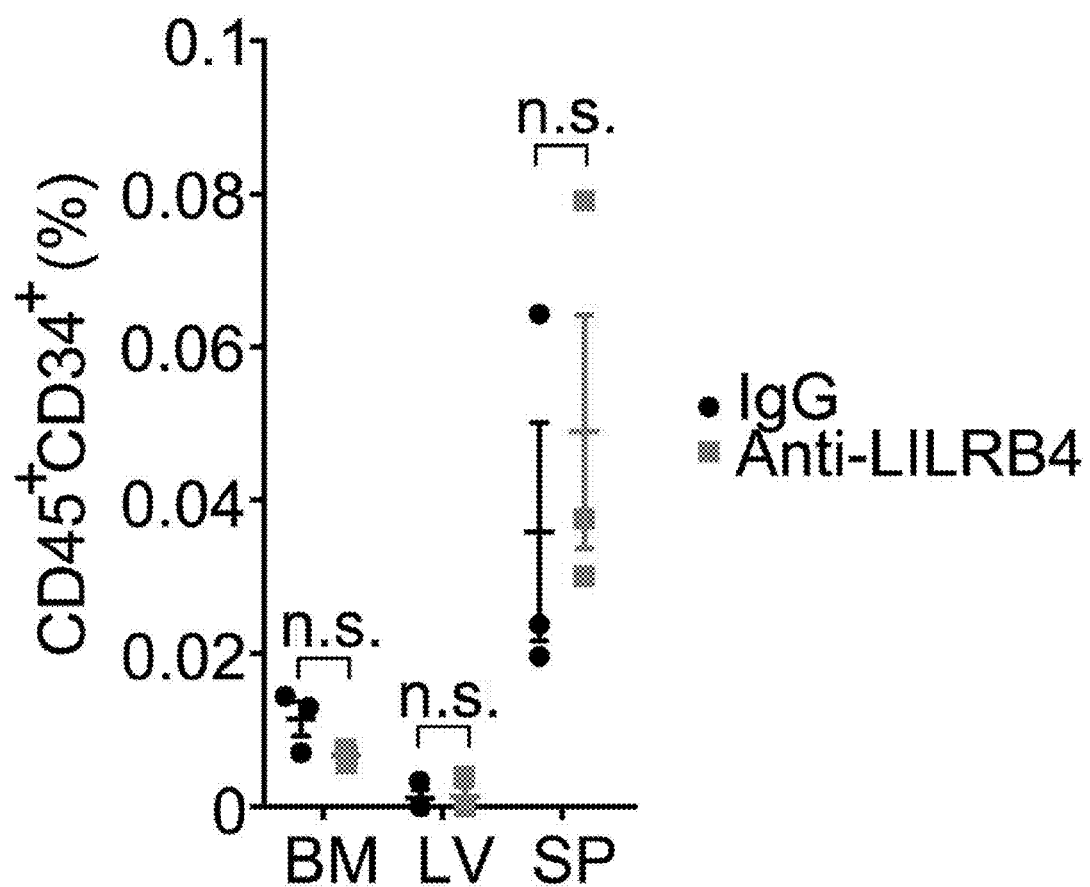

FIG. 91—Anti-LILRB4 antibody did not affect homing of normal HSCs. Human cord blood mononuclear cells ($1\times10^7$) were injected into NSG mice followed immediately by antibody treatment, and then the mice (n=3) were sacrificed at 20 hrs after transplant. The number of $CD45^+CD34^+$ HSCs in liver, spleen, and bone marrow were normalized to that in peripheral blood as determined by flow cytometry.

Figure 92A:
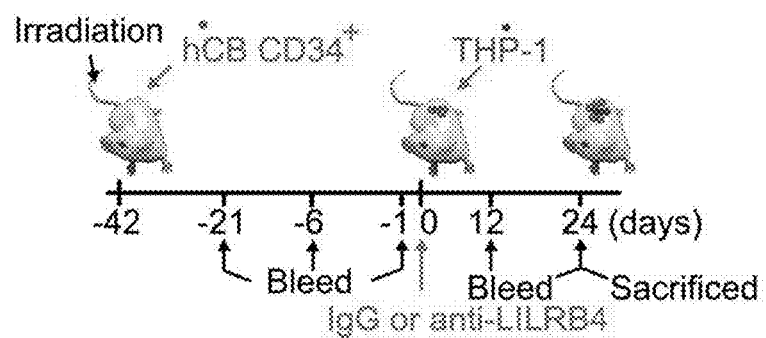
Figure 92B:
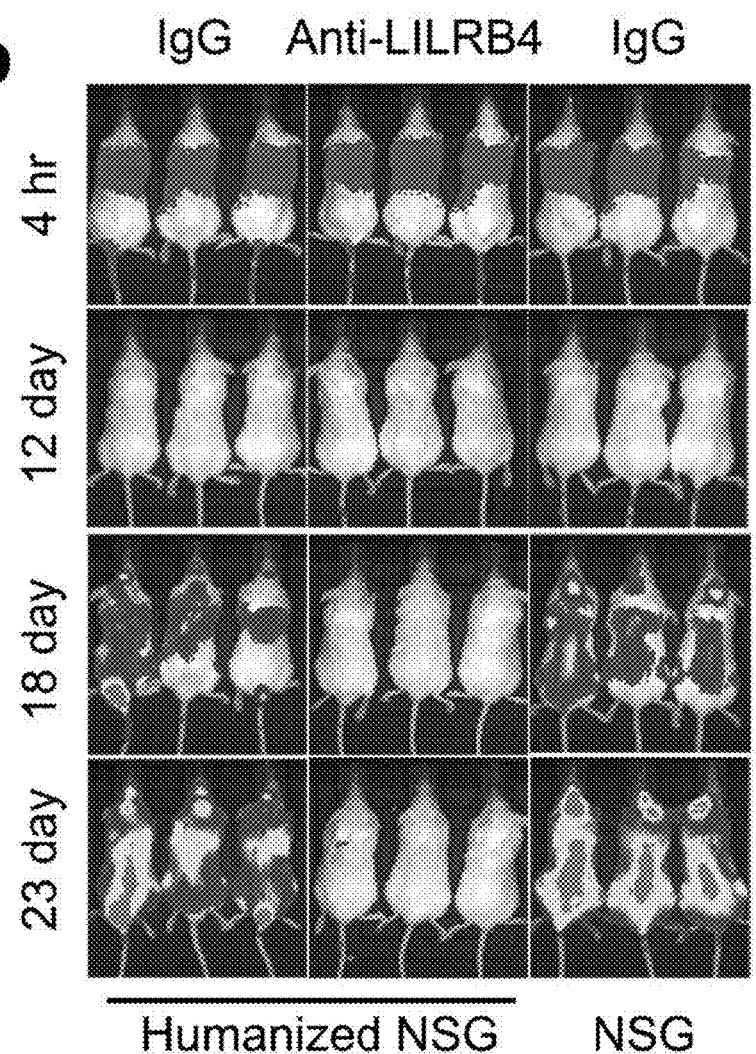
Figure 92C:
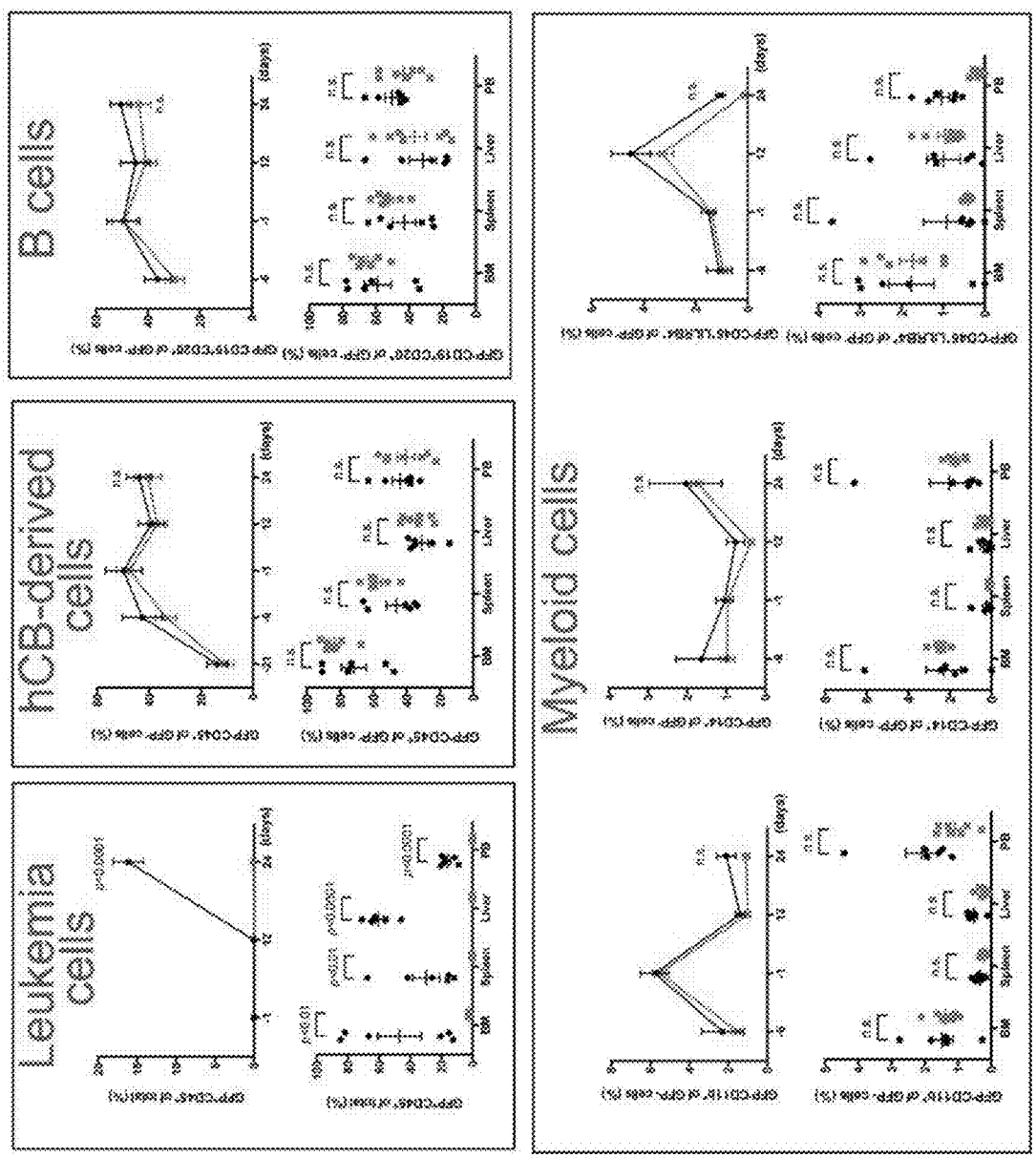
Figure 92D:
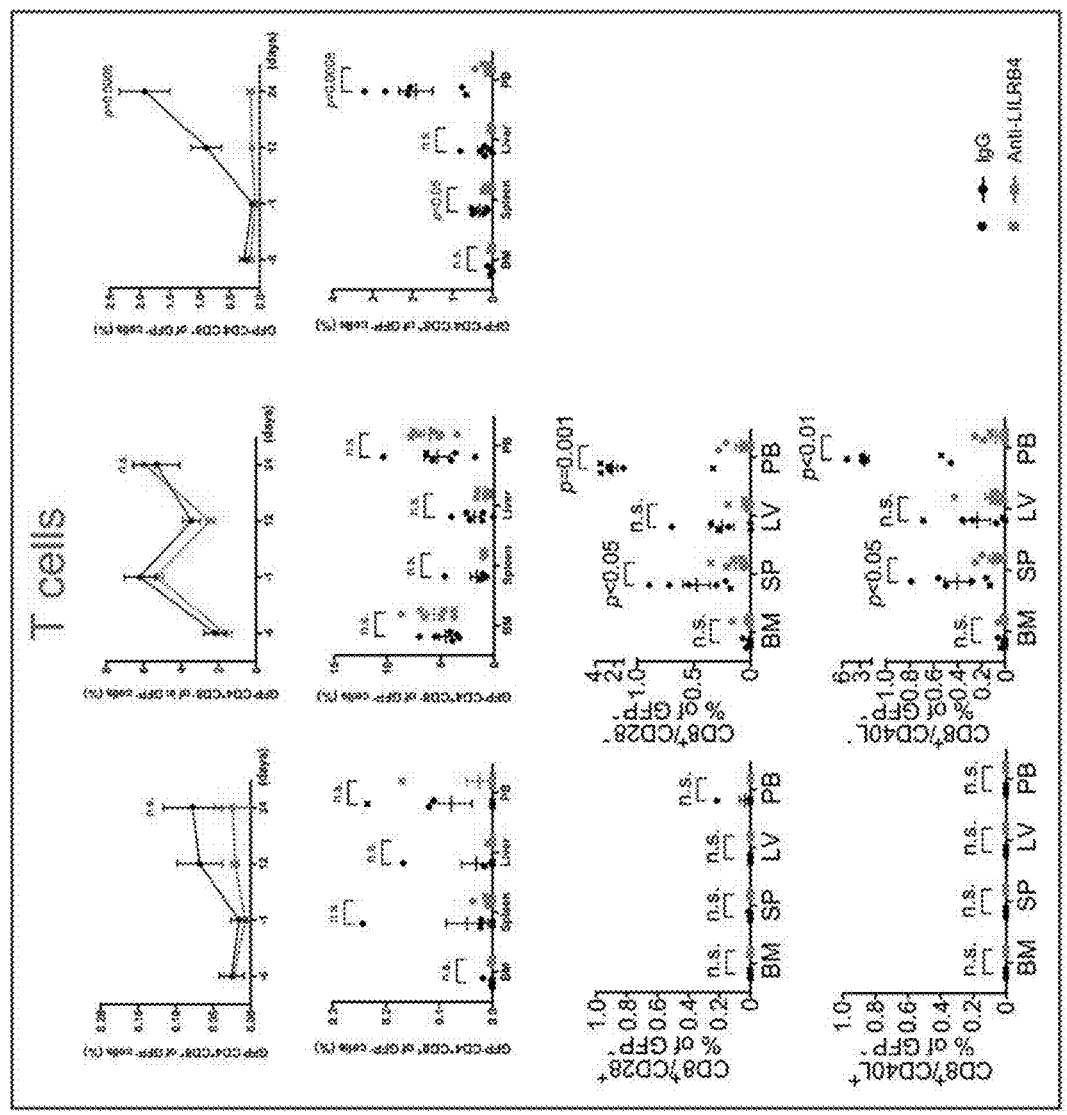

FIGS. 92a-92d—Anti-LILRB4 antibodies inhibit leukemia development in hCB-humanized NSG mice. FIG. 92a: Strategy to test whether anti-LILRB4 antibody C84 inhibits leukemia development in hCB-humanized NSG mice. FIG. 92b: Leukemia development was monitored over time by luminescence imaging. FIG. 92c and FIG. 92d: Frequency of engrafted leukemia, normal human cells, including human B cells, human myeloid cells and human T cells in peripheral blood over time and hematopoietic tissues of hCB-humanized mice at the 24 days after leukemia transplantation. BM: bone marrow; LV: liver; SP: spleen; PB: peripheral blood.

DESCRIPTION OF ILLUSTRATIVE EMBODIMENTS

The inventors have developed a number of anti-LILRB mAb, each of which efficiently block human AML development in various xenografted mouse models. These exciting results indicate that LILRBs support the activity of leukemia stem cells and leukemia development, but are not critical for normal hematopoiesis. In particular, for the first time, the inventors demonstrate that anti-LILRB4 inhibit development of human AML (including human patient AML developed in xenografted mice). Importantly, they obtained sequences of variable regions of ten anti-LILRB mAbs, and produced chimeric antibodies with human constant regions. The inventors showed that one such chimeric antibody (MHC-C84) not only retains the same binding properties as the original mAb C84, but has enhanced anti-leukemia activity in xenograft models. Thus, anti-LILRB antibodies can be used to treat leukemia and other cancers that express the relevant LILRB on their cell surface. They can also be used to treat immune diseases that have an LILRB component. These and other aspects of the disclosure are discussed below.

I. DEFINITIONS

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989), incorporated by reference herein.

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000), incorporated by reference herein. The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989), each incorporated by reference herein. The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999), incorporated by reference herein. The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itsself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

An "antigen binding protein" ("ABP") as used herein means any protein that binds a specified target antigen. In the instant application, the specified target antigen is the LILRB protein or fragment thereof "Antigen binding protein" includes but is not limited to antibodies and antigen-binding fragment thereof. Peptibodies are another example of antigen binding proteins.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. In certain embodiments, the antigen-binding fragment is not derived from an antibody but rather is derived from a receptor. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies. In certain embodiments, the antigen-binding fragment is derived from a receptor and contains one or more mutations. In certain embodiments, the antigen-binding fragment does not bind to the natural ligand of the receptor from which the antigen-binding fragment is derived.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the LILRB4 specific antibodies of the present invention are specific to LILRB4. In some embodiments, the antibody that binds to LILRB4 has a dissociation constant (Kd) of ≤100 nM, ≤10 nM, nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

The term "compete" when used in the context of antigen binding proteins (e.g., atnibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., LILRB or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, an "isolated" biological component (such as a nucleic acid, peptide or cell) has been substantially separated, produced apart from, or purified away from other biological components or cells of the organism in which the component naturally occurs, i.e., other chromosomal and extrachromosomal DNA and RNA, cells and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass LILRB antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a LILRB-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

As used herein, an "effective amount" or "therapeutically effective amount" means the amount of agent that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. LILRS

The leukocyte immunoglobulin-like receptors (LILR) are a family of receptors possessing extracellular immunoglobulin domains. They are also known as CD85, ILTs and LIR, and can exert immunomodulatory effects on a wide range of immune cells. The human genes encoding these receptors are found in a gene cluster at chromosomal region 19q13.4. They include, LILRA1, LILRA2, LILRA3, LILRA4, LILRA5, LILRA6, LILRB1, LILRB2, LILRB3, LILRB4, LILRB5, LILRB6 or LILRA6, and LILRB7 or LILRA5. A subset of LILRs recognize MHC class I molecules (also known as HLA class I in humans). Of these, the inhibitory receptors LILRB1 and LILRB2 show a broad specificity for classical and non-classical MHC alleles with preferential binding to b2m-associated complexes. In contrast, the activating receptors LILRA1 and LILRA3 prefer b2m-independent free heavy chains of MHC class I, and in particular HLA-C alleles.

A. LILRB 1

Leukocyte immunoglobulin-like receptor subfamily B member 1 is a protein that in humans is encoded by the LILRB1 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. LILRB1 was also reported to be expressed in human gastric cancer cells and may enhance tumor growth (see Zhang et al., 2012). It is thought to control inflammatory responses and cytotoxicity to help focus the immune response and limit autoreactivity. Multiple transcript variants encoding different isoforms have been found for this gene.

B. LILRB2

Leukocyte immunoglobulin-like receptor subfamily B member 2 is a protein that in humans is encoded by the LILRB2 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. The receptor is also expressed on human non-small cell lung cancer cells (see Sun et al., 2008). Multiple transcript variants encoding different isoforms have been found for this gene. LILRB2 has been shown to interact with PTPN6.

C. LILRB3

Leukocyte immunoglobulin-like receptor subfamily B member 3 is a protein that in humans is encoded by the LILRB3 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. Multiple transcript variants encoding different isoforms have been found for this gene.

D. LILRB4

Leukocyte immunoglobulin-like receptor subfamily B member 4 is a protein that in humans is encoded by the LILRB4 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. The receptor can also function in antigen capture and presentation. It is thought to control inflammatory responses and cytotoxicity to help focus the immune response and limit autoreactivity. LILRB4 is also expressed in human gastric cancer cells and may enhance tumor growth (Zhang et al., 2012). Multiple transcript variants encoding different isoforms have been found for this gene. LILRB4 has been shown to interact with PTPN6.

E. LAIR1

Leukocyte-associated immunoglobulin-like receptor 1 is a protein that in humans is encoded by the LAIR1 gene. LAIR1 has also been designated as CD305 (cluster of differentiation 305). LAIR1 is a type I transmembrane glycoprotein that contains one extracellular Ig-like domain and two intracellular ITIMs. Like the genes that encode LILRBs, lair1 is localized to the leukocyte receptor complex (LRC) on human chromosome 19q13.4. LAIR1 binds collagens, and its ITIMs recruit SHP-1 and SHP-2. LAIR1 is expressed in T cells, B cells, natural killer (NK) cells, macrophages, and dendritic cells, as well as hematopoietic progenitors including human $CD34^+$ cells. The inventors have demonstrated that LAIR1 is expressed on AML stem cells and differentiated AML and ALL cells and its inhibition blocks AML-SC activity and leukemia development (unpublished data).

III. CANCERS

A. Cancers

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the tubulysin analogs described herein may be used to lead to decreased cell counts and as such can potentially be used to treat a variety of types of cancer lines. In some aspects, it is anticipated that the tubulysin analogs described herein may be used to treat virtually any malignancy. Here, the only requirement is the presence of LILRBs on the surface of the cancer cell, and in particular on the surface of cancer stem cells.

Cancer cells that may be treated according to the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

B. Acute Myeloid Leukemia

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified, but the specific cause is not clear. As an acute leukemia, AML progresses rapidly and is typically fatal within weeks or months if left untreated.

AML has several subtypes; treatment and prognosis varies among subtypes. Five-year survival varies from 15-70%, and relapse rate varies from 33-78%, depending on subtype. AML is treated initially with chemotherapy aimed at inducing a remission; patients may go on to receive additional chemotherapy or a hematopoietic stem cell transplant. Recent research into the genetics of AML has resulted in the availability of tests that can predict which drug or drugs may work best for a particular patient, as well as how long that patient is likely to survive.

Most signs and symptoms of AML are caused by the replacement of normal blood cells with leukemic cells. A lack of normal white blood cell production makes the patient susceptible to infections; while the leukemic cells themselves are derived from white blood cell precursors, they have no infection-fighting capacity. A drop in red blood cell count (anemia) can cause fatigue, paleness, and shortness of breath. A lack of platelets can lead to easy bruising or bleeding with minor trauma.

The early signs of AML are often vague and nonspecific, and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections.

Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML.

Some patients with AML may experience swelling of the gums because of infiltration of leukemic cells into the gum tissue. Rarely, the first sign of leukemia may be the development of a solid leukemic mass or tumor outside of the bone marrow, called a chloroma. Occasionally, a person may show no symptoms, and the leukemia may be discovered incidentally during a routine blood test.

A number of risk factors for developing AML have been identified, including: other blood disorders, chemical exposures, ionizing radiation, and genetics.

"Preleukemic" blood disorders, such as myelodysplastic syndrome or myeloproliferative disease, can evolve into AML; the exact risk depends on the type of MDS/MPS. Exposure to anticancer chemotherapy, in particular alkylating agents, can increase the risk of subsequently developing AML. The risk is highest about three to five years after chemotherapy. Other chemotherapy agents, specifically epipodophyllotoxins and anthracyclines, have also been associated with treatment-related leukemia. These treatment-related leukemias are often associated with specific chromosomal abnormalities in the leukemic cells. Occupational chemical exposure to benzene and other aromatic organic solvents is controversial as a cause of AML. Benzene and many of its derivatives are known to be carcinogenic in vitro. While some studies have suggested a link between occupational exposure to benzene and increased risk of AML, others have suggested the attributable risk, if any, is slight. High amounts of ionizing radiation exposure can increase the risk of AML. A hereditary risk for AML appears to exist. Multiple cases of AML developing in a family at a rate higher than predicted by chance alone have been reported. Several congenital conditions may increase the risk of leukemia; the most common is probably Down syndrome, which is associated with a 10- to 18-fold increase in the risk of AML.

The first clue to a diagnosis of AML is typically an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made via examination of the peripheral blood smear when there are circulating leukemic blasts, a definitive diagnosis usually requires an adequate bone marrow aspiration and biopsy.

Marrow or blood is examined via light microscopy, as well as flow cytometry, to diagnose the presence of leukemia, to differentiate AML from other types of leukemia (e.g., acute lymphoblastic leukemia—ALL), and to classify the subtype of disease (see below). A sample of marrow or blood is typically also tested for chromosomal abnormalities by routine cytogenetics or fluorescent in situ hybridization. Genetic studies may also be performed to look for specific mutations in genes such as FLT3, nucleophosmin, and KIT, which may influence the outcome of the disease.

Cytochemical stains on blood and bone marrow smears are helpful in the distinction of AML from ALL, and in subclassification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The diagnosis and classification of AML can be challenging, and should be performed by a qualified hematopathologist or hematologist. In straightforward cases, the presence of certain morphologic features (such as Auer rods) or specific flow cytometry results can distinguish AML from other leukemias; however, in the absence of such features, diagnosis may be more difficult.

According to the widely used WHO criteria, the diagnosis of AML is established by demonstrating involvement of more than 20% of the blood and/or bone marrow by leukemic myeloblasts. The French-American-British (FAB) classification is a bit more stringent, requiring a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently.

Because acute promyelocytic leukemia (APL) has the highest curability and requires a unique form of treatment, it is important to quickly establish or exclude the diagnosis of this subtype of leukemia. Fluorescent in situ hybridization performed on blood or bone marrow is often used for this purpose, as it readily identifies the chromosomal translocation [t(15;17)(q22;q12);] that characterizes APL. There is also a need to molecularly detect the presence of PML/RARA fusion protein, which is an oncogenic product of that translocation.

First-line treatment of AML consists primarily of chemotherapy, and is divided into two phases: induction and post-remission (or consolidation) therapy. The goal of induction therapy is to achieve a complete remission by reducing the number of leukemic cells to an undetectable level; the goal of consolidation therapy is to eliminate any residual undetectable disease and achieve a cure. Hematopoietic stem cell transplantation is usually considered if induction chemotherapy fails or after a patient relapses, although transplantation is also sometimes used as front-line therapy for patients with high-risk disease.

All FAB subtypes except M3 are usually given induction chemotherapy with cytarabine (ara-C) and an anthracycline (most often daunorubicin). This induction chemotherapy regimen is known as "7+3" (or "3+7"), because the cytarabine is given as a continuous IV infusion for seven consecutive days while the anthracycline is given for three consecutive days as an IV push. Up to 70% of patients will achieve a remission with this protocol. Other alternative induction regimens, including high-dose cytarabine alone, FLAG-like regimens or investigational agents, may also be used. Because of the toxic effects of therapy, including myelosuppression and an increased risk of infection, induction chemotherapy may not be offered to the very elderly, and the options may include less intense chemotherapy or palliative care.

The M3 subtype of AML, also known as acute promyelocytic leukemia (APL), is almost universally treated with the drug all-trans-retinoic acid (ATRA) in addition to induction chemotherapy, usually an anthracycline. Care must be taken to prevent disseminated intravascular coagulation (DIC), complicating the treatment of APL when the promyelocytes release the contents of their granules into the peripheral circulation. APL is eminently curable, with well-documented treatment protocols.

The goal of the induction phase is to reach a complete remission. Complete remission does not mean the disease has been cured; rather, it signifies no disease can be detected with available diagnostic methods. Complete remission is obtained in about 50%-75% of newly diagnosed adults, although this may vary based on the prognostic factors described above. The length of remission depends on the prognostic features of the original leukemia. In general, all remissions will fail without additional consolidation therapy.

Even after complete remission is achieved, leukemic cells likely remain in numbers too small to be detected with current diagnostic techniques. If no further post-remission or consolidation therapy is given, almost all patients will eventually relapse. Therefore, more therapy is necessary to eliminate non-detectable disease and prevent relapse—that is, to achieve a cure.

The specific type of post-remission therapy is individualized based on a patient's prognostic factors (see above) and general health. For good-prognosis leukemias (i.e., inv(16), t(8;21), and t(15;17)), patients will typically undergo an additional three to five courses of intensive chemotherapy, known as consolidation chemotherapy. For patients at high risk of relapse (e.g., those with high-risk cytogenetics, underlying MDS, or therapy-related AML), allogeneic stem cell transplantation is usually recommended if the patient is able to tolerate a transplant and has a suitable donor. The best post-remission therapy for intermediate-risk AML (normal cytogenetics or cytogenetic changes not falling into good-risk or high-risk groups) is less clear and depends on the specific situation, including the age and overall health of the patient, the patient's personal values, and whether a suitable stem cell donor is available.

For patients who are not eligible for a stem cell transplant, immunotherapy with a combination of histamine dihydrochloride (Ceplene) and interleukin 2 (Proleukin) after the completion of consolidation has been shown to reduce the absolute relapse risk by 14%, translating to a 50% increase in the likelihood of maintained remission.

For patients with relapsed AML, the only proven potentially curative therapy is a hematopoietic stem cell transplant, if one has not already been performed. In 2000, the monoclonal antibody-linked cytotoxic agent gemtuzumab ozogamicin (Mylotarg) was approved in the United States for patients aged more than 60 years with relapsed AML who are not candidates for high-dose chemotherapy. This drug was voluntarily withdrawn from the market by its manufacturer, Pfizer in 2010. Since treatment options for relapsed AML are so limited, palliative care may be offered.

Patients with relapsed AML who are not candidates for stem cell transplantation, or who have relapsed after a stem cell transplant, may be offered treatment in a clinical trial, as conventional treatment options are limited. Agents under investigation include cytotoxic drugs such as clofarabine, as well as targeted therapies, such as farnesyl transferase inhibitors, decitabine, and inhibitors of MDR1 (multidrug-resistance protein). For relapsed acute promyelocytic leukemia (APL), arsenic trioxide has been tested in trials and approved by the U.S. FDA. Like ATRA, arsenic trioxide does not work with other subtypes of AML.

While acute myeloid leukemia is a curable disease, the chance of cure for a specific patient depends on a number of prognostic factors. The single most important prognostic factor in AML is cytogenetics, or the chromosomal structure of the leukemic cell. Certain cytogenetic abnormalities are associated with very good outcomes (for example, the (15:17) translocation in acute promyelocytic leukemia). About half of AML patients have "normal" cytogenetics; they fall into an intermediate risk group. A number of other cytogenetic abnormalities are known to associate with a poor prognosis and a high risk of relapse after treatment.

AML which arises from a pre-existing myelodysplastic syndrome (MDS) or myeloproliferative disease (so-called secondary AML) has a worse prognosis, as does treatment-related AML arising after chemotherapy for another previous malignancy. Both of these entities are associated with a high rate of unfavorable cytogenetic abnormalities.

In some studies, age >60 years and elevated lactate dehydrogenase level were also associated with poorer outcomes. As with most forms of cancer, performance status (i.e., the general physical condition and activity level of the patient) plays a major role in prognosis as well.

FLT3 internal tandem duplications (ITDs) have been shown to confer a poorer prognosis in AML. Treating these patients with more aggressive therapy, such as stem-cell transplantation in first remission, has not been shown to enhance long-term survival. ITDs of FLT3 may be associated with leukostasis. In 2012, the FLT3 inhibitor quizartinib showed positive phase II trial results in AML patients with FLT3-ITD mutations.

Researchers are investigating the clinical significance of c-KIT mutations in AML. These are prevalent, and clinically relevant because of the availability of tyrosine kinase inhibitors, such as imatinib and sunitinib that can block the activity of c-KIT pharmacologically. Other genes being investigated as prognostic factors or therapeutic targets include CEBPA, BAALC, ERG, and NPM1.

C. Acute Lymphoblastic Leukemia (ALL)

Acute lymphoblastic leukemia (ALL) or acute lymphoid leukemia is an acute form of leukemia, or cancer of the white blood cells, characterized by the overproduction of cancerous, immature white blood cells—known as lymphoblasts. In persons with ALL, lymphoblasts are overproduced in the bone marrow and continuously multiply, causing damage and death by inhibiting the production of normal cells—such as red and white blood cells and platelets—in the bone marrow and by infiltrating to other organs. ALL is most common in childhood with a peak incidence at 2-5 years of age, and another peak in old age.

The symptoms of ALL are indicative of a reduced production of functional blood cells, because the leukemia wastes the resources of the bone marrow, which are normally used to produce new, functioning blood cells. These symptoms can include fever, increased risk of infection (especially bacterial infections like pneumonia, due to neutropenia; symptoms of such an infection include shortness of breath, chest pain, cough, vomiting, changes in bowel or bladder habits), increased tendency to bleed (due to thrombocytopenia) and signs indicative of anemia including pallor, tachycardia (high heart rate), fatigue and headache.

About 6,000 cases are reported in the U.S. every year; statistics from other countries are difficult to come by, although it is known to be more common in the United States, Italy and Costa Rica. Cure is a realistic goal and is achieved in over 80% of affected children, although only 20-40% of adults can be cured. "Acute" refers to the relatively short time course of the disease to differentiate it from chronic lymphocytic leukemia, which has a potential time course of many years.

The symptoms are not specific to ALL, but worsen to the point that medical help is sought. They result from the lack of normal and healthy blood cells because they are crowded out by malignant and immature leukocytes (white blood cells). Therefore, people with ALL experience symptoms from malfunctioning of their erythrocytes (red blood cells), leukocytes, and platelets. Laboratory tests that might show abnormalities include blood count tests, renal function tests, electrolyte tests, and liver enzyme tests.

The signs and symptoms of ALL are variable but follow from bone marrow replacement and/or organ infiltration, and include generalized weakness and fatigue, anemia, dizziness, frequent or unexplained fever and infection, weight loss and/or loss of appetite, excessive and unexplained bruising, bone pain, joint pain (caused by the spread of "blast" cells to the surface of the bone or into the joint from the marrow cavity), breathlessness, enlarged lymph nodes, liver and/or spleen, pitting edema (swelling) in the lower limbs and/or abdomen, and petechiae, which are tiny red spots or lines in the skin due to low platelet levels.

In general, cancer is caused by damage to DNA that leads to uncontrolled cellular growth and spreads throughout the body, either by increasing chemical signals that cause growth or by interrupting chemical signals that control growth. Damage can be caused through the formation of fusion genes, as well as the dysregulation of a proto-oncogene via juxtaposition of it to the promoter of another gene, e.g., the T-cell receptor gene. This damage may be caused by environmental factors such as chemicals, drugs or radiation, and occurs naturally during mitosis or other normal processes (although cells have numerous mechanisms of DNA repair that help to reduce this).

ALL is associated with exposure to radiation and chemicals in animals and humans. High level radiation exposure is a known risk factor for developing leukemia, as found by studies of survivors of atom bomb exposure in Hiroshima and Nagasaki. In animals, exposure to benzene and other chemicals can cause leukemia. Epidemiological studies have associated leukemia with workplace exposure to chemicals, but these studies are not as conclusive. Some evidence suggests that secondary leukemia can develop in individuals treated for other cancers with radiation and chemotherapy as a result of that treatment.

Diagnosing ALL begins with a medical history, physical examination, complete blood count, and blood smears. Because the symptoms are so general, many other diseases with similar symptoms must be excluded. Typically, the higher the white blood cell count the worse the prognosis. Blast cells are seen on blood smear in the majority of cases (blast cells are precursors (stem cells) to all immune cell lines). A bone marrow biopsy is conclusive proof of ALL. A lumbar puncture (also known as a spinal tap) will indicate if the spinal column and brain have been invaded.

Pathological examination, cytogenetics (in particular the presence of Philadelphia chromosome), and immunophenotyping establish whether myeloblastic (neutrophils, eosinophils, or basophils) or lymphoblastic (B lymphocytes or T lymphocytes) cells are the problem. RNA testing can establish how aggressive the disease is; different mutations have been associated with shorter or longer survival. Immunohistochemical testing may reveal TdT or CALLA antigens on the surface of leukemic cells. TdT is a protein expressed early in the development of pre-T and pre-B cells, whereas CALLA is an antigen found in 80% of ALL cases and also in the "blast crisis" of CML. Medical imaging (such as ultrasound or CT scanning) can find invasion of other organs commonly the lung, liver, spleen, lymph nodes, brain, kidneys, and reproductive organs.

The earlier acute lymphocytic leukemia is detected, the more effective the treatment. The aim is to induce a lasting remission, defined as the absence of detectable cancer cells in the body (usually less than 5% blast cells in the bone marrow). Treatment for acute leukemia can include chemotherapy, steroids, radiation therapy, intensive combined treatments (including bone marrow or stem cell transplants), and growth factors.

Chemotherapy is the initial treatment of choice. Most ALL patients will receive a combination of different treatments. There are no surgical options, due to the body-wide distribution of the malignant cells. In general, cytotoxic chemotherapy for ALL combines multiple antileukemic drugs in various combinations. Chemotherapy for ALL consists of three phases: remission induction, intensification, and maintenance therapy.

As the chemotherapy regimens can be intensive and protracted (often about 2 years in case of the GMALL UKALL, HyperCVAD or CALGB protocols; for ALL about 3 years, 2 months for males on COG protocols; 2 years, 2 months for females—longer for males, as testicles are a potential reservoir), many patients have an intravenous catheter inserted into a large vein (termed a central venous catheter or a Hickman line), or a Portacath, a cone-shaped port with a silicone nose that is surgically planted under the skin, usually near the collar bone, and the most effective product available, due to low infection risks and the long-term viability of a portacath.

Radiation therapy (or radiotherapy) is used on painful bony areas, in high disease burdens, or as part of the preparations for a bone marrow transplant (total body irradiation). Radiation in the form of whole-brain radiation is also used for central nervous system prophylaxis, to prevent recurrence of leukemia in the brain. Whole-brain prophylaxis radiation used to be a common method in treatment of children's ALL. Recent studies showed that CNS chemotherapy provided results as favorable but with less developmental side-effects. As a result, the use of whole-brain radiation has been more limited. Most specialists in adult leukemia have abandoned the use of radiation therapy for CNS prophylaxis, instead using intrathecal chemotherapy.

For some subtypes of relapsed ALL, aiming at biological targets such as the proteasome, in combination with chemotherapy, has given promising results in clinical trials. Selection of biological targets on the basis of their combinatorial effects on the leukemic lymphoblasts can lead to clinical trials for improvement in the effects of ALL treatment. In ongoing clinical trials, a CD19-CD3 bi-specific monoclonal murine antibody—Blinatumomab, is showing great promise.

Chimeric antigen receptors (CARs) have been developed as a promising therapy for ALL. This technology uses a single chain variable fragment (scFv) designed to recognize the cell surface marker CD19 as a method of treating ALL. CD19 is a molecule found on all B-cells and can be used as a means of distinguishing the potentially malignant B-cell population in the patient. In this therapy, mice are immunized with the CD19 antigen and produce anti-CD19 antibodies. Hybridomas developed from the mouse spleen cells fused to a myeloma cell line can be developed as a source for the cDNA encoding the CD19 specific antibody. The cDNA is sequenced and the sequence encoding the variable heavy and variable light chains of these antibodies are cloned together using a small peptide linker. This resulting sequence encodes the scFv. This can be cloned into a transgene encoding what will become the endodomain of the CAR. There are varying arrangements of subunits used as the endodomain but they generally consist of the hinge region that attaches to the scFv, a transmembrane region, the intracellular region of a costimulatory molecule such as CD28, and the intracellular domain of CD3-zeta containing ITAM repeats. Other sequences frequently included are: 4-1bb and OX40. The final transgene sequence, containing the scFv and endodomain sequences is then inserted into immune effector cells that are obtained from the patient and expanded in vitro. In previous trials these have been a type of T-cell capable of cytotoxicity. Inserting the DNA into the effector cell can be accomplished by several methods. Most commonly, this is done using a lentivirus which encodes the transgene. Pseudotyped, self-inactivating lentiviruses have been shown to be an effective method for the stable insertion of a desired transgene into the target cell genomic DNA. Other methods include electroporation and transfection but these are limited in their efficacy as transgene expression will diminish over time. The gene-modified effector cells are then transplanted back into the patient. Typically this process is done in conjunction with a conditioning regiment such as cyclophosphamide which has been shown to potentiate the effects of infused T-cells. This effect has been attributed to the creation of an immunologic space niche. The process as a whole results in an effector cell, typically a T-cell that can recognize a tumor cell antigen in a major histocompatibility complex independent manner and initiate a cytotoxic response D. Chronic Lymphoblastic Leukemia (CLL)

B-cell chronic lymphocytic leukemia (B-CLL), also known as chronic lymphoid leukemia (CLL), is the most common type of leukemia (a type of cancer of the white blood cells) in adults. CLL affects B cell lymphocytes, which originate in the bone marrow, develop in the lymph nodes, and normally fight infection by producing antibodies. In CLL, B cells grow out of control and accumulate in the bone marrow and blood, where they crowd out healthy blood cells. CLL is a stage of small lymphocytic lymphoma (SLL), a type of B-cell lymphoma, which presents primarily in the lymph nodes. CLL and SLL are considered the same underlying disease, just with different appearances. CLL is a disease of adults. Most (>75%) people newly diagnosed with CLL are over the age of 50, and the majority are men. However, in rare cases, it can occur in teenagers and occasionally in children. Some of these may relate to an inherited predisposition.

Most people are diagnosed without symptoms as the result of a routine blood test that returns a high white blood cell count, but, as it advances, CLL results in swollen lymph nodes, spleen, and liver, and eventually anemia and infections. Early CLL is not treated, and late CLL is treated with chemotherapy and monoclonal antibodies.

DNA analysis has distinguished two major types of CLL, with different survival times. CLL that is positive for the marker ZAP-70 has an average survival of 8 years, while CLL negative for ZAP-70 has an average survival of more than 25 years. Many patients, especially older ones, with slowly progressing disease can be reassured and may not need any treatment in their lifetimes.

Most people are diagnosed without symptoms as the result of a routine blood test that returns a high white blood cell count. Less commonly, CLL may present with enlarged lymph nodes without a high white blood cell count or no evidence of the disease in the blood. This is referred to as small lymphocytic lymphoma. In some individuals the disease comes to light only after the neoplastic cells overwhelm the bone marrow resulting in anemia producing tiredness or weakness.

CLL is usually first suspected by the presence of lymphocytosis, an increase in a type of white blood cell, on a complete blood count (CBC) test. This frequently is an incidental finding on a routine physician visit. Most often the lymphocyte count is greater than 4000 cells per microliter (µl) of blood, but can be much higher. The presence of a lymphocytosis in an elderly individual should raise strong suspicion for CLL, and a confirmatory diagnostic test, in particular flow cytometry, should be performed unless clinically unnecessary.

The diagnosis of CLL is based on the demonstration of an abnormal population of B lymphocytes in the blood, bone marrow, or tissues that display an unusual but characteristic pattern of molecules on the cell surface. This atypical molecular pattern includes the coexpression of cells surface markers cluster of differentiation 5 (CD5) and cluster of differentiation 23 (CD23). In addition, all the CLL cells within one individual are clonal, that is, genetically identical. In practice, this is inferred by the detection of only one of the mutually exclusive antibody light chains, kappa or lambda, on the entire population of the abnormal B cells. Normal B lymphocytes consist of a stew of different antibody-producing cells, resulting in a mixture of both kappa and lambda expressing cells. The lack of the normal distribution of kappa and lambda producing B cells is one basis for demonstrating clonality, the key element for establishing a diagnosis of any B cell malignancy (B cell non-Hodgkin lymphoma).

The combination of the microscopic examination of the peripheral blood and analysis of the lymphocytes by flow cytometry to confirm clonality and marker molecule expression is needed to establish the diagnosis of CLL. Both are easily accomplished on a small amount of blood. A flow cytometer is an instrument that can examine the expression of molecules on individual cells in fluids. This requires the use of specific antibodies to marker molecules with fluorescent tags recognized by the instrument. In CLL, the lymphocytes are genetically clonal, of the B cell lineage (expressing marker molecules cluster of differentiation 19 (CD19) and CD20), and characteristically express the marker molecules CD5 and CD23. These B cells resemble normal lymphocytes under the microscope, although slightly smaller, and are fragile when smeared onto a glass slide, giving rise to many broken cells, which are called "smudge" or "smear" cells.

The Matutes's CLL score allows the identification of a homogeneous subgroup of classical CLL, that differs from atypical/mixed CLL for the five markers' expression (CD5, CD23, FMC7, CD22 and immunoglobulin light chain) Matutes's CLL scoring system is very helpful for the differential diagnosis between classical CLL and the other B cell chronic lymphoproliferative disorders, but not for the immunological distinction between mixed/atypical CLL and mantle cell lymphoma (MCL malignant B cells). Discrimination between CLL and MCL can be improved by adding non-routine markers such as CD54 and CD200. Among routine markers, the most discriminating feature is the CD20/CD23 mean fluorescence intensity ratio. In contrast, FMC7 expression can surprisingly be misleading for borderline cases.

Staging, determining the extent of the disease, is done with the Rai staging system or the Binet classification (see details) and is based primarily on the presence of a low platelet or red cell count. Early stage disease does not need to be treated.

CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes).

Initial CLL treatments vary depending on the exact diagnosis and the progression of the disease, and even with the preference and experience of the health care practitioner. Dozens of agents are used for CLL therapy. An initial treatment regimen that contains fludarabine, cyclophosphamide, and rituximab (known as FCR) has demonstrated higher overall response rates and complete response rates.

A study carried out by the researchers at the University of Pennsylvania used genetically modified T cells to attack cells that expressed the CD19 protein to fight the disease. In 2013, the researchers announced that 26 of 59 patients had achieved complete remission and that the original patient had remained tumor-free.

Leukemia is rarely associated with pregnancy, affecting only about 1 in 10,000 pregnant women. Treatment for chronic lymphocytic leukemias can often be postponed until after the end of the pregnancy. If treatment is necessary, then giving chemotherapy during the second or third trimesters is less likely to result in pregnancy loss or birth defects than treatment during the first trimester.

While generally considered incurable, CLL progresses slowly in most cases. Many people with CLL lead normal and active lives for many years—in some cases for decades. Because of its slow onset, early-stage CLL is, in general, not treated since it is believed that early CLL intervention does not improve survival time or quality of life. Instead, the condition is monitored over time to detect any change in the disease pattern.

The decision to start CLL treatment is taken when the patient's clinical symptoms or blood counts indicate that the disease has progressed to a point where it may affect the patient's quality of life. Clinical "staging systems" such as the Rai 4-stage system and the Binet classification can help to determine when and how to treat the patient. Determining when to start treatment and by what means is often difficult; studies have shown there is no survival advantage to treating the disease too early. The National Cancer Institute Working Group has issued guidelines for treatment, with specific markers that should be met before it is initiated.

Combination chemotherapy regimens are effective in both newly diagnosed and relapsed CLL. Combinations of fludarabine with alkylating agents (cyclophosphamide) produce higher response rates and a longer progression-free survival than single agents:

FC (fludarabine with cyclophosphamide)
FR (fludarabine with rituximab)
FCR (fludarabine, cyclophosphamide, and rituximab)
CHOP (cyclophosphamide, doxorubicin, vincristine and prednisolone)

Although the purine analogue fludarabine was shown to give superior response rates to chlorambucil as primary therapy, there is no evidence early use of fludarabine improves overall survival, and some clinicians prefer to reserve fludarabine for relapsed disease.

Chemoimmunotherapy with FCR has shown to improve response rates, progression-free survival and overall survival in a large randomized trial in CLL patients selected for good physical fitness. This has been the first clinical trial demonstrating that the choice of a first line therapy can improve the overall survival of patients with CLL. Alkylating agents approved for CLL include bendamustine and cyclophosphamide.

Targeted therapy attacks cancer cells at a specific target, with the aim of not harming normal cells. Monoclonal antibodies, such as alemtuzumab (directed against CD52), and rituximab and ofatumumab (directed against CD20), are used in CLL. Tyrosine kinase inhibitor therapy can also be used in CLL. In February 2014, the FDA granted ibrutinib approval to treat chronic lymphocytic leukemia. Ibrutinib is a Bruton's tyrosine kinase (BTK) inhibitor. In July 2014, the FDA and EMA granted idelalisib approval to treat different types of leukemia. Idelalisib is a PI3K inhibitor that targets the PI3Kδ pathway. It is taken orally.

Autologous stem cell transplantation, using the recipient's own cells, is not curative. Younger individuals, if at high risk for dying from CLL, may consider allogeneic hematopoietic stem cell transplantation (HSCT). Myeloablative (bone marrow killing) forms of allogeneic stem cell transplantation, a high-risk treatment using blood cells from a healthy donor, may be curative, but treatment-related toxicity is significant. An intermediate level, called reduced-intensity conditioning allogeneic stem cell transplantation, may be better tolerated by older or frail patients.

"Refractory" CLL is a disease that no longer responds favorably to treatment. In this case, more aggressive therapies, including lenalidomide, flavopiridol, and bone marrow (stem cell) transplantation, are considered. The monoclonal antibody, alemtuzumab (directed against CD52), may be used in patients with refractory, bone marrow-based disease.

Complications include Richter's syndrome, hypogammaglobulinemia leading to recurrent infection, warm autoimmune hemolytic anemia in 10-15% of patients, transformation to high grade lymphoma. Chronic lymphocytic leukemia may transform into Richter's syndrome, the development of fast-growing diffuse large B cell lymphoma, prolymphocytic leukemia, Hodgkin's lymphoma, or acute leukemia in a patient who has chronic lymphocytic leukemia. Its incidence is estimated to be around 5 percent in patients with CLL.

Gastrointestinal (GI) involvement can rarely occur with chronic lymphocytic leukemia. Some of the reported manifestations include intussusception, small intestinal bacterial contamination, colitis and others. Usually, GI complications with CLL occur after Richter transformation. There have been two case reports to date of GI involvement in chronic lymphocytic leukemia without Richter's transformation.

E. Non-Small Cell Lung Cancer

Non-small-cell lung carcinoma (NSCLC) is any type of epithelial lung cancer other than small cell lung carcinoma (SCLC). As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy).

The most common types of NSCLC are squamous cell carcinoma, large cell carcinoma, and adenocarcinoma, but there are several other types that occur less frequently, and all types can occur in unusual histologic variants and as mixed cell-type combinations. Sometimes the phrase "non-small-cell lung cancer" ("not otherwise specified", or NOS) is used generically, usually when a more specific diagnosis cannot be made. This is most often the case when a pathologist examines a small amount of malignant cells or tissue in a cytology or biopsy specimen.

Lung cancer in never-smokers is almost universally NSCLC, with a sizeable majority being adenocarcinoma. On relatively rare occasions, malignant lung tumors are found to contain components of both SCLC and NSCLC. In these cases, the tumors should be classified as combined small cell lung carcinoma (c-SCLC), and are (usually) treated like "pure" SCLC.

Adenocarcinoma of the lung is currently the most common type of lung cancer in "never smokers" (lifelong non-smokers). Adenocarcinomas account for approximately 40% of lung cancers. Historically, adenocarcinoma was more often seen peripherally in the lungs than small cell lung cancer and squamous cell lung cancer, both of which tended to be more often centrally located. Interestingly, however, recent studies suggest that the "ratio of centrally-to-peripherally occurring" lesions may be converging toward unity for both adenocarcinoma and squamous cell carcinoma.

Squamous cell carcinoma (SCC) of the lung is more common in men than in women. It is closely correlated with a history of tobacco smoking, more so than most other types of lung cancer. According to the Nurses' Health Study, the relative risk of SCC is approximately 5.5, both among those with a previous duration of smoking of 1 to 20 years, and those with 20 to 30 years, compared to never-smokers. The relative risk increases to approximately 16 with a previous smoking duration of 30 to 40 years, and approximately 22 with more than 40 years.

Large cell lung carcinoma (LCLC) is a heterogeneous group of undifferentiated malignant neoplasms originating from transformed epithelial cells in the lung. LCLC's have typically comprised around 10% of all NSCLC in the past, although newer diagnostic techniques seem to be reducing the incidence of diagnosis of "classic" LCLC in favor of more poorly differentiated squamous cell carcinomas and adenocarcinomas. LCLC is, in effect, a "diagnosis of exclusion", in that the tumor cells lack light microscopic characteristics that would classify the neoplasm as a small-cell carcinoma, squamous-cell carcinoma, adenocarcinoma, or other more specific histologic type of lung cancer. LCLC is differentiated from small cell lung carcinoma (SCLC) primarily by the larger size of the anaplastic cells, a higher cytoplasmic-to-nuclear size ratio, and a lack of "salt-and-pepper" chromatin.

More than one kind of treatment is often used, depending on the stage of the cancer, the individual's overall health, age, response to chemotherapy, and other factors such as the likely side effects of the treatment. NSCLCs are usually not very sensitive to chemotherapy and/or radiation, so surgery is the treatment of choice if diagnosed at an early stage, often with adjuvant (ancillary) chemotherapy involving cisplatin. Other treatment choices are chemotherapy, radiation therapy (radiotherapy), and targeted therapy.

New methods of giving radiation treatment allow doctors to be more accurate in treating lung cancers. This means less radiation affects nearby healthy tissues. New methods include Cyberknife and stereotactic radiosurgery (SRS). Other treatments are radiofrequency ablation and chemoembolization.

A wide variety of chemotherapies are used in advanced (metastatic) NSCLC. Some patients with particular mutations in the EGFR gene respond to EGFR tyrosine kinase inhibitors such as gefitinib. About 7% of NSCLC have EML4-ALK translocations; these may benefit from ALK inhibitors which are in clinical trials. Crizotinib gained FDA approval in August 2011.

F. Gastric Cancer

Stomach cancer or gastric cancer is cancer developing from the lining of the stomach. Early symptoms may include heartburn, upper abdominal pain, nausea and loss of appetite. Later signs and symptoms may include weight loss, yellow skin, vomiting, difficulty swallowing, and blood in the stool among others. The cancer may spread from the stomach to other parts of the body, particularly the liver, lungs, bones, lining of the abdomen and lymph nodes. The prognosis of stomach cancer is generally poor, due to the fact the tumor has often metastasized by the time of discovery and the fact that most people with the condition are elderly (median age is between 70 and 75 years) at presentation. The κ-year survival rate for stomach cancer is reported to be less than 10%.

The most common cause is infection by the bacteria *Helicobacter pylori*, which accounts for more than 60% of cases. Certain types of *H. pylori* have greater risks than others. Other common causes include eating pickled vegetables and smoking. About 10% of cases run in families and between 1% and 3% of cases are due to genetic syndromes inherited from a person's parents such as hereditary diffuse gastric cancer. Most cases of stomach cancers are gastric carcinomas. This type can be divided into a number of subtypes. Lymphomas and mesenchymal tumors may also develop within the stomach. Most of the time, stomach cancer develops through a number of stages over a number of years. Diagnosis is usually by biopsy done during endoscopy. This is then followed by medical imaging to determine if the disease has spread to other parts of the body. Japan and South Korea, two countries that have high rates of disease, screen for stomach cancer.

A Mediterranean diet lowers the risk of cancer as does the stopping of smoking. There is tentative evidence that treating *H. pylori* decreases the future risk. If cancer is treated early, many cases can be cured. Treatments may include some combination of surgery, chemotherapy, radiation therapy, and targeted therapy. If treated late, palliative care may be advised. Outcomes are often poor with a less than 10% 5-year survival rate globally. This is largely because most people with the condition present with advanced disease. In the United States 5-year survival is 28% while in South Korea it is over 65% partly due to screening efforts.

Globally stomach cancer is the fifth leading cause of cancer and the third leading cause of death from cancer making up 7% of cases and 9% of deaths. In 2012 it occurred in 950,000 people and caused 723,000 deaths. Before the 1930s in much of the world, including the United States and the United Kingdom, it was the most common cause of death from cancer. Rates of death have been decreasing in many areas of the world since then. This is believed to be due to the eating of less salted and pickled foods as a result of the development of refrigeration as a method of keeping food fresh. Stomach cancer occurs most commonly in East Asia and Eastern Europe and it occurs twice as often in males as in females.

Stomach cancer is often either asymptomatic (producing no noticeable symptoms) or it may cause only nonspecific symptoms (symptoms that are specific not only to stomach cancer, but also to other related or unrelated disorders) in its early stages. By the time symptoms occur, the cancer has often reached an advanced stage (see below) and may have also metastasized (spread to other, perhaps distant, parts of the body), which is one of the main reasons for its relatively poor prognosis. Early cancers may be associated with indigestion or a burning sensation (heartburn). However, less than 1 in every 50 people referred for endoscopy due to indigestion has cancer. Abdominal discomfort and loss of appetite, especially for meat, can occur.

Gastric cancers that have enlarged and invaded normal tissue can cause weakness, fatigue, bloating of the stomach after meals, abdominal pain in the upper abdomen, nausea and occasional vomiting, diarrhea or constipation. Further enlargement may cause weight loss or bleeding with vomiting blood or having blood in the stool, the latter apparent as black discolouration (melena) and sometimes leading to anemia. Dysphagia suggests a tumour in the cardia or extension of the gastric tumor into the esophagus.

Gastric cancer is a multifactorial disease. *Helicobacter pylori* infection is an essential risk factor in 65-80% of gastric cancers, but in only 2% of such infections. The mechanism by which *H. pylori* induces stomach cancer potentially involves chronic inflammation, or the action of *H. pylori* virulence factors such as CagA. Smoking increases the risk of developing gastric cancer significantly, from 40% increased risk for current smokers to 82% increase for heavy smokers. Gastric cancers due to smoking mostly occur in the upper part of the stomach near the esophagus. Some studies show increased risk with alcohol consumption as well.

Dietary factors are not proven causes, but some foods including smoked foods, salt and salt-rich foods, red meat, processed meat, pickled vegetables, and bracken are associated with a higher risk of stomach cancer. Nitrates and nitrites in cured meats can be converted by certain bacteria, including *H. pylori*, into compounds that have been found to cause stomach cancer in animals. On the other hand, fresh fruit and vegetable intake, citrus fruit intake, and antioxidant intake are associated with a lower risk of stomach cancer. A Mediterranean diet is also associated with lower rates of stomach cancer as does regular aspirin use.

There is a correlation between iodine deficiency and gastric cancer. Gastric cancer shows a male predominance in its incidence as up to two males are affected for every female. Estrogen may protect women against the development of this cancer form. Approximately 10% of cases show a genetic component.

People may possess certain risk factors, such as those that are physical or genetic, that can alter their susceptibility for gastric cancer. Obesity is one such physical risk factor that has been found to increase the risk of gastric adenocarcinoma by contributing to the development of gastroesphageal reflux disease (GERD). The exact mechanism by which obesity causes GERD is not completely known. Studies hypothesize that increased dietary fat leading to increased pressure on the stomach and the lower esophageal sphincter, due to excess adipose tissue, could play a role, yet no statistically significant data has been collected. However, the risk of gastric cardia adenocarcinoma, with GERD present, has been found to increase more than 2 times for an obese person. A genetic risk factor for gastric cancer is a genetic defect of the CDH1 gene known as hereditary diffuse gastric cancer (HDGC). The CDH1 gene, which codes for E-cadherin, lies on the 16th chromosome. When the gene experiences a particular mutation, gastric cancer develops through a mechanism that is not fully understood. This mutation is considered autosomal dominant meaning that half of a carrier's children will likely experience the same mutation. Diagnosis of hereditary diffuse gastric cancer usually takes place when at least two cases involving a family member, such as a parent or grandparent, are diagnosed, with at least one diagnosed before the age of 50. The diagnosis can also be made if there are at least three cases in the family, in which case age is not considered.

The International Cancer Genome Consortium is leading efforts to identify genomic changes involved in stomach cancer. A very small percentage of diffuse-type gastric cancers (see Histopathology below) arise from an inherited abnormal CDH1 gene. Genetic testing and treatment options are available for families at risk.

Other factors associated with increased risk are AIDS, diabetes, pernicious anemia, chronic atrophic gastritis, Menetrier's disease (hyperplastic, hypersecretory gastropathy), and intestinal metaplasia.

To find the cause of symptoms, the doctor asks about the patient's medical history, does a physical exam, and may order laboratory studies. Gastroscopic exam is the diagnostic method of choice. This involves insertion of a fibre optic camera into the stomach to visualize it. Upper GI series (may be called barium roentgenogram). Computed tomography or CT scanning of the abdomen may reveal gastric cancer, but is more useful to determine invasion into adjacent tissues, or the presence of spread to local lymph nodes. Wall thickening of more than 1 cm that is focal, eccentric and enhancing favours malignancy.

Abnormal tissue seen in a gastroscope examination will be biopsied by the surgeon or gastroenterologist. This tissue is then sent to a pathologist for histological examination under a microscope to check for the presence of cancerous cells. A biopsy, with subsequent histological analysis, is the only sure way to confirm the presence of cancer cells.

Various gastroscopic modalities have been developed to increase yield of detected mucosa with a dye that accentuates the cell structure and can identify areas of dysplasia. Endocytoscopy involves ultra-high magnification to visualise cellular structure to better determine areas of dysplasia. Other gastroscopic modalities such as optical coherence tomography are also being tested investigationally for similar applications.

A number of cutaneous conditions are associated with gastric cancer. A condition of darkened hyperplasia of the skin, frequently of the axilla and groin, known as acanthosis nigricans, is associated with intra-abdominal cancers such as gastric cancer. Other cutaneous manifestations of gastric cancer include tripe palms (a similar darkening hyperplasia of the skin of the palms) and the Leser-Trelat sign, which is the rapid development of skin lesions known as seborrheic keratoses. Various blood tests may be performed including a complete blood count (CBC) to check for anaemia, and a fecal occult blood test to check for blood in the stool.

Getting rid of *H. pylori* in those who are infected decreases the risk of stomach cancer, at least in those who are Asian. Low doses of vitamins, especially from a healthy diet, decrease the risk of stomach cancer. A previous review of supplementation did not find supporting evidence and possibly worse outcomes.

Cancer of the stomach is difficult to cure unless it is found at an early stage (before it has begun to spread). Unfortunately, because early stomach cancer causes few symptoms, the disease is usually advanced when the diagnosis is made. Treatment for stomach cancer may include surgery, chemotherapy, and/or radiation therapy. New treatment approaches such as biological therapy and improved ways of using current methods are being studied in clinical trials.

Surgery remains the only curative therapy for stomach cancer. Of the different surgical techniques, endoscopic mucosal resection (EMR) is a treatment for early gastric cancer (tumor only involves the mucosa) that has been pioneered in Japan, but is also available in the United States at some centers. In this procedure, the tumor, together with the inner lining of stomach (mucosa), is removed from the wall of the stomach using an electrical wire loop through the endoscope. The advantage is that it is a much smaller operation than removing the stomach. Endoscopic submucosal dissection (ESD) is a similar technique pioneered in Japan, used to resect a large area of mucosa in one piece. If the pathologic examination of the resected specimen shows incomplete resection or deep invasion by tumor, the patient would need a formal stomach resection.

Those with metastatic disease at the time of presentation may receive palliative surgery and while it remains controversial, due to the possibility of complications from the surgery itself and the fact that it may delay chemotherapy the data so far is mostly positive, with improved survival rates being seen in those treated with this approach.

The use of chemotherapy to treat stomach cancer has no firmly established standard of care. Unfortunately, stomach cancer has not been particularly sensitive to these drugs, and chemotherapy, if used, has usually served to palliatively reduce the size of the tumor, relieve symptoms of the disease and increase survival time. Some drugs used in stomach cancer treatment have included: 5-FU (fluorouracil) or its analog capecitabine, BCNU (carmustine), methyl-CCNU (semustine) and doxorubicin (Adriamycin), as well as mitomycin C, and more recently cisplatin and taxotere, often using drugs in various combinations. The relative benefits of these different drugs, alone and in combination, are unclear. Clinical researchers have explored the benefits of giving chemotherapy before surgery to shrink the tumor, or as adjuvant therapy after surgery to destroy remaining cancer cells. Recently, a targeted treatment called trastuzumab has become available for use with chemotherapy for the treatment of those overexpressing the HER2 gene in their tumor cells.

Radiation therapy (also called radiotherapy) may also be used to treat stomach cancer, often as an adjuvant to chemotherapy and/or surgery.

IV. MONOCLONAL ANTIBODIES AND PRODUCTION THEREOF

The monoclonal antibodies described herein were prepared using standard methods, followed by screening, characterization and functional assessment. Variable regions were sequenced and then subcloned into a human expression vector to produce the chimeric antibody genes, which were then expressed and purified. These chimeric antibodies were tested for antigen binding, signaling blocking, and in xenograft experiments.

A. General Methods

It will be understood that monoclonal antibodies binding to LILRBs will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

1. Antibodies to LILRB

Antibodies or antigen-binding fragments thereof according to the present disclosure may be defined, in the first instance, by their binding specificity, which in this case is for LILRBs. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to LILRB4. In some embodiments, when bound to LILRB4, such antibodies modulate the activation of LILRB4. In certain embodiments, the antibody or antigen-binding fragment, when bound to LILRB4, activates LILRB4. In certain embodiments, the antibody or antigen-binding fragment, when bound to LILRB4, suppresses activation of LILRB4. In certain embodiments, the antibody or antigen-binding fragment, when bound to LILRB4, can specifically interfere with, block or reduce the interaction between ApoE and LILRB4. In certain embodiments, the antibody or antigen-binding fragment provided herein is capable of inhibiting ApoE-mediated activity of LILRB4. In certain embodiments, the antibodies or antigen-binding fragments provided herein specifically or selectively bind to human LILRB4 (SEQ ID NO: 238).

In some embodiments, the antibodies or antigen-binding fragments bind specifically to human LILRB4 and/or substantially inhibits binding of human LILRB4 to ApoE by at least about 20%-40%, 40-60%, 60-80%, 80-85%, or more (for example, by an assay as disclosed in the Example). In some embodiments, the antibody or antigen-binding fragment has a Kd of less (binding more tightly) than $10^{-7}$, $10^{-8}$, $10^{-9}$, $10^{-10}$, $10^{-11}$, $10^{-12}$, $10^{-13}$ M. In some embodiments, the antibody or antigen-binding fragment has an IC50 for blocking the binding of ApoE to LILRB4 of less than 1 uM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some embodiments, the antibodies or antigen-binding fragments provided herein having clone-paired CDR's from the heavy and light chains as illustrated in FIG. 17 or FIG. 22. Such antibodies may be produced by the clones discussed below in the Examples section using methods described herein. In certain embodiments, each CDR is defined in accordance with Kabat definition, the Chothia definition, the combination of Kabat definition and Chothia definition, the AbM definition, or the contact definition of CDR. In certain embodiments, the antibody or antigen-binding fragment is characterized by clone-paired heavy and light chain CDR sequences from FIG. 17 or FIG. 22.

In certain embodiments, the antibodies may be defined by their variable sequence, which include additional "framework" regions. The antibody is characterized by clone-paired heavy chain and light chain amino acid sequences from FIG. 16 or FIG. 21. Furthermore, the antibodies sequences may vary from these sequences, particularly in regions outside the CDRs. For example, the amino acids may vary from those set out above by a given percentage, e.g., 80%, 85%, 90%, 91%, 92%, 93%, 94%, 95%, 96%, 97%, 98% or 99% homology, or the amino acids may vary from those set out above by permitting conservative substitutions (discussed below). Each of the foregoing apply to the amino acid sequences of FIG. 16 and FIG. 21. In another embodiment, the antibody derivatives of the present disclosure comprise VL and VH domains having up to 0, 1, 2, 3, 4, 5, 6, 7, 8, 9, 10 or more conservative or non-conservative amino acid substitutions, while still exhibiting the desired binding and functional properties.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (Clq) of the classical complement system. Thus, the term "antibody" includes intact immunoglobulins of types IgA, IgG, IgE, IgD, IgM (as well as subtypes thereof), wherein the light chains of the immunoglobulin may be of types kappa or lambda. Within light and heavy chains, the variable and constant regions are joined by a 35 "J" region of about 12 or more amino acids, with the heavy chain also including a "D" region of about 10 more amino acids. See generally, Fundamental Immunology Ch. 7 (Paul, W., ed., $2n^d$ ed. Raven Press, N.Y. (1989).

The present disclosure further comprises nucleic acids which hybridize to nucleic acids encoding the antibodies disclosed herein. In general, the nucleic acids hybridize under moderate or high stringency conditions to nucleic acids that encode antibodies disclosed herein and also encode antibodies that maintain the ability to specifically bind to an LILRB. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., supra). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

2. Exemplary Epitopes

In another aspect, the present disclosure provides epitopes to which anti-LILRB4 antibodies bind.

In some embodiments, epitopes that are bound by the antibodies described herein are useful. In certain embodiments, an epitope provided herein can be utilized to isolate antibodies or antigen binding proteins that bind to LILRB4. In certain embodiments, an epitope provided herein can be utilized to generate antibodies or antigen binding proteins which bind to LILRB4. In certain embodiments, an epitope or a sequence comprising an epitope provided herein can be utilized as an immunogen to generate antibodies or antigen binding proteins that bind to LILRB4. In certain embodiments, an epitope described herein or a sequence comprising an epitope described herein can be utilized to interfere with biological activity of LILRB4.

In some embodiments, antibodies or antigen-binding fragments thereof that bind to any of the epitopes are particularly useful. In some embodiments, an epitope provided herein, when bound by an antibody, modulates the biological activity of LILRB4. In some embodiments, an epitope provided herein, when bound by an antibody, activates LILRB4. In some embodiments, an epitope provided herein, when bound by an antibody, suppress the activation of LILRB4. In some embodiments, an epitope provided herein, when bound by an antibody, block the interaction between ApoE and LILRB4.

In some embodiments, the domain(s)/region(s) containing residues that are in contact with or are buried by an antibody can be identified by mutating specific residues in LILRB4 and determining whether the antibody can bind the mutated LILRB4 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In certain embodiments, the antibody or antigen-binding fragment disclosed herein specifically binds to the Ig1 domain of LILRB4 comprising amino acid residues 27-118 of SEQ ID NO: 238. In certain embodiments, the antibody or antigen-binding fragment disclosed herein specifically binds to the Ig1 domain of LILRB4 comprising amino acid residues 119-218 of SEQ ID NO: 238. In certain embodiments, the antibody or antigen-binding fragment disclosed herein binds to the stalk domain of LILRB4 comprising amino acid residues 219-259 of SEQ ID NO: 238.

In certain embodiments, the antibody or antigen-binding fragment disclosed herein binds to an epitope of LILRB4 comprising amino acid residues 238-244 of SEQ ID NO: 238. In certain embodiments, the antibody or antigen-binding fragment binds to an epitope in a fragment of LILRB4 comprising amino acid residues 200-211 of SEQ ID NO: 238. In certain embodiments, the antibody or antigen-binding fragment binds to an epitope in a fragment of LILRB4 comprising amino acid residues 129-140 of SEQ ID NO: 238. In certain embodiments, the antibody or antigen-binding fragment binds to an epitope in a fragment of LILRB4 comprising amino acid residues 219-230 of SEQ ID NO: 238. In certain embodiments, the antibody or antigen-binding fragment binds to an epitope of a fragment of LILRB4 comprising amino acid residues 173-184 of SEQ ID NO: 238. In certain embodiments, the antibody or antigen-binding fragment binds to an epitope of LILRB4 comprising amino acid residues 245-250 of SEQ ID NO: 238.

In certain embodiments, the antibody or antigen-binding fragment binds to at least one of the following residues: P35, W106 and Y121 of SEQ ID NO: 238. In certain embodiments, the antibody or antigen-binding fragment binds to at least one of the following residues: E54, R56, P103 and W106 of SEQ ID NO: 238. In certain embodiments, the antibody or antigen-binding fragment binds to at least one of the following residues: S220, L221, P224 and P226 of SEQ ID NO: 238. In certain embodiments, the antibody or antigen-binding fragment binds to at least one of the following residues: A67 and Q72 of SEQ ID NO: 238. In certain embodiments, the antibody or antigen-binding fragment binds to at least one of the following residues: R59, A67, Y99, R101 and W106 of SEQ ID NO: 238.

3. Competing Antigen Binding Proteins

In another aspect, the present disclosure provides antigen-binding proteins that compete with one of the exemplified antibodies or antigen-binding fragment binding to the epitope described herein for specific binding to LILRB. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the heavy and light chain variable regions and CDRs included in FIGS. 16, 17, 21 and 22.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies may be generated by subcloning heavy and light chain Fv DNAs from the cloning vector into an IgG plasmid vector, transfected into 293 Freestyle cells or CHO cells, and antibodies collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4); sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328. In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result in removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyl-transferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (See for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3 GlcNAc2; GlcNAc2Man3GlcNAc2; GalGlcNAc2Man3 GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an $\alpha 1,3$-linkage with the GlcNAc at the reducing end of the N-glycan, an $\alpha 1,6$-linkage with the GlcNAc at the reducing end of the N-glycan, an $\alpha 1,2$-linkage with the Gal at the non-reducing end of the N-glycan, an $\alpha 1,3$-linkage with the GlcNac at the non-reducing end of the N-glycan, or an $\alpha 1,4$-linkage with a GlcNAc at the non-reducing end of the N-glycan.

Therefore, in particular aspects of the above the glycoprotein compositions, the glycoform is in an $\alpha 1,3$-linkage or $\alpha 1,6$-linkage fucose to produce a glycoform selected from the group consisting of Man5GlcNAc2(Fuc), GlcNAcMan5GlcNAc2(Fuc), Man3GlcNAc2(Fuc), GlcNAcMan3GlcNAc2(Fuc), GlcNAc2Man3GlcNAc2 (Fuc), GalGlcNAc2Man3GlcNAc2(Fuc), Gal2GlcNAc2Man3GlcNAc2(Fuc), NANAGal2GlcNAc2Man3GlcNAc2(Fuc), and NANA2Gal2GlcNAc2Man3GlcNAc2(Fuc); in an $\alpha 1,3$-linkage or $\alpha 1,4$-linkage fucose to produce a glycoform selected from the group consisting of GlcNAc(Fuc) Man5GlcNAc2, GlcNAc(Fuc)Man3GlcNAc2, GlcNAc2 (Fuc1-2)Man3GlcNAc2, GalGlcNAc2(Fuc1-2) Man3GlcNAc2, Gal2GlcNAc2(Fuc1-2)Man3GlcNAc2, NANAGal2GlcNAc2(Fuc1-2)Man3GlcNAc2, and NANA2Gal2GlcNAc2(Fuc1-2)Man3GlcNAc2; or in an $\alpha 1,2$-linkage fucose to produce a glycoform selected from the group consisting of Gal(Fuc)GlcNAc2Man3GlcNAc2, Gal2(Fuc1-2)GlcNAc2Man3GlcNAc2, NANAGal2(Fuc1-2)GlcNAc2Man3GlcNAc2, and NANA2Gal2(Fuc1-2) GlcNAc2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated bisected and multiantennary species. As used herein, the terms "N-glycan" and "glycoform" are used interchangeably and refer to an N-linked oligosaccharide, for example, one that is attached by an asparagine-Nacetylglucosamine linkage to an asparagine residue of a polypeptide. N-linked glycoproteins contain an N-acetylglucosamine residue linked to the amide nitrogen of an asparagine residue in the protein.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well.

Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

V. TREATMENT OF CANCER

A. Formulation and Administration

The present disclosure provides pharmaceutical compositions comprising anti-LILRB antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethyl-amino ethanol, histidine, procaine, and the like.

Passive transfer of antibodies, known as artificially acquired passive immunity, generally will involve the use of intravenous injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-DC-HIL antibody or the other therapy will be desired. Various combinations may be employed, where the antibody is "A," and the other therapy is "B," as exemplified below:

| | |
|---|---|
| A/B/A | B/A/B |
| B/B/A | A/A/B |
| B/A/A | A/B/B |
| B/B/B/A | B/B/A/B |
| A/A/B/B | A/B/A/B |
| A/B/B/A | B/B/A/A |
| B/A/B/A | B/A/A/B |
| B/B/B/A | A/A/A/B |
| B/A/A/A | A/B/A/A |
| A/A/B/A | A/B/B/B |
| B/A/B/B | B/B/A/B |

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene) and interleukin 2 (Proleukin) after the completion of consolidation therapy, gemtuzumab ozogamicin (Mylotarg) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are selected from the groups consisting of an anthracycline topoisomerase inhibitor, a daunorubicin, a nucleoside metabolic inhibitor, a cytarabine, a combination of daunorubicin and cytarabine, a daunorubicin and cytarabine liposome for injection, Vyxeos, an all-trans-retinoic acid (ATRA), an arsenic, an arsenic trioxide, a histamine dihydrochloride, Ceplene, an interleukin-2, Proleukin, a gemtuzumab ozogamicin, Mylotarg, a clofarabine, a farnesyl transferase inhibitor, a decitabine, an IDH1 inhibitor, an IDH2 inhibitor, an enasidenib, Idhifa, an IDO inhibitor, an epacadostat, a platinum complex derivative, oxaliplatin, a kinase inhibitor, a tyrosine kinase inhibitor, a PI3 kinase inhibitor, a BTK inhibitor, ibrutinib, a PD-1 antibody, a PD-L1 antibody, a CTLA-4 antibody, a LAG3 antibody, an ICOS antibody, a TIGIT antibody, a TIM3 antibody, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a topoisomerase inhibitor, a hormone therapy medicine, a hormone antagonist, an aromatase inhibitor, and a P-glycoprotein inhibitor.

VI. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VII. IMMUNODETECTION METHODS

In still further embodiments, the present disclosure concerns immunodetection methods for binding, purifying, removing, quantifying and otherwise generally detecting LILRB-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LILRBs also is provided. The steps of various useful immunodetection methods have been described in the scientific literature, such as, e.g., Doolittle and Ben-Zeev (1999), Gulbis and Galand 11993), De Jager et al. (1993), and Nakamura et al. (1987). In general, the immunobinding methods include obtaining a sample suspected of containing LILRB-related cancers, and contacting the sample with a first antibody in accordance with the present disclosure, as the case may be, under conditions effective to allow the formation of immunocomplexes.

These methods include methods for detecting or purifying LILRBs or LILRB-related cancer cells from a sample. The antibody will preferably be linked to a solid support, such as in the form of a column matrix, and the sample suspected of containing the LILRB-related cancer cells will be applied to the immobilized antibody. The unwanted components will be washed from the column, leaving the LILRB-expressing cells immunocomplexed to the immobilized antibody, which is then collected by removing the organism or antigen from the column.

The immunobinding methods also include methods for detecting and quantifying the amount of LILRB-related cancer cells or related components in a sample and the detection and quantification of any immune complexes formed during the binding process. Here, one would obtain a sample suspected of containing LILRB-related cancer cells, and contact the sample with an antibody that binds LILRBs or components thereof, followed by detecting and quantifying the amount of immune complexes formed under the specific conditions. In terms of antigen detection, the biological sample analyzed may be any sample that is suspected of containing LILRB-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LILRBs. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the LILRB-related cancer cells is added to the wells. After binding and washing to remove non-specifically bound immune complexes, the bound antigen may be detected. Detection may be achieved by the addition of another anti-LILRB antibody that is linked to a detectable label. This type of ELISA is a simple "sandwich ELISA." Detection may also be achieved by the addition of a second anti-LILRB antibody, followed by the addition of a third antibody that has binding affinity for the second antibody, with the third antibody being linked to a detectable label.

In another exemplary ELISA, the samples suspected of containing the LILRB-related cancer cells are immobilized onto the well surface and then contacted with the anti-LILRB antibodies of the disclosure. After binding and washing to remove non-specifically bound immune complexes, the bound anti-LILRB antibodies are detected. Where the initial anti-LILRB antibodies are linked to a detectable label, the immune complexes may be detected directly. Again, the immune complexes may be detected using a second antibody that has binding affinity for the first anti-LILRB antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect LILRB-related cancer cells, the antibodies may be included in the kit. The immunodetection kits will thus comprise, in suitable container means, a first antibody that binds to an LILRB, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of LILRBs, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VIII. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

This example illustrates that LILRBs and LAIR1 are highly expressed on AML cells including AML-SCs and their expression inversely correlates with survival of AML patients.

The inventors analyzed the surface expression of LILRB1-4 on human AML patients and found that they are expressed by significant percentages of these patients (FIG. 1a). LILRB1,2,3,4 are expressed on 8, 8, 12, and 18 out of a total of 37 tested human AML cases respectively. LILRBs including LILRB4 can be co-expressed with the leukemia stem cell marker CD34 (FIG. 1a). The inventors' in silico analysis indicated that the expression of several closely related LILRB family members, LILRBs 1, 2, 3, and 4, and LAIR1 inversely correlates with the overall survival of AML patients (FIGS. 2a-2d). These receptors are more highly expressed on human AML cells than on normal counterparts. Importantly, the LILRB$^+$/LAIR1$^+$ cells are enriched for the activity of AML-SCs (Kang et al., 2015).

LILRBs and LAIR1 are essential for growth and xenograft of human leukemia cells. To study the potential function of LILRBs and LAIR1 in human leukemia, the inventors knockdown expression of LILRBs and LAIR1 individually using shRNAs in human leukemia lines that have high levels of surface expression of these receptors including MV4-11 (AML), THP-1 (AML), U937 (AML), 697 (B-ALL), Kasumi2 (B-ALL), and RCH-ACV (B-ALL). The silencing of expression of individual LILRB2, 3, 4 or LAIR1 dramatically inhibited cell growth. Representative data from THP-1 and MV4-11, two AML lines with a rearranged MLL gene, are shown in FIGS. 3a-3d. Importantly, inhibition of expression of LILRBs or LAIR1 in any of seven primary human AML samples almost completely abolished leukemia development in xenografted NSG mice (Kang et al., 2015). These results indicate that several LILRBs are essential for the growth of human AML cells.

To gain a deeper understanding of the mechanism by which LILRBs support AML development, the inventors studied acute leukemia development in LILRB3-null, LILRB4-null, or LAIR1-null mice (Tang et al., 2012; Rojo et al., 2000, Zheng et al., 2012). These mice have normal hematopoiesis and HSC activity (Tang et al., 2012; Rojo et al., 2000, Zheng et al., 2012). The inventors used MLL-AF9, AML1-ETO, or N-Myc transplantation AML or acute lymphoblastic leukemia (ALL) mouse models (Sugihara et al., 2011; Kristov et al., 2006; Somervaille and Clearly, 2006; Yan et al., 2006) for this study. The mice transplanted with LILRB- or LAIR1-null leukemia cells developed the disease more slowly upon serial transplantation than did controls and eventually were free of leukemia. The survival and self-renewal of LILRB- or LAIR1-null phenotypic AML-SC enriched cells decreased over time whereas their ability to differentiate increased. The inventors further discovered that SHP-1 and CAMKI are key components in the LILRB/LAIR1 signaling pathway in AML-SCs (Kang et al. 2015). These results indicate that LILRBs and LAIR1 support the activity of AML-SCs.

Example 2

This example illustrates the identification of anti-LILRB monoclonal antibodies (mAbs).

The inventors developed antibodies against individual LILRBs as determined by their binding to LILRBs in Western blotting (FIG. 4) and flow cytometry (FIG. 5). Because there was no reporter for LILRB/LAIR1-mediated signaling, the inventors generated a stable chimeric receptor reporter cell system to test the ability of an antibody to bind to the extracellular domain (ECD) of LILRB or LAIR1 and trigger the activation or inhibition of the chimerically fused intracellular domain of paired immunoglobulin-like receptor 13, which signals through the adaptor DAP-12 to activate NFAT promoter-driven GFP expression (FIG. 6 right and FIG. 7, left). This reporter system serves as a sensitive surrogate that enables us to screen for blocking antibodies and stimulating antibodies.

Using this system, the inventors have identified a group of novel monoclonal antibodies (mAbs) that inhibit the LILRB2-4 signaling activation (FIGS. 6-7). For example, soluble anti-LILRB4 mAbs including C84, C53, C92, C201 inhibit GFP induction in the chimeric receptor reporter system for LILRB4 (FIG. 7).

Example 3

This example illustrates the anti-LILRB mAbs that block leukemia development.

The inventors identified several anti-LILRB mAbs effectively block AML development in xenograft models. For example, C84, an anti-LILRB4 mAb, blocked AML development in xenografted mouse models. In these models, human leukemia cells THP-1 or MV4-11 (positive for LILRB4 surface expression as shown in FIGS. 8-9) or primary human AML cells from three individual patients were subcutaneously (sc) or intravenously (iv) to transplanted into the immune-deficient NSG mice (FIGS. 10-13 and FIG. 15 for AML cell lines implanted xenograft models; FIG. 14 for patient AML xenograft models). By contrast, C84 administration did not inhibit cancer development if LILRB4 is not expressed by the cancer cells (FIG. 13). Therefore, the anti-LILRB4 mAb C84 had a striking specific inhibitory effect on the development of human AML that express LILRB4. Importantly, six independent experiments using different xenografted models gave similar results.

In addition to C84, the inventors identified additional nine mAbs C201, C53, C92, C39, C3, C193, C290, C102, and C287 that are against LILRBs have anti-leukemia effects in xenograft models. The anti-leukemia potency and the cross-reactivity of these mAbs are summarized in FIG. 19.

The inventors determined the isotype and also sequenced variable regions of mAbs that are effective to inhibit leukemia development. The inventors obtained the isotypes and sequencing of variable regions of mAbs C84, C201, C53, C92, C39, C3, C193, C290, C102, and C287 (FIGS. 20-22).

The inventors also produced chimeric antibodies that demonstrated their anti-leukemia potency. To express the chimeric antibodies, the inventors subcloned the variable regions of mouse mAbs into an expression vector encoding human constant regions, and transfected into 293T cells. The inventors collected the conditioned medium from the transfected 293T cells and purified the chimeric antibodies. FIG. 23 shows the expression and purification of chimeric anti-C84 (Mouse/Human Chimeric ab MHC-C84) as determined by SDS-PAGE.

The inventors compared the LILRB binding, signaling blocking, and leukemia inhibition activities of chimeric antibodies and the original mAbs. Chimeric ab MHC-C84 binds LILRB4 on THP-1 cells (FIG. 24) and on LILRB4 chimeric receptor reporter cells (FIG. 25) respectively as C84, as determined by flow cytometry. The inventors also found that the chimeric antibody MHC-C84 is a blocking antibody for LILRB4 as C84, as determined by chimeric receptor reporter assay (FIG. 26). Most importantly, the chimeric antibody MHC-C84 inhibits AML development in xenograft models (with the same or better effect than the original mAb C84) as determined by flow cytometry analysis of liver, bone marrow, spleen, and peripheral blood of AML xenografted mice (FIG. 27) or by luminescence imaging of tumor development in AML xenografted mice over time (FIG. 28). Strikingly, in these experiments, the inventors only administrated MHC-C84 or C84 one time (a total of 200 μg antibody/mouse) for the whole experiment period. These results indicate that chimeric anti-LILRBs have the same or greater capacities to block leukemia development than the original mAbs.

In summary, these data demonstrated that: 1) LILRB/LAIR1 are highly expressed by human AML cells and LILRB$^+$/LAIR1$^+$ cells are enriched in AML-SC activity; 2) LILRB/LAIR1 expression inversely correlates with the overall survival of AML patients; 3) LILRB/LAIR1 are essential for growth of primary and immortalized human leukemia cells in vitro and in vivo; and 4) the inventors have identified several novel anti-human LILRB4 mAb and chimeric antibodies that essentially block human AML development in various xenograft models including in patient AML derived xenograft models. It is noteworthy that there is no apparent effect of knockout of individual LILRB genes or lair1 on normal hematopoiesis (Tang et al., 2012; Rojo et al., 2000, Zheng et al., 2012). In addition, inhibition of LILRB stimulated immunity and indirectly boosted antitumor effects. Therefore, LILRB/LAIR1 represent ideal targets for treating AML.

As the inventors identified multiple potential ligand binding sites for LILRB2 (Deng et al., 2014), they envision that a large molecule such as a blocking antibody rather than a small molecule chemical will be a more appropriate LILRB blocker. Indeed, as the inventors demonstrated, even a single time administration of an anti-LILRB mAb or chimeric antibody was capable of very efficiently blocking human AML development in xenograft models. These results provide proof-of-principle that anti-LILRB mAbs or chimeric antibodies are promising drug candidates for treating AML.

Example 4

This example illustrates the interaction between LILRB4 and ApoE, and that APOE activates LILRB4 to support AML infiltration.

Anti-LILRB4 antibody blockade that efficiently suppresses immune inhibitory and migration functions of acute monocytic leukemia cells suggests that the function of LILRB4 on leukemia cell surface may be ligand dependent. To identify potential agonists and antagonists of LILRBs, the inventors generated individual stable chimeric receptor reporter cells based on fusion of the extracellular domain (ECD) of individual LILRBs and their mouse orthologues PirB and gp49B1, with the intracellular domain of paired immunoglobulin-like receptor (3, which signals through the adaptor DAP-12 to activate NFAT promoter-driven GFP expression (FIG. 33a). With help from this system, the generated novel anti-LILRB4 blocking antibodies to further assess LILRB4-mediated signaling (FIG. 33). The inventors sought to identify the extracellular binding protein(s) for LILRB4. Intergrin-αvβ3 was previously identified as the ligand for gp49B1, a mouse LILRB4 orthologue. However, a variety of intergrin-αβ complexes did not activate human LILRB4 reporter cells (FIG. 34).

Surprisingly, the inventors found that human serum and mouse serum were capable of specifically stimulating the reporter for LILRB4 reporter (FIG. 34) but not other LILRBs (FIG. 35a). Through fast protein liquid chromatography (FPLC) fractionation followed by reporter assays and mass spectrometry (FIGS. 36a-36c), the inventors identified human and mouse APOE specifically activated LILRB4 reporter (FIG. 35b and FIG. 37). Purified APOE from different sources all activated LILRB4 (FIG. 38a). All three isoforms of human APOE activated LILRB4 in both immobilized and soluble conditions (FIG. 38b). Interestingly, recombinant APOE specifically activated the mouse PirB, but not gp49B1 (FIG. 35b) that is considered to be the mouse orthologue of LILRB4. The serum from wild-type but not APOE-null mice activated the LILRB4 reporter (FIG. 35c). In addition, liposome-reconstituted APOE protein (APOE-POPC) had the same ability as lipid-free APOE protein in activation of LILRB4 reporter cells (FIG. 35d). The binding of APOE to THP-1 cells was significantly decreased by LILRB4 KO (FIG. 35e).

The inventors confirmed the specific binding of recombinant APOE to LILRB4 using surface plasmon resonance (SPR), bio-layer interferometry (Octet) and microscale thermophoresis (MST), with a dissociation constant of 2 nM as determined by SPR (FIG. 35f and FIG. 39). APOE (SEQ ID: 282) contains two functional domains, the N-terminal domain that contains its receptor LDLR binding site (residues 136-150), and a C-terminal domain (residues 222-299). To determine which domain of APOE is required for binding to LILRB4, the inventors generated a N-terminal mutant (Mut-N: R142A/K143A/R145A/K146A/R147A/R150A) and two C-terminal mutants (Mut-C1: deletion of residues 245-299; and Mut-C2: deletion of residues 279-299) of human APOE. The N-terminal mutant significantly reduced the LILRB4 activation (FIG. 35g). The inventors further designed a series of site-specific mutations in amino acids potentially critical to the binding of ligand to LILRB4 based on the molecular modeling of LILRB4 to APOE (FIGS. 40a-40b). The inventors found that P35 and W106 in the first Ig-domain and Y121 in the linker region between two Ig-domains are critical for APOE activation of the LILRB4 reporter (FIG. 35h). APOE activation of the immune inhibitory receptor LILRB4 is in line with the well-documented immune-suppressive function of APOE.

To further determine whether ApoE regulates LILRB4 function, the inventors compared the homing of mouse C1498 AML cells with and without ectopic-expressing LILRB4 in wild-type and apoe-knockout mice. Expression of LILRB4 significantly increased C1498 cell homing to bone marrow and liver in wild-type mice, but not in APOE-null recipients (FIGS. 35i-35l). Together, APOE binds and activates LILRB4 to support migration of human acute monocytic leukemia cells.

Example 5

This example illustrates rabbit monoclonal antibodies against LILRB4 and epitope binning of the anti-LILRB4 antibodies provided herein.

Figure 18F:
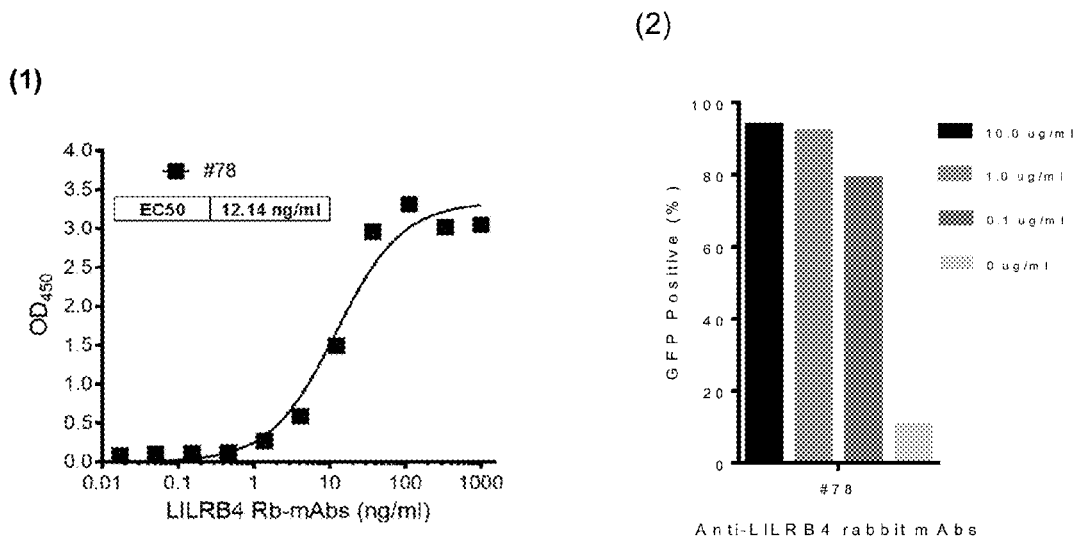

Using the reporter assay system described in FIG. 33a, the inventors tested the single B cell clones from rabbit immunization for their effects on activation of LILRB4. As shown in FIG. 41a, 18 rabbit clones activated LILRB4. From the 18 rabbit B cell clones, 21 anti-LILRB4 rabbit monoclonal antibodies were generated. The inventors also tested whether the 21 anti-LILRB4 rabbit monoclonal antibodies can block APOE-mediated activation of LILRB4. As shown in FIG. 41b, antibody #128-3 and #216-1 block the APOE activation of LILRB4 according to the LILRB4 reporter assays.

The inventors further measured the binding of the 21 anti-LILRB4 rabbit monoclonal antibodies using an ELISA assay. The results showed that all these 21 monoclonal antibodies are high binders, with $EC_{50}$ from 0.05 to 0.3 nM (FIG. 42 and Table 1). The activation of LILRB4 reporter by the 21 anti-LILRB4 rabbit monoclonal antibodies was also tested. The results showed that 19 monoclonal antibodies activated LILRB4 when coating antibodies in plates, as shown in FIG. 43.

The inventors then conducted BLI analysis of the 21 anti-LILRB4 rabbit monoclonal antibodies using classic sandwich epitope binning assay. The results are shown in FIG. 44 and the node plot of the epitope bins of the 21 rabbit anti-LILRB4 rabbit monoclonal antibodies are shown in FIG. 45. This effort identified seven epitope bins (bin 1 to bin 7) for these 21 monoclonal antibodies. For each eqitope bin, one representative antibody (#216-2: bin 1; #140: bin 2; #129: bin 3; #128-3: bin 4, #210: bin 5; #8: bin 6 and #139: bin 7) was selected for the following ELISA assays.

The inventors also tested the cross-reactivity of representative anti-LILRB4 antibodies for their binding to other LILRBs. The results are shown in FIG. 46. Antibody #216-2 (bin 1) has cross-reactivity with LILRB1, LILRB2 and LILIR5 except LILRB4. Antibody #210 (bin 5) has cross-reactivity with LILRB3 and LILRB5 except LILRB4. Antibody #139 (bin 7) has cross-reactivity with LILRB2, LILRB3 and LILRB5 except LILRB4. Antibody #140 (bin 2), #129 (bin 3), #128-3 (bin 4) and #8 (bin 6) are LILRB4 specific antibodies.

The extracellular domain (ECD) of LILRB4 contains four regions: signal peptide region (SP domain, residues 1-27), the first Ig-like domain (D1 domain, residues 27-118), the second Ig-like domain (D2 domain, residues 119-218, which contains linker region, residues 119-123) and the stalk region (SR domain, residues 219-259). To investigate to which region the antibodies provided herein specifically bind, the inventors generated a series mutated forms of LILRB4 ECD-Fc fusion proteins as shown in FIG. 47. The results of the binning assay using these LILRB4 ECD-Fc fusion proteins for the representative antibodies are shown in FIG. 48. Among the seven epitope bins, three epitope bins (bin 3, bin 4 and bin 5) are located on D1, one epitope bin (bin 7) on D2 and three epitope bins (bin 1, bin 2 and bin 6) are on SR.

Among the 21 rabbit anti-LILRB4 antibodies, the inventors found the antibody #128-3 of particular interest as it blocks the APOE activation of LILRB4. The binning assay showed that the antibody #128-3 binds to the D1 region of LILRB4 (FIG. 49). To further analyse the antibody #128-3, the inventors simulated the interaction between the Fv domain of the antibody #128-3 and LILRB4. The simulating model showed that the antibody #128-3 binds to the "head region" of D1 domain (FIGS. 50 and 51). Detailed 128-3/LILRB4 interaction results showed that eight amino acid residues (E54, R56, E57, K78, R101, P103, V104 and W106) on D1 of LILRB4 are on the antibody #128-3/LILRB4 interface.

To further map the residues in epitopes of LILRB4 that are recognized by the antibody #128-3, the inventors generated a series LILRB4 mutated proteins with single residue mutation (FIG. 52). Considering that D1 of LILRB3 is the closest relative of LILRB4 and that antibody #128-3 is a LILRB4 specific antibody, the inventors replaced the LILRB4 amino acid by that of LILRB3 if the residues are different in LILRB4 and LILRB3. If the residues are conserved in LILRB4 and LILRB3, they were mutated to alanine. The binding assay showed that four residues (E54, R56, P103 and W106) are critical for the binding of antibody #128-3 to LILRB4. These key amino acid residues are located on the binding surface of LILRB4 by antibody #128-3 (FIG. 54). The amino acid sequences at and around the antibody #128-3 binding epitope (motif) are shown in FIG. 55. For comparison, sequences of LILRB1, LILRB2, LILRB3 and LILRB5 are aligned to LILRB4 in FIG. 55.

The inventors then analysed the domains and epitopes of LILRB4 bound by other rabbit monoclonal antibodies. The results are shown in FIGS. 56-72 and compiled in the Table 1 below.

Epitope mapping data showed that antibodies #140 (bin 2), #216-2 (bin 1) and #8 (bin 6) binding to SR of LILRB4 (FIG. 73). Antibody #216-2 recognizes a conformational epitope on SR, and amino acid sequence (PEDQPLM; SEQ ID NO: 283) is the key region for antibody #216-2 binding. Antibody # 8 recognizes a linear epitope of amino acid sequence (PTGSVP; SEQ ID NO: 284) on SR.

FIG. 74 illustrates a binding model of the representative antibodies. As shown in FIG. 74, antibody #128-3, which binds to D1 of LILRB4 can block LILRB4 activation by APOE. Antibody #216-2, which has cross-reactivity with LILRB1, LILRB2 and LILRB5 recognizes a conformational epitope on SR of LILRB4. On the other hand, LILRB4 specific antibody #8 recognizes a linear epitope on SR.

TABLE 1

| Antibody | Heavy Chain/Light chain SEQ ID NO. | EC50 (nM) | LILRB4 Domain/Epitopes bound |
|---|---|---|---|
| #6 | 39/40 | 0.07673 | D1 |
| #8 | 13/14 | 0.06289 | Stalk<br>P245, T246, G247, S248, V249, P250<br>(SEQ ID NO: 284) |
| #71-1 | 41/42 | 0.1337 | D1 |
| #78 | 11/12 | 0.08093 | Stalk<br>P238-M244 |
| #101 | 25/26 | 0.11813 | Stalk<br>S220, L221, P224, P226 |
| #120 | 9/10 | 0.07953 | Stalk<br>P238-M244 |
| #128-1 | 15/16 | 0.139 | Stalk<br>P238-M244 |
| #128-3 | 17/18 | 0.18393 | D1<br>E54, R56, P103, W106 |
| #129 | 33/34 | 0.09007 | D1 |
| #139 | 29/30 | 0.0832 | D2 |
| #140 | 19/20 | 0.18293 | Stalk<br>S220, L221, P224, P226 |
| #156-1 | 31/32 | 0.0828 | D1<br>A67, Q72 |
| #161-1 | 3/4 | 0.06907 | Stalk<br>P238-M244 |
| #161-2 | 5/6 | 0.084 | Stalk<br>P238-M244 |
| #192 | 1/2 | 0.14 | Stalk<br>P238-M244 |
| #208 | 7/8 | 0.1318 | Stalk<br>P238-M244 |
| #210 | 37/38 | 0.09967 | D1<br>A67, Q72 |
| #214 | 35/36 | 0.05091 | D1 |
| #216-1 | 21/22 | 0.30567 | D1<br>R59, A67, Y99, R101, W106 |
| #216-2 | 23/24 | 0.06468 | Stalk<br>P238-M244 |
| #223 | 27/28 | 0.08967 | D1<br>A67, Q72 |
| #C53 | 220/221 | TBD | D2 (200-211 GFSHYLLSHPSD (SEQ ID NO: 285)) |
| #C84 | 222/223 | 0.56827 | D2 (129-140 LPSPLVTSGKSV (SEQ ID NO: 286))<br>(Close to Y121) |

TABLE 1-continued

| Antibody | Heavy Chain/Light chain SEQ ID NO. | EC50 (nM) | LILRB4 Domain/Epitopes bound |
|---|---|---|---|
| #C92 | 224/225 | TBD | Stalk (219-230 GSLEDPRPSPTR (SEQ ID NO: 287)) |
| #C201 | 226/227 | TBD | D2 (173-184 AQQHQAEFPMSP (SEQ ID NO: 288)) |
| #C3 | 148/149 | TBD | LILRB3 PEPLDRNNPLEP (SEQ ID NO: 289) But cross-reacts with LILRB4 |
| #C193 | 154/155 | TBD | LILRB2 PDSVITQGSPVT (SEQ ID NO: 290) NOT cross-reacts with LILRB4 |
| #C287 | 156/157 | TBD | LILRB3 PSPVVASGGNMT (SEQ ID NO: 291) NOT cross-reacts with LILRB4 |
| #C39 | 150/151 | TBD | LILRB2 TFLLTKAGAADA (SEQ ID NO: 292) But cross-reacts with LILRB4 |
| #C102 | 152/153 | TBD | LILRB2 DAPLRLRSIHEY (SEQ ID NO: 293) NOT cross-reacts with LILRB4 |
| #C290 | 158/159 | TBD | LILRB3 DPLEILPSGVSR (SEQ ID NO: 294) But cross-reacts with LILRB4 |

TBD: to be determined.

Example 6

This example illustrates that LILRB4 expressed on leukemia cells leads to T cell suppression.

To identify novel mechanism and molecular targets for immune evasion of leukemia, the inventors analyzed the correlation between gene expression of 50 known conceptual co-stimulating and co-inhibitory receptors and the overall survivals of 173 AML patients in TCGA AML database. The inventors found that the expression of lilrb4, an immune inhibitory receptor, most significantly negatively correlated with AML patient survival.

LILRB4 has a restrictive expression pattern on normal monocytic cells, and is higher expressed in monocytic AML (or acute monocytic leukemia, which are developed from monocytic lineage and belong to FAB M4 and M5 AML subtypes) cells than in those from other subtypes of AML (FIG. 76). The inventors analyzed the surface expression of LILRB4 on leukemia blasts from 118 AML patient samples from the UT Southwestern Medical Center (UTSW), and found that LILRB4 was only present on the blasts of M4 and M5 monocytic AML but not on other AML subtypes (FIG. 77a). These results are consistent with a previous report that LILRB4 is a specific marker for monocytic AML. Importantly, LILRB4 levels were higher on monocytic AML cells than on normal monocytes (FIGS. 77b-77c), and is not expressed on normal hematopoietic stem cells (HSCs) (FIG. 78). These results suggest that LILRB4, a monocytic AML marker, represents an attractive target for treating this type of leukemia.

To test whether LILRB4 expressed on AML cells have immune-suppressive function, the inventors co-cultured LILRB4-positive or LILRB4-negative leukemia cells, or normal hematopoietic cells with either autologous T cells or T cells from healthy donors. LILRB4-positive monocytic AML cells significantly suppressed T cell proliferation (FIGS. 79a-79f). The inventors then deleted LILRB4 in the human monocytic AML THP-1 cells using an inducible CRISPR/Cas9 system with lilrb4-specific guide RNA. The T cell suppressive ability of THP-1 cells was lost upon lilrb4 knockout (KO) (FIGS. 77d-77f). Conversely, forced expression of wild-type lilrb4, but not the intracellular domain-deleted mutant lilrb4, on lilrb4-KO THP-1 cells, rescued such T cell inhibitory function (FIGS. 77d-77f). Therefore, LILRB4 on tumor cells efficiently suppresses human T cell activity, and this function of LILRB4 depends on its intracellular signaling domain. This is in contrast to a previous study reporting that the extracellular domain of LILRB4 was responsible for inhibition of T cell activities. Surprisingly, the separation of wild-type THP-1 cells and human T cells in transwells still enabled T cell inhibition. In contrast, the lilrb4-KO THP-1 cells lost this ability.

The inventors sought to determine if antagonizing LILRB4 could prevent AML development by reversing LILRB4-mediated immune inhibition. Although anti-LILRB4 had no effect on cell activation or proliferation of T cells or THP-1 cells per se (FIGS. 80a-80b), anti-LILRB4 antibody treatment blocked the LILRB4-mediated T cell suppression. Furthermore, the treatment of this blocking antibody significantly decreased THP-1 cell number and increased CTL number and cytokine production by CTLs, in a co-culture of THP-1 cells and CTLs (FIG. 77g-77k). Together, these in vitro results indicate that LILRB4 expressed by AML cells inhibits T cell activity, and that anti-LILRB4 blocking antibody reverses this immune checkpoint function, making tumor cells susceptible to cytotoxic killing by T cells.

Example 7

This example illustrates that LILRB4 supports infiltration of leukemia cells.

One of the characteristic features of monocytic AML is enhanced extramedullary infiltration of tumor cells. The inventors observed that the antibody blockade of LILRB4 results in significant decrease of leukemic infiltration into internal organs, including bone marrow, liver, and brain. The inventors hypothesized that, in addition to T cell inhibition, LILRB4 can promote leukemia infiltration for immune evasion. To test this hypothesis, the inventors performed trans-endothelial migration and homing assays and monitored leukemia infiltration relative to LILRB4 expression. LILRB4 KO in human AML THP-1 cells decreased trans-endothelial migration in vitro (FIG. 81a), reduced short-term (20 hours) homing to liver and bone marrow (FIG. 81b), lowered long-term (21 days) engraftment to hematopoietic organs (FIG. 81c), prolonged survival of xenografted mice (FIG. 81d), and delayed the body weight loss (FIG. 81e). In contrast, forced expression of human LILRB4 in mouse AML C1498 or WEHI-3 cells had the opposite effects (FIGS. 81f-j and FIG. 82). Of note, KO or ectopic expression of LILRB4 did not significantly affect leukemia growth in vitro and in vivo (FIG. 83a-b). Because NSG mice are defective of functional T cells, these results, especially those from the xenograft experiments, reveal a distinct role of LILRB4 in AML—to promote migration and leukemia infiltration. This is consistent with previous studies showing that the frequency of circulating LILRB4+ AML blasts is significantly lower than that of the LILRB4-AML blasts and LILRB4+ chronic lymphocytic leukemia cells more commonly associate with lymphoid tissue involvement.

To further investigate whether LILRB4 regulates cell migration/infiltration, the inventors treated LILRB4-positive (THP-1 and MV4-11) and LILRB4-negative (U937) human AML cells (FIG. 84) with anti-LILRB4 antibodies in in vitro transwell and in vivo homing assays and a xenograft model. The inventors found that antibody-mediated LILRB4 blockade had the same effect as LILRB4 KO for LILRB4-expressing MV4-11 and THP-1 AML cells (FIG. 81k-t) but had no effect on U937 cells that do not express LILRB4 (FIG. 85). Importantly, whole animal and ex vivo bioluminescence imaging showed anti-LILRB4 antibody significantly blocked leukemia infiltration into lung, liver, bone marrow, brain, kidney, spleen and gastrointestinal tract (FIGS. 81u-v, FIG. 86 and FIG. 87).

Example 8

This example illustrates synergistic effect of anti-LILRB4 antibody with chemotherapy drugs.

LILRB4 may become the Achilles' heel for acute monocytic leukemia and thus represents an ideal target for treating this disease. Targeting LILRB4 may reactivate multiple immune cell types including T cells and perhaps monocytes/macrophages, block tumor infiltration into tissues/organs, and directly kill tumor cells (by antibody-dependent cell-mediated cytotoxicity or phagocytosis), thus perfectly combining immunotherapy and targeted therapies. In addition, anti-LILRB4 may retain leukemia cells in peripheral blood (FIG. 89) and a combination of LILRB4 targeting with other therapies such as chemo-treatment can be beneficial as the anti-LILRB4 treatment results in migration of leukemia cells out of niche into the blood stream where these cells may be more susceptible to cytotoxic chemotherapy (FIG. 90). Importantly, the functional dependence of acute monocytic leukemia on LILRB4 suggests that the possibility of LILRB4 downregulation-led drug resistance for the LILRB4 blockade strategy is low. Even more, because LILRB4 is restrictively expressed on normal monocytic cells but is expressed at higher levels on human monocytic AML cells, and anti-LILRB4 blocking antibody didn't affect normal HSC homing (FIG. 91) and normal haematopoiesis in human cord blood cell-reconstituted mice (FIG. 92), LILRB4 targeting may have minimal toxicity.

The inventors identified new mechanisms for tumor progression and immune evasion of acute monocytic leukemia, and also demonstrated that an ITIM-containing receptor can initiate primary immune escape signaling in tumor cells. To evade immune attack, acute monocytic leukemia depends on LILRB4 for T cell inhibition; different from a previous finding, these data indicate that the intracellular signaling of LILRB4 in cancer cells is required for this immune suppression. Consistently, LILRB4 guides tumor cells to migrate to internal organs/tissues including the immune privileged sites. Of note, this also explained the characteristic extramedullary infiltration of monocytic AML.

The tumor invasion mechanisms for acute monocytic leukemia as the inventors have demonstrated are unique. Different from the direct immune inhibition through cell-cell contact as exemplified by PD-L1/PD-1 engagement, these leukemia cells utilize LILRB4-mediated signaling to infiltrate into tissues and suppress T cell activities—thus to create a new immune suppressive microenvironment. The inventors' finding suggests that a tumor blockade strategy that is different from the existing ones is needed to treat acute monocytic leukemia.

Besides AML, LILRB4 may play roles in other hematopoietic malignancies and solid cancers. LILRB4 is unregulated in chronic lymphocytic leukemia and certain solid cancer cells. LILRB4 is also expressed on tumor-associated macrophages, myeloid-derived suppressor cells, and tolerogenic dendritic cells, likely contributing to an immune-suppressive environment for many tumors. An extrapolation of these results in AML may suggest that LILRB4 potentially promotes metastasis of LILRB4-positive solid cancer cells. Moreover, monocytic cells are reported to be the source of IL-6, the main cytokine responsible for the life-threatening cytokine release syndrome associated with some immunotherapies. Targeting these LILRB4-postive monocytic cells may thus control the cytokine release syndrome. Blocking LILRB4 signaling may prove to be a novel strategy for treating different types of cancers with minimal side effects.

Example 9

Mice. C57 BL/6J and NOD-scid IL2Rγ null (NSG) mice were purchased from and maintained at the animal core facility of University of Texas Southwestern Medical Center (UTSW). APOE-null mice were previously described. All animal experiments were performed with the approval of the Committee on Animal Care.

Chimeric receptor reporter cells. The inventors constructed a stable chimeric receptor reporter cell system as described to test the ability of a ligand to bind to the ECD of individual LILRBs, PirB, and gp49B1 and to trigger the activation or inhibition of the chimerically fused intracellular domain of paired immunoglobulin-like receptor 13, which signals through the adaptor DAP-12 to activate the NFAT promoter. If an agonist or antagonist binds the ECD and activates or suppresses the chimeric signaling domain, an increase or decrease, respectively, in GFP expression is observed.

APOE competition assay was used to screen LILRB4 blocking antibodies. Briefly, APOE proteins were pre-coated on 96-well plate at 37° C. for 3 hrs. After 2 times washing by PBS, $2 \times 10^4$ LILRB4 reporter cells were seeded in each well; meanwhile, indicated anti-LILRB4 antibodies were added into culture media. After 16 hrs, the percentage of GFP$^+$ reporter cells was analysed by flow cytometry.

K562 co-culture assay was used to screen anti-LILRB4 antibodies that may enhance LILRB4 activity. Briefly, $2 \times 10^4$ LILRB4 reporter cells and $2 \times 10^4$ K562 cells were mixed and cultured in a well of 96-well plate; meanwhile, indicated anti-LILRB4 antibodies were added into culture media. After 16 hrs, the percentage of mouse CD45$^+$ GFP$^+$ cells was determined by flow cytometry.

Flow cytometry. For flow cytometry analyses of mouse AML cells, peripheral blood or bone marrow cells were stained with anti-Mac-1-APC (M1/70, BD Pharmingen), anti-Gr-1-PE (RB6-8C5, BD Pharmingen), anti-CD3-APC (145-2C11, BD Pharmingen), anti-B220-PE (RA3-6B2, BD Pharmingen), or anti-Kit-PE (B8, BD Pharmingen) monoclonal antibodies. For analysis of human hematopoietic engraftment in NSG mice, a previously published protocol was followed. The inventors used anti-human CD45-PE (HI30, BD Pharmingen), anti-human CD34-FITC (555821, BD Pharmingen), anti-human CD19-PE (HIB19, eBioscience), anti-human CD2O-PE (555623, BD Pharmingen), anti-human CD11b-APC (ICRF44, eBioscience), anti-human LILRB4-APC (ZM4.1, eBioscience), anti-human CD14-APC (61D3, eBioscience), anti-human CD4-APC (RPA-T4, eBioscience), anti-human CD8-PE (555367, BD Pharmingen), anti-human CD28-APC (CD28.2, eBioscience), and anti-human CD40L-APC (24-31, eBioscience) antibodies to quantify the engraftment of different human hematopoietic lineage cells.

Virus construction/infection and AML transplantation. For virus packaging, retroviral constructs MSCV-MLL-AF9-IRES-YFP, XZ201-IRES-GFP, XZ201-LILRB4-IRES-GFP were mixed with PCL-ECO (2:1), followed by transfection into 293T cells using Lipofectamine 2000 (Invitrogen, Calif.). Virus-containing supernatant was collected 48-72 hours post-transfection and used for infection as described previously. Infected mouse Lin⁻ cells ($3 \times 10^5$) or mouse leukemia C1498 cells ($1 \times 10^6$) were transplanted into lethally irradiated (1,000 rad) or sub-lethally irradiated (250 rad) C57BL/6J mice (6-8 weeks old) by retro-orbital injection. C1498 cells were purchased from ATCC. For the secondary transplantation, the inventors used FACS to isolate YFP⁺ BM cells from primary recipient mice and transplanted 3000 cells into non-irradiated recipient mice including wild-type C57BL/6J and APOE-null mice. The inventors monitored the survival, examined the size and histological properties of bone marrow, spleen, and liver, and analysed the numbers and infiltration of leukemia cells in peripheral blood, bone marrow, spleen, and liver. The inventors also determined the different populations of leukemia cells using flow cytometry.

Human and mouse leukemia cells. Primary human AML samples were obtained from UTSW. Informed consent was obtained under a protocol reviewed and approved by the Institutional Review Board at UTSW. The UTSW cohort included 105 AML patients, representative of AML subtypes M1 (n=9), M2 (n=34), M3 (n=10), M4 (n=34), M5 (n=25), M6 (n=2), and M7 (n=1) and patients with undifferentiated leukemia (AUL; n=1) and transient myeloproliferative disorder (TAM; n=2). LILRB4 expression of samples were analysed by flow cytometry. Human leukemia cells (THP-1, MV4-11, and U937) and mouse leukemia cells (WEHI-3) (purchased from the ATCC) were cultured in RPMI-1640 supplemented with 10% FBS at 37° C. in 5% $CO_2$ and the normal level of $O_2$. Mouse leukemia cells (C1498) (purchased from the ATCC) were cultured in DMEM supplemented with 10% FBS at 37° C. in 5% $CO_2$ and the normal level of $O_2$.

TCGA analyses. Data were obtained from the TCGA acute myeloid leukemia database (Version: Oct. 29, 2015). The patients were classified into AML subtypes MO (n=16), M1 (n=42), M2 (n=39), M3 (n=16), M4 (n=35), M5 (n=18), M6 (n=2), M7 (n=3);

two cases were not classified by subtype. The levels of LILRB4 mRNA were determined by RNAseq (Illumina-HiSeq). RESM-normalized counts are reported, and data were visualized with UCSC Xena (xena.ucsc.edu). For analysis of overall survival, 160 patients with available survival data were separated into three groups based on whether they had high (n=55), moderate (n=48), or low (n=57) LILRB4 expression.

Bio-layer Interferometry. Analyses of the binding interactions between LILRB4-Fc with APOE2, APOE3, and APOE4 were performed using the Octet RED96 (ForteBio, Pall Corporation). All assays were performed with the protein A dip-and-read biosensors (ForteBio) to capture LILRB4-Fc in a kinetics assay buffer (Fortebio), both association (300 s) and dissociation (600 s) of APOEs were monitored. Background wavelength shifts were measured from reference sensors with loading of LILRB4-Fc only and buffer.

Microscale Thermophoresis (MST). MST experiments were performed on a Monolith NT.115 system (NanoTemper Technologies) using 80% LED and 20% IR-laser power. Laser on and off times were set at 30 s and 5 s, respectively. Recombinant LILRB4-ECD protein (SinoBio) was labeled with 4488-NHS (NanoTemper Technologies) and applied at a final concentration of 5.9 nM. A two-fold dilution series was prepared for unlabeled His-APOE (#CI06, Novoprotein) in PBS and each dilution point was similarly transferred to LILRB4-ECD solution. The final concentrations of His-APOE ranged from 12 µM to 0.36 nM. Samples were filled into standard-treated capillaries (NanoTemper Technologies) for measurement.

Tumor cell/T cell co-culture assay. Human T cells isolated from health donor peripheral blood (PB009-1-0, Allcells) were co-cultured with irradiated (28 Gy) THP-1 cells in a U-bottom 96 well-plate for 3-7 days. Anti-CD3/CD28-coated beads (#11161D, Thermo Fisher), 50 U/ml recombinant human IL-2, and 5 ng/ml recombinant human IL-7 were supplemented to the medium. In some experiments, THP-1 cells were cultured in the upper chamber of transwell inserts (pore size is 3 µM, #09-761-80, Thermo Fisher) for the U-bottom 96 well-plate. For primary AML or B-ALL samples, patient CD3⁺ T cells were collected and patient leukemia cells were sorted as CD33⁺ and CD19⁺ for AML and B-ALL, respectively.

CD8⁺ T cells ($5 \times 10^4$ per well) isolated from hPBMCs of a healthy donor (Interstate Blood Bank) were stimulated with anti-CD3/CD28/CD137-coated beads (11163D, Thermo Fisher) or cultured without stimulation for 2 days in a 96-well plate. Then, $5 \times 10^3$ human leukemia THP-1-Luc-GFP cells and 50 to 500 µg/ml anti-LILRB4 antibody C84 or control antibody mIgG were added. Cell numbers were determined on day 7 in triplicate wells. Anti-CD8 and anti-CD28 were used to detect human CTL cells; THP-1 cells were positive for GFP. Cell supernatants from co-cultures of stimulated CTL cells and THP-1 cells treated with C84 or mIgG were used to examine cytokine production using human cytokine arrays (AAH-CYT-6, RayBiotech). The experiment was repeated three times with similar results.

Transwell assay. To test the cell plasticity, $1 \times 10^5$ MV4-11 cells were labelled with CFSE (Invitrogen) and treated with 100 µg/ml of anti-LILRB4 antibody C84 or control antibody mIgG and cultured in the upper chamber of well in a transwell plate (Corning). After 18 h, cells in lower chamber were counted. To test the ability of AML cells to migrate through endothelial cells, $3 \times 10^5$ human umbilical vein endothelial cells (HUVEC) cells were cultured on the transwell membrane. After 3 days, $1 \times 10^5$ CFSE-labelled MV4-

11 cells were seeded in the upper chamber with 100 µg/ml of C84 or mIgG. After 18 h, cells in lower chamber were counted.

Homing and mobilization of leukemia and HSC cells. CFSE-labelled MV4-11 cells ($5 \times 10^6$ cells per mouse) were injected intravenously into NSG mice. Animals were treated with 200 µg of control antibody mIgG or anti-LILRB4 antibody C84 or 10% serum immediately after injection of leukemia cells. Mice were sacrificed after 8 or 20 h. Peripheral blood, bone marrow, liver, and spleen were harvested, and single-cell suspensions were examined by flow cytometry. CFSE or anti-human CD45 was used to detect human leukemia cells. Numbers of leukemia cells in recipient liver, spleen, and bone marrow are reported as a percentage relative to cell numbers in peripheral blood. To test HSC homing, $1 \times 10^7$ human cord blood mononuclear cells were injected intravenously into an NSG mouse. Mice were treated with 200 µg of mIgG or C84 immediately after injection of mononuclear cells and were sacrificed after 20 h. Anti-human CD45 and anti-human CD34 were used to detect human HSCs by flow cytometry. To test the homing of mouse leukemia cells, $5 \times 10^6$ C1498-GFP-hLILRB4 cells or C1498-GFP were injected intravenously into wild-type C57BL/6J or APOE-null mice. Mice were sacrificed after 20 h. GFP was used to detect leukemia cells by flow cytometry. The number of leukemia cells in recipient liver, spleen, and bone marrow were normalized to numbers in peripheral blood and are reported as a percentage. To test mobilization of leukemia cells, $5 \times 10^6$ MV4-11 cells were injected intravenously into each NSG mouse. Three days after transplantation, mice were injected intravenously with 200 µg C84 or mIgG. The day of first administration was assigned as day 0. Mice were then treated with another dose of 200 µg C84 or mIgG, respectively, on the next day. Leukemia cells in peripheral blood were examined at 4 hr (on day 0) and at 1 and 4 days after first administration of antibodies. Mice were sacrificed on day 4. Anti-human CD45 was used to detect human leukemia cells by flow cytometry.

Human AML xenograft. Briefly, 6-8 week-old NSG mice were used for transplantation. Human leukemia cells were resuspended in 200 µl PBS containing 1% FBS. Mice were given $1 \times 10^6$ human cultured leukemia cells or 5 to $10 \times 10^6$ human primary AML cells via tail-vein injection. One to four months after transplantation, the peripheral blood, bone marrow, spleen, and liver were assessed for the engraftment.

For hPBMC xenograft model, $1 \times 10^7$ human PBMCs were injected intravenously into each NSG mouse. Three weeks after implantation, mice had 30 to 50% engraftment of human T cells. At 3 weeks post implantation, $1 \times 10^6$ human AML THP-1 cells that stably express luciferase (THP-1-Luc-GFP cells) were subcutaneously implanted. Mice were immediately given 200 µg C84 or mIgG intravenously and were treated twice a week until euthanization. Tumor growth was monitored over time by luminescence imaging.

For the human cord blood (hCB) HSC reconstituted xenograft model, $3 \times 10^4$ human cord blood CD34$^+$ cells were injected intravenously via the retro-orbital route into sub-lethally irradiated (2.5 Gy) 6-8 weeks old NSG mice. Multi-lineage human hematopoietic reconstitution was confirmed at various time points between day 21 and day 41 post-transplantation by flow cytometry. At day 42, $1 \times 10^6$ human THP-1-Luc-GFP cells were intravenously implanted. The mice were immediately given 200 µg C84 or mouse IgG by intravenous injection. Tumor growth was monitored over time by luminescence imaging. Multi-lineage human hematopoietic reconstitution was examined at various time points at day 12 to day 24 post-transplantation of leukemia cells by flow cytometry. CD19 and CD20 were used to identify human B cells; CD11b, CD14, and LILRB4 human myeloid cells; CD4, CD8, CD28, and CD40L populations of human T cells.

For survival curve experiments, the death of mice was recorded when the moribund animals were euthanized.

CRISPR/Cas9-based LILRB4 knockout in AML cells. THP1 cells were infected with doxycycline-inducible Cas9-expressing lentivirus (pCW-Cas9, Addgene 50661). After 1 µg/ml puromycin selection, the survived cells were infected with sgRNA-expressing lentivirus, produced by the plasmid modified from pSLQ1651 (Addgene 51024) by replacing the puro-mcherry with GFP for sorting. One control sgRNA (control sgRNA 5'-GAACGACTAGTTAGGCGTGTA-3' (SEQ ID NO: 295)) and three LILRB4 targeting sgRNA (sgRNA1 5'-TGTTACTATCGCAGCCCTGT-3' (SEQ ID NO: 296); sgRNA2 5'-GTAGGTCCCCCCGTGCACTG-3' (SEQ ID NO: 297); sgRNA3 5'-CCTGTGACCTCAGTG-CACGG-3' (SEQ ID NO: 298)) which were designed by an online tool, were cloned into the sgRNA plasmid, respectively. After treated with 1 µg/ml doxycycline for 1 week, these cells were staining with anti-LILRB4 antibody and the LILRB4 negative cells were sorted as LILRB4 knockout cells.

SDS-PAGE and Cytoplasmic/nuclear protein isolation. For SDS-PAGE, samples were mixed with 4× loading buffer with β-mercaptoethanol (BME) and loaded on 10% SDS gels. Nuclear and cytoplasmic cellular compartments were isolated by NE-nuclear/cytoplasmic extraction kit (#78833, Thermo Fisher) and these protein extracts were mixed with 4× loading buffer with β-mercaptoethanol (BME) and loaded on 10% SDS gels. Anti-SHP-1 (#3759), anti-SHP-2 (#3397), anti-SHIP (#2727), anti-phospho-SHP-2 (Tyr580) (#3703), anti-Nf-kB p65 (#8242), anti-IKKa (#11930), anti-IKKb (#8943), anti-phospho-IKKa/b (Ser176/180) (#2697), anti-phospho-Stat1 (Tyr701) (#7649), anti-phospho-Stat-3 (Ser727) (#9134), anti-Lamin-B2 (#12255) and anti-Arginase-1 (#9819) were purchased from Cell Signaling Technology Inc. Anti-uPAR antibody (MON R-4-02, Thermo Fisher) and anti-alpha-tubulin (#MABT205, Sigma) were purchased from other companies.

RNA-seq analysis. RNA was purified from sorted cells with Qiagen RNeasy Mini Kit and then reverse-transcribed with SuperScript III Reverse Transcriptase (Invitrogen) according to the manufacturer's instructions. RNA-seq was performed at the UTSW Genomics and Microarray Core Facility. The cDNA was sonicated using a Covaris S2 ultrasonicator, and libraries were prepared with the KAPA High Throughput Library Preparation Kit. Samples were end-repaired and the 3' ends were adenylated and barcoded with multiplex adapters. PCR-amplified libraries were purified with AmpureXP beads and validated on the Agilent 2100 Bioanalyzer. Before being normalized and pooled, samples were quantified by Qubit (Invitrogen) and then run on an Illumina Hiseq 2500 instrument using PE100 SBS v3 reagents to generate 51-bp single-end reads. Before mapping, reads were trimmed to remove low-quality regions in the ends. Trimmed reads were mapped to the human genome (HM19) using TopHat v2.0.1227 with the UCSC iGenomes GTF file from Illumina.

Methods for data normalization and analysis are based on the use of "internal standards" that characterize some aspects of the system's behavior, such as technical variability, as presented elsewhere. Genes with $\log_2$ (fold change) >2, P<0.01 and RPKM>0.1 were deemed to be significantly differentially expressed between the two conditions, and used for pathway analysis and upstream transcription factor analysis. Pathway analysis was conducted using the DAVID. Upstream transcription-factor analysis was conducted using QIAGEN's Ingenuity tool. Gene heat maps were clustered by hierarchical clustering (Cluster and Java Treeview).

Quantitative RT-PCR. Total RNA was extracted using RNAeasy kit (QIAGEN) and reverse transcribed into cDNA using SuperScript III Reverse Transcriptase (Invitrogen) according to the protocol provided. Real-time PCR was performed with the primers listed in Table 2 using SYBR Green Master Mix (Bio-Rad). mRNA levels were normalized to the level of GAPDH or 18S rRNA transcripts present in the same sample.

Statistical analyses. Data are expressed as means±SEM. Data were analysed by Student's t test and were considered statistically significant if p<0.05. The survival rates of the two groups were analysed using a log-rank test and were considered statistically significant if p<0.05. In all figures, * indicates p<0.05;  indicates p<0.01; * indicates p<0.001; **** indicates p<0.0001; otherwise, p values are represented as precise values.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Abe and Kufe, *Cancer Res.*, 49(11):2834-2839, 1989.
Ahmad et al., *Nat. Cell Biol.*, 9:1419-1427, 2007.
Allred et al., *Arch. Surg.*, 125(1), 107-113, 1990.
Atherton et al., Biol. of Reproduction, 32, 155-171, 1985.
Baldus et al., *Clin. Cancer Res.*, 10(8):2790-2796, 2004.
Beidler et al., *J. Immunol.*, 141(11):4053-4060, 1988.
Brown et al., *J. Immunol. Meth.*, 12;130(1), :111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
Daeron et al., *Immunol Rev* 224, 11-43, 2008.
De Jager et al., *Semin. Nucl. Med.* 23(2), 165-179, 1993.
Deng et al. *Blood*, 124(6):924-35, 2014.
Dholakia et al., *J. Biol. Chem.*, 264, 20638-20642, 1989.
Doolittle and Ben-Zeev, *Methods Mol. Biol.*, 109, 215-237, 1999.
Duraisamy et al., *Gene*, 373:28-34, 2006.
EP Application 125,023
EP Application 171,496
EP Application 173,494
EP Application 184,187
Gefter et al., *Somatic Cell Genet.*, 3:231-236, 1977.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Gulbis and Galand, *Hum. Pathol.* 24(12), 1271-1285, 1993.
Guo et al., *Sci. Transl. Med.* 3:99 ra85, 2001.
Hodel et al., *Mol. Cell*, 10(2):347-58, 2002.
Huang et al., *Cancer Biol Ther.*, 2:702-706, 2003.
Huang et al., *Cancer Res.*, 65:10413-10422, 2005.
Jones et al., *Nature*, 321:522-525, 1986.
Kau et al., *Nat. Rev. Cancer*, 4(2):106-17, 2004.
Khatoon et al., *Ann. of Neurology*, 26, 210-219, 1989.
King et al., *J. Biol. Chem.*, 269, 10210-10218, 1989.
Kinlough et al., *J. Biol. Chem.*, 279(51):53071-53077, 2004.
Kinoshita et al., *Biochem. Biophys. Res. Commun.*, 394:205-210, 2010.
Kohler and Milstein, *Eur. J. Immunol.*, 6, 511-519, 1976.
Kang et al., *Nature Cell Biology* 17(5):665-677, 2015.
Katz, H. R., *Adv Immunol* 91, 251-272, 2006.
Kohler and Milstein, *Nature*, 256, 495-497, 1975.
Kufe et al., *Hybridoma*, 3:223-232, 1984.
Kyte and Doolittle, *J. Mol. Biol.*, 157(1):105-132, 1982.
Leng et al., *J. Biol. Chem.*, 282:19321-19330, 2007.
Levitan et al., *J. Biol. Chem.*, 280:33374-33386, 2005.
Li et al., *Cancer Biol. Ther.*, 2:187-193, 2003b.
Li et al., *J. Biol. Chem.*, 276:35239-35242, 2001.
Li et al., *J. Biol. Chem.*, 276:6061-6064, 2001.
Li et al., *Mol. Cancer Res.*, 1:765-775, 2003c.
Li et al., *Mol. Cell Biol.*, 18:7216-7224, 1998.
Li et al., *Oncogene*, 22:6107-6110, 2003a.
Ligtenberg et al., *J. Biol. Chem.*, 267, 6171-6177, 1992.
Krivtsov et al., *Nature*, 442(7104): p. 818-22, 2006.
Ma et al., *Immunity* 34, 385-395, 2011.
Macao, Nat. Struct. Mol. Biol., 13, 71-76, 2006.
Merlo et al., *Cancer Res.*, 49, 6966-6971, 1989.
Mori et al., *J. Immunol* 181, 4742-4751, 2008.
Morrison, *Science*, 229(4719):1202-1207, 1985.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.

Owens and Haley, *J. Biol. Chem.*, 259, 14843-14848, 1987.
Owens and Haley, *J. Biol. Chem.*, 259:14843-14848, 1987.
PCT Application PCT/US86/02269
PCT Application WO 86/01533
Percipalle et al., *J. Mol. Biol.*, (4):722-32, 1997.
Perey et al., *Cancer Res.*, 52(22):6365-6370, 1992.
Persic et al., *Gene* 187:1, 1997
Posner et al., *Hybridoma* 6, 611-625, 1987.
Potter and Haley, *Meth. Enzymol.*, 91, 613-633, 1983.
Raina et al., *EMBO J.*, 25:3774-3783, 2006.
Raina et al., *J. Biol. Chem.*, 279:20607-20612, 2004.
Remington's Pharmaceutical Sciences, 15th Ed., 3:624-652, 1990.
Ren et al., *Cancer Cell*, 5:163-175, 2004.
Ren et al., *J. Biol. Chem.*, 277:17616-17622, 2002.
Rojo et al., *Mol Cell Biol*, 20(19): p. 7178-82, 2000.
Ryan and Wente, *Curr. Opin. Cell Biol.*, 12(3):361-71, 2000.
Schroeder et al., *J. Biol. Chem.*, 276(16):13057-13064, 2001.
Schroeder et al., *Oncogene*, 23:5739-5747, 2004.
Shaw et al., *J. Natl. Cancer Inst.*, 80(19):1553-1559, 1988.
Siddiqui et al., *Proc. Natl. Acad. Sci. USA*, 85:2320-2323, 1988.
Somervaille and Cleary, *Cancer Cell*, 10(4): p. 257-68, 2006.
Sugihara et al., *Oncogene*, 31:2849-61, 2011.
Suh and Gumbiner, *Exp. Cell Res.*, 290(2):447-56, 2003.
Sun et al., *J. Steroid Biochem.*, 26(1):83-92, 1987.
Sun et al., *Chest* 134: 783-788, 2008.
Takai et al., T, *J Biomed Biotechnol*, 2011:275302, 2011.
Tang et al., *J Immunol*, 188(2): p. 548-58, 2012.
Tang et al., *J. Biol. Chem.*, 271:28324-28330, 1996.
Truscott et al., *J Cell Biol.*, 163(4):707-713, 2003.
Verhoeyen et al., *Science*, 239(4847):1534-1536, 1988.
Vermeer et al., *Nature*, 422(6929):322-6, 2003.
Wawrzynczak & Thorpe, In: *Immunoconjugates, Antibody Conuugates In Radioimaging And Therapy Of Cancer*, Vogel (Ed.), NY, Oxford University Press, 28, 1987.
Wei et al., *Cancer Cell*, 7:167-178, 2005.
Weis, *Cell*, 112(4):441-51, 2003.
Wen et al., *J. Biol. Chem.*, 278:38029-38039, 2003.
Wood et al., *J. Clin. Lab. Immunol.*, 17(4):167-171, 1985.
Yamamoto et al., *J. Biol. Chem.*, 272:12492-12494, 1997.
Yan et al., *Nat Med*, 12(8): p. 945-9, 2006.
Yin et al., *J. Biol. Chem.*, 278:35458-35464, 2003.
Yin et al., *J. Biol. Chem.*, 279:45721-45727, 2004.
Yin et al., *J. Biol. Chem.*, 282:257-266, 2007.
Young et al., *Cell.* 112(1):41-50, 2003.
Zheng et al., *Nature*, 485(7400): p. 656-60, 2012.

What is claimed is:

1. An isolated monoclonal antibody or an antigen-binding fragment that binds to LILRB4 thereof comprising:
   (a) a heavy chain variable region comprising the complementary determining regions (CDRs) of SEQ ID NOS: 73, 74 and 75 in that order; and
   a light chain variable region comprising the CDR of SEQ ID NO: 76, TAS and SEQ ID NO: 77 in that order;
   (b) a heavy chain variable region comprising the CDRs of SEQ ID NOS: 83, 84 and 85 in that order; and a light chain variable region comprising the CDRs of SEQ ID NO: 86, RAS and SEQ ID NO: 87 in that order;
   (c) a heavy chain variable region comprising the CDRs of SEQ ID NOS: 98, 99 and 100 in that order; and a light chain variable region comprising the CDRs of SEQ ID NO: 101, EAS and SEQ ID NO: 102 in that order; or
   (d) a heavy chain variable region comprising the CDRs of SEQ ID NOS: 166, 167 and 168 in that order; and a light chain variable region comprising the CDRs of SEQ ID NOS: 169, 170 and 171 in that order.

2. The isolated monoclonal antibody or an antigen-binding fragment thereof of claim 1, wherein the antigen-binding fragment is a recombinant ScFv (single chain fragment variable) antibody, Fab fragment, F(ab')$_2$ fragment, or Fv fragment.

3. The isolated monoclonal antibody or an antigen binding fragment thereof of claim 1, wherein the isolated monoclonal antibody is a chimeric, humanized, or human antibody.

4. A pharmaceutical composition comprising the isolated monoclonal antibody or an antigen-binding fragment thereof of claim 1, and a pharmaceutically acceptable carrier.

5. An isolated nucleic acid that encodes the isolated monoclonal antibody of claim 1.

6. A vector comprising the isolated nucleic acid of claim 5.

7. A host cell comprising the vector of claim 6.

8. The host cell of claim 7, wherein the host cell is a mammalian cell.

9. The host cell of claim 7, wherein the host cell is a CHO cell.

10. A hybridoma or engineered cell encoding or producing the isolated monoclonal antibody of claim 1.

11. A process of producing an antibody, comprising culturing the host cell of claim 7 under conditions suitable for expressing the antibody, and recovering the antibody.

12. A method of treating or ameliorating the effect of a cancer in a subject, the method comprising administering to said subject a therapeutically effective amount of the antibody or an antigen-binding fragment thereof of claim 1.

13. The method of claim 12, wherein the cancer is acute myeloid leukemia.

14. The method of claim 12, wherein the antibody or an antigen-binding fragment thereof is administered intravenously, intra-arterially, intra-tumorally, or subcutaneously.

15. The method of claim 12, further comprising administering to the subject one or more drugs selected from the group consisting of an anthracycline topoisomerase inhibitor, a daunorubicin, a nucleoside metabolic inhibitor, a cytarabine, a combination of daunorubicin and cytarabine, a daunorubicin and cytarabine liposome for injection, Vyxeos, an all-trans-retinoic acid (ATRA), an arsenic, an arsenic trioxide, a histamine dihydrochloride, Ceplene, an interleukin-2, Proleukin, a gemtuzumab ozogamicin, Mylotarg, a clofarabine, a farnesyl transferase inhibitor, a decitabine, an IDH1 inhibitor, an IDH2 inhibitor, an enasidenib, Idhifa, an IDO inhibitor, an epacadostat, a platinum complex derivative, oxaliplatin, a kinase inhibitor, a tyrosine kinase inhibitor, a PI3 kinase inhibitor, a BTK inhibitor, ibrutinib, a PD-1 antibody, a PD-L1 antibody, a CTLA-4 antibody, a LAG3 antibody, an ICOS antibody, a TIGIT antibody, a TIM3 antibody, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a topoisomerase inhibitor, a hormone therapy medicine, a hormone antagonist, an aromatase inhibitor, and a P-glycoprotein inhibitor.

16. A method of detecting a cancer cell or cancer stem cell in a sample or subject comprising:
   (a) contacting a subject or a sample from the subject with the antibody or an antigen-binding fragment thereof of claim 1; and
   (b) detecting binding of said antibody to a cancer cell or cancer stem cell in said subject or sample.

17. The method of claim 16, wherein the sample is a body fluid or biopsy.

18. The method of claim 16, wherein the sample is blood, sputum, tears, saliva, mucous, serum, urine or feces.

19. The method of claim 16, wherein detection comprises immunohistochemistry, ELISA, RIA or Western blot.

20. The method of claim 16, further comprising performing steps (a) and (b) a second time and determining a change in detection levels as compared to the first time.

21. The isolated monoclonal antibody or an antigen-binding fragment thereof of claim 1, further characterized as comprising:
   (a) a heavy chain variable region having an amino acid sequence at least about 90% identical to SEQ ID NO: 13; and
   a light chain variable region having an amino acid sequence at least about 90% identical to SEQ ID NO: 14;
   (b) a heavy chain variable region having an amino acid sequence at least about 90% identical to SEQ ID NO: 17; and a light chain variable region having an amino acid sequence at least about 90% identical to SEQ ID NO: 18;

(c) a heavy chain variable region having an amino acid sequence at least about 90% identical to SEQ ID NO: 23; and a light chain variable region having an amino acid sequence at least about 90% identical to SEQ ID NO: 24; or
(d) a heavy chain variable region having an amino acid sequence at least about 90% identical to SEQ ID NO: 222; and a light chain variable region having an amino acid sequence at least about 90% identical to SEQ ID NO: 223.

22. The isolated monoclonal antibody or an antigen-binding fragment thereof of claim 21, wherein
   (a) the heavy chain variable region has an amino acid sequence of SEQ ID NO: 13, and wherein the light chain variable region has an amino acid sequence of SEQ ID NO: 14 ;
   (b) the heavy chain variable region has an amino acid sequence of SEQ ID NO: 17, and wherein the light chain variable region has an amino acid sequence of SEQ ID NO: 18;
   (c) the heavy chain variable region has an amino acid sequence of SEQ ID NO: 23, and wherein the light chain variable region has an amino acid sequence of SEQ ID NO: 24; or
   (d) the heavy chain variable region has an amino acid sequence of SEQ ID NO: 222, and wherein the light chain variable region has an amino acid sequence of SEQ ID NO: 223.

23. The isolated monoclonal antibody or an antigen-binding fragment thereof of claim 21, wherein the antigen-binding fragment is a recombinant ScFv antibody, Fab fragment, F(ab')2 fragment, or Fv fragment.

24. The isolated monoclonal antibody or an antigen binding fragment thereof of claim 21, wherein the isolated monoclonal antibody is a chimeric, humanized, or human antibody.

* * * * *

UNITED STATES PATENT AND TRADEMARK OFFICE
CERTIFICATE OF CORRECTION

| | | |
|---|---|---|
| PATENT NO. | : 10,501,538 B2 | |
| APPLICATION NO. | : 15/696972 | |
| DATED | : December 10, 2019 | |
| INVENTOR(S) | : Zhang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 308

<210> SEQ ID NO 1
<211> LENGTH: 115
<212> TYPE: PRT
<213> ORGANISM: Artificial sequence
<220> FEATURE:
<223> OTHER INFORMATION: Synthetic peptide

<400> SEQUENCE: 1

Glu Gln Ser Leu Glu Glu Ser Gly Gly Gly Leu Val Thr Pro Gly Gly
1               5                   10                  15

Thr Leu Thr Leu Thr Cys Thr Val Ser Gly Phe Ser Leu Ser Asn Asn
            20                  25                  30

Ala Met Ser Trp Val Arg Gln Ala Pro Gly Lys Gly Leu Glu Trp Ile
        35                  40                  45

Gly Val Ile Leu Leu Ala Gly Pro Thr Tyr Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Ile Ala
                85                  90                  95

Ile Gly Ser Arg Pro Phe Ala Leu Trp Gly Gln Gly Thr Leu Val Thr
            100                 105                 110

Ile Ser Ser
        115

<210> SEQ ID NO 2
<211> LENGTH: 109
<212> TYPE: PRT
<213> ORGANISM: Artificial sequence
<220> FEATURE:
<223> OTHER INFORMATION: Synthetic peptide

<400> SEQUENCE: 2

Glu Leu Val Leu Thr Gln Thr Pro Ser Ser Thr Ser Ala Ala Val Gly
```

```
1               5                   10                  15
Gly Thr Val Thr Ile Asn Cys Gln Ser Ser Gln Ser Val Tyr Ser Asn
                20                  25                  30

Trp Leu Ser Trp Phe Gln Gln Lys Pro Gly Gln Pro Pro Lys Pro Leu
                35                  40                  45

Ile Tyr Leu Ala Ser Thr Leu Ala Ser Gly Val Pro Ser Arg Phe Ser
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Gly Tyr Asn Gly Asn
                85                  90                  95

Ile Tyr Thr Phe Gly Gly Gly Thr Glu Val Val Val Lys
                100                 105

<210> SEQ ID NO 3
<211> LENGTH: 112
<212> TYPE: PRT
<213> ORGANISM: Artificial sequence
<220> FEATURE:
<223> OTHER INFORMATION: Synthetic peptide

<400> SEQUENCE: 3

Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Val Tyr Leu
                20                  25                  30

Met Ser Trp Val Arg His Ser Pro Gly Lys Gly Leu Glu Tyr Ile Gly
                35                  40                  45

Phe Ile Asn Ser Ala Gly Ile Thr Ala Tyr Ala Thr Trp Ala Lys Gly
        50                  55                  60

Arg Phe Ile Ile Ser Lys Thr Ser Thr Thr Val Asp Leu Lys Val Thr
65                  70                  75                  80

Ser Pro Thr Thr Glu Asp Thr Ala Thr Tyr Phe Cys Ala Arg Asn Trp
                85                  90                  95

Ile Arg Leu Asp Leu Trp Gly Gln Gly Thr Leu Val Thr Ile Ser Ser
                100                 105                 110

<210> SEQ ID NO 4
<211> LENGTH: 110
<212> TYPE: PRT
<213> ORGANISM: Artificial sequence
<220> FEATURE:
<223> OTHER INFORMATION: Synthetic peptide

<400> SEQUENCE: 4

Glu Leu Asp Leu Thr Gln Thr Pro Ala Ser Val Ser Ala Ala Val Gly
1               5                   10                  15

Gly Thr Val Thr Ile Ser Cys Gln Ser Ser Glu Thr Ile Tyr Lys Asn
                20                  25                  30

Tyr Leu Ser Trp Phe Gln Gln Lys Pro Gly Gln Pro Pro Lys Leu Leu
                35                  40                  45

Ile Tyr Glu Ser Ser Lys Leu Ala Ser Gly Val Pro Ser Arg Phe Ser
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Thr Asp Gly
                85                  90                  95
```

```
Arg Asp Thr Ile Phe Gly Gly Gly Thr Glu Leu Glu Ile Lys
            100                 105                 110
```

<210> SEQ ID NO 5
<211> LENGTH: 112
<212> TYPE: PRT
<213> ORGANISM: Artificial sequence
<220> FEATURE:
<223> OTHER INFORMATION: Synthetic peptide

<400> SEQUENCE: 5

```
Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Val Tyr Leu
            20                  25                  30

Met Ser Trp Val Arg His Ser Pro Gly Lys Gly Leu Glu Tyr Ile Gly
        35                  40                  45

Phe Ile Asn Ser Ala Gly Ile Thr Ala Tyr Ala Thr Trp Ala Lys Gly
    50                  55                  60

Arg Phe Ile Ile Ser Lys Thr Ser Thr Val Asp Leu Lys Val Thr
65                  70                  75                  80

Ser Pro Thr Thr Glu Asp Thr Ala Thr Tyr Phe Cys Ala Arg Asn Trp
                85                  90                  95

Ile Arg Leu Asp Leu Trp Gly Gln Gly Thr Leu Val Thr Ile Ser Ser
            100                 105                 110
```

<210> SEQ ID NO 6
<211> LENGTH: 106
<212> TYPE: PRT
<213> ORGANISM: Artificial sequence
<220> FEATURE:
<223> OTHER INFORMATION: Synthetic peptide

<400> SEQUENCE: 6

```
Thr Gln Thr Pro Ala Ser Val Ser Ala Ala Val Gly Gly Thr Val Thr
1               5                   10                  15

Ile Ser Cys Gln Ser Ser Glu Thr Ile Tyr Lys Asn Tyr Leu Ser Trp
            20                  25                  30

Phe Gln Gln Lys Pro Gly Gln Pro Pro Lys Leu Leu Ile Tyr Glu Ser
        35                  40                  45

Ser Lys Leu Ala Ser Gly Val Pro Ser Arg Phe Ser Gly Ser Gly Ser
    50                  55                  60

Gly Thr Gln Phe Thr Leu Thr Ile Ser Asp Val Gln Cys Asp Asp Ala
65                  70                  75                  80

Ala Thr Tyr Tyr Cys Leu Gly Gly Tyr Thr Asp Gly Arg Asp Thr Ile
                85                  90                  95

Phe Gly Gly Gly Thr Glu Val Glu Ile Lys
            100                 105
```

<210> SEQ ID NO 7
<211> LENGTH: 115
<212> TYPE: PRT
<213> ORGANISM: Artificial sequence
<220> FEATURE:
<223> OTHER INFORMATION: Synthetic peptide

<400> SEQUENCE: 7

```
Glu Gln Ser Val Glu Glu Ser Gly Gly Gly Leu Val Thr Pro Gly Gly
1               5                   10                  15

Thr Leu Thr Leu Thr Cys Thr Val Ser Gly Phe Ser Leu Ser Asn Asn
```

20                  25                  30
Ala Met Ser Trp Val Arg Gln Ala Pro Gly Lys Gly Leu Glu Trp Ile
                35                  40                  45

Gly Val Ile Leu Leu Ser Gly Thr Thr Tyr Tyr Ala Ser Trp Ala Lys
     50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Ile Ala
                 85                  90                  95

Ile Gly Ser Arg Pro Phe Ala Leu Trp Gly Gln Gly Thr Leu Val Thr
                100                 105                 110

Ile Ser Ser
        115

<210> SEQ ID NO 8
<211> LENGTH: 109
<212> TYPE: PRT
<213> ORGANISM: Artificial sequence
<220> FEATURE:
<223> OTHER INFORMATION: Synthetic peptide

<400> SEQUENCE: 8

Glu Leu Val Met Thr Gln Thr Pro Ser Ser Thr Ser Ala Ala Val Gly
 1               5                  10                  15

Gly Thr Val Thr Ile Asn Cys Gln Ser Ser Gln Ser Val Tyr Ser Asn
                20                  25                  30

Trp Leu Ser Trp Phe Gln Gln Lys Pro Gly Gln Pro Pro Lys Pro Leu
            35                  40                  45

Ile Tyr Leu Ala Ser Thr Leu Ala Ser Gly Val Pro Ser Arg Phe Ser
     50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Gln Gly Gly Tyr Asn Gly Asn
                 85                  90                  95

Ile Tyr Thr Phe Gly Gly Gly Thr Glu Val Val Val Lys
                100                 105

<210> SEQ ID NO 9
<211> LENGTH: 112
<212> TYPE: PRT
<213> ORGANISM: Artificial sequence
<220> FEATURE:
<223> OTHER INFORMATION: Synthetic peptide

<400> SEQUENCE: 9

Gln Ser Leu Glu Glu Ser Gly Gly Arg Leu Val Thr Pro Gly Thr Pro
 1               5                  10                  15

Leu Thr Leu Thr Cys Thr Val Ser Gly Ile Asp Leu Asn Lys Tyr Ala
                20                  25                  30

Met Thr Trp Val Arg Gln Ala Pro Gly Lys Gly Leu Glu Tyr Ile Gly
            35                  40                  45

Phe Ile Asn Ile Val Gly Ile Ala Gly Tyr Ala Thr Trp Ala Lys Gly
     50                  55                  60

Arg Phe Thr Ile Ser Lys Thr Ser Thr Thr Val Asp Leu Lys Val Thr
 65                  70                  75                  80

Ser Pro Thr Thr Glu Asp Thr Ala Thr Tyr Phe Cys Ala Arg Asn Trp
                 85                  90                  95

Ile Arg Leu Asp Leu Trp Gly Gln Gly Thr Leu Val Thr Val Ser Ser
            100                 105                 110

<210> SEQ ID NO 10
<211> LENGTH: 111
<212> TYPE: PRT
<213> ORGANISM: Artificial sequence
<220> FEATURE:
<223> OTHER INFORMATION: Synthetic peptide

<400> SEQUENCE: 10

Glu Leu Asp Leu Thr Gln Thr Pro Ala Ser Val Ser Ala Ala Val Gly
1               5                   10                  15

Gly Thr Val Thr Ile Ser Cys Gln Ser Ser Glu Ser Leu Tyr Lys Lys
            20                  25                  30

Asn Tyr Leu Ser Trp Phe Gln Gln Lys Pro Gly Gln Pro Pro Lys Leu
        35                  40                  45

Leu Ile Phe Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Ser Tyr Tyr Cys Leu Gly Asp Tyr Thr Asn
                85                  90                  95

Gly Arg Asp Thr Thr Phe Gly Gly Gly Thr Glu Val Val Val Lys
            100                 105                 110

<210> SEQ ID NO 11
<211> LENGTH: 112
<212> TYPE: PRT
<213> ORGANISM: Artificial sequence
<220> FEATURE:
<223> OTHER INFORMATION: Synthetic peptide

<400> SEQUENCE: 11

Gln Ser Leu Gln Glu Ser Gly Gly Arg Leu Val Thr Pro Gly Thr Pro
1               5                   10                  15

Leu Thr Leu Thr Cys Thr Val Ser Gly Ile Asp Leu Ser Val Tyr Leu
            20                  25                  30

Met Ser Trp Val Arg Gln Ser Pro Gly Lys Gly Leu Glu Tyr Ile Gly
        35                  40                  45

Phe Ile Asn Ser Ala Gly Ile Thr Ala Tyr Ala Thr Trp Ala Lys Gly
    50                  55                  60

Arg Phe Ile Ile Ser Lys Thr Ser Thr Thr Val Asp Leu Lys Val Thr
65                  70                  75                  80

Ser Pro Thr Thr Glu Asp Thr Ala Thr Tyr Phe Cys Ala Arg Asn Trp
                85                  90                  95

Ile Arg Leu Asp Leu Trp Gly Gln Gly Thr Leu Val Thr Ile Ser Ser
            100                 105                 110

<210> SEQ ID NO 12
<211> LENGTH: 110
<212> TYPE: PRT
<213> ORGANISM: Artificial sequence
<220> FEATURE:
<223> OTHER INFORMATION: Synthetic peptide

<400> SEQUENCE: 12

Glu Leu Val Leu Thr Gln Thr Pro Ala Ser Val Ser Ala Ala Val Gly
1               5                   10                  15

Gly Thr Val Thr Ile Ser Cys Gln Ser Ser Glu Ser Ile Tyr Lys Asn

```
            20                  25                  30

Tyr Leu Ser Trp Phe Gln Gln Lys Pro Gly Gln Pro Pro Lys Leu Leu
            35                  40                  45

Ile Tyr Glu Thr Ser Lys Leu Ala Ser Gly Val Pro Ser Arg Phe Ser
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Thr Asn Gly
                85                  90                  95

Arg Asp Thr Ile Phe Gly Gly Gly Thr Glu Leu Glu Ile Lys
            100                 105                 110

<210> SEQ ID NO 13
<211> LENGTH: 110
<212> TYPE: PRT
<213> ORGANISM: Artificial sequence
<220> FEATURE:
<223> OTHER INFORMATION: Synthetic peptide

<400> SEQUENCE: 13

Gln Ser Val Lys Glu Ser Gly Gly Gly Leu Val Thr Pro Gly Gly Thr
1               5                   10                  15

Leu Thr Leu Thr Cys Thr Ala Ser Gly Phe Ser Leu Ile Ser Tyr Asp
            20                  25                  30

Met Tyr Trp Val Arg Gln Ala Pro Gly Lys Gly Leu Glu Tyr Ile Gly
            35                  40                  45

Ile Ile Tyr Ser Asp Gly Tyr Thr Phe Tyr Ala Thr Gly Ala Lys Gly
        50                  55                  60

Arg Ile Thr Ile Ser Arg Thr Ser Thr Val Asp Leu Lys Ile Thr
65                  70                  75                  80

Ser Pro Thr Thr Glu Asp Thr Ala Thr Tyr Phe Cys Ala Thr Asn Ala
                85                  90                  95

Phe Ala Leu Trp Gly Gln Gly Thr Leu Val Thr Ile Ser Ser
            100                 105                 110

<210> SEQ ID NO 14
<211> LENGTH: 110
<212> TYPE: PRT
<213> ORGANISM: Artificial sequence
<220> FEATURE:
<223> OTHER INFORMATION: Synthetic peptide

<400> SEQUENCE: 14

Glu Leu Asp Leu Thr Gln Thr Pro Ser Ser Val Ser Ala Ala Val Gly
1               5                   10                  15

Gly Thr Val Thr Ile Ser Cys Gln Ser Ser Gln Asn Val Tyr Asn Asn
            20                  25                  30

Asn Trp Leu Val Trp Leu Gln Gln Lys Pro Gly Gln Pro Pro Lys Arg
            35                  40                  45

Leu Ile Tyr Thr Ala Ser Ser Leu Ala Ser Gly Val Pro Ser Arg Phe
        50                  55                  60

Ala Gly Ser Gly Ser Ala Thr Gln Phe Thr Leu Thr Ile Ser Asp Leu
65                  70                  75                  80

Glu Cys Gly Asp Ala Ala Thr Tyr Tyr Cys Ala Gly Gly Tyr Ser Gly
                85                  90                  95

Pro Ile Tyr Thr Phe Gly Gly Gly Thr Glu Val Glu Ile Lys
            100                 105                 110
```

<210> SEQ ID NO 15
<211> LENGTH: 113
<212> TYPE: PRT
<213> ORGANISM: Artificial sequence
<220> FEATURE:
<223> OTHER INFORMATION: Synthetic peptide

<400> SEQUENCE: 15

```
Glu Gln Ser Val Glu Glu Ser Glu Gly Arg Leu Val Thr Pro Gly Gly
1               5                   10                  15

Ser Leu Thr Leu Thr Cys Thr Val Ser Gly Phe Gly Leu Ser Ser Trp
            20                  25                  30

Ala Met Ala Trp Val Arg Gln Ala Pro Gly Lys Gly Leu Glu Trp Ile
        35                  40                  45

Gly Ile Ile Gly Val Ser Gly Lys Ile Tyr Tyr Pro Thr Trp Ala Lys
    50                  55                  60

Gly Arg Phe Thr Ile Ser Arg Thr Ser Thr Thr Val Asp Leu Lys Ile
65                  70                  75                  80

Ala Ser Pro Thr Thr Glu Asp Thr Ala Thr Tyr Phe Cys Ala Arg Glu
                85                  90                  95

Pro Tyr Gly Asp Ser Leu Trp Gly Gln Gly Thr Leu Val Thr Ile Ser
            100                 105                 110

Ser
```

<210> SEQ ID NO 16
<211> LENGTH: 110
<212> TYPE: PRT
<213> ORGANISM: Artificial sequence
<220> FEATURE:
<223> OTHER INFORMATION: Synthetic peptide

<400> SEQUENCE: 16

```
Glu Leu Val Met Thr Gln Thr Pro Ser Pro Val Ser Ala Ala Val Gly
1               5                   10                  15

Gly Thr Val Thr Ile Ser Cys Gln Ser Ser Gln Asn Ile Ser Thr Tyr
            20                  25                  30

Leu Ser Trp Tyr Gln Gln Lys Pro Gly Gln Pro Pro Lys Phe Leu Ile
        35                  40                  45

Tyr Gln Ala Ser Lys Leu Ala Ser Gly Val Ser Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Ser Tyr Tyr Cys Ala Gly Trp Lys Ser Tyr Ser Asn
                85                  90                  95

Asp Asp Asn Asp Phe Gly Gly Gly Thr Glu Val Val Val Lys
            100                 105                 110
```

<210> SEQ ID NO 17
<211> LENGTH: 121
<212> TYPE: PRT
<213> ORGANISM: Artificial sequence
<220> FEATURE:
<223> OTHER INFORMATION: Synthetic peptide

<400> SEQUENCE: 17

```
Glu Gln Ser Leu Glu Glu Ser Gly Gly Asp Leu Val Thr Pro Gly Ala
1               5                   10                  15

Ser Leu Thr Leu Thr Cys Lys Ala Ser Gly Ile Asp Phe Ser Asn His
            20                  25                  30
```

```
Tyr Tyr Ile Tyr Trp Val Arg Gln Ala Pro Gly Lys Gly Leu Glu Trp
        35                  40                  45

Ile Gly Cys Ile Phe Ser Gly Asp Ser Ala Ser Thr Tyr Tyr Ala Ser
     50                  55                  60

Trp Ala Lys Gly Arg Phe Thr Ile Ser Lys Ser Ser Pro Thr Val
 65                  70                  75                  80

Thr Leu Gln Met Thr Ser Leu Thr Ala Ala Asp Thr Ala Thr Tyr Phe
                 85                  90                  95

Cys Ala Arg Gly Met Ser Thr Asn Asp Trp Ala Ser Asp Leu Trp Gly
             100                 105                 110

Pro Gly Thr Met Val Thr Val Ser Ser
             115                 120
```

<210> SEQ ID NO 18
<211> LENGTH: 111
<212> TYPE: PRT
<213> ORGANISM: Artificial sequence
<220> FEATURE:
<223> OTHER INFORMATION: Synthetic peptide

<400> SEQUENCE: 18

```
Glu Leu Val Met Thr Gln Thr Pro Ala Ser Val Ser Ala Ala Val Gly
 1               5                  10                  15

Gly Thr Val Thr Ile Asn Cys Gln Ala Ser Glu Ser Ile Asn Ser Ile
                 20                  25                  30

Tyr Leu Ala Trp Tyr Gln Gln Lys Pro Gly Gln Arg Pro Lys Leu Leu
             35                  40                  45

Ile Tyr Arg Ala Ser Thr Leu Ala Ser Gly Val Ser Ser Arg Phe Lys
         50                  55                  60

Gly Ser Ala Ser Gly Thr Gly Phe Thr Leu Thr Ile Ser Asp Leu Glu
 65                  70                  75                  80

Cys Ala Asp Ala Ala Thr Tyr Tyr Cys Gln Gln Ser Tyr Asp Trp Gly
                 85                  90                  95

Asp Val Glu Asn Thr Phe Gly Gly Gly Thr Glu Val Glu Ile Lys
             100                 105                 110
```

<210> SEQ ID NO 19
<211> LENGTH: 127
<212> TYPE: PRT
<213> ORGANISM: Artificial sequence
<220> FEATURE:
<223> OTHER INFORMATION: Synthetic peptide

<400> SEQUENCE: 19

```
Glu Gln Ser Leu Lys Glu Ser Gly Gly Arg Leu Val Thr Pro Gly Thr
 1               5                  10                  15

Pro Leu Thr Leu Thr Cys Thr Ala Ser Gly Phe Ser Leu Ser Thr Tyr
                 20                  25                  30

Asp Met Ser Trp Val Arg Gln Ala Pro Gly Lys Gly Leu Glu Trp Ile
             35                  40                  45

Gly Ile Ile Ser Thr Ser Tyr Ser Ile Tyr Tyr Thr Tyr Tyr Ala Ser
         50                  55                  60

Trp Ala Lys Gly Arg Phe Thr Ile Ser Arg Thr Ser Ser Thr Thr Val
 65                  70                  75                  80

Asp Leu Lys Met Thr Ser Leu Thr Thr Glu Asp Thr Ala Thr Tyr Phe
                 85                  90                  95

Cys Val Gly Gly Gly Gly Lys Leu Asn Ser Val Val Tyr Tyr Ile Arg
```

```
                   100                 105                 110
Gly Leu Arg Phe Trp Gly Gln Gly Thr Leu Val Thr Ile Ser Ser
            115                 120                 125

<210> SEQ ID NO 20
<211> LENGTH: 110
<212> TYPE: PRT
<213> ORGANISM: Artificial sequence
<220> FEATURE:
<223> OTHER INFORMATION: Synthetic peptide

<400> SEQUENCE: 20

Glu Leu Val Met Thr Gln Thr Pro Ser Ser Thr Ser Ala Ala Val Gly
1               5                   10                  15

Gly Thr Val Thr Ile Asn Cys Gln Ala Ser Gln Ser Val Tyr Asp Asp
            20                  25                  30

Asn Trp Cys Ser Trp Tyr Gln Gln Lys Pro Gly Gln Pro Pro Lys Leu
        35                  40                  45

Leu Ile Tyr Asp Ala Ser Thr Leu Pro Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Ser Asp
                85                  90                  95

Asn Ile Tyr Val Phe Gly Gly Gly Thr Glu Val Glu Ile Lys
            100                 105                 110

<210> SEQ ID NO 21
<211> LENGTH: 124
<212> TYPE: PRT
<213> ORGANISM: Artificial sequence
<220> FEATURE:
<223> OTHER INFORMATION: Synthetic peptide

<400> SEQUENCE: 21

Glu Gln Ser Val Glu Glu Ser Gly Gly Gly Leu Val Lys Pro Gly Ala
1               5                   10                  15

Ser Leu Thr Leu Thr Cys Ile Ala Ser Gly Phe Ser Phe Ser Ser Ser
            20                  25                  30

Tyr Val Met Cys Trp Val Arg Gln Ala Pro Gly Lys Gly Leu Glu Leu
        35                  40                  45

Ile Ala Cys Ile His Ala Gly Gly Ser Gly Ser Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Tyr Asn Tyr His Phe Tyr Tyr Ile Gly Asp Tyr Ser Asp
            100                 105                 110

Leu Trp Gly Pro Gly Thr Leu Val Thr Val Ser Ser
        115                 120

<210> SEQ ID NO 22
<211> LENGTH: 110
<212> TYPE: PRT
<213> ORGANISM: Artificial sequence
<220> FEATURE:
<223> OTHER INFORMATION: Synthetic peptide

<400> SEQUENCE: 22
```

```
Glu Leu Val Met Thr Gln Thr Pro Ser Ser Val Ser Ala Ala Val Gly
1               5                   10                  15

Gly Thr Val Thr Ile Lys Cys Gln Ala Ser Glu Asp Ile Asp Ser Tyr
            20                  25                  30

Leu Ala Trp Tyr Gln Gln Lys Pro Gly Gln Arg Pro Lys Val Leu Ile
        35                  40                  45

Tyr Arg Ala Ser Thr Leu Ala Ser Gly Val Pro Ser Arg Phe Lys Gly
50                  55                  60

Ser Gly Ser Gly Thr Glu Phe Thr Leu Thr Ile Ser Gly Leu Glu Cys
65                  70                  75                  80

Asp Asp Ala Ala Thr Tyr Tyr Cys Gln Gln Gly Trp Ser Asn Asp Val
                85                  90                  95

Gly Ser Asn Ala Phe Gly Gly Gly Thr Lys Val Glu Ile Lys
                100                 105                 110

<210> SEQ ID NO 23
<211> LENGTH: 113
<212> TYPE: PRT
<213> ORGANISM: Artificial sequence
<220> FEATURE:
<223> OTHER INFORMATION: Synthetic peptide

<400> SEQUENCE: 23

Glu Gln Ser Leu Lys Glu Ser Gly Gly Arg Leu Val Thr Pro Gly Thr
1               5                   10                  15

Pro Leu Thr Leu Thr Cys Thr Val Ser Gly Ile Asp Leu Ser Ser Tyr
            20                  25                  30

Ala Met Thr Trp Val Arg Gln Val Pro Gly Lys Gly Leu Glu Tyr Ile
        35                  40                  45

Gly Phe Ile Asn Ile Val Gly Ile Ala Gly Tyr Ala Thr Trp Ala Lys
    50                  55                  60

Gly Arg Phe Thr Ile Ser Lys Thr Ser Thr Thr Val Asp Leu Lys Val
65                  70                  75                  80

Thr Ser Pro Thr Thr Glu Asp Thr Ala Thr Tyr Phe Cys Ala Arg Asn
                85                  90                  95

Trp Ile Arg Leu Asp Leu Trp Gly Gln Gly Thr Leu Val Thr Val Ser
                100                 105                 110

Ser

<210> SEQ ID NO 24
<211> LENGTH: 111
<212> TYPE: PRT
<213> ORGANISM: Artificial sequence
<220> FEATURE:
<223> OTHER INFORMATION: Synthetic peptide

<400> SEQUENCE: 24

Glu Leu Val Met Thr Gln Thr Pro Ala Ser Val Ser Ala Ala Val Gly
1               5                   10                  15

Gly Thr Val Thr Ile Ser Cys Gln Ser Ser Glu Ser Leu Tyr Lys Lys
            20                  25                  30

Asn Tyr Leu Ser Trp Phe Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80
```

```
Gln Cys Asp Asp Ala Ala Ser Tyr Tyr Cys Leu Gly Asp Tyr Thr Asn
                85                  90                  95

Gly Arg Asp Thr Thr Phe Gly Gly Gly Thr Glu Val Glu Ile Lys
            100                 105                 110
```

<210> SEQ ID NO 25
<211> LENGTH: 112
<212> TYPE: PRT
<213> ORGANISM: Artificial sequence
<220> FEATURE:
<223> OTHER INFORMATION: Synthetic peptide

<400> SEQUENCE: 25

```
His Ser Val Lys Glu Ser Gly Gly Gly Leu Val Thr Pro Gly Glu Ser
 1               5                  10                  15

Leu Lys Leu Thr Cys Lys Ala Ser Gly Met Asp Phe Ser Lys Tyr Trp
                20                  25                  30

Ile Cys Trp Val Arg Gln Ala Pro Gly Lys Gly Leu Glu Trp Ile Ala
            35                  40                  45

Cys Ile Asp Thr Gly Arg Ser Ala Ile Thr Val Tyr Ala Lys Trp Ala
        50                  55                  60

Lys Gly Arg Phe Thr Ile Ser Lys Thr Ser Thr Thr Val Thr Leu
 65                  70                  75                  80

Gln Met Thr Thr Leu Thr Ala Ala Asp Thr Ala Thr Tyr Phe Cys Glu
                85                  90                  95

Thr Ser Val Asp Leu Trp Gly Pro Gly Thr Leu Val Thr Ile Ser Ser
            100                 105                 110
```

<210> SEQ ID NO 26
<211> LENGTH: 112
<212> TYPE: PRT
<213> ORGANISM: Artificial sequence
<220> FEATURE:
<223> OTHER INFORMATION: Synthetic peptide

<400> SEQUENCE: 26

```
Glu Leu Asp Leu Thr Gln Thr Pro Ala Ser Val Glu Ala Ala Val Gly
 1               5                  10                  15

Gly Thr Val Thr Ile Lys Cys Gln Ala Ser Glu Ser Ile Tyr Ser Gly
                20                  25                  30

Leu Ala Trp Tyr Lys Gln Lys Pro Gly Gln Pro Lys Phe Leu Ile
            35                  40                  45

Leu Ser Ala Ser Thr Gln Ala Ser Gly Val Pro Ser Arg Phe Lys Gly
        50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Ser Arg His Tyr Gly Ser Ser
                85                  90                  95

Arg Ser Tyr Gly Phe Ala Phe Gly Gly Gly Thr Glu Val Glu Ile Lys
            100                 105                 110
```

<210> SEQ ID NO 27
<211> LENGTH: 113
<212> TYPE: PRT
<213> ORGANISM: Artificial sequence
<220> FEATURE:
<223> OTHER INFORMATION: Synthetic peptide

<400> SEQUENCE: 27

Glu Gln Ser Val Lys Glu Gly Gly Arg Leu Val Thr Pro Gly Thr
1               5                   10                  15

Pro Leu Thr Leu Thr Cys Ile Val Ser Gly Phe Ser Leu Asn Asn Tyr
            20                  25                  30

Ala Ile Ser Trp Val Arg Gln Ala Pro Glu Lys Gly Leu Glu Trp Ile
        35                  40                  45

Gly Met Ile Arg Ser Asp Gly His Val Asp Tyr Ala Thr Trp Ala Lys
50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Gly
            85                  90                  95

Gly His Phe Phe Asn Pro Trp Gly Pro Gly Thr Leu Val Thr Ile Ser
            100                 105                 110

Ser

<210> SEQ ID NO 28
<211> LENGTH: 112
<212> TYPE: PRT
<213> ORGANISM: Artificial sequence
<220> FEATURE:
<223> OTHER INFORMATION: Synthetic peptide

<400> SEQUENCE: 28

Glu Leu Val Met Thr Gln Thr Pro Ser Pro Val Ser Ala Ala Val Gly
1               5                   10                  15

Gly Thr Val Thr Ile Ser Cys Gln Ser Ser Gln Thr Val Tyr Asn Tyr
            20                  25                  30

Asn Glu Leu Ala Trp Tyr Gln Gln Lys Pro Gly Gln Pro Pro Lys Leu
        35                  40                  45

Leu Ile Asp Ala Ala Ser Thr Leu Ala Ser Gly Val Pro Ser Arg Phe
50                  55                  60

Ser Gly Ser Gly Ser Gly Thr Gln Phe Thr Leu Lys Ile Ser Glu Val
65                  70                  75                  80

Gln Cys Asp Asp Ala Ala Thr Tyr Tyr Cys Gln Gly Thr Tyr Tyr Ile
            85                  90                  95

Ser Gly Trp Tyr Tyr Thr Phe Gly Gly Gly Thr Glu Val Val Val Lys
            100                 105                 110

<210> SEQ ID NO 29
<211> LENGTH: 115
<212> TYPE: PRT
<213> ORGANISM: Artificial sequence
<220> FEATURE:
<223> OTHER INFORMATION: Synthetic peptide

<400> SEQUENCE: 29

Glu Gln Ser Leu Glu Glu Ser Gly Gly Arg Leu Val Thr Pro Gly Thr
1               5                   10                  15

Pro Leu Thr Leu Thr Cys Thr Val Ser Gly Phe Ser Leu Asn Ser Tyr
            20                  25                  30

Ala Met Ala Trp Val Arg Gln Ala Pro Gly Lys Gly Leu Glu Trp Ile
        35                  40                  45

Gly Ile Ile Gly Leu Ser Thr Met Thr Tyr Tyr Ala Ser Trp Val Asn
50                  55                  60

Gly Arg Phe Thr Ile Ser Lys Thr Ser Thr Thr Val Asp Leu Lys Met
65                  70                  75                  80

```
Thr Ser Leu Thr Thr Glu Asp Thr Ala Thr Tyr Phe Cys Val Arg Asn
                85                  90                  95

Asp Val Tyr Trp Ala Phe Asn Leu Trp Gly Gln Gly Thr Leu Val Thr
            100                 105                 110

Val Ser Ser
        115

<210> SEQ ID NO 30
<211> LENGTH: 112
<212> TYPE: PRT
<213> ORGANISM: Artificial sequence
<220> FEATURE:
<223> OTHER INFORMATION: Synthetic peptide

<400> SEQUENCE: 30

Glu Leu Asp Leu Thr Gln Thr Pro Ser Ser Val Ser Ala Gly Val Gly
1               5                   10                  15

Gly Thr Val Ser Ile Ser Cys Gln Ser Ser Glu Ser Val Val Asn Asn
            20                  25                  30

His Ala Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Ala Gln Phe Thr Leu Thr Ile Ser Gly Val
65                  70                  75                  80

Gln Cys Asp Asp Ala Ala Thr Tyr Tyr Cys Gln Gly Gly Phe Tyr Ser
                85                  90                  95

Gly Ile Ser Asp Tyr Pro Phe Gly Gly Gly Thr Glu Val Glu Ile Lys
            100                 105                 110

<210> SEQ ID NO 31
<211> LENGTH: 123
<212> TYPE: PRT
<213> ORGANISM: Artificial sequence
<220> FEATURE:
<223> OTHER INFORMATION: Synthetic peptide

<400> SEQUENCE: 31

Gln Ser Val Lys Glu Ser Glu Gly Asp Leu Val Lys Pro Gly Ala Ser
1               5                   10                  15

Leu Thr Leu Thr Cys Arg Ala Ser Gly Phe Ser Phe Ser Ser Asp Tyr
            20                  25                  30

Asn Met Cys Trp Val Arg Gln Ala Ala Gly Lys Gly Leu Glu Trp Ile
        35                  40                  45

Ala Cys Ile Gly Val Gly Thr Ser Gly Lys Thr Ala Tyr Ala Thr Trp
    50                  55                  60

Ala Lys Gly Arg Phe Thr Ile Ser Arg Ser Ser Thr Thr Val Ala
65                  70                  75                  80

Leu Gln Met Thr Ser Leu Thr Val Ala Asp Thr Ala Thr Tyr Phe Cys
                85                  90                  95

Ala Arg Pro Ser Tyr Gly Ser Gly Gly Glu Gly Gly Ser Gly Leu
            100                 105                 110

Trp Gly Pro Gly Thr Leu Val Thr Ile Ser Ser
        115                 120

<210> SEQ ID NO 32
<211> LENGTH: 111
<212> TYPE: PRT
<213> ORGANISM: Artificial sequence
```

<220> FEATURE:
<223> OTHER INFORMATION: Synthetic peptide

<400> SEQUENCE: 32

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile His Ser Asp
            20                  25                  30

Leu Ala Trp Tyr Gln Gln Lys Pro Gly Gln Arg Pro Lys Leu Leu Ile
        35                  40                  45

Tyr Val Ala Ser Tyr Leu Ala Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Thr Tyr Tyr Gly Ser Asp
                85                  90                  95

Tyr Val Gly Gly Ala Phe Gly Gly Gly Thr Glu Val Val Val Lys
            100                 105                 110

<210> SEQ ID NO 33
<211> LENGTH: 124
<212> TYPE: PRT
<213> ORGANISM: Artificial sequence
<220> FEATURE:
<223> OTHER INFORMATION: Synthetic peptide

<400> SEQUENCE: 33

Glu Gln Ser Val Lys Glu Ser Gly Gly Gly Leu Val Lys Pro Gly Ala
1               5                   10                  15

Ser Leu Thr Leu Thr Cys Thr Ala Ser Gly Phe Ser Phe Ser Ser Ser
            20                  25                  30

Tyr His Met Cys Trp Val Arg Gln Ala Pro Gly Lys Gly Leu Glu Trp
        35                  40                  45

Ile Gly Cys Ile Ala Thr Gly Tyr Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Val Pro Ser Leu Thr Ala Ala Asp Thr Ala Thr Cys Phe Cys
                85                  90                  95

Ala Arg Gly Tyr Tyr Arg Tyr Ser Asp Ser Tyr Gly Tyr Phe Asp
            100                 105                 110

Leu Trp Gly Pro Gly Thr Leu Val Thr Ile Ser Ser
        115                 120

<210> SEQ ID NO 34
<211> LENGTH: 112
<212> TYPE: PRT
<213> ORGANISM: Artificial sequence
<220> FEATURE:
<223> OTHER INFORMATION: Synthetic peptide

<400> SEQUENCE: 34

Glu Leu Val Leu Thr Gln Thr Ala Ser Pro Val Ser Ala Ala Val Gly
1               5                   10                  15

Gly Thr Val Thr Val Asn Cys Gln Ala Ser Gln Ser Ile Ser Ser Gly
            20                  25                  30

Tyr Leu Ser Trp Tyr Gln Gln Lys Pro Gly Gln Pro Pro Lys Leu Leu
        35                  40                  45

```
Ile Tyr Tyr Ala Ser Arg Leu Ala Ser Gly Val Pro Ser Arg Phe Ser
 50                  55                  60

Gly Ser Gly Ser Gly Thr Glu Tyr Thr Leu Thr Ile Ser Gly Val Gln
 65                  70                  75                  80

Cys Asp Asp Ala Ala Thr Tyr Tyr Cys Leu Tyr Val Ser Tyr Asp Gly
                 85                  90                  95

Thr Thr Thr Asp Asn Ala Phe Gly Gly Thr Glu Val Glu Ile Lys
            100                 105                 110
```

<210> SEQ ID NO 35
<211> LENGTH: 109
<212> TYPE: PRT
<213> ORGANISM: Artificial sequence
<220> FEATURE:
<223> OTHER INFORMATION: Synthetic peptide

<400> SEQUENCE: 35

```
Gln Ser Val Lys Glu Ser Gly Gly Arg Leu Val Thr Pro Gly Thr Pro
 1               5                  10                  15

Leu Thr Leu Thr Cys Thr Val Ser Gly Phe Ser Leu Ser Ser Tyr Trp
                20                  25                  30

Met His Trp Val Arg Gln Ala Pro Gly Lys Gly Leu Glu Trp Val Gly
             35                  40                  45

Val Val Ser Val Ser Gly Asn Phe Tyr Tyr Ala Thr Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Ile Glu Asp Thr Ala Phe Tyr Phe Cys Thr Met Ser Phe
                 85                  90                  95

Ala Leu Trp Gly Gln Gly Thr Leu Val Thr Ile Ser Ser
            100                 105
```

<210> SEQ ID NO 36
<211> LENGTH: 113
<212> TYPE: PRT
<213> ORGANISM: Artificial sequence
<220> FEATURE:
<223> OTHER INFORMATION: Synthetic peptide

<400> SEQUENCE: 36

```
Glu Leu Val Met Thr Gln Thr Ala Ser Pro Val Ser Ala Ala Val Gly
 1               5                  10                  15

Gly Thr Val Thr Ile Asn Cys Gln Ser Ser Gln Ser Val Tyr Ser Asn
                20                  25                  30

Asn Asn Leu Gly Trp Leu Lys Gln Lys Pro Gly Gln Pro Pro Lys Glu
            35                  40                  45

Leu Ile Tyr Tyr Ala Ser Thr Leu Ala Ser Gly Val Pro Ser Arg Phe
         50                  55                  60

Lys Gly Ser Gly Ser Gly Thr Gln Phe Thr Leu Thr Ile Ser Asp Leu
 65                  70                  75                  80

Glu Cys Asp Asp Ala Ala Thr Tyr Tyr Cys Val Gly Gly Tyr Gly Cys
                 85                  90                  95

Ser Ser Ala Asp Cys Ser Val Phe Gly Gly Thr Glu Val Glu Ile
            100                 105                 110

Lys
```

<210> SEQ ID NO 37
<211> LENGTH: 117

```
<212> TYPE: PRT
<213> ORGANISM: Artificial sequence
<220> FEATURE:
<223> OTHER INFORMATION: Synthetic peptide

<400> SEQUENCE: 37

Glu Gln Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
                20                  25                  30

Ile Met Gly Trp Val Arg Gln Ala Arg Gly Lys Gly Leu Glu Tyr Ile
            35                  40                  45

Gly Ala Ile Asn Thr Asp Gly Ala Thr Tyr Tyr Ala Thr Trp Ala Lys
50                  55                  60

Gly Arg Phe Thr Ile Ser Arg Thr Ser Thr Thr Val His Leu Lys Val
65                  70                  75                  80

Thr Ser Pro Thr Thr Glu Asp Thr Ala Thr Tyr Phe Cys Ala Arg Ser
                85                  90                  95

Leu Ala Pro Gly Asp Ser Asn Ile Asn Leu Trp Gly Gln Gly Thr Leu
                100                 105                 110

Val Thr Ile Ser Ser
            115

<210> SEQ ID NO 38
<211> LENGTH: 110
<212> TYPE: PRT
<213> ORGANISM: Artificial sequence
<220> FEATURE:
<223> OTHER INFORMATION: Synthetic peptide

<400> SEQUENCE: 38

Glu Leu Val Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Arg Asn
                20                  25                  30

Asn Arg Leu Ala Trp Tyr Gln Gln Lys Pro Gly Gln Pro Pro Lys Arg
            35                  40                  45

Leu Ile Tyr Leu Ala Ser Thr Leu Ala Ser Gly Val Pro Ser Arg Phe
50                  55                  60

Lys Gly Ser Gly Ser Gly Thr Gln Phe Thr Leu Thr Ile Ser Asp Val
65                  70                  75                  80

Gln Cys Asp Asp Ala Ala Ala Tyr Tyr Cys Ala Gly Asp Ser Gly Val
                85                  90                  95

Gly Ile Ile Ala Phe Gly Gly Gly Thr Glu Val Glu Ile Lys
                100                 105                 110

<210> SEQ ID NO 39
<211> LENGTH: 112
<212> TYPE: PRT
<213> ORGANISM: Artificial sequence
<220> FEATURE:
<223> OTHER INFORMATION: Synthetic peptide

<400> SEQUENCE: 39

Gln Ser Val Lys Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
                20                  25                  30

Ile Asp Trp Val Arg Gln Ala Pro Gly Arg Gly Leu Glu Tyr Ile Gly
```

```
            35                  40                  45
Val Ile Asn Pro Gly Gly Ser Ala Val Tyr Ala Thr Trp Ala Lys Gly
 50                  55                  60

Arg Phe Thr Ile Ser Arg Thr Ser Thr Val Asp Leu Lys Met Thr
 65                  70                  75                  80

Ser Leu Thr Thr Glu Asp Thr Ala Thr Tyr Phe Cys Ala Arg Gly Trp
                     85                  90                  95

Ser Arg Gly Asp Leu Trp Gly Gln Gly Thr Leu Val Thr Ile Ser Ser
                    100                 105                 110
```

<210> SEQ ID NO 40
<211> LENGTH: 111
<212> TYPE: PRT
<213> ORGANISM: Artificial sequence
<220> FEATURE:
<223> OTHER INFORMATION: Synthetic peptide

<400> SEQUENCE: 40

```
Glu Leu Asp Met Thr Gln Thr Pro Ser Pro Val Ser Ala Ala Val Gly
 1               5                  10                  15

Gly Thr Val Thr Ile Lys Cys Gln Ser Ser Gln Asn Val Tyr Asp Asp
                 20                  25                  30

Asp Thr Leu Ser Trp Tyr Gln Gln Lys Pro Gly Gln Pro Pro Lys Leu
             35                  40                  45

Leu Ile Tyr Asp Ala Ser Lys Leu Ala Ser Gly Val Pro Ser Arg Phe
         50                  55                  60

Lys Gly Ser Gly Ser Gly Thr Gln Phe Thr Leu Thr Ile Ser Gly Val
 65                  70                  75                  80

Gln Cys Asp Asp Ala Ala Thr Tyr Tyr Cys Leu Gly Val Phe His Asp
                 85                  90                  95

Ala Ala Asp Asn Ala Phe Gly Gly Gly Thr Glu Leu Glu Ile Lys
                100                 105                 110
```

<210> SEQ ID NO 41
<211> LENGTH: 123
<212> TYPE: PRT
<213> ORGANISM: Artificial sequence
<220> FEATURE:
<223> OTHER INFORMATION: Synthetic peptide

<400> SEQUENCE: 41

```
Gln Ser Val Glu Glu Ser Gly Gly Gly Leu Val Lys Pro Gly Ala Ser
 1               5                  10                  15

Leu Thr Leu Thr Cys Thr Ala Ser Gly Phe Ser Phe Ser Ser Ser Tyr
                 20                  25                  30

His Met Cys Trp Val Arg Gln Ala Pro Gly Lys Gly Leu Glu Trp Ile
             35                  40                  45

Gly Cys Ile Ala Thr Gly Tyr Gly Ser Thr Tyr Tyr Ala Ser Trp Ala
         50                  55                  60

Lys Gly Arg Phe Thr Ile Ser Lys Thr Ser Thr Thr Val Thr Leu
 65                  70                  75                  80

Gln Val Pro Ser Leu Thr Ala Ala Asp Thr Ala Thr Cys Phe Cys Ala
                 85                  90                  95

Arg Gly Tyr Tyr Arg Tyr Thr Ser Asp Ser Tyr Gly Tyr Phe Asp Leu
                100                 105                 110

Trp Gly Pro Gly Thr Leu Val Thr Ile Ser Ser
                115                 120
```

<210> SEQ ID NO 42
<211> LENGTH: 112
<212> TYPE: PRT
<213> ORGANISM: Artificial sequence
<220> FEATURE:
<223> OTHER INFORMATION: Synthetic peptide

<400> SEQUENCE: 42

Glu Leu Asp Leu Thr Gln Thr Ala Ser Pro Val Ser Ala Ala Val Gly
1               5                   10                  15

Gly Thr Val Thr Val Asn Cys Gln Ala Ser Gln Ser Ile Ser Ser Gly
                20                  25                  30

Tyr Leu Ser Trp Tyr Gln Gln Lys Pro Gly Gln Pro Pro Lys Leu Leu
            35                  40                  45

Ile Tyr Tyr Ala Ser Arg Leu Ala Ser Gly Val Pro Ser Arg Phe Ser
    50                  55                  60

Gly Ser Gly Ser Gly Thr Glu Tyr Thr Leu Thr Ile Ser Gly Val Gln
65                  70                  75                  80

Cys Asp Asp Ala Ala Thr Tyr Tyr Cys Leu Tyr Val Ser Tyr Ser Gly
                85                  90                  95

Thr Thr Thr Asp Asn Ala Phe Gly Gly Gly Thr Asp Val Glu Ile Lys
            100                 105                 110

<210> SEQ ID NO 43
<211> LENGTH: 8
<212> TYPE: PRT
<213> ORGANISM: Artificial sequence
<220> FEATURE:
<223> OTHER INFORMATION: Synthetic peptide

<400> SEQUENCE: 43

Gly Phe Ser Leu Ser Asn Asn Ala
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic peptide

<400> SEQUENCE: 44

Ile Leu Leu Ala Gly Pro Thr
1               5

<210> SEQ ID NO 45
<211> LENGTH: 11
<212> TYPE: PRT
<213> ORGANISM: Artificial sequence
<220> FEATURE:
<223> OTHER INFORMATION: Synthetic peptide

<400> SEQUENCE: 45

Ala Ile Ala Ile Gly Ser Arg Pro Phe Ala Leu
1               5                   10

<210> SEQ ID NO 46
<211> LENGTH: 7
<212> TYPE: PRT
<213> ORGANISM: Artificial sequence
<220> FEATURE:
<223> OTHER INFORMATION: Synthetic peptide

<400> SEQUENCE: 46

```
Gln Ser Val Tyr Ser Asn Trp
1               5
```

<210> SEQ ID NO 47
<211> LENGTH: 10
<212> TYPE: PRT
<213> ORGANISM: Artificial sequence
<220> FEATURE:
<223> OTHER INFORMATION: Synthetic peptide

<400> SEQUENCE: 47

```
Gln Gly Gly Tyr Asn Gly Asn Ile Tyr Thr
1               5                   10
```

<210> SEQ ID NO 48
<211> LENGTH: 8
<212> TYPE: PRT
<213> ORGANISM: Artificial sequence
<220> FEATURE:
<223> OTHER INFORMATION: Synthetic peptide

<400> SEQUENCE: 48

```
Gly Ile Asp Leu Ser Val Tyr Leu
1               5
```

<210> SEQ ID NO 49
<211> LENGTH: 7
<212> TYPE: PRT
<213> ORGANISM: Artificial sequence
<220> FEATURE:
<223> OTHER INFORMATION: Synthetic peptide

<400> SEQUENCE: 49

```
Ile Asn Ser Ala Gly Ile Thr
1               5
```

<210> SEQ ID NO 50
<211> LENGTH: 9
<212> TYPE: PRT
<213> ORGANISM: Artificial sequence
<220> FEATURE:
<223> OTHER INFORMATION: Synthetic peptide

<400> SEQUENCE: 50

```
Ala Arg Asn Trp Ile Arg Leu Asp Leu
1               5
```

<210> SEQ ID NO 51
<211> LENGTH: 7
<212> TYPE: PRT
<213> ORGANISM: Artificial sequence
<220> FEATURE:
<223> OTHER INFORMATION: Synthetic peptide

<400> SEQUENCE: 51

```
Glu Thr Ile Tyr Lys Asn Tyr
1               5
```

<210> SEQ ID NO 52
<211> LENGTH: 11
<212> TYPE: PRT
<213> ORGANISM: Artificial sequence
<220> FEATURE:
<223> OTHER INFORMATION: Synthetic peptide

<400> SEQUENCE: 52

Leu Gly Gly Tyr Thr Asp Gly Arg Asp Thr Ile
1               5                   10

<210> SEQ ID NO 53
<211> LENGTH: 8
<212> TYPE: PRT
<213> ORGANISM: Artificial sequence
<220> FEATURE:
<223> OTHER INFORMATION: Synthetic peptide

<400> SEQUENCE: 53

Gly Ile Asp Leu Ser Val Tyr Leu
1               5

<210> SEQ ID NO 54
<211> LENGTH: 7
<212> TYPE: PRT
<213> ORGANISM: Artificial sequence
<220> FEATURE:
<223> OTHER INFORMATION: Synthetic peptide

<400> SEQUENCE: 54

Ile Asn Ser Ala Gly Ile Thr
1               5

<210> SEQ ID NO 55
<211> LENGTH: 9
<212> TYPE: PRT
<213> ORGANISM: Artificial sequence
<220> FEATURE:
<223> OTHER INFORMATION: Synthetic peptide

<400> SEQUENCE: 55

Ala Arg Asn Trp Ile Arg Leu Asp Leu
1               5

<210> SEQ ID NO 56
<211> LENGTH: 7
<212> TYPE: PRT
<213> ORGANISM: Artificial sequence
<220> FEATURE:
<223> OTHER INFORMATION: Synthetic peptide

<400> SEQUENCE: 56

Glu Thr Ile Tyr Lys Asn Tyr
1               5

<210> SEQ ID NO 57
<211> LENGTH: 11
<212> TYPE: PRT
<213> ORGANISM: Artificial sequence
<220> FEATURE:
<223> OTHER INFORMATION: Synthetic peptide

<400> SEQUENCE: 57

Leu Gly Gly Tyr Thr Asp Gly Arg Asp Thr Ile
1               5                   10

<210> SEQ ID NO 58
<211> LENGTH: 8
<212> TYPE: PRT
<213> ORGANISM: Artificial sequence
<220> FEATURE:
<223> OTHER INFORMATION: Synthetic peptide

<400> SEQUENCE: 58

Gly Phe Ser Leu Ser Asn Asn Ala

```
1               5

<210> SEQ ID NO 59
<211> LENGTH: 7
<212> TYPE: PRT
<213> ORGANISM: Artificial sequence
<220> FEATURE:
<223> OTHER INFORMATION: Synthetic peptide

<400> SEQUENCE: 59

Ile Leu Leu Ser Gly Thr Thr
1               5

<210> SEQ ID NO 60
<211> LENGTH: 11
<212> TYPE: PRT
<213> ORGANISM: Artificial sequence
<220> FEATURE:
<223> OTHER INFORMATION: Synthetic peptide

<400> SEQUENCE: 60

Ala Ile Ala Ile Gly Ser Arg Pro Phe Ala Leu
1               5                   10

<210> SEQ ID NO 61
<211> LENGTH: 7
<212> TYPE: PRT
<213> ORGANISM: Artificial sequence
<220> FEATURE:
<223> OTHER INFORMATION: Synthetic peptide

<400> SEQUENCE: 61

Gln Ser Val Tyr Ser Asn Trp
1               5

<210> SEQ ID NO 62
<211> LENGTH: 10
<212> TYPE: PRT
<213> ORGANISM: Artificial sequence
<220> FEATURE:
<223> OTHER INFORMATION: Synthetic peptide

<400> SEQUENCE: 62

Gln Gly Gly Tyr Asn Gly Asn Ile Tyr Thr
1               5                   10

<210> SEQ ID NO 63
<211> LENGTH: 8
<212> TYPE: PRT
<213> ORGANISM: Artificial sequence
<220> FEATURE:
<223> OTHER INFORMATION: Synthetic peptide

<400> SEQUENCE: 63

Gly Ile Asp Leu Asn Lys Tyr Ala
1               5

<210> SEQ ID NO 64
<211> LENGTH: 7
<212> TYPE: PRT
<213> ORGANISM: Artificial sequence
<220> FEATURE:
<223> OTHER INFORMATION: Synthetic peptide

<400> SEQUENCE: 64

Ile Asn Ile Val Gly Ile Ala
1               5
```

<210> SEQ ID NO 65
<211> LENGTH: 9
<212> TYPE: PRT
<213> ORGANISM: Artificial sequence
<220> FEATURE:
<223> OTHER INFORMATION: Synthetic peptide

<400> SEQUENCE: 65

Ala Arg Asn Trp Ile Arg Leu Asp Leu
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic peptide

<400> SEQUENCE: 66

Glu Ser Leu Tyr Lys Lys Asn Tyr
1               5

<210> SEQ ID NO 67
<211> LENGTH: 11
<212> TYPE: PRT
<213> ORGANISM: Artificial sequence
<220> FEATURE:
<223> OTHER INFORMATION: Synthetic peptide

<400> SEQUENCE: 67

Leu Gly Asp Tyr Thr Asn Gly Arg Asp Thr Thr
1               5                   10

<210> SEQ ID NO 68
<211> LENGTH: 8
<212> TYPE: PRT
<213> ORGANISM: Artificial sequence
<220> FEATURE:
<223> OTHER INFORMATION: Synthetic peptide

<400> SEQUENCE: 68

Gly Ile Asp Leu Ser Val Tyr Leu
1               5

<210> SEQ ID NO 69
<211> LENGTH: 7
<212> TYPE: PRT
<213> ORGANISM: Artificial sequence
<220> FEATURE:
<223> OTHER INFORMATION: Synthetic peptide

<400> SEQUENCE: 69

Ile Asn Ser Ala Gly Ile Thr
1               5

<210> SEQ ID NO 70
<211> LENGTH: 9
<212> TYPE: PRT
<213> ORGANISM: Artificial sequence
<220> FEATURE:
<223> OTHER INFORMATION: Synthetic peptide

<400> SEQUENCE: 70

Ala Arg Asn Trp Ile Arg Leu Asp Leu
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic peptide

<400> SEQUENCE: 71

Glu Ser Ile Tyr Lys Asn Tyr
1               5

<210> SEQ ID NO 72
<211> LENGTH: 11
<212> TYPE: PRT
<213> ORGANISM: Artificial sequence
<220> FEATURE:
<223> OTHER INFORMATION: Synthetic peptide

<400> SEQUENCE: 72

Leu Gly Gly Tyr Thr Asn Gly Arg Asp Thr Ile
1               5                   10

<210> SEQ ID NO 73
<211> LENGTH: 8
<212> TYPE: PRT
<213> ORGANISM: Artificial sequence
<220> FEATURE:
<223> OTHER INFORMATION: Synthetic peptide

<400> SEQUENCE: 73

Gly Phe Ser Leu Ile Ser Tyr Asp
1               5

<210> SEQ ID NO 74
<211> LENGTH: 7
<212> TYPE: PRT
<213> ORGANISM: Artificial sequence
<220> FEATURE:
<223> OTHER INFORMATION: Synthetic peptide

<400> SEQUENCE: 74

Ile Tyr Ser Asp Gly Tyr Thr
1               5

<210> SEQ ID NO 75
<211> LENGTH: 7
<212> TYPE: PRT
<213> ORGANISM: Artificial sequence
<220> FEATURE:
<223> OTHER INFORMATION: Synthetic peptide

<400> SEQUENCE: 75

Ala Thr Asn Ala Phe Ala Leu
1               5

<210> SEQ ID NO 76
<211> LENGTH: 8
<212> TYPE: PRT
<213> ORGANISM: Artificial sequence
<220> FEATURE:
<223> OTHER INFORMATION: Synthetic peptide

<400> SEQUENCE: 76

Gln Asn Val Tyr Asn Asn Asn Trp
1               5

```
<210> SEQ ID NO 77
<211> LENGTH: 10
<212> TYPE: PRT
<213> ORGANISM: Artificial sequence
<220> FEATURE:
<223> OTHER INFORMATION: Synthetic peptide

<400> SEQUENCE: 77

Ala Gly Gly Tyr Ser Gly Pro Ile Tyr Thr
1               5                   10

<210> SEQ ID NO 78
<211> LENGTH: 8
<212> TYPE: PRT
<213> ORGANISM: Artificial sequence
<220> FEATURE:
<223> OTHER INFORMATION: Synthetic peptide

<400> SEQUENCE: 78

Gly Phe Gly Leu Ser Ser Trp Ala
1               5

<210> SEQ ID NO 79
<211> LENGTH: 7
<212> TYPE: PRT
<213> ORGANISM: Artificial sequence
<220> FEATURE:
<223> OTHER INFORMATION: Synthetic peptide

<400> SEQUENCE: 79

Ile Gly Val Ser Gly Lys Ile
1               5

<210> SEQ ID NO 80
<211> LENGTH: 9
<212> TYPE: PRT
<213> ORGANISM: Artificial sequence
<220> FEATURE:
<223> OTHER INFORMATION: Synthetic peptide

<400> SEQUENCE: 80

Ala Arg Glu Pro Tyr Gly Asp Ser Leu
1               5

<210> SEQ ID NO 81
<211> LENGTH: 6
<212> TYPE: PRT
<213> ORGANISM: Artificial sequence
<220> FEATURE:
<223> OTHER INFORMATION: Synthetic peptide

<400> SEQUENCE: 81

Gln Asn Ile Ser Thr Tyr
1               5

<210> SEQ ID NO 82
<211> LENGTH: 12
<212> TYPE: PRT
<213> ORGANISM: Artificial sequence
<220> FEATURE:
<223> OTHER INFORMATION: Synthetic peptide

<400> SEQUENCE: 82

Ala Gly Trp Lys Ser Tyr Ser Asn Asp Asp Asn Asp
1               5                   10

<210> SEQ ID NO 83
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 83

Gly Ile Asp Phe Ser Asn His Tyr Tyr
1               5

<210> SEQ ID NO 84
<211> LENGTH: 9
<212> TYPE: PRT
<213> ORGANISM: Artificial sequence
<220> FEATURE:
<223> OTHER INFORMATION: Synthetic peptide

<400> SEQUENCE: 84

Ile Phe Ser Gly Asp Ser Ala Ser Thr
1               5

<210> SEQ ID NO 85
<211> LENGTH: 13
<212> TYPE: PRT
<213> ORGANISM: Artificial sequence
<220> FEATURE:
<223> OTHER INFORMATION: Synthetic peptide

<400> SEQUENCE: 85

Ala Arg Gly Met Ser Thr Asn Asp Trp Ala Ser Asp Leu
1               5                   10

<210> SEQ ID NO 86
<211> LENGTH: 7
<212> TYPE: PRT
<213> ORGANISM: Artificial sequence
<220> FEATURE:
<223> OTHER INFORMATION: Synthetic peptide

<400> SEQUENCE: 86

Glu Ser Ile Asn Ser Ile Tyr
1               5

<210> SEQ ID NO 87
<211> LENGTH: 12
<212> TYPE: PRT
<213> ORGANISM: Artificial sequence
<220> FEATURE:
<223> OTHER INFORMATION: Synthetic peptide

<400> SEQUENCE: 87

Gln Gln Ser Tyr Asp Trp Gly Asp Val Glu Asn Thr
1               5                   10

<210> SEQ ID NO 88
<211> LENGTH: 9
<212> TYPE: PRT
<213> ORGANISM: Artificial sequence
<220> FEATURE:
<223> OTHER INFORMATION: Synthetic peptide

<400> SEQUENCE: 88

Gly Phe Ser Leu Ser Thr Tyr Asp Met
1               5

<210> SEQ ID NO 89
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 89

Ser Thr Ser Tyr Ser Ile Tyr Tyr Thr
1               5

<210> SEQ ID NO 90
<211> LENGTH: 19
<212> TYPE: PRT
<213> ORGANISM: Artificial sequence
<220> FEATURE:
<223> OTHER INFORMATION: Synthetic peptide

<400> SEQUENCE: 90

Val Gly Gly Gly Gly Lys Leu Asn Ser Val Val Tyr Tyr Ile Arg Gly
1               5                   10                  15

Leu Arg Phe

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Gln Ser Val Tyr Asp Asp Asn Trp
1               5

<210> SEQ ID NO 92
<211> LENGTH: 10
<212> TYPE: PRT
<213> ORGANISM: Artificial sequence
<220> FEATURE:
<223> OTHER INFORMATION: Synthetic peptide

<400> SEQUENCE: 92

Ala Gly Ala Tyr Ser Asp Asn Ile Tyr Val
1               5                   10

<210> SEQ ID NO 93
<211> LENGTH: 9
<212> TYPE: PRT
<213> ORGANISM: Artificial sequence
<220> FEATURE:
<223> OTHER INFORMATION: Synthetic peptide

<400> SEQUENCE: 93

Gly Phe Ser Phe Ser Ser Ser Tyr Val
1               5

<210> SEQ ID NO 94
<211> LENGTH: 9
<212> TYPE: PRT
<213> ORGANISM: Artificial sequence
<220> FEATURE:
<223> OTHER INFORMATION: Synthetic peptide

<400> SEQUENCE: 94

Ile His Ala Gly Gly Ser Gly Ser Thr
1               5

<210> SEQ ID NO 95
```

<211> LENGTH: 16
<212> TYPE: PRT
<213> ORGANISM: Artificial sequence
<220> FEATURE:
<223> OTHER INFORMATION: Synthetic peptide

<400> SEQUENCE: 95

Ala Arg Tyr Asn Tyr His Phe Tyr Tyr Ile Gly Asp Tyr Ser Asp Leu
1               5                   10                  15

<210> SEQ ID NO 96
<211> LENGTH: 6
<212> TYPE: PRT
<213> ORGANISM: Artificial sequence
<220> FEATURE:
<223> OTHER INFORMATION: Synthetic peptide

<400> SEQUENCE: 96

Glu Asp Ile Asp Ser Tyr
1               5

<210> SEQ ID NO 97
<211> LENGTH: 12
<212> TYPE: PRT
<213> ORGANISM: Artificial sequence
<220> FEATURE:
<223> OTHER INFORMATION: Synthetic peptide

<400> SEQUENCE: 97

Gln Gln Gly Trp Ser Asn Asp Val Gly Ser Asn Ala
1               5                   10

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Gly Ile Asp Leu Ser Ser Tyr Ala
1               5

<210> SEQ ID NO 99
<211> LENGTH: 7
<212> TYPE: PRT
<213> ORGANISM: Artificial sequence
<220> FEATURE:
<223> OTHER INFORMATION: Synthetic peptide

<400> SEQUENCE: 99

Ile Asn Ile Val Gly Ile Ala
1               5

<210> SEQ ID NO 100
<211> LENGTH: 9
<212> TYPE: PRT
<213> ORGANISM: Artificial sequence
<220> FEATURE:
<223> OTHER INFORMATION: Synthetic peptide

<400> SEQUENCE: 100

Ala Arg Asn Trp Ile Arg Leu Asp Leu
1               5

<210> SEQ ID NO 101
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 101

Glu Ser Leu Tyr Lys Lys Asn Tyr
1               5

<210> SEQ ID NO 102
<211> LENGTH: 11
<212> TYPE: PRT
<213> ORGANISM: Artificial sequence
<220> FEATURE:
<223> OTHER INFORMATION: Synthetic peptide

<400> SEQUENCE: 102

Leu Gly Asp Tyr Thr Asn Gly Arg Asp Thr Thr
1               5                   10

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Gly Met Asp Phe Ser Lys Tyr Trp
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Ile Asp Thr Gly Arg Ser Ala Ile
1               5

<210> SEQ ID NO 105
<211> LENGTH: 6
<212> TYPE: PRT
<213> ORGANISM: Artificial sequence
<220> FEATURE:
<223> OTHER INFORMATION: Synthetic peptide

<400> SEQUENCE: 105

Glu Thr Ser Val Asp Leu
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic peptide

<400> SEQUENCE: 106

Glu Ser Ile Tyr Ser Gly
1               5

<210> SEQ ID NO 107
<211> LENGTH: 14
<212> TYPE: PRT
```

<213> ORGANISM: Artificial sequence
<220> FEATURE:
<223> OTHER INFORMATION: Synthetic peptide

<400> SEQUENCE: 107

Gln Ser Arg His Tyr Gly Ser Ser Arg Ser Tyr Gly Phe Ala
1               5                   10

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Gly Phe Ser Leu Asn Asn Tyr Ala
1               5

<210> SEQ ID NO 109
<211> LENGTH: 7
<212> TYPE: PRT
<213> ORGANISM: Artificial sequence
<220> FEATURE:
<223> OTHER INFORMATION: Synthetic peptide

<400> SEQUENCE: 109

Ile Arg Ser Asp Gly His Val
1               5

<210> SEQ ID NO 110
<211> LENGTH: 9
<212> TYPE: PRT
<213> ORGANISM: Artificial sequence
<220> FEATURE:
<223> OTHER INFORMATION: Synthetic peptide

<400> SEQUENCE: 110

Ala Arg Gly Gly His Phe Phe Asn Pro
1               5

<210> SEQ ID NO 111
<211> LENGTH: 8
<212> TYPE: PRT
<213> ORGANISM: Artificial sequence
<220> FEATURE:
<223> OTHER INFORMATION: Synthetic peptide

<400> SEQUENCE: 111

Gln Thr Val Tyr Asn Tyr Asn Glu
1               5

<210> SEQ ID NO 112
<211> LENGTH: 12
<212> TYPE: PRT
<213> ORGANISM: Artificial sequence
<220> FEATURE:
<223> OTHER INFORMATION: Synthetic peptide

<400> SEQUENCE: 112

Gln Gly Thr Tyr Tyr Ile Ser Gly Trp Tyr Tyr Thr
1               5                   10

<210> SEQ ID NO 113
<211> LENGTH: 8
<212> TYPE: PRT
<213> ORGANISM: Artificial sequence

```
<220> FEATURE:
<223> OTHER INFORMATION: Synthetic peptide

<400> SEQUENCE: 113

Gly Phe Ser Leu Asn Ser Tyr Ala
1               5

<210> SEQ ID NO 114
<211> LENGTH: 7
<212> TYPE: PRT
<213> ORGANISM: Artificial sequence
<220> FEATURE:
<223> OTHER INFORMATION: Synthetic peptide

<400> SEQUENCE: 114

Ile Gly Leu Ser Thr Met Thr
1               5

<210> SEQ ID NO 115
<211> LENGTH: 11
<212> TYPE: PRT
<213> ORGANISM: Artificial sequence
<220> FEATURE:
<223> OTHER INFORMATION: Synthetic peptide

<400> SEQUENCE: 115

Val Arg Asn Asp Val Tyr Trp Ala Phe Asn Leu
1               5                   10

<210> SEQ ID NO 116
<211> LENGTH: 8
<212> TYPE: PRT
<213> ORGANISM: Artificial sequence
<220> FEATURE:
<223> OTHER INFORMATION: Synthetic peptide

<400> SEQUENCE: 116

Glu Ser Val Val Asn Asn His Ala
1               5

<210> SEQ ID NO 117
<211> LENGTH: 12
<212> TYPE: PRT
<213> ORGANISM: Artificial sequence
<220> FEATURE:
<223> OTHER INFORMATION: Synthetic peptide

<400> SEQUENCE: 117

Gln Gly Gly Phe Tyr Ser Gly Ile Ser Asp Tyr Pro
1               5                   10

<210> SEQ ID NO 118
<211> LENGTH: 9
<212> TYPE: PRT
<213> ORGANISM: Artificial sequence
<220> FEATURE:
<223> OTHER INFORMATION: Synthetic peptide

<400> SEQUENCE: 118

Gly Phe Ser Phe Ser Ser Asp Tyr Asn
1               5

<210> SEQ ID NO 119
<211> LENGTH: 9
<212> TYPE: PRT
<213> ORGANISM: Artificial sequence
<220> FEATURE:
```

```
<223> OTHER INFORMATION: Synthetic peptide

<400> SEQUENCE: 119

Ile Gly Val Gly Thr Ser Gly Lys Thr
1               5

<210> SEQ ID NO 120
<211> LENGTH: 16
<212> TYPE: PRT
<213> ORGANISM: Artificial sequence
<220> FEATURE:
<223> OTHER INFORMATION: Synthetic peptide

<400> SEQUENCE: 120

Ala Arg Pro Ser Tyr Gly Ser Gly Gly Glu Gly Gly Gly Ser Gly Leu
1               5                   10                  15

<210> SEQ ID NO 121
<211> LENGTH: 6
<212> TYPE: PRT
<213> ORGANISM: Artificial sequence
<220> FEATURE:
<223> OTHER INFORMATION: Synthetic peptide

<400> SEQUENCE: 121

Gln Ser Ile His Ser Asp
1               5

<210> SEQ ID NO 122
<211> LENGTH: 13
<212> TYPE: PRT
<213> ORGANISM: Artificial sequence
<220> FEATURE:
<223> OTHER INFORMATION: Synthetic peptide

<400> SEQUENCE: 122

Gln Ser Thr Tyr Tyr Gly Ser Asp Tyr Val Gly Gly Ala
1               5                   10

<210> SEQ ID NO 123
<211> LENGTH: 9
<212> TYPE: PRT
<213> ORGANISM: Artificial sequence
<220> FEATURE:
<223> OTHER INFORMATION: Synthetic peptide

<400> SEQUENCE: 123

Gly Phe Ser Phe Ser Ser Ser Tyr His
1               5

<210> SEQ ID NO 124
<211> LENGTH: 7
<212> TYPE: PRT
<213> ORGANISM: Artificial sequence
<220> FEATURE:
<223> OTHER INFORMATION: Synthetic peptide

<400> SEQUENCE: 124

Ile Ala Thr Gly Tyr Gly Ser
1               5

<210> SEQ ID NO 125
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 125

Ala Arg Gly Tyr Tyr Arg Tyr Thr Ser Asp Ser Tyr Gly Tyr Phe Asp
1               5                   10                  15
Leu

<210> SEQ ID NO 126
<211> LENGTH: 7
<212> TYPE: PRT
<213> ORGANISM: Artificial sequence
<220> FEATURE:
<223> OTHER INFORMATION: Synthetic peptide

<400> SEQUENCE: 126

Gln Ser Ile Ser Ser Gly Tyr
1               5

<210> SEQ ID NO 127
<211> LENGTH: 13
<212> TYPE: PRT
<213> ORGANISM: Artificial sequence
<220> FEATURE:
<223> OTHER INFORMATION: Synthetic peptide

<400> SEQUENCE: 127

Leu Tyr Val Ser Tyr Asp Gly Thr Thr Asp Asn Ala
1               5                   10

<210> SEQ ID NO 128
<211> LENGTH: 8
<212> TYPE: PRT
<213> ORGANISM: Artificial sequence
<220> FEATURE:
<223> OTHER INFORMATION: Synthetic peptide

<400> SEQUENCE: 128

Gly Phe Ser Leu Ser Ser Tyr Trp
1               5

<210> SEQ ID NO 129
<211> LENGTH: 7
<212> TYPE: PRT
<213> ORGANISM: Artificial sequence
<220> FEATURE:
<223> OTHER INFORMATION: Synthetic peptide

<400> SEQUENCE: 129

Val Ser Val Ser Gly Asn Phe
1               5

<210> SEQ ID NO 130
<211> LENGTH: 6
<212> TYPE: PRT
<213> ORGANISM: Artificial sequence
<220> FEATURE:
<223> OTHER INFORMATION: Synthetic peptide

<400> SEQUENCE: 130

Thr Met Ser Phe Ala Leu
1               5

<210> SEQ ID NO 131
<211> LENGTH: 8
<212> TYPE: PRT
<213> ORGANISM: Artificial sequence
<220> FEATURE:
```

```
<223> OTHER INFORMATION: Synthetic peptide

<400> SEQUENCE: 131

Gln Ser Val Tyr Ser Asn Asn Asn
1               5

<210> SEQ ID NO 132
<211> LENGTH: 13
<212> TYPE: PRT
<213> ORGANISM: Artificial sequence
<220> FEATURE:
<223> OTHER INFORMATION: Synthetic peptide

<400> SEQUENCE: 132

Val Gly Gly Tyr Gly Cys Ser Ser Ala Asp Cys Ser Val
1               5                   10

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133

Gly Phe Ser Leu Ser Ser Tyr Ile
1               5

<210> SEQ ID NO 134
<211> LENGTH: 7
<212> TYPE: PRT
<213> ORGANISM: Artificial sequence
<220> FEATURE:
<223> OTHER INFORMATION: Synthetic peptide

<400> SEQUENCE: 134

Ile Asn Thr Asp Gly Ala Thr
1               5

<210> SEQ ID NO 135
<211> LENGTH: 13
<212> TYPE: PRT
<213> ORGANISM: Artificial sequence
<220> FEATURE:
<223> OTHER INFORMATION: Synthetic peptide

<400> SEQUENCE: 135

Ala Arg Ser Leu Ala Pro Gly Asp Ser Asn Ile Asn Leu
1               5                   10

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Glu Ser Val Tyr Arg Asn Asn Arg
1               5

<210> SEQ ID NO 137
<211> LENGTH: 10
<212> TYPE: PRT
<213> ORGANISM: Artificial sequence
<220> FEATURE:
<223> OTHER INFORMATION: Synthetic peptide
```

<400> SEQUENCE: 137

Ala Gly Asp Ser Gly Val Gly Ile Ile Ala
1               5                   10

<210> SEQ ID NO 138
<211> LENGTH: 8
<212> TYPE: PRT
<213> ORGANISM: Artificial sequence
<220> FEATURE:
<223> OTHER INFORMATION: Synthetic peptide

<400> SEQUENCE: 138

Gly Phe Ser Leu Ser Thr Tyr Tyr
1               5

<210> SEQ ID NO 139
<211> LENGTH: 7
<212> TYPE: PRT
<213> ORGANISM: Artificial sequence
<220> FEATURE:
<223> OTHER INFORMATION: Synthetic peptide

<400> SEQUENCE: 139

Ile Asn Pro Gly Gly Ser Ala
1               5

<210> SEQ ID NO 140
<211> LENGTH: 9
<212> TYPE: PRT
<213> ORGANISM: Artificial sequence
<220> FEATURE:
<223> OTHER INFORMATION: Synthetic peptide

<400> SEQUENCE: 140

Ala Arg Gly Trp Ser Arg Gly Asp Leu
1               5

<210> SEQ ID NO 141
<211> LENGTH: 8
<212> TYPE: PRT
<213> ORGANISM: Artificial sequence
<220> FEATURE:
<223> OTHER INFORMATION: Synthetic peptide

<400> SEQUENCE: 141

Gln Asn Val Tyr Asp Asp Asp Thr
1               5

<210> SEQ ID NO 142
<211> LENGTH: 11
<212> TYPE: PRT
<213> ORGANISM: Artificial sequence
<220> FEATURE:
<223> OTHER INFORMATION: Synthetic peptide

<400> SEQUENCE: 142

Leu Gly Val Phe His Asp Ala Ala Asp Asn Ala
1               5                   10

<210> SEQ ID NO 143
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 143

Gly Phe Ser Phe Ser Ser Ser Tyr His
1               5

<210> SEQ ID NO 144
<211> LENGTH: 7
<212> TYPE: PRT
<213> ORGANISM: Artificial sequence
<220> FEATURE:
<223> OTHER INFORMATION: Synthetic peptide

<400> SEQUENCE: 144

Ile Ala Thr Gly Tyr Gly Ser
1               5

<210> SEQ ID NO 145
<211> LENGTH: 17
<212> TYPE: PRT
<213> ORGANISM: Artificial sequence
<220> FEATURE:
<223> OTHER INFORMATION: Synthetic peptide

<400> SEQUENCE: 145

Ala Arg Gly Tyr Tyr Arg Tyr Thr Ser Asp Ser Tyr Gly Tyr Phe Asp
1               5                   10                  15

Leu

<210> SEQ ID NO 146
<211> LENGTH: 7
<212> TYPE: PRT
<213> ORGANISM: Artificial sequence
<220> FEATURE:
<223> OTHER INFORMATION: Synthetic peptide

<400> SEQUENCE: 146

Gln Ser Ile Ser Ser Gly Tyr
1               5

<210> SEQ ID NO 147
<211> LENGTH: 13
<212> TYPE: PRT
<213> ORGANISM: Artificial sequence
<220> FEATURE:
<223> OTHER INFORMATION: Synthetic peptide

<400> SEQUENCE: 147

Leu Tyr Val Ser Tyr Ser Gly Thr Thr Thr Asp Asn Ala
1               5                   10

<210> SEQ ID NO 148
<211> LENGTH: 119
<212> TYPE: PRT
<213> ORGANISM: Artificial sequence
<220> FEATURE:
<223> OTHER INFORMATION: Synthetic peptide

<400> SEQUENCE: 148

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Asn Tyr
                20                  25                  30

Ala Met Asn Trp Gly Arg Gln Ala Pro Gly Lys Gly Leu Glu Trp Val
            35                  40                  45

Ala Arg Ile Arg Ser Lys Arg Asn Asn Tyr Ala Thr His Tyr Asp Asp
```

```
            50                  55                  60
Ser Val Lys Asp Arg Phe Thr Ile Ser Arg Asp Asp Ser Gln Asn Met
 65                  70                  75                  80

Leu Tyr Leu Gln Leu Asn Asn Leu Lys Thr Glu Asp Thr Ala Met Tyr
                 85                  90                  95

Tyr Cys Val Arg Asp Gly Pro Tyr Ala Met Asp Tyr Trp Gly Gln Gly
            100                 105                 110

Thr Ser Val Thr Val Ser Ser
        115

<210> SEQ ID NO 149
<211> LENGTH: 113
<212> TYPE: PRT
<213> ORGANISM: Artificial sequence
<220> FEATURE:
<223> OTHER INFORMATION: Synthetic peptide

<400> SEQUENCE: 149

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
         50                 55                  60

Pro Asp Arg Phe Thr Gly Ser Gly Ser Gly Thr Asp Phe Thr Leu Thr
 65                 70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 150
<211> LENGTH: 123
<212> TYPE: PRT
<213> ORGANISM: Artificial sequence
<220> FEATURE:
<223> OTHER INFORMATION: Synthetic peptide

<400> SEQUENCE: 150

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Leu Val
            35                  40                  45

Ala Thr Ile Asp Ser Asn Gly Gly Thr Tyr Tyr Pro Asp Ser Val
         50                 55                  60

Lys Gly Arg Phe Thr Ile Ser Arg Asp Asn Ala Lys Asn Thr Leu Tyr
 65                 70                  75                  80

Leu Gln Met Ser Ser Leu Lys Ser Glu Asp Thr Ala Met His Tyr Cys
                85                  90                  95

Ala Arg Asp Gly Gly Ser Tyr Gly Tyr Tyr Tyr Ala Met Asp Tyr
            100                 105                 110

Trp Gly Gln Gly Thr Ser Val Thr Val Ser Ser
```

115                 120

<210> SEQ ID NO 151
<211> LENGTH: 113
<212> TYPE: PRT
<213> ORGANISM: Artificial sequence
<220> FEATURE:
<223> OTHER INFORMATION: Synthetic peptide

<400> SEQUENCE: 151

Asp Ile Val Met Ser Gln Ser Pro Ser Ser Leu Ala Val Ser Ala Gly
1               5                   10                  15

Glu Lys Val Thr Met Arg Cys Lys Ser Ser Gln Ser Leu Leu Asn Ser
            20                  25                  30

Arg Thr Arg Lys Ser Tyr Leu Ala Trp Tyr Gln Gln Lys Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro Trp Thr Phe Gly Gly Gly Thr Lys Leu Glu Ile
            100                 105                 110

Lys

<210> SEQ ID NO 152
<211> LENGTH: 116
<212> TYPE: PRT
<213> ORGANISM: Artificial sequence
<220> FEATURE:
<223> OTHER INFORMATION: Synthetic peptide

<400> SEQUENCE: 152

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Tyr Trp Asp Tyr Phe Asp Tyr Trp Gly Gln Gly Thr Thr Leu
            100                 105                 110

Thr Val Ser Ser
        115

<210> SEQ ID NO 153
<211> LENGTH: 112
<212> TYPE: PRT
<213> ORGANISM: Artificial sequence
<220> FEATURE:
<223> OTHER INFORMATION: Synthetic peptide

<400> SEQUENCE: 153

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Gln Ile Pro Pro Thr Phe Gly Gly Gly Thr Lys Leu Glu Ile Lys
            100                 105                 110
```

<210> SEQ ID NO 154
<211> LENGTH: 114
<212> TYPE: PRT
<213> ORGANISM: Artificial sequence
<220> FEATURE:
<223> OTHER INFORMATION: Synthetic peptide

<400> SEQUENCE: 154

```
Glu Val Gln Leu Val Glu Ser Gly Gly Gly Leu Val Gln Pro Lys Gly
1               5                   10                  15

Ser Leu Arg Leu Ser Cys Ala Ala Ser Gly Phe Ile Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Lys Tyr Ala Thr Tyr Tyr Val Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Gly Ile Trp Gly Gln Gly Thr Leu Val Thr Val
            100                 105                 110

Ser Ala
```

<210> SEQ ID NO 155
<211> LENGTH: 113
<212> TYPE: PRT
<213> ORGANISM: Artificial sequence
<220> FEATURE:
<223> OTHER INFORMATION: Synthetic peptide

<400> SEQUENCE: 155

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr His Gln Lys Pro Gly Gln
        35                  40                  45

Pro Pro Lys Leu Leu Ile Tyr Trp Ala Phe Thr Arg Glu Ser Gly Val
    50                  55                  60

Pro Asp Arg Phe Thr Gly Ser Gly Ser Gly Thr Asp Phe Thr Leu Thr
65                  70                  75                  80
```

-continued

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ser Gly Thr Lys Leu Glu Ile
            100                 105                 110

Lys

<210> SEQ ID NO 156
<211> LENGTH: 118
<212> TYPE: PRT
<213> ORGANISM: Artificial sequence
<220> FEATURE:
<223> OTHER INFORMATION: Synthetic peptide

<400> SEQUENCE: 156

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Ile Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Gly Ser Ala Lys Gly Gly Phe Phe Tyr Trp Gly Gln Gly Thr
            100                 105                 110

Leu Val Thr Val Ser Ala
        115

<210> SEQ ID NO 157
<211> LENGTH: 112
<212> TYPE: PRT
<213> ORGANISM: Artificial sequence
<220> FEATURE:
<223> OTHER INFORMATION: Synthetic peptide

<400> SEQUENCE: 157

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110

<210> SEQ ID NO 158
<211> LENGTH: 123
<212> TYPE: PRT
<213> ORGANISM: Artificial sequence
<220> FEATURE:

<223> OTHER INFORMATION: Synthetic peptide

<400> SEQUENCE: 158

```
Glu Val Gln Leu Leu Gln Ser Gly Pro Glu Leu Val Lys Pro Gly Ala
1               5                   10                  15

Ser Val Lys Ile Ser Cys Arg Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Thr Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Lys Arg Ser Arg Gly Glu Leu Asp Ser Thr Met Asp Tyr
                100                 105                 110

Trp Gly Gln Gly Thr Ser Val Thr Val Ser Ser
            115                 120
```

<210> SEQ ID NO 159
<211> LENGTH: 112
<212> TYPE: PRT
<213> ORGANISM: Artificial sequence
<220> FEATURE:
<223> OTHER INFORMATION: Synthetic peptide

<400> SEQUENCE: 159

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Met Leu Glu Ile Lys
                100                 105                 110
```

<210> SEQ ID NO 160
<211> LENGTH: 10
<212> TYPE: PRT
<213> ORGANISM: Artificial sequence
<220> FEATURE:
<223> OTHER INFORMATION: Synthetic peptide

<400> SEQUENCE: 160

```
Gly Phe Thr Phe Ser Asn Tyr Trp Met Asn
1               5                   10
```

<210> SEQ ID NO 161
<211> LENGTH: 19
<212> TYPE: PRT
<213> ORGANISM: Artificial sequence
<220> FEATURE:
<223> OTHER INFORMATION: Synthetic peptide

<400> SEQUENCE: 161

Glu Ile Arg Leu Lys Tyr Asn Asn Tyr Ala Thr His Tyr Ala Glu Ser
1               5                   10                  15

Val Lys Gly

<210> SEQ ID NO 162
<211> LENGTH: 9
<212> TYPE: PRT
<213> ORGANISM: Artificial sequence
<220> FEATURE:
<223> OTHER INFORMATION: Synthetic peptide

<400> SEQUENCE: 162

Thr Arg Tyr Gly Ser Ser Leu Asp Tyr
1               5

<210> SEQ ID NO 163
<211> LENGTH: 17
<212> TYPE: PRT
<213> ORGANISM: Artificial sequence
<220> FEATURE:
<223> OTHER INFORMATION: Synthetic peptide

<400> SEQUENCE: 163

Lys Ser Ser Gln Asn Leu Phe Tyr Ser Thr Asn Gln Lys Asn Tyr Leu
1               5                   10                  15

Ala

<210> SEQ ID NO 164
<211> LENGTH: 7
<212> TYPE: PRT
<213> ORGANISM: Artificial sequence
<220> FEATURE:
<223> OTHER INFORMATION: Synthetic peptide

<400> SEQUENCE: 164

Trp Ala Ser Thr Arg Glu Ser
1               5

<210> SEQ ID NO 165
<211> LENGTH: 9
<212> TYPE: PRT
<213> ORGANISM: Artificial sequence
<220> FEATURE:
<223> OTHER INFORMATION: Synthetic peptide

<400> SEQUENCE: 165

Gln Gln Tyr Tyr Asn Tyr Pro Leu Thr
1               5

<210> SEQ ID NO 166
<211> LENGTH: 10
<212> TYPE: PRT
<213> ORGANISM: Artificial sequence
<220> FEATURE:
<223> OTHER INFORMATION: Synthetic peptide

<400> SEQUENCE: 166

Gly Tyr Thr Phe Thr Asn Tyr Gly Met Asn
1               5                   10

<210> SEQ ID NO 167
<211> LENGTH: 17
<212> TYPE: PRT

<213> ORGANISM: Artificial sequence
<220> FEATURE:
<223> OTHER INFORMATION: Synthetic peptide

<400> SEQUENCE: 167

Trp Ile Asn Thr Tyr Thr Gly Glu Pro Thr Tyr Ala Asp Asp Phe Lys
1               5                   10                  15

Gly

<210> SEQ ID NO 168
<211> LENGTH: 12
<212> TYPE: PRT
<213> ORGANISM: Artificial sequence
<220> FEATURE:
<223> OTHER INFORMATION: Synthetic peptide

<400> SEQUENCE: 168

Ile Tyr Tyr His Thr Ser Leu Trp Tyr Phe Asp Val
1               5                   10

<210> SEQ ID NO 169
<211> LENGTH: 16
<212> TYPE: PRT
<213> ORGANISM: Artificial sequence
<220> FEATURE:
<223> OTHER INFORMATION: Synthetic peptide

<400> SEQUENCE: 169

Arg Ser Ser Gln Asn Ile Val His Ser Asn Gly Asn Thr Tyr Leu Glu
1               5                   10                  15

<210> SEQ ID NO 170
<211> LENGTH: 7
<212> TYPE: PRT
<213> ORGANISM: Artificial sequence
<220> FEATURE:
<223> OTHER INFORMATION: Synthetic peptide

<400> SEQUENCE: 170

Arg Val Ser Asn Arg Phe Ser
1               5

<210> SEQ ID NO 171
<211> LENGTH: 9
<212> TYPE: PRT
<213> ORGANISM: Artificial sequence
<220> FEATURE:
<223> OTHER INFORMATION: Synthetic peptide

<400> SEQUENCE: 171

Phe Gln Gly Ser His Val Pro Leu Thr
1               5

<210> SEQ ID NO 172
<211> LENGTH: 10
<212> TYPE: PRT
<213> ORGANISM: Artificial sequence
<220> FEATURE:
<223> OTHER INFORMATION: Synthetic peptide

<400> SEQUENCE: 172

Gly Tyr Thr Phe Thr Asn Tyr Gly Met Asn
1               5                   10

<210> SEQ ID NO 173
<211> LENGTH: 17

```
<212> TYPE: PRT
<213> ORGANISM: Artificial sequence
<220> FEATURE:
<223> OTHER INFORMATION: Synthetic peptide

<400> SEQUENCE: 173

Trp Ile Asn Thr Tyr Thr Gly Glu Pro Thr Tyr Ala Asp Asp Phe Lys
1               5                   10                  15

Gly

<210> SEQ ID NO 174
<211> LENGTH: 12
<212> TYPE: PRT
<213> ORGANISM: Artificial sequence
<220> FEATURE:
<223> OTHER INFORMATION: Synthetic peptide

<400> SEQUENCE: 174

Ile Tyr Tyr His Thr Ser Leu Trp Tyr Phe Asp Val
1               5                   10

<210> SEQ ID NO 175
<211> LENGTH: 16
<212> TYPE: PRT
<213> ORGANISM: Artificial sequence
<220> FEATURE:
<223> OTHER INFORMATION: Synthetic peptide

<400> SEQUENCE: 175

Arg Ser Ser Gln Ser Leu Val His Ser Asn Gly Asn Thr Tyr Leu His
1               5                   10                  15

<210> SEQ ID NO 176
<211> LENGTH: 7
<212> TYPE: PRT
<213> ORGANISM: Artificial sequence
<220> FEATURE:
<223> OTHER INFORMATION: Synthetic peptide

<400> SEQUENCE: 176

Lys Val Ser Asn Arg Phe Ser
1               5

<210> SEQ ID NO 177
<211> LENGTH: 9
<212> TYPE: PRT
<213> ORGANISM: Artificial sequence
<220> FEATURE:
<223> OTHER INFORMATION: Synthetic peptide

<400> SEQUENCE: 177

Ser Gln Ser Thr His Val Pro Tyr Thr
1               5

<210> SEQ ID NO 178
<211> LENGTH: 11
<212> TYPE: PRT
<213> ORGANISM: Artificial sequence
<220> FEATURE:
<223> OTHER INFORMATION: Synthetic peptide

<400> SEQUENCE: 178

Gly Tyr Ser Ile Thr Ser Asp Tyr Ala Trp Asn
1               5                   10

<210> SEQ ID NO 179
```

```
<211> LENGTH: 16
<212> TYPE: PRT
<213> ORGANISM: Artificial sequence
<220> FEATURE:
<223> OTHER INFORMATION: Synthetic peptide

<400> SEQUENCE: 179

Tyr Ile Ser Tyr Ser Gly Gly Thr Ser Tyr Asn Pro Ser Leu Lys Ser
1               5                   10                  15

<210> SEQ ID NO 180
<211> LENGTH: 7
<212> TYPE: PRT
<213> ORGANISM: Artificial sequence
<220> FEATURE:
<223> OTHER INFORMATION: Synthetic peptide

<400> SEQUENCE: 180

Leu His Tyr Gly Tyr Asp Tyr
1               5

<210> SEQ ID NO 181
<211> LENGTH: 16
<212> TYPE: PRT
<213> ORGANISM: Artificial sequence
<220> FEATURE:
<223> OTHER INFORMATION: Synthetic peptide

<400> SEQUENCE: 181

Arg Ser Ser Gln Ser Ile Val His Ser Asn Gly Asn Thr Tyr Leu Glu
1               5                   10                  15

<210> SEQ ID NO 182
<211> LENGTH: 7
<212> TYPE: PRT
<213> ORGANISM: Artificial sequence
<220> FEATURE:
<223> OTHER INFORMATION: Synthetic peptide

<400> SEQUENCE: 182

Lys Val Ser Asn Arg Phe Ser
1               5

<210> SEQ ID NO 183
<211> LENGTH: 9
<212> TYPE: PRT
<213> ORGANISM: Artificial sequence
<220> FEATURE:
<223> OTHER INFORMATION: Synthetic peptide

<400> SEQUENCE: 183

Phe Gln Gly Leu His Val Pro Pro Thr
1               5

<210> SEQ ID NO 184
<211> LENGTH: 10
<212> TYPE: PRT
<213> ORGANISM: Artificial sequence
<220> FEATURE:
<223> OTHER INFORMATION: Synthetic peptide

<400> SEQUENCE: 184

Gly Phe Thr Phe Asn Asn Tyr Ala Met Asn
1               5                   10

<210> SEQ ID NO 185
<211> LENGTH: 19
```

```
<212> TYPE: PRT
<213> ORGANISM: Artificial sequence
<220> FEATURE:
<223> OTHER INFORMATION: Synthetic peptide

<400> SEQUENCE: 185

Arg Ile Arg Ser Lys Arg Asn Asn Tyr Ala Thr His Tyr Asp Asp Ser
1               5                   10                  15

Val Lys Asp

<210> SEQ ID NO 186
<211> LENGTH: 8
<212> TYPE: PRT
<213> ORGANISM: Artificial sequence
<220> FEATURE:
<223> OTHER INFORMATION: Synthetic peptide

<400> SEQUENCE: 186

Asp Gly Pro Tyr Ala Met Asp Tyr
1               5

<210> SEQ ID NO 187
<211> LENGTH: 17
<212> TYPE: PRT
<213> ORGANISM: Artificial sequence
<220> FEATURE:
<223> OTHER INFORMATION: Synthetic peptide

<400> SEQUENCE: 187

Lys Ser Ser Gln Ser Leu Leu Tyr Ser Ser Asn Gln Lys Asn Tyr Leu
1               5                   10                  15

Ala

<210> SEQ ID NO 188
<211> LENGTH: 7
<212> TYPE: PRT
<213> ORGANISM: Artificial sequence
<220> FEATURE:
<223> OTHER INFORMATION: Synthetic peptide

<400> SEQUENCE: 188

Trp Ala Ser Thr Arg Glu Ser
1               5

<210> SEQ ID NO 189
<211> LENGTH: 9
<212> TYPE: PRT
<213> ORGANISM: Artificial sequence
<220> FEATURE:
<223> OTHER INFORMATION: Synthetic peptide

<400> SEQUENCE: 189

Gln Gln Tyr Tyr Ser Tyr Pro Tyr Thr
1               5

<210> SEQ ID NO 190
<211> LENGTH: 10
<212> TYPE: PRT
<213> ORGANISM: Artificial sequence
<220> FEATURE:
<223> OTHER INFORMATION: Synthetic peptide

<400> SEQUENCE: 190

Gly Phe Ile Phe Asn Thr Tyr Ala Met Asn
1               5                   10
```

```
<210> SEQ ID NO 191
<211> LENGTH: 19
<212> TYPE: PRT
<213> ORGANISM: Artificial sequence
<220> FEATURE:
<223> OTHER INFORMATION: Synthetic peptide

<400> SEQUENCE: 191

Arg Ile Arg Ser Lys Ser Asn Lys Tyr Ala Thr Tyr Tyr Val Asp Ser
1               5                   10                  15

Val Lys Asp

<210> SEQ ID NO 192
<211> LENGTH: 3
<212> TYPE: PRT
<213> ORGANISM: Artificial sequence
<220> FEATURE:
<223> OTHER INFORMATION: Synthetic peptide

<400> SEQUENCE: 192

Asp Gly Ile
1

<210> SEQ ID NO 193
<211> LENGTH: 17
<212> TYPE: PRT
<213> ORGANISM: Artificial sequence
<220> FEATURE:
<223> OTHER INFORMATION: Synthetic peptide

<400> SEQUENCE: 193

Lys Ser Ser Gln Ser Leu Leu Asn Ser Gly Asn Gln Lys Asn Tyr Leu
1               5                   10                  15

Thr

<210> SEQ ID NO 194
<211> LENGTH: 7
<212> TYPE: PRT
<213> ORGANISM: Artificial sequence
<220> FEATURE:
<223> OTHER INFORMATION: Synthetic peptide

<400> SEQUENCE: 194

Trp Ala Phe Thr Arg Glu Ser
1               5

<210> SEQ ID NO 195
<211> LENGTH: 9
<212> TYPE: PRT
<213> ORGANISM: Artificial sequence
<220> FEATURE:
<223> OTHER INFORMATION: Synthetic peptide

<400> SEQUENCE: 195

Gln Asn Asp Tyr Ser Tyr Pro Leu Thr
1               5

<210> SEQ ID NO 196
<211> LENGTH: 10
<212> TYPE: PRT
<213> ORGANISM: Artificial sequence
<220> FEATURE:
<223> OTHER INFORMATION: Synthetic peptide

<400> SEQUENCE: 196
```

```
Gly Tyr Thr Phe Thr Asn Tyr Gly Ile Asn
1               5                   10
```

<210> SEQ ID NO 197
<211> LENGTH: 14
<212> TYPE: PRT
<213> ORGANISM: Artificial sequence
<220> FEATURE:
<223> OTHER INFORMATION: Synthetic peptide

<400> SEQUENCE: 197

```
Trp Val Lys Gln Ala Pro Gly Lys Gly Leu Lys Trp Met Gly
1               5                   10
```

<210> SEQ ID NO 198
<211> LENGTH: 9
<212> TYPE: PRT
<213> ORGANISM: Artificial sequence
<220> FEATURE:
<223> OTHER INFORMATION: Synthetic peptide

<400> SEQUENCE: 198

```
Gly Ser Ala Lys Gly Gly Phe Phe Tyr
1               5
```

<210> SEQ ID NO 199
<211> LENGTH: 16
<212> TYPE: PRT
<213> ORGANISM: Artificial sequence
<220> FEATURE:
<223> OTHER INFORMATION: Synthetic peptide

<400> SEQUENCE: 199

```
Lys Ser Ser Gln Ser Leu Leu Tyr Ser Asn Gly Arg Thr Tyr Leu Asn
1               5                   10                  15
```

<210> SEQ ID NO 200
<211> LENGTH: 7
<212> TYPE: PRT
<213> ORGANISM: Artificial sequence
<220> FEATURE:
<223> OTHER INFORMATION: Synthetic peptide

<400> SEQUENCE: 200

```
Leu Val Ser Lys Leu Asp Ser
1               5
```

<210> SEQ ID NO 201
<211> LENGTH: 9
<212> TYPE: PRT
<213> ORGANISM: Artificial sequence
<220> FEATURE:
<223> OTHER INFORMATION: Synthetic peptide

<400> SEQUENCE: 201

```
Val Gln Gly Thr His Phe Pro Tyr Thr
1               5
```

<210> SEQ ID NO 202
<211> LENGTH: 10
<212> TYPE: PRT
<213> ORGANISM: Artificial sequence
<220> FEATURE:
<223> OTHER INFORMATION: Synthetic peptide

<400> SEQUENCE: 202

```
Gly Phe Thr Phe Ser Ser Tyr Gly Met Ser
```

```
<210> SEQ ID NO 203
<211> LENGTH: 17
<212> TYPE: PRT
<213> ORGANISM: Artificial sequence
<220> FEATURE:
<223> OTHER INFORMATION: Synthetic peptide

<400> SEQUENCE: 203

Thr Ile Asp Ser Asn Gly Gly Gly Thr Tyr Tyr Pro Asp Ser Val Lys
1               5                   10                  15
Gly

<210> SEQ ID NO 204
<211> LENGTH: 14
<212> TYPE: PRT
<213> ORGANISM: Artificial sequence
<220> FEATURE:
<223> OTHER INFORMATION: Synthetic peptide

<400> SEQUENCE: 204

Asp Gly Gly Gly Ser Tyr Gly Tyr Tyr Tyr Ala Met Asp Tyr
1               5                   10

<210> SEQ ID NO 205
<211> LENGTH: 17
<212> TYPE: PRT
<213> ORGANISM: Artificial sequence
<220> FEATURE:
<223> OTHER INFORMATION: Synthetic peptide

<400> SEQUENCE: 205

Lys Ser Ser Gln Ser Leu Leu Asn Ser Arg Thr Arg Lys Ser Tyr Leu
1               5                   10                  15
Ala

<210> SEQ ID NO 206
<211> LENGTH: 7
<212> TYPE: PRT
<213> ORGANISM: Artificial sequence
<220> FEATURE:
<223> OTHER INFORMATION: Synthetic peptide

<400> SEQUENCE: 206

Trp Ala Ser Thr Arg Glu Ser
1               5

<210> SEQ ID NO 207
<211> LENGTH: 9
<212> TYPE: PRT
<213> ORGANISM: Artificial sequence
<220> FEATURE:
<223> OTHER INFORMATION: Synthetic peptide

<400> SEQUENCE: 207

Lys Gln Ser Tyr Asn Leu Pro Trp Thr
1               5

<210> SEQ ID NO 208
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 208

Gly Tyr Thr Phe Thr Glu Tyr Thr Met His
1               5                   10

<210> SEQ ID NO 209
<211> LENGTH: 17
<212> TYPE: PRT
<213> ORGANISM: Artificial sequence
<220> FEATURE:
<223> OTHER INFORMATION: Synthetic peptide

<400> SEQUENCE: 209

Gly Ile Asn Pro Asn Asn Gly Gly Thr Ser Tyr Asn Gln Lys Phe Lys
1               5                   10                  15

Gly

<210> SEQ ID NO 210
<211> LENGTH: 7
<212> TYPE: PRT
<213> ORGANISM: Artificial sequence
<220> FEATURE:
<223> OTHER INFORMATION: Synthetic peptide

<400> SEQUENCE: 210

Tyr Trp Asp Tyr Phe Asp Tyr
1               5

<210> SEQ ID NO 211
<211> LENGTH: 16
<212> TYPE: PRT
<213> ORGANISM: Artificial sequence
<220> FEATURE:
<223> OTHER INFORMATION: Synthetic peptide

<400> SEQUENCE: 211

Arg Ser Ser Gln Ser Ile Val His Ser Asn Gly Asn Thr Tyr Leu Glu
1               5                   10                  15

<210> SEQ ID NO 212
<211> LENGTH: 7
<212> TYPE: PRT
<213> ORGANISM: Artificial sequence
<220> FEATURE:
<223> OTHER INFORMATION: Synthetic peptide

<400> SEQUENCE: 212

Lys Val Ser Asn Arg Phe Ser
1               5

<210> SEQ ID NO 213
<211> LENGTH: 9
<212> TYPE: PRT
<213> ORGANISM: Artificial sequence
<220> FEATURE:
<223> OTHER INFORMATION: Synthetic peptide

<400> SEQUENCE: 213

Phe Gln Gly Ser Gln Ile Pro Pro Thr
1               5

<210> SEQ ID NO 214
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 214

Gly Tyr Thr Phe Thr Glu Tyr Thr Met His
1               5                   10

<210> SEQ ID NO 215
<211> LENGTH: 17
<212> TYPE: PRT
<213> ORGANISM: Artificial sequence
<220> FEATURE:
<223> OTHER INFORMATION: Synthetic peptide

<400> SEQUENCE: 215

Gly Ile Asn Thr Asn Asn Gly Gly Thr Ser Tyr Asn Gln Lys Phe Lys
1               5                   10                  15
Gly

<210> SEQ ID NO 216
<211> LENGTH: 14
<212> TYPE: PRT
<213> ORGANISM: Artificial sequence
<220> FEATURE:
<223> OTHER INFORMATION: Synthetic peptide

<400> SEQUENCE: 216

Asp Lys Arg Ser Arg Gly Glu Leu Asp Ser Thr Met Asp Tyr
1               5                   10

<210> SEQ ID NO 217
<211> LENGTH: 16
<212> TYPE: PRT
<213> ORGANISM: Artificial sequence
<220> FEATURE:
<223> OTHER INFORMATION: Synthetic peptide

<400> SEQUENCE: 217

Arg Ser Ser Lys Ser Leu Leu His Ser Asn Gly Asn Thr Tyr Leu Tyr
1               5                   10                  15

<210> SEQ ID NO 218
<211> LENGTH: 7
<212> TYPE: PRT
<213> ORGANISM: Artificial sequence
<220> FEATURE:
<223> OTHER INFORMATION: Synthetic peptide

<400> SEQUENCE: 218

Arg Met Ser Asn Leu Ala Ser
1               5

<210> SEQ ID NO 219
<211> LENGTH: 9
<212> TYPE: PRT
<213> ORGANISM: Artificial sequence
<220> FEATURE:
<223> OTHER INFORMATION: Synthetic peptide

<400> SEQUENCE: 219

Met Gln His Leu Glu Tyr Pro Phe Thr
1               5

<210> SEQ ID NO 220
<211> LENGTH: 120
<212> TYPE: PRT
<213> ORGANISM: Artificial Sequence
<220> FEATURE:
```

<223> OTHER INFORMATION: Synthetic peptide

<400> SEQUENCE: 220

Glu Val Asn Leu Glu Ser Gly Gly Gly Leu Val Gln Pro Gly Gly
1               5                   10                  15

Ser Met Lys Leu Ser Cys Ile Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Tyr Asn Asn Tyr Ala Thr His Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Asn Leu Arg Ala Glu Asp Thr Gly Ile Tyr
                85                  90                  95

Tyr Cys Thr Gly Thr Arg Tyr Gly Ser Ser Leu Asp Tyr Trp Gly Gln
            100                 105                 110

Gly Thr Ser Val Thr Val Ser Ser
            115                 120

<210> SEQ ID NO 221
<211> LENGTH: 113
<212> TYPE: PRT
<213> ORGANISM: Artificial Sequence
<220> FEATURE:
<223> OTHER INFORMATION: Synthetic peptide

<400> SEQUENCE: 221

Asp Ile Val Met Ser Gln Ser Pro Ser Ser Leu Ala Val Ser Val Gly
1               5                   10                  15

Glu Lys Val Thr Met Ser Cys Lys Ser Ser Gln Asn Leu Phe Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Ala Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Ala Gly Thr Lys Leu Glu Leu
            100                 105                 110

Lys

<210> SEQ ID NO 222
<211> LENGTH: 121
<212> TYPE: PRT
<213> ORGANISM: Artificial Sequence
<220> FEATURE:
<223> OTHER INFORMATION: Synthetic peptide

<400> SEQUENCE: 222

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
            50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                85                  90                  95

Ala Ser Ile Tyr Tyr His Thr Ser Leu Trp Tyr Phe Asp Val Trp Gly
                100                 105                 110

Ala Gly Thr Thr Val Thr Val Ser Ser
            115                 120

<210> SEQ ID NO 223
<211> LENGTH: 112
<212> TYPE: PRT
<213> ORGANISM: Artificial Sequence
<220> FEATURE:
<223> OTHER INFORMATION: Synthetic peptide

<400> SEQUENCE: 223

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Arg Val Ser Asn Arg Phe Ser Gly Val Pro
 50                  55                  60

Val Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
                100                 105                 110

<210> SEQ ID NO 224
<211> LENGTH: 121
<212> TYPE: PRT
<213> ORGANISM: Artificial Sequence
<220> FEATURE:
<223> OTHER INFORMATION: Synthetic peptide

<400> SEQUENCE: 224

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                85                  90                  95

Ala Ser Ile Tyr Tyr His Thr Ser Leu Trp Tyr Phe Asp Val Trp Gly
                100                 105                 110

Ala Gly Thr Thr Val Thr Val Ser Ser
            115

<210> SEQ ID NO 225
<211> LENGTH: 112
<212> TYPE: PRT
<213> ORGANISM: Artificial Sequence
<220> FEATURE:
<223> OTHER INFORMATION: Synthetic peptide

<400> SEQUENCE: 225

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 226
<211> LENGTH: 116
<212> TYPE: PRT
<213> ORGANISM: Artificial Sequence
<220> FEATURE:
<223> OTHER INFORMATION: Synthetic peptide

<400> SEQUENCE: 226

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Gly Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Leu His Tyr Gly Tyr Asp Tyr Trp Gly Leu Gly Thr Thr Leu
            100                 105                 110

Thr Val Ser Ser
        115
```

<210> SEQ ID NO 227
<211> LENGTH: 112
<212> TYPE: PRT
<213> ORGANISM: Artificial Sequence
<220> FEATURE:
<223> OTHER INFORMATION: Synthetic peptide

<400> SEQUENCE: 227

```
Asp Val Leu Met Thr Gln Thr Pro Leu Ser Leu Pro Val Ser Leu Gly
1               5                   10                  15
```

```
Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Leu His Val Pro Pro Thr Phe Gly Gly Gly Thr Lys Leu Glu Ile Lys
            100                 105                 110

<210> SEQ ID NO 228
<211> LENGTH: 1953
<212> TYPE: DNA
<213> ORGANISM: Homo sapiens

<400> SEQUENCE: 228
```

| | | | | |
|---|---|---|---|---|
| atgacccca tcctcacggt | cctgatctgt | ctcgggctga | gtctgggccc | ccggacccac | 60 |
| gtgcaggcag ggcacctccc | caagcccacc | ctctgggctg | aaccaggctc | tgtgatcacc | 120 |
| caggggagtc ctgtgaccct | caggtgtcag | ggggccagg | agaccagga | gtaccgtcta | 180 |
| tatagagaaa agaaaacagc | acctggatt | acacggatcc | cacaggagct | tgtgaagaag | 240 |
| ggccagttcc ccatcccatc | catcacctgg | aacacacag | ggcggtatcg | ctgttactat | 300 |
| ggtagcgaca ctgcaggccg | ctcagagagc | agtgacccc | tggagctggt | ggtgacagga | 360 |
| gcctacatca acccaccct | ctcagcccag | cccagcccg | tggtgaactc | aggagggaat | 420 |
| gtaaccctcc agtgtgactc | acaggtgca | tttgatggct | tcattctgtg | taaggaagga | 480 |
| gaagatgaac cccacaatg | cctgaactcc | cagccccatg | cccgtgggtc | gtcccgcgcc | 540 |
| atcttctccg tgggccccgt | gagcccgagt | cgcaggtggt | ggtacaggtg | ctatgcttat | 600 |
| gactcgaact ctccctatga | gtggtctcta | cccagtgatc | tcctggagct | cctggtccta | 660 |
| ggtgtttcta agaagccatc | actctcagtg | cagccaggtc | ctatcgtggc | ccctgaggag | 720 |
| accctgactc tgcagtgtgg | ctctgatgct | ggctacaaca | gatttgttct | gtataaggac | 780 |
| ggggaacgtg acttccttca | gctcgctggc | gcacagcccc | aggctgggct | ctcccaggcc | 840 |
| aacttcaccc tgggccctgt | gagccgctcc | tacggggcc | agtacagatg | ctacggtgca | 900 |
| cacaacctct cctccgagtg | gtcggccccc | agcgaccccc | tggacatcct | gatcgcagga | 960 |
| cagttctatg acagagtctc | cctctcggtg | cagccgggcc | ccacggtggc | ctcaggagag | 1020 |
| aacgtgaccc tgctgtgtca | gtcacaggga | tggatgcaaa | cttttccttct | gaccaaggag | 1080 |
| ggggcagctg atgacccatg | gcgtctaaga | tcaacgtacc | aatctcaaaa | ataccaggct | 1140 |
| gaattcccca tggtcctgt | gacctcagcc | catgcgggga | cctacaggtg | ctacggctca | 1200 |
| cagagctcca aacctacct | gctgactcac | cccagtgacc | cctggagct | cgtggtctca | 1260 |
| ggaccgtctg ggggcccag | ctccccgaca | caggcccca | cctccacatc | tggccctgag | 1320 |
| gaccagcccc tcacccccac | cggtcggat | cccagagtg | gtctgggaag | gcacctgggg | 1380 |
| gttgtgatcg gcatcttggt | ggccgtcatc | ctactgctcc | tcctcctcct | cctcctcttc | 1440 |
| ctcatcctcc gacatcgacg | tcagggcaaa | cactggacat | cgacccagag | aaaggctgat | 1500 |
| ttccaacatc ctgcagggc | tgtggggcca | gagcccacag | acagaggcct | gcagtggagg | 1560 |

```
tccagcccag ctgccgatgc ccaggaagaa aacctctatg ctgccgtgaa gcacacacag    1620
cctgaggatg gggtggagat ggacactcgg agcccacacg atgaagaccc ccaggcagtg    1680
acgtatgccg aggtgaaaca ctccagacct aggagagaaa tggcctctcc tccttcccca    1740
ctgtctgggg aattcctgga cacaaaggac agacaggcgg aagaggacag gcagatggac    1800
actgaggctg ctgcatctga agccccccag gatgtgacct acgcccagct gcacagcttg    1860
accctcagac gggaggcaac tgagcctcct ccatcccagg aagggccctc tccagctgtg    1920
cccagcatct acgccactct ggccatccac tag                                 1953
```

<210> SEQ ID NO 229
<211> LENGTH: 650
<212> TYPE: PRT
<213> ORGANISM: Homo sapiens

<400> SEQUENCE: 229

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300
```

```
Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
            325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
            405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
            485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys His Thr Gln Pro Glu Asp Gly
            530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
            565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ala Ser Glu Ala
            595                 600                 605

Pro Gln Asp Val Thr Tyr Ala Gln Leu His Ser Leu Thr Leu Arg Arg
            610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
            645                 650

<210> SEQ ID NO 230
<211> LENGTH: 438
<212> TYPE: PRT
<213> ORGANISM: Homo sapiens

<400> SEQUENCE: 230

Gly His Leu Pro Lys Pro Thr Leu Trp Ala Glu Pro Gly Ser Val Ile
1               5                   10                  15

Thr Gln Gly Ser Pro Val Thr Leu Arg Cys Gln Gly Gly Gln Glu Thr
            20                  25                  30
```

Gln Glu Tyr Arg Leu Tyr Arg Glu Lys Lys Thr Ala Leu Trp Ile Thr
        35                  40                  45

Arg Ile Pro Gln Glu Leu Val Lys Lys Gly Gln Phe Pro Ile Pro Ser
 50                  55                  60

Ile Thr Trp Glu His Ala Gly Arg Tyr Arg Cys Tyr Tyr Gly Ser Asp
 65                  70                  75                  80

Thr Ala Gly Arg Ser Glu Ser Ser Asp Pro Leu Glu Leu Val Val Thr
                 85                  90                  95

Gly Ala Tyr Ile Lys Pro Thr Leu Ser Ala Gln Pro Ser Pro Val Val
                100                 105                 110

Asn Ser Gly Gly Asn Val Ile Leu Gln Cys Asp Ser Gln Val Ala Phe
            115                 120                 125

Asp Gly Phe Ser Leu Cys Lys Glu Gly Glu Asp Glu His Pro Gln Cys
        130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Leu Val Leu Gly Val Ser Lys Lys Pro Ser Leu Ser Val Gln
            195                 200                 205

Pro Gly Pro Ile Val Ala Pro Glu Glu Thr Leu Thr Leu Gln Cys Gly
        210                 215                 220

Ser Asp Ala Gly Tyr Asn Arg Phe Val Leu Tyr Lys Asp Gly Glu Arg
225                 230                 235                 240

Asp Phe Leu Gln Leu Ala Gly Ala Gln Pro Gln Ala Gly Leu Ser Gln
                245                 250                 255

Ala Asn Phe Thr Leu Gly Pro Val Ser Arg Ser Tyr Gly Gly Gln Tyr
                260                 265                 270

Arg Cys Tyr Gly Ala His Asn Leu Ser Ser Glu Trp Ser Ala Pro Ser
            275                 280                 285

Asp Pro Leu Asp Ile Leu Ile Ala Gly Gln Phe Tyr Asp Arg Val Ser
        290                 295                 300

Leu Ser Val Gln Pro Gly Pro Thr Val Ala Ser Gly Glu Asn Val Thr
305                 310                 315                 320

Leu Leu Cys Gln Ser Gln Gly Trp Met Gln Thr Phe Leu Leu Thr Lys
                325                 330                 335

Glu Gly Ala Ala Asp Asp Pro Trp Arg Leu Arg Ser Thr Tyr Gln Ser
                340                 345                 350

Gln Lys Tyr Gln Ala Glu Phe Pro Met Gly Pro Val Thr Ser Ala His
            355                 360                 365

Ala Gly Thr Tyr Arg Cys Tyr Gly Ser Gln Ser Ser Lys Pro Tyr Leu
        370                 375                 380

Leu Thr His Pro Ser Asp Pro Leu Glu Leu Val Val Ser Gly Pro Ser
385                 390                 395                 400

Gly Gly Pro Ser Ser Pro Thr Thr Gly Pro Thr Ser Thr Ser Gly Pro
                405                 410                 415

Glu Asp Gln Pro Leu Thr Pro Thr Gly Ser Asp Pro Gln Ser Gly Leu
            420                 425                 430

Gly Arg His Leu Gly Val
            435

<210> SEQ ID NO 231
<211> LENGTH: 1797
<212> TYPE: DNA
<213> ORGANISM: Homo sapiens

<400> SEQUENCE: 231

```
atgacccca tcgtcacagt cctgatctgt ctcgggctga gtctgggccc caggacccgc      60
gtgcagacag ggaccatccc caagcccacc ctgtgggctg agccagactc tgtgatcacc     120
caggggagtc ccgtcaccct cagttgtcag gggagccttg aagcccagga gtaccgtcta     180
tatagggaga aaaaatcagc atcttggatt acacggatac gaccagagct tgtgaagaac     240
ggccagttcc acatcccatc catcacctgg gaacacacag ggcgatatgg ctgtcagtat     300
tacagccgcg ctcggtggtc tgagctcagt gaccccctgg tgctggtgat gacaggagcc     360
tacccaaaac ccaccctctc agcccagccc agccctgtgg tgacctcagg aggaagggtg     420
accctccagt gtgagtcaca ggtggcattt ggcggcttca ttctgtgtaa ggaaggagaa     480
gatgaacacc cacaatgcct gaactcccag cccatgccc gtgggtcgtc ccgcgccatc      540
ttctccgtgg gccccgtgag cccgaatcgc aggtggtcgc acaggtgcta tggttatgac     600
ttgaactctc cctatgtgtg gtcttcaccc agtgatctcc tggagctcct ggtcccaggt     660
gtttctaaga agccatcact ctcagtgcag ccgggtcctg tcatggcccc tggggaaagc     720
ctgacccctcc agtgtgtctc tgatgtcggc tatgacagat ttgttctgta caaggagggg     780
gaacgtgacc ttcgccagct ccctggccgg cagccccagg ctgggctctc ccaggccaac     840
ttcacccctg gccctgtgag ccgctcctac ggggggccagt acagatgcta cggtgcacac     900
aacctctcct ctgagtgctc ggccccagc gaccccctgg acatcctgat cacaggacag     960
atccgtggca cacccttcat ctcagtgcag ccaggcccca gtgggcctc aggagagaac    1020
gtgaccctgc tgtgtcagtc atggcggcag ttccacactt tccttctgac caaggcggga    1080
gcagctgatg ccccactccg tctaagatca atacacgaat atcctaagta ccaggctgaa    1140
ttcccccatga gtcctgtgac ctcagcccac gcggggacct acaggtgcta cggctcactc    1200
aactccgacc cctacctgct gtctcacccc agtgagcccc tggagctcgt ggtctcagga    1260
ccctccatgg gttccagccc ccacccacc ggtcccatct ccacacctgc aggccctgag    1320
gaccagcccc tcaccccac tgggtcggat cccaaagtg gtctgggaag cacctgggg     1380
gttgtgatcg gcatcttggt ggccgtcgtc ctactgctcc tcctcctcct cctcctcttc    1440
ctcatcctcc gacatcgacg tcagggcaaa cactggacat cgacccagag aaaggctgat    1500
ttccaacatc ctgcagggc tgtggggcca gagcccacag acagaggcct gcagtggagg    1560
tccagcccag ctgccgacgc ccaggaagaa aacctctatg ctgccgtgaa ggacacacag    1620
cctgaagatg gggtggagat ggacactcgg gctgctgcat ctgaagcccc ccaggatgtg    1680
acctacgccc agctgcacag cttgacccta gacggaagg caactgagcc tcctccatcc    1740
caggaagggg aacctccagc tgagcccagc atctacgcca ccctggccat ccactag      1797
```

<210> SEQ ID NO 232
<211> LENGTH: 598
<212> TYPE: PRT
<213> ORGANISM: Homo sapiens

<400> SEQUENCE: 232

```
Met Thr Pro Ile Val Thr Val Leu Ile Cys Leu Gly Leu Ser Leu Gly
1               5                   10                  15
```

```
Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
            130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
            195                 200                 205

Ser Pro Ser Asp Leu Leu Glu Leu Leu Val Pro Gly Val Ser Lys Lys
            210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
            275                 280                 285

Ser Tyr Gly Gly Gln Tyr Arg Cys Tyr Gly Ala His Asn Leu Ser Ser
            290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
            325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
            370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
```

```
                       435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
            580                 585                 590

Ala Thr Leu Ala Ile His
        595

<210> SEQ ID NO 233
<211> LENGTH: 440
<212> TYPE: PRT
<213> ORGANISM: Homo sapiens

<400> SEQUENCE: 233

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile
    50                  55                  60

Pro Ser Ile Thr Trp Glu His Thr Gly Arg Tyr Gly Cys Gln Tyr Tyr
65                  70                  75                  80

Ser Arg Ala Arg Trp Ser Glu Leu Ser Asp Pro Leu Val Leu Val Met
                85                  90                  95

Thr Gly Ala Tyr Pro Lys Pro Thr Leu Ser Ala Gln Pro Ser Pro Val
            100                 105                 110

Val Thr Ser Gly Gly Arg Val Thr Leu Gln Cys Glu Ser Gln Val Ala
        115                 120                 125

Phe Gly Gly Phe Ile Leu Cys Lys Glu Gly Glu Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
        195                 200                 205
```

Gln Pro Gly Pro Val Val Ala Pro Gly Glu Ser Leu Thr Leu Gln Cys
    210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Cys Ser Ala Pro
        275                 280                 285

Ser Asp Pro Leu Asp Ile Leu Ile Thr Gly Gln Ile Arg Gly Thr Pro
    290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val
        435                 440

<210> SEQ ID NO 234
<211> LENGTH: 1896
<212> TYPE: DNA
<213> ORGANISM: Homo sapiens

<400> SEQUENCE: 234
atgacgcccg ccctcacagc cctgctctgc cttgggctga gtctgggccc caggacccgc      60
atgcaggcag ggcccttccc caaacccacc ctctgggctg agccaggctc tgtgatcagc     120
tgggggagcc ccgtgaccat ctggtgtcag gggagcctgg aggcccagga gtaccaactg     180
gataaagagg gaagcccaga gccctgggac agaaataacc cactggaacc caagaacaag     240
gccagattct ccatcccatc catgacacag caccatgcag ggagataccg ctgccactat     300
tacagctctg caggctggtc agagcccagc gaccccctgg agctggtgat gacaggattc     360
tacaacaaac ccaccctctc agccctgccc agccctgtgg tggcctcagg ggggaatatg     420
accctccgat gtggctcaca gaagggatat caccattttg ttctgatgaa ggaaggagaa     480
caccagctcc cccggaccct ggactcacag cagctccaca gtggggggtt ccaggccctg     540
ttccctgtgg gccccgtgac ccccagccac aggtggaggt tcacatgcta ttactattat     600
acaaacaccc cctgggtgtg gtcccacccc agtgaccccc tggagattct gccctcaggc     660
gtgtctagga gccctccct cctgaccctg cagggccctg tcctggcccc tgggcagagc     720
ctgacccctc agtgtggctc tgatgtcggc tacgacagat ttgttctgta taaggagggg     780

```
gaacgtgact tcctccagcg ccctggccag cagccccagg ctgggctctc ccaggccaac    840
ttcaccctgg gccctgtgag ccgctcctac gggggccagt acaggtgcta tggtgcacac    900
aacctctcct ccgagtggtc ggcccccagt gacccctgg acatcctgat cacaggacag    960
atctatgaca ccgtctccct gtcagcacag ccggggccca cagtggcctc aggagagaac   1020
atgaccctgc tgtgtcagtc acgggggtat tttgacactt tccttctgac caaagaaggg   1080
gcagcccatc ccccactgcg tctgagatca atgtacggag ctcataagta ccaggctgaa   1140
ttccccatga gtcctgtgac ctcagcccac gcggggacct acaggtgcta cggctcacgc   1200
agctccaacc cccacctgct gtctttcccc agtgagcccc tggaactcat ggtctcagga   1260
cactctggag gctccagcct cccacccaca gggccgccct ccacacctgg tctgggaaga   1320
tacctggagg ttttgattgg ggtctcggtg gccttcgtcc tgctgctctt cctcctcctc   1380
ttcctcctcc tcctccgtca gcgtcacagc aaacacagga catctgacca gagaaagact   1440
gatttccagc gtcctgcagg ggctgcggag acagagccca aggacagggg cctgctgagg   1500
aggtccagcc cagctgctga cgtccaggaa gaaaacctct atgctgctgt gaaggacaca   1560
cagtctgagg acagggtgga gctggacagt cagagcccac acgatgaaga ccccaggca   1620 gtgacgtatg ccccggtgaa acactccagt cctaggagag aaatggcctc tcctccctcc   1680
tcactgtctg gggaattcct ggacacaaag gacagacagg tggaagagga caggcagatg   1740
gacactgagg ctgctgcatc tgaagcctcc caggatgtga cctacgccca gctgcacagc   1800 ttgacccta gacggaaggc aactgagcct cctccatccc aggaagggga acctccagct   1860
gagcccagca tctacgccac tctggccatc cactag                              1896
```

<210> SEQ ID NO 235
<211> LENGTH: 631
<212> TYPE: PRT
<213> ORGANISM: Homo sapiens

<400> SEQUENCE: 235

```
Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Gln Glu Ala Gln Glu Tyr Arg Leu His Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Met Val Met Thr Gly Ala Tyr Ser Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Arg Gly
                165                 170                 175
```

```
Phe Gln Ala Leu Phe Pro Val Gly Pro Val Thr Pro Ser His Arg Trp
                180             185                 190
Arg Phe Thr Cys Tyr Tyr Tyr Thr Asn Thr Pro Trp Val Trp Ser
            195             200             205
His Pro Ser Asp Pro Leu Glu Ile Leu Pro Ser Gly Val Ser Arg Lys
        210             215                 220
Pro Ser Leu Leu Thr Leu Gln Gly Pro Val Leu Ala Pro Gly Gln Ser
225             230             235                 240
Leu Thr Leu Gln Cys Gly Ser Asp Val Gly Tyr Asn Arg Phe Val Leu
                245             250                 255
Tyr Lys Glu Gly Glu Arg Asp Phe Leu Gln Arg Pro Gly Gln Gln Pro
                260             265                 270
Gln Ala Gly Leu Ser Gln Ala Asn Phe Thr Leu Gly Pro Val Ser Pro
                275             280             285
Ser Asn Gly Gly Gln Tyr Arg Cys Tyr Gly Ala His Asn Leu Ser Ser
        290             295             300
Glu Trp Ser Ala Pro Ser Asp Pro Leu Asn Ile Leu Met Ala Gly Gln
305             310             315                 320
Ile Tyr Asp Thr Val Ser Leu Ser Ala Gln Pro Gly Pro Thr Val Ala
                325             330                 335
Ser Gly Glu Asn Val Thr Leu Leu Cys Gln Ser Trp Trp Gln Phe Asp
            340             345             350
Thr Phe Leu Leu Thr Lys Glu Gly Ala Ala His Pro Pro Leu Arg Leu
            355             360             365
Arg Ser Met Tyr Gly Ala His Lys Tyr Gln Ala Glu Phe Pro Met Ser
370             375             380
Pro Val Thr Ser Ala His Ala Gly Thr Tyr Arg Cys Tyr Gly Ser Tyr
385             390             395             400
Ser Ser Asn Pro His Leu Leu Ser His Pro Ser Glu Pro Leu Glu Leu
            405             410             415
Val Val Ser Gly His Ser Gly Gly Ser Ser Leu Pro Pro Thr Gly Pro
            420             425             430
Pro Ser Thr Pro Gly Leu Gly Arg Tyr Leu Glu Val Leu Ile Gly Val
            435             440             445
Ser Val Ala Phe Val Leu Leu Leu Phe Leu Leu Leu Phe Leu Leu Leu
450             455             460
Arg Arg Gln Arg His Ser Lys His Arg Thr Ser Asp Gln Arg Lys Thr
465             470             475             480
Asp Phe Gln Arg Pro Ala Gly Ala Ala Glu Thr Glu Pro Lys Asp Arg
            485             490             495
Gly Leu Leu Arg Arg Ser Ser Pro Ala Ala Asp Val Gln Glu Glu Asn
            500             505             510
Leu Tyr Ala Ala Val Lys Asp Thr Gln Ser Glu Asp Arg Val Glu Leu
            515             520             525
Asp Ser Gln Ser Pro His Asp Glu Asp Pro Gln Ala Val Thr Tyr Ala
            530             535             540
Pro Val Lys His Ser Ser Pro Arg Arg Glu Met Ala Ser Pro Pro Ser
545             550             555             560
Ser Leu Ser Gly Glu Phe Leu Asp Thr Lys Asp Arg Gln Val Glu Glu
            565             570             575
Asp Arg Gln Met Asp Thr Glu Ala Ala Ala Ser Glu Ala Ser Gln Asp
            580             585             590
Val Thr Tyr Ala Gln Leu His Ser Leu Thr Leu Arg Arg Lys Ala Thr
```

```
                     595                 600                 605
Glu Pro Pro Ser Gln Glu Gly Glu Pro Ala Glu Pro Ser Ile
            610                 615                 620

Tyr Ala Thr Leu Ala Ile His
625                 630

<210> SEQ ID NO 236
<211> LENGTH: 420
<212> TYPE: PRT
<213> ORGANISM: Homo sapiens

<400> SEQUENCE: 236

Gly Pro Phe Pro Lys Pro Thr Leu Trp Ala Glu Pro Gly Ser Val Ile
1               5                  10                  15

Ser Trp Gly Ser Pro Val Thr Ile Trp Cys Gln Gly Ser Gln Glu Ala
            20                  25                  30

Gln Glu Tyr Arg Leu His Lys Glu Gly Ser Pro Glu Pro Leu Asp Arg
        35                  40                  45

Asn Asn Pro Leu Glu Pro Lys Asn Lys Ala Arg Phe Ser Ile Pro Ser
    50                  55                  60

Met Thr Glu His His Ala Gly Arg Tyr Arg Cys His Tyr Tyr Ser Ser
65                  70                  75                  80

Ala Gly Trp Ser Glu Pro Ser Asp Pro Leu Glu Met Val Met Thr Gly
                85                  90                  95

Ala Tyr Ser Lys Pro Thr Leu Ser Ala Leu Pro Ser Pro Val Val Ala
            100                 105                 110

Ser Gly Gly Asn Met Thr Leu Arg Cys Gly Ser Gln Lys Gly Tyr His
        115                 120                 125

His Phe Val Leu Met Lys Glu Gly Glu His Gln Leu Pro Arg Thr Leu
    130                 135                 140

Asp Ser Gln Gln Leu His Ser Arg Gly Phe Gln Ala Leu Phe Pro Val
145                 150                 155                 160

Gly Pro Val Thr Pro Ser His Arg Trp Arg Phe Thr Cys Tyr Tyr Tyr
                165                 170                 175

Tyr Thr Asn Thr Pro Trp Val Trp Ser His Pro Ser Asp Pro Leu Glu
            180                 185                 190

Ile Leu Pro Ser Gly Val Ser Arg Lys Pro Ser Leu Leu Thr Leu Gln
        195                 200                 205

Gly Pro Val Leu Ala Pro Gly Gln Ser Leu Thr Leu Gln Cys Gly Ser
    210                 215                 220

Asp Val Gly Tyr Asn Arg Phe Val Leu Tyr Lys Glu Gly Glu Arg Asp
225                 230                 235                 240

Phe Leu Gln Arg Pro Gly Gln Gln Pro Gln Ala Gly Leu Ser Gln Ala
                245                 250                 255

Asn Phe Thr Leu Gly Pro Val Ser Pro Ser Asn Gly Gly Gln Tyr Arg
            260                 265                 270

Cys Tyr Gly Ala His Asn Leu Ser Ser Glu Trp Ser Ala Pro Ser Asp
        275                 280                 285

Pro Leu Asn Ile Leu Met Ala Gly Gln Ile Tyr Asp Thr Val Ser Leu
    290                 295                 300

Ser Ala Gln Pro Gly Pro Thr Val Ala Ser Gly Glu Asn Val Thr Leu
305                 310                 315                 320

Leu Cys Gln Ser Trp Trp Gln Phe Asp Thr Phe Leu Leu Thr Lys Glu
                325                 330                 335
```

| | | | | | | | | | | | |
|---|---|---|---|---|---|---|---|---|---|---|---|
|Gly|Ala|Ala|His|Pro|Pro|Leu|Arg|Leu|Arg|Ser|Met|Tyr|Gly|Ala|His|
| | | |340| | | |345| | | |350|

Lys Tyr Gln Ala Glu Phe Pro Met Ser Pro Val Thr Ser Ala His Ala
            355                 360                 365

Gly Thr Tyr Arg Cys Tyr Gly Ser Tyr Ser Ser Asn Pro His Leu Leu
    370                 375                 380

Ser His Pro Ser Glu Pro Leu Glu Leu Val Val Ser Gly His Ser Gly
385                 390                 395                 400

Gly Ser Ser Leu Pro Pro Thr Gly Pro Pro Ser Thr Pro Gly Leu Gly
                405                 410                 415

Arg Tyr Leu Glu
            420

<210> SEQ ID NO 237
<211> LENGTH: 1347
<212> TYPE: DNA
<213> ORGANISM: Homo sapiens

<400> SEQUENCE: 237

```
atgatcccca ccttcacggc tctgctctgc ctcgggctga gtctgggccc caggacccac    60
atgcaggcag ggcccctccc caaacccacc ctctgggctg agccaggctc tgtgatcagc   120
tgggggaact ctgtgaccat ctggtgtcag ggaccctgg aggctcggga gtaccgtctg   180
gataaagagg aaagcccagc accctgggac agacagaacc cactggagcc aagaacaag   240
gccagattct ccatcccatc catgacagag gactatgcag ggagataccg ctgttactat   300
cgcagccctg taggctggtc acagcccagt gaccccctgg agctggtgat gacaggagcc   360
tacagtaaac ccaccctttc agccctgccg agtcctcttg tgacctcagg aaagagcgtg   420
accctgctgt gtcagtcacg gagcccaatg gacactttc ttctgatcaa ggagcgggca   480
gcccatcccc tactgcatct gagatcagag cacggagctc agcagcacca ggctgaattc   540
cccatgagtc ctgtgacctc agtgcacggg gggacctaca ggtgcttcag ctcacacggc   600
ttctcccact acctgctgtc acacccagt gacccctgg agctcatagt ctcaggatcc   660
ttggagggtc ccaggccctc acccacaagg tccgtctcaa cagctgcagg ccctgaggac   720
cagcccctca tgcctacagg gtcagtcccc cacagtggtc tgagaaggca ctgggaggta   780
ctgatcgggg tcttggtggt ctccatcctg cttctctccc tcctcctctt cctcctcctc   840
caacactggc gtcagggaaa acacaggaca ttggcccaga gacaggctga tttccaacgt   900
cctccagggg ctgccgagcc agagcccaag gacgggggcc tacagaggag gtccagccca   960
gctgctgacg tccagggaga aaacttctgt gctgccgtga gaacacaca gcctgaggac  1020
ggggtggaaa tggacactcg gcagagccca cacgatgaag accccaggc agtgacgtat  1080
gccaaggtga acactccag acctaggaga gaaatggcct ctcctccctc cccactgtct  1140
ggggaattcc tggacacaaa ggacagacag gcagaagagg acagacagat ggacactgag  1200
gctgctgcat ctgaagcccc caggatgtg acctacgccc ggctgacag ctttacccctc  1260
agacagaagg caactgagcc tcctccatcc caggaagggg cctctccagc tgagcccagt  1320
gtctatgcca ctctggccat ccactaa                                       1347
```

<210> SEQ ID NO 238
<211> LENGTH: 448
<212> TYPE: PRT
<213> ORGANISM: Homo sapiens

<400> SEQUENCE: 238

```
Met Ile Pro Thr Phe Thr Ala Leu Leu Cys Leu Gly Leu Ser Leu Gly
1               5                   10                  15

Pro Arg Thr His Met Gln Ala Gly Pro Leu Pro Lys Pro Thr Leu Trp
                20                  25                  30

Ala Glu Pro Gly Ser Val Ile Ser Trp Gly Asn Ser Val Thr Ile Trp
            35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
        100                 105                 110

Leu Glu Leu Val Met Thr Gly Ala Tyr Ser Lys Pro Thr Leu Ser Ala
            115                 120                 125

Leu Pro Ser Pro Leu Val Thr Ser Gly Lys Ser Val Thr Leu Leu Cys
130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Asp Pro
210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
            245                 250                 255

His Trp Glu Val Leu Ile Gly Val Leu Val Val Ser Ile Leu Leu Leu
        260                 265                 270

Ser Leu Leu Leu Phe Leu Leu Leu Gln His Trp Arg Gln Gly Lys His
    275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
            325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
        355                 360                 365

Arg Arg Glu Met Ala Ser Pro Pro Ser Pro Leu Ser Gly Glu Phe Leu
370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
                405                 410                 415
```

```
Ser Phe Thr Leu Arg Gln Lys Ala Thr Glu Pro Pro Ser Gln Glu
                420                 425                 430

Gly Ala Ser Pro Ala Glu Pro Ser Val Tyr Ala Thr Leu Ala Ile His
            435                 440                 445

<210> SEQ ID NO 239
<211> LENGTH: 238
<212> TYPE: PRT
<213> ORGANISM: Homo sapiens

<400> SEQUENCE: 239

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Gly Ser Pro Ala Pro Trp
        35                  40                  45

Asp Arg Gln Asn Pro Leu Glu Pro Lys Asn Lys Ala Arg Phe Ser Ile
    50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
            100                 105                 110

Val Thr Ser Gly Lys Ser Val Thr Leu Leu Cys Gln Ser Arg Ser Pro
        115                 120                 125

Met Asp Thr Phe Leu Leu Ile Lys Glu Arg Ala Ala His Pro Leu Leu
    130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
            180                 185                 190

Glu Leu Ile Val Ser Gly Ser Leu Glu Asp Pro Arg Pro Ser Pro Thr
        195                 200                 205

Arg Ser Val Ser Thr Ala Ala Gly Pro Glu Asp Gln Pro Leu Met Pro
    210                 215                 220

Thr Gly Ser Val Pro His Ser Gly Leu Arg Arg His Trp Glu
225                 230                 235

<210> SEQ ID NO 240
<211> LENGTH: 1773
<212> TYPE: DNA
<213> ORGANISM: Homo sapiens

<400> SEQUENCE: 240
atgaccctca ccctctcagt cctgatttgc ctcgggctga gtgtgggccc caggacctgc      60
gtgcaggcag gcaccctccc caaacccacc ctctgggctg agccagcctc tgtgatagct     120
cgggggaagc ccgtgaccct ctggtgtcag gggcccctgg agactgagga gtaccgtctg     180
gataaggagg gactcccatg ggcccggaag agacagaacc cactggagcc tggagccaag     240
gccaagttcc acattccatc cacggtgtat gacagtgcag gcgataccg ctgctactat     300 gagacccctg caggctggtc agagcccagt gaccccctgg agctggtggc gacaggattc     360
```

```
tatgcagaac ccactcttt agccctgccg agtcctgtgg tggcctcagg aggaaatgtg    420
accctccagt gtgatacact ggacggactt ctcacgtttg ttcttgttga ggaagaacag    480
aagctcccca ggaccctgta ctcacagaag ctccccaaag gccatccca ggccctgttc     540
cctgtgggtc ccgtgacccc cagctgcagg tggaggttca gatgctatta ctattacagg    600
aaaaaccctc aggtgtggtc gaaccccagt gacctcctgg agattctggt cccaggcgtg    660
tctaggaagc cctccctcct gatcccgcag ggctctgtcg tggcccgcgg aggcagcctg    720
accctgcagt gtcgctctga tgtcggctat gacatattcg ttctgtacaa ggaggggaa     780
catgacctcg tccagggctc tggccagcag ccccaggctg gctctccca ggccaacttc     840
accctgggcc ctgtgagccg ctcccacggg ggccagtaca gatgctacgg tgcacacaac    900
ctctccccta ggtggtcggc ccccagcgac ccctggaca tcctgatcgc aggactgatc     960
cctgacatac ccgccctctc ggtgcagccg ggccccaagg tggcctcagg agagaacgtg   1020
accctgctgt gtcagtcatg gcatcagata gacactttct ttttgaccaa ggagggggca   1080
gcccatcccc cgctgtgtct aaagtcaaag taccagtctt atagacacca ggctgaattc   1140
tccatgagtc ctgtgacctc agcccagggt ggaacctacc gatgctacag cgcaatcagg   1200
tcctacccct acctgctgtc cagccctagt taccccccagg agctcgtggt ctcaggaccc   1260
tctggggatc ccagcctctc acctacaggc tccaccccca cacctggccc tgaggaccag   1320
cccctcaccc ccacggggtt ggatcccag agtggtctgg aaggcacct ggggttgtg     1380
actggggtct cagtggcctt cgtcctgctg ctgttcctcc tcctcttcct cctcctccga   1440
catcggcatc agagcaaaca caggacatcg gcccatttct accgtcctgc aggggctgcg   1500
gggccagagc ccaaggacca gggcctgcag aagagggcca gcccagttgc tgacatccag   1560
gaggaaattc tcaatgctgc cgtgaaggac acacagccca aggacggggt ggagatggat   1620
gctccggctg ctgcatctga agccccccag gatgtgacct acgcccagct gcacagcttg   1680
accctcagac gggaggcaac tgagcctcct ccatcccagg aaagggaacc tccagctgaa   1740
cccagcatct acgccccct ggccatccac tag                                 1773
```

<210> SEQ ID NO 241
<211> LENGTH: 590
<212> TYPE: PRT
<213> ORGANISM: Homo sapiens

<400> SEQUENCE: 241

```
Met Thr Leu Thr Leu Ser Val Leu Ile Cys Leu Gly Leu Ser Val Gly
1               5                   10                  15

Pro Arg Thr Cys Val Gln Ala Gly Thr Leu Pro Lys Pro Thr Leu Trp
            20                  25                  30

Ala Glu Pro Ala Ser Val Ile Ala Arg Gly Lys Pro Val Thr Leu Trp
        35                  40                  45

Cys Gln Gly Pro Leu Glu Thr Glu Glu Tyr Arg Leu Asp Lys Glu Gly
    50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                85                  90                  95

Arg Cys Tyr Tyr Glu Thr Pro Ala Gly Trp Ser Glu Pro Ser Asp Pro
            100                 105                 110

Leu Glu Leu Val Ala Thr Gly Phe Tyr Ala Glu Pro Thr Leu Leu Ala
        115                 120                 125
```

```
Leu Pro Ser Pro Val Val Ala Ser Gly Gly Asn Val Thr Leu Gln Cys
    130                 135                 140
Asp Thr Leu Asp Gly Leu Leu Thr Phe Val Leu Val Glu Glu Glu Gln
145                 150                 155                 160
Lys Leu Pro Arg Thr Leu Tyr Ser Gln Lys Leu Pro Lys Gly Pro Ser
                165                 170                 175
Gln Ala Leu Phe Pro Val Gly Pro Val Thr Pro Ser Cys Arg Trp Arg
                180                 185                 190
Phe Arg Cys Tyr Tyr Tyr Tyr Arg Lys Asn Pro Gln Val Trp Ser Asn
                195                 200                 205
Pro Ser Asp Leu Leu Glu Ile Leu Val Pro Gly Val Ser Arg Lys Pro
210                 215                 220
Ser Leu Leu Ile Pro Gln Gly Ser Val Val Ala Arg Gly Gly Ser Leu
225                 230                 235                 240
Thr Leu Gln Cys Arg Ser Asp Val Gly Tyr Asp Ile Phe Val Leu Tyr
                245                 250                 255
Lys Glu Gly Glu His Asp Leu Val Gln Gly Ser Gly Gln Gln Pro Gln
                260                 265                 270
Ala Gly Leu Ser Gln Ala Asn Phe Thr Leu Gly Pro Val Ser Arg Ser
                275                 280                 285
His Gly Gly Gln Tyr Arg Cys Tyr Gly Ala His Asn Leu Ser Pro Arg
                290                 295                 300
Trp Ser Ala Pro Ser Asp Pro Leu Asp Ile Leu Ile Ala Gly Leu Ile
305                 310                 315                 320
Pro Asp Ile Pro Ala Leu Ser Val Gln Pro Gly Pro Lys Val Ala Ser
                325                 330                 335
Gly Glu Asn Val Thr Leu Leu Cys Gln Ser Trp His Gln Ile Asp Thr
                340                 345                 350
Phe Phe Leu Thr Lys Glu Gly Ala Ala His Pro Pro Leu Cys Leu Lys
                355                 360                 365
Ser Lys Tyr Gln Ser Tyr Arg His Gln Ala Glu Phe Ser Met Ser Pro
                370                 375                 380
Val Thr Ser Ala Gln Gly Gly Thr Tyr Arg Cys Tyr Ser Ala Ile Arg
385                 390                 395                 400
Ser Tyr Pro Tyr Leu Leu Ser Ser Pro Ser Tyr Pro Gln Glu Leu Val
                405                 410                 415
Val Ser Gly Pro Ser Gly Asp Pro Ser Leu Ser Pro Thr Gly Ser Thr
                420                 425                 430
Pro Thr Pro Gly Pro Glu Asp Gln Pro Leu Thr Pro Thr Gly Leu Asp
                435                 440                 445
Pro Gln Ser Gly Leu Gly Arg His Leu Gly Val Val Thr Gly Val Ser
450                 455                 460
Val Ala Phe Val Leu Leu Leu Phe Leu Leu Leu Phe Leu Leu Leu Arg
465                 470                 475                 480
His Arg His Gln Ser Lys His Arg Thr Ser Ala His Phe Tyr Arg Pro
                485                 490                 495
Ala Gly Ala Ala Gly Pro Glu Pro Lys Asp Gln Gly Leu Gln Lys Arg
                500                 505                 510
Ala Ser Pro Val Ala Asp Ile Gln Glu Glu Ile Leu Asn Ala Ala Val
                515                 520                 525
Lys Asp Thr Gln Pro Lys Asp Gly Val Glu Met Asp Ala Arg Ala Ala
530                 535                 540
```

```
Ala Ser Glu Ala Pro Gln Asp Val Thr Tyr Ala Gln Leu His Ser Leu
545                 550                 555                 560

Thr Leu Arg Arg Glu Ala Thr Glu Pro Pro Ser Gln Glu Arg Glu
            565                 570                 575

Pro Pro Ala Glu Pro Ser Ile Tyr Ala Pro Leu Ala Ile His
            580                 585                 590

<210> SEQ ID NO 242
<211> LENGTH: 435
<212> TYPE: PRT
<213> ORGANISM: Homo sapiens

<400> SEQUENCE: 242

Gly Thr Leu Pro Lys Pro Thr Leu Trp Ala Glu Pro Ala Ser Val Ile
1               5                   10                  15

Ala Arg Gly Lys Pro Val Thr Leu Trp Cys Gln Gly Pro Leu Glu Thr
            20                  25                  30

Glu Glu Tyr Arg Leu Asp Lys Glu Gly Leu Pro Trp Ala Arg Lys Arg
        35                  40                  45

Gln Asn Pro Leu Glu Pro Gly Ala Lys Ala Lys Phe His Ile Pro Ser
    50                  55                  60

Thr Val Tyr Asp Ser Ala Gly Arg Tyr Arg Cys Tyr Tyr Glu Thr Pro
65                  70                  75                  80

Ala Gly Trp Ser Glu Pro Ser Asp Pro Leu Glu Leu Val Ala Thr Gly
                85                  90                  95

Phe Tyr Ala Glu Pro Thr Leu Leu Ala Leu Pro Ser Pro Val Val Ala
            100                 105                 110

Ser Gly Gly Asn Val Thr Leu Gln Cys Asp Thr Leu Asp Gly Leu Leu
        115                 120                 125

Thr Phe Val Leu Val Glu Glu Glu Gln Lys Leu Pro Arg Thr Leu Tyr
130                 135                 140

Ser Gln Lys Leu Pro Lys Gly Pro Ser Gln Ala Leu Phe Pro Val Gly
145                 150                 155                 160

Pro Val Thr Pro Ser Cys Arg Trp Arg Phe Arg Cys Tyr Tyr Tyr Tyr
                165                 170                 175

Arg Lys Asn Pro Gln Val Trp Ser Asn Pro Ser Asp Leu Leu Glu Ile
            180                 185                 190

Leu Val Pro Gly Val Ser Arg Lys Pro Ser Leu Leu Ile Pro Gln Gly
        195                 200                 205

Ser Val Val Ala Arg Gly Gly Ser Leu Thr Leu Gln Cys Arg Ser Asp
    210                 215                 220

Val Gly Tyr Asp Ile Phe Val Leu Tyr Lys Glu Gly Glu His Asp Leu
225                 230                 235                 240

Val Gln Gly Ser Gly Gln Gln Pro Gln Ala Gly Leu Ser Gln Ala Asn
                245                 250                 255

Phe Thr Leu Gly Pro Val Ser Arg Ser His Gly Gly Gln Tyr Arg Cys
            260                 265                 270

Tyr Gly Ala His Asn Leu Ser Pro Arg Trp Ser Ala Pro Ser Asp Pro
        275                 280                 285

Leu Asp Ile Leu Ile Ala Gly Leu Ile Pro Asp Ile Pro Ala Leu Ser
    290                 295                 300

Val Gln Pro Gly Pro Lys Val Ala Ser Gly Glu Asn Val Thr Leu Leu
305                 310                 315                 320

Cys Gln Ser Trp His Gln Ile Asp Thr Phe Phe Leu Thr Lys Glu Gly
                325                 330                 335
```

Ala Ala His Pro Pro Leu Cys Leu Lys Ser Lys Tyr Gln Ser Tyr Arg
        340                 345                 350

His Gln Ala Glu Phe Ser Met Ser Pro Val Thr Ser Ala Gln Gly Gly
        355                 360                 365

Thr Tyr Arg Cys Tyr Ser Ala Ile Arg Ser Tyr Pro Tyr Leu Leu Ser
        370                 375                 380

Ser Pro Ser Tyr Pro Gln Glu Leu Val Val Ser Gly Pro Ser Gly Asp
385                 390                 395                 400

Pro Ser Leu Ser Pro Thr Gly Ser Thr Pro Thr Pro Gly Pro Glu Asp
        405                 410                 415

Gln Pro Leu Thr Pro Thr Gly Leu Asp Pro Gln Ser Gly Leu Gly Arg
        420                 425                 430

His Leu Gly
        435

<210> SEQ ID NO 243
<211> LENGTH: 2526
<212> TYPE: DNA
<213> ORGANISM: Mus musculus

<400> SEQUENCE: 243

```
atgtcctgca ccttcacagc cctgctccgt cttggactga ctctgagcct ctggatccca    60
gtgctgacag ggtccctccc taagcctatc ctcagagtac agccagactc tgtggtctcc   120
aggaggacta aggtgacctt cttgtgtgaa gagacaattg gagccaatga gtaccgcctc   180
tataaagatg gaaagctata taaaaccgta acaaagaaca acagaagcc agaaaacaag   240
gctgaattct cattctcaaa tgtagacctg agtaatgcag tcaatatcg atgttcctac   300
agcacccagt ataaatcatc aggctacagt gacctcctgg agctggtggt gacaggacac   360
tactggacac ccagcctttt agcccaagcc agccctgtgg taacttcagg agggtatgtc   420
accctccagt gtgagtcctg cacaacgat cacaagttca ttctgactgt agaaggacca   480
cagaagctct cgtggacaca agactcacag tataattact ctacaaggaa gtaccacgcc   540
ctgttctctg tgggccctgt gacccccaac cagagatgga tatgcagatg ttacagttat   600
gacaggaaca gaccatatgt gtggtcacct ccaagtgaat ccgtggagct cctggtctca   660
ggtaatctcc aaaaaccaac catcaaggct gaaccaggat ctgtgatcac ctccaaaaga   720
gcaatgacca tctggtgtca ggggaacctg gatgcagaag tatattttct gcataatgag   780
aaaagccaaa aaacacagag cacacagacc tacaggagc tgggaacaa gggcaagttc   840
ttcatccctt ctgtgacact acaacatgca gggcaatatc gctgttattg ttacggctca   900
gctggttggt cacagcccag tgacaccctg agctggtgg tgacaggaat ctatgaatac   960
tatgaaccca ggctgtcagt actgcccagc cctgtggtga cagctggagg gaacatgaca  1020
ctccactgtg cctcagactt tccctacgat aaattcattc tcaccaagga agataagaaa  1080
ttcggcaact cactggacac agagcatata tcttctagtg acagtaccg agccctgttt  1140
attataggac ccacaacccc aacccataca ggggcattca gatgttacgg ttactacaag  1200
aatgccccac agctgtggtc agtacctagt gctctccaac aaatactcat tcagggctg  1260
tccaagaagc cctctctgct gactcaccaa ggccatatcc tggaccctgg aatgaccctc  1320
accctgcagt gtttctctga catcaactat gacagatttg ctctgcacaa ggtgggggga  1380
gctgacatca tgcagcactc tagccagcag actgacactg gcttctctgt ggccaacttc  1440
acactgggct atgtgagtag ctccactgga ggccaataca gatgctatgg tgcacacaac  1500
```

```
ctctcctctg agtggtcagc ctccagtgag cccctggaca tcctgatcac aggacagctc   1560
cctctcactc cttccctctc agtgcagcct aaccacacag tgcactcagg agagaccgtg   1620
agcctgctgt gttggtcaat ggactctgtg gatactttca ttctgtccaa ggagggatca   1680
gcccagcaac ccctgcgact aaaatcaaag tcccatgatc agcagtccca ggcagaattc   1740
tccatgagtg ctgtgacctc ccatctctca ggcacctaca ggtgctatgg agctcaagac   1800
tcatctttct acctcttgtc atctgccagt gcccctgtgg agctcacagt ctcaggaccc   1860
atcgaaacct ctaccccgcc acccacaatg tccatgccac taggtggact gcatatgtac   1920
ctgaaggctc tcattggagt gtctgtggcc ttcatcctgt tcctcttcat cttcatcttc   1980
attcttcttc gacgaagaca tcggggaaaa ttcaggaaag atgtccagaa agagaaagac   2040
ttgcaacttt cttcaggagc tgaagagccc ataaccagga aaggagaact ccagaagagg   2100
cccaacccag ctgctgccac caggaagaa agcctatatg cttcagtgga ggacatgcaa   2160
actgaggatg gagtggagct gaacagctgg acaccacctg aggaagatcc ccagggagag   2220
acttatgccc aggtgaaacc ctccaggctc aggaaggcag acatgtctc accttctgtc   2280 atgtcaaggg aacaactgaa acagaatat gaacaagcag aagagggcca aggagcaaac   2340
aatcaggctg ccgaatctgg ggagtcccag gatgtgacct atgcccagct gtgcagcagg   2400
acactcagac aggggcagc tgcatctcct ctctcccagg caggggaagc cccagaggag   2460
cccagtgtat atgctactct ggcggctgct cgtccagagg ctgttcccaa ggacatggag   2520
caatga                                                             2526

<210> SEQ ID NO 244
<211> LENGTH: 841
<212> TYPE: PRT
<213> ORGANISM: Mus musculus

<400> SEQUENCE: 244

Met Ser Cys Thr Phe Thr Ala Leu Leu Arg Leu Gly Leu Thr Leu Ser
1               5                   10                  15

Leu Trp Ile Pro Val Leu Thr Gly Ser Leu Pro Lys Pro Ile Leu Arg
            20                  25                  30

Val Gln Pro Asp Ser Val Val Ser Arg Arg Thr Lys Val Thr Phe Leu
        35                  40                  45

Cys Glu Glu Thr Ile Gly Ala Asn Glu Tyr Arg Leu Tyr Lys Asp Gly
    50                  55                  60

Lys Leu Tyr Lys Thr Val Thr Lys Asn Gln Lys Pro Glu Asn Lys
65                  70                  75                  80

Ala Glu Phe Ser Phe Ser Asn Val Asp Leu Ser Asn Ala Gly Gln Tyr
                85                  90                  95

Arg Cys Ser Tyr Ser Thr Gln Tyr Lys Ser Ser Gly Tyr Ser Asp Leu
            100                 105                 110

Leu Glu Leu Val Val Thr Gly His Tyr Trp Thr Pro Ser Leu Leu Ala
        115                 120                 125

Gln Ala Ser Pro Val Val Thr Ser Gly Gly Tyr Val Thr Leu Gln Cys
    130                 135                 140

Glu Ser Trp His Asn Asp His Lys Phe Ile Leu Thr Val Glu Gly Pro
145                 150                 155                 160

Gln Lys Leu Ser Trp Thr Gln Asp Ser Gln Tyr Asn Tyr Ser Thr Arg
                165                 170                 175

Lys Tyr His Ala Leu Phe Ser Val Gly Pro Val Thr Pro Asn Gln Arg
```

```
            180                 185                 190
Trp Ile Cys Arg Cys Tyr Ser Tyr Asp Arg Asn Arg Pro Tyr Val Trp
            195                 200                 205
Ser Pro Pro Ser Glu Ser Val Glu Leu Leu Val Ser Gly Asn Leu Gln
            210                 215                 220
Lys Pro Thr Ile Lys Ala Glu Pro Gly Ser Val Ile Thr Ser Lys Arg
225                 230                 235                 240
Ala Met Thr Ile Trp Cys Gln Gly Asn Leu Asp Ala Glu Val Tyr Phe
                245                 250                 255
Leu His Asn Glu Lys Ser Gln Lys Thr Gln Ser Thr Gln Thr Leu Gln
                260                 265                 270
Glu Pro Gly Asn Lys Gly Lys Phe Phe Ile Pro Ser Val Thr Leu Gln
            275                 280                 285
His Ala Gly Gln Tyr Arg Cys Tyr Cys Tyr Gly Ser Ala Gly Trp Ser
            290                 295                 300
Gln Pro Ser Asp Thr Leu Glu Leu Val Val Thr Gly Ile Tyr Glu Tyr
305                 310                 315                 320
Tyr Glu Pro Arg Leu Ser Val Leu Pro Ser Pro Val Val Thr Ala Gly
                325                 330                 335
Gly Asn Met Thr Leu His Cys Ala Ser Asp Phe Pro Tyr Asp Lys Phe
                340                 345                 350
Ile Leu Thr Lys Glu Asp Lys Lys Phe Gly Asn Ser Leu Asp Thr Glu
                355                 360                 365
His Ile Ser Ser Ser Gly Gln Tyr Arg Ala Leu Phe Ile Ile Gly Pro
            370                 375                 380
Thr Thr Pro Thr His Thr Gly Ala Phe Arg Cys Tyr Gly Tyr Tyr Lys
385                 390                 395                 400
Asn Ala Pro Gln Leu Trp Ser Val Pro Ser Ala Leu Gln Gln Ile Leu
                405                 410                 415
Ile Ser Gly Leu Ser Lys Lys Pro Ser Leu Leu Thr His Gln Gly His
                420                 425                 430
Ile Leu Asp Pro Gly Met Thr Leu Thr Leu Gln Cys Phe Ser Asp Ile
            435                 440                 445
Asn Tyr Asp Arg Phe Ala Leu His Lys Val Gly Gly Ala Asp Ile Met
            450                 455                 460
Gln His Ser Ser Gln Gln Thr Asp Thr Gly Phe Ser Val Ala Asn Phe
465                 470                 475                 480
Thr Leu Gly Tyr Val Ser Ser Ser Thr Gly Gly Gln Tyr Arg Cys Tyr
                485                 490                 495
Gly Ala His Asn Leu Ser Ser Glu Trp Ser Ala Ser Ser Glu Pro Leu
                500                 505                 510
Asp Ile Leu Ile Thr Gly Gln Leu Pro Leu Thr Pro Ser Leu Ser Val
            515                 520                 525
Gln Pro Asn His Thr Val His Ser Gly Glu Thr Val Ser Leu Leu Cys
            530                 535                 540
Trp Ser Met Asp Ser Val Asp Thr Phe Ile Leu Ser Lys Glu Gly Ser
545                 550                 555                 560
Ala Gln Gln Pro Leu Arg Leu Lys Ser Lys Ser His Asp Gln Gln Ser
                565                 570                 575
Gln Ala Glu Phe Ser Met Ser Ala Val Thr Ser His Leu Ser Gly Thr
                580                 585                 590
Tyr Arg Cys Tyr Gly Ala Gln Asp Ser Ser Phe Tyr Leu Leu Ser Ser
            595                 600                 605
```

Ala Ser Ala Pro Val Glu Leu Thr Val Ser Gly Pro Ile Glu Thr Ser
610                 615                 620

Thr Pro Pro Thr Met Ser Met Pro Leu Gly Gly Leu His Met Tyr
625                 630                 635                 640

Leu Lys Ala Leu Ile Gly Val Ser Val Ala Phe Ile Leu Phe Leu Phe
            645                 650                 655

Ile Phe Ile Phe Ile Leu Leu Arg Arg Arg His Arg Gly Lys Phe Arg
            660                 665                 670

Lys Asp Val Gln Lys Glu Lys Asp Leu Gln Leu Ser Ser Gly Ala Glu
            675                 680                 685

Glu Pro Ile Thr Arg Lys Gly Glu Leu Gln Lys Arg Pro Asn Pro Ala
690                 695                 700

Ala Ala Thr Gln Glu Glu Ser Leu Tyr Ala Ser Val Glu Asp Met Gln
705                 710                 715                 720

Thr Glu Asp Gly Val Glu Leu Asn Ser Trp Thr Pro Pro Glu Glu Asp
            725                 730                 735

Pro Gln Gly Glu Thr Tyr Ala Gln Val Lys Pro Ser Arg Leu Arg Lys
            740                 745                 750

Ala Gly His Val Ser Pro Ser Val Met Ser Arg Glu Gln Leu Asn Thr
            755                 760                 765

Glu Tyr Glu Gln Ala Glu Glu Gly Gln Gly Ala Asn Asn Gln Ala Ala
770                 775                 780

Glu Ser Gly Glu Ser Gln Asp Val Thr Tyr Ala Gln Leu Cys Ser Arg
785                 790                 795                 800

Thr Leu Arg Gln Gly Ala Ala Ser Pro Leu Ser Gln Ala Gly Glu
            805                 810                 815

Ala Pro Glu Glu Pro Ser Val Tyr Ala Thr Leu Ala Ala Arg Pro
            820                 825                 830

Glu Ala Val Pro Lys Asp Met Glu Gln
            835                 840

<210> SEQ ID NO 245
<211> LENGTH: 618
<212> TYPE: PRT
<213> ORGANISM: Mus musculus

<400> SEQUENCE: 245

Ser Leu Pro Lys Pro Ile Leu Arg Val Gln Pro Asp Ser Val Val Ser
1               5                   10                  15

Arg Arg Thr Lys Val Thr Phe Leu Cys Glu Glu Thr Ile Gly Ala Asn
            20                  25                  30

Glu Tyr Arg Leu Tyr Lys Asp Gly Lys Leu Tyr Lys Thr Val Thr Lys
        35                  40                  45

Asn Lys Gln Lys Pro Glu Asn Lys Ala Glu Phe Ser Phe Ser Asn Val
50                  55                  60

Asp Leu Ser Asn Ala Gly Gln Tyr Arg Cys Ser Tyr Ser Thr Gln Tyr
65                  70                  75                  80

Lys Ser Ser Gly Tyr Ser Asp Leu Leu Glu Leu Val Val Thr Gly His
            85                  90                  95

Tyr Trp Thr Pro Ser Leu Leu Ala Gln Ala Ser Pro Val Val Thr Ser
            100                 105                 110

Gly Gly Tyr Val Thr Leu Gln Cys Glu Ser Trp His Asn Asp His Lys
        115                 120                 125

Phe Ile Leu Thr Val Glu Gly Pro Gln Lys Leu Ser Trp Thr Gln Asp

-continued

```
    130                 135                 140

Ser Gln Tyr Asn Tyr Ser Thr Arg Lys Tyr His Ala Leu Phe Ser Val
145                 150                 155                 160

Gly Pro Val Thr Pro Asn Gln Arg Trp Ile Cys Arg Cys Tyr Ser Tyr
                165                 170                 175

Asp Arg Asn Arg Pro Tyr Val Trp Ser Pro Pro Ser Glu Ser Val Glu
            180                 185                 190

Leu Leu Val Ser Gly Asn Leu Gln Lys Pro Thr Ile Lys Ala Glu Pro
        195                 200                 205

Gly Ser Val Ile Thr Ser Lys Arg Ala Met Thr Ile Trp Cys Gln Gly
    210                 215                 220

Asn Leu Asp Ala Glu Val Tyr Phe Leu His Asn Glu Lys Ser Gln Lys
225                 230                 235                 240

Thr Gln Ser Thr Gln Thr Leu Gln Glu Pro Gly Asn Lys Gly Lys Phe
                245                 250                 255

Phe Ile Pro Ser Val Thr Leu Gln His Ala Gly Gln Tyr Arg Cys Tyr
            260                 265                 270

Cys Tyr Gly Ser Ala Gly Trp Ser Gln Pro Ser Asp Thr Leu Glu Leu
        275                 280                 285

Val Val Thr Gly Ile Tyr Glu Tyr Tyr Glu Pro Arg Leu Ser Val Leu
    290                 295                 300

Pro Ser Pro Val Val Thr Ala Gly Gly Asn Met Thr Leu His Cys Ala
305                 310                 315                 320

Ser Asp Phe Pro Tyr Asp Lys Phe Ile Leu Thr Lys Glu Asp Lys Lys
                325                 330                 335

Phe Gly Asn Ser Leu Asp Thr Glu His Ile Ser Ser Ser Gly Gln Tyr
            340                 345                 350

Arg Ala Leu Phe Ile Ile Gly Pro Thr Thr Pro Thr His Thr Gly Ala
        355                 360                 365

Phe Arg Cys Tyr Gly Tyr Tyr Lys Asn Ala Pro Gln Leu Trp Ser Val
    370                 375                 380

Pro Ser Ala Leu Gln Gln Ile Leu Ile Ser Gly Leu Ser Lys Lys Pro
385                 390                 395                 400

Ser Leu Leu Thr His Gln Gly His Ile Leu Asp Pro Gly Met Thr Leu
                405                 410                 415

Thr Leu Gln Cys Phe Ser Asp Ile Asn Tyr Asp Arg Phe Ala Leu His
            420                 425                 430

Lys Val Gly Gly Ala Asp Ile Met Gln His Ser Ser Gln Gln Thr Asp
        435                 440                 445

Thr Gly Phe Ser Val Ala Asn Phe Thr Leu Gly Tyr Val Ser Ser Ser
    450                 455                 460
Thr Gly Gly Gln Tyr Arg Cys Tyr Gly Ala His Asn Leu Ser Ser Glu
465                 470                 475                 480

Trp Ser Ala Ser Ser Glu Pro Leu Asp Ile Leu Ile Thr Gly Gln Leu
                485                 490                 495

Pro Leu Thr Pro Ser Leu Ser Val Gln Pro Asn His Thr Val His Ser
            500                 505                 510

Gly Glu Thr Val Ser Leu Leu Cys Trp Ser Met Asp Ser Val Asp Thr
        515                 520                 525

Phe Ile Leu Ser Lys Glu Gly Ser Ala Gln Gln Pro Leu Arg Leu Lys
    530                 535                 540

Ser Lys Ser His Asp Gln Gln Ser Gln Ala Glu Phe Ser Met Ser Ala
545                 550                 555                 560
```

Val Thr Ser His Leu Ser Gly Thr Tyr Arg Cys Tyr Gly Ala Gln Asp
            565                 570                 575

Ser Ser Phe Tyr Leu Leu Ser Ala Ser Ala Pro Val Glu Leu Thr
        580                 585                 590

Val Ser Gly Pro Ile Glu Thr Ser Thr Pro Pro Thr Met Ser Met
    595                 600                 605

Pro Leu Gly Gly Leu His Met Tyr Leu Lys
    610                 615

<210> SEQ ID NO 246
<211> LENGTH: 1008
<212> TYPE: DNA
<213> ORGANISM: Mus musculus

<400> SEQUENCE: 246

```
atgatcgcca tgctcacagt gctgctatac cttggtctta ttctggaacc caggactgca      60
gtacaggcag acacctccc aaagcccatc atctgggctg agccaggctc tgtgatcgct     120
gcgtatacat ctgtgattac ctggtgtcag ggttcctggg aggcccagta ttatcatctg     180
tataaagaga aaagtgtaaa tccttgggac actcaagtcc ctctggaaac aggaataag      240
gccaagttca acattccaag catgacaacc tcatatgcag catatataa gtgttactat      300
gagagtgctg ctggcttctc agagcacagt gatgccatgg agctggtgat gacaggagca     360
tatgaaaatc ccagcctgtc agtctatccc agctctaatg tgacctctgg agtttccata     420
tcctttagtt gcagctcatc catagtattt ggcagattca ttctgatcca ggaaggaaag     480
catggcctct cttggaccct ggactcacag catcaggcca atcagccatc ctatgctact     540
tttgttctgg atgctgttac tcccaaccac aatggaacat tcagatgcta tggctacttt     600
agaaatgaac cacaggtgtg gtcaaaacca gtaactccc tagacctcat gatctcagaa      660
accaaggacc agtcctctac acccactgaa gatggactgg aaacatacca gaagatttg      720
attggagtcc tggtgtcatt cctcctgctt ttcttcctcc tgcttttct catcctcatc      780
ggataccagt atgggcacaa aagaaggct aatgcttctg tgaagaacac acaatctgag      840
aacaatgcag agctgaacag ttggaaccca caaaatgaag acccccaggg aattgtctac     900
gcccaggtaa aaccctccag gcttcagaag gacactgcat gcaaagagac ccaggatgta     960
acctatgccc agttgtgcat caggacacag gaacagaaca acagctga                1008
```

<210> SEQ ID NO 247
<211> LENGTH: 335
<212> TYPE: PRT
<213> ORGANISM: Mus musculus

<400> SEQUENCE: 247

Met Ile Ala Met Leu Thr Val Leu Leu Tyr Leu Gly Leu Ile Leu Glu
1               5                   10                  15

Pro Arg Thr Ala Val Gln Ala Gly His Leu Pro Lys Pro Ile Ile Trp
            20                  25                  30

Ala Glu Pro Gly Ser Val Ile Ala Ala Tyr Thr Ser Val Ile Thr Trp
        35                  40                  45

Cys Gln Gly Ser Trp Glu Ala Gln Tyr Tyr His Leu Tyr Lys Glu Lys
    50                  55                  60

Ser Val Asn Pro Trp Asp Thr Gln Val Pro Leu Glu Thr Arg Asn Lys
65                  70                  75                  80

Ala Lys Phe Asn Ile Pro Ser Met Thr Thr Ser Tyr Ala Gly Ile Tyr

```
                        85                  90                  95
Lys Cys Tyr Tyr Glu Ser Ala Ala Gly Phe Ser Glu His Ser Asp Ala
                100                 105                 110
Met Glu Leu Val Met Thr Gly Ala Tyr Glu Asn Pro Ser Leu Ser Val
                115                 120                 125
Tyr Pro Ser Ser Asn Val Thr Ser Gly Val Ser Ile Ser Phe Ser Cys
130                 135                 140
Ser Ser Ser Ile Val Phe Gly Arg Phe Ile Leu Ile Gln Glu Gly Lys
145                 150                 155                 160
His Gly Leu Ser Trp Thr Leu Asp Ser Gln His Gln Ala Asn Gln Pro
                165                 170                 175
Ser Tyr Ala Thr Phe Val Leu Asp Ala Val Thr Pro Asn His Asn Gly
                180                 185                 190
Thr Phe Arg Cys Tyr Gly Tyr Phe Arg Asn Glu Pro Gln Val Trp Ser
                195                 200                 205
Lys Pro Ser Asn Ser Leu Asp Leu Met Ile Ser Glu Thr Lys Asp Gln
                210                 215                 220
Ser Ser Thr Pro Thr Glu Asp Gly Leu Glu Thr Tyr Gln Lys Ile Leu
225                 230                 235                 240
Ile Gly Val Leu Val Ser Phe Leu Leu Phe Leu Leu Leu Phe
                245                 250                 255
Leu Ile Leu Ile Gly Tyr Gln Tyr Gly His Lys Lys Ala Asn Ala
                260                 265                 270
Ser Val Lys Asn Thr Gln Ser Glu Asn Asn Ala Glu Leu Asn Ser Trp
                275                 280                 285
Asn Pro Gln Asn Glu Asp Pro Gln Gly Ile Val Tyr Ala Gln Val Lys
                290                 295                 300
Pro Ser Arg Leu Gln Lys Asp Thr Ala Cys Lys Glu Thr Gln Asp Val
305                 310                 315                 320
Thr Tyr Ala Gln Leu Cys Ile Arg Thr Gln Glu Gln Asn Asn Ser
                325                 330                 335

<210> SEQ ID NO 248
<211> LENGTH: 215
<212> TYPE: PRT
<213> ORGANISM: Mus musculus

<400> SEQUENCE: 248

Gly His Leu Pro Lys Pro Ile Ile Trp Ala Glu Pro Gly Ser Val Ile
1               5                   10                  15
Ala Ala Tyr Thr Ser Val Ile Thr Trp Cys Gln Gly Ser Trp Glu Ala
                20                  25                  30
Gln Tyr Tyr His Leu Tyr Lys Glu Lys Ser Val Asn Pro Trp Asp Thr
                35                  40                  45
Gln Val Pro Leu Glu Thr Arg Asn Lys Ala Lys Phe Asn Ile Pro Ser
50                  55                  60
Met Thr Thr Ser Tyr Ala Gly Ile Tyr Lys Cys Tyr Tyr Glu Ser Ala
65                  70                  75                  80
Ala Gly Phe Ser Glu His Ser Asp Ala Met Glu Leu Val Met Thr Gly
                85                  90                  95
Ala Tyr Glu Asn Pro Ser Leu Ser Val Tyr Pro Ser Ser Asn Val Thr
                100                 105                 110
Ser Gly Val Ser Ile Ser Phe Ser Cys Ser Ser Ser Ile Val Phe Gly
                115                 120                 125
```

```
Arg Phe Ile Leu Ile Gln Glu Gly Lys His Gly Leu Ser Trp Thr Leu
130                 135                 140

Asp Ser Gln His Gln Ala Asn Gln Pro Ser Tyr Ala Thr Phe Val Leu
145                 150                 155                 160

Asp Ala Val Thr Pro Asn His Asn Gly Thr Phe Arg Cys Tyr Gly Tyr
                165                 170                 175

Phe Arg Asn Glu Pro Gln Val Trp Ser Lys Pro Ser Asn Ser Leu Asp
            180                 185                 190

Leu Met Ile Ser Glu Thr Lys Asp Gln Ser Ser Thr Pro Thr Glu Asp
                195                 200                 205

Gly Leu Glu Thr Tyr Gln Lys
    210                 215

<210> SEQ ID NO 249
<211> LENGTH: 864
<212> TYPE: DNA
<213> ORGANISM: Homo sapiens

<400> SEQUENCE: 249
atgtctcccc accccaccgc cctcctgggc ctagtgctct gcctggccca gaccatccac      60
acgcaggagg aagatctgcc cagaccctcc atctcggctg agccaggcac cgtgatcccc     120
ctggggagcc atgtgacttt cgtgtgccgg ggcccggttg gggttcaaac attccgcctg     180
gagagggaca gtagatccac atacaatgat actgaagatg tgtctcaagc tagtccatct     240
gagtcagagg ccagattccg cattgactca gtaagagaag gaaatgccgg ctttatcgc      300
tgcatctatt ataagccccc taaatggtct gagcagagtg actacctgga gctgctggtg     360
aaagaaagct ctggaggccc ggactccccg gacacagagc ccggctcctc agctggaccc     420
acgcagaggc cgtcggacaa cagtcacaat gagcatgcac ctgcttccca aggcctgaaa     480
gctgagcatc tgtatattct catcggggtc tcagtggtct tcctcttctg tctcctcctc     540
ctggtcctct tctgcctcca tcgccagaat cagataaagc aggggccccc cagaagcaag     600
gacgaggagc agaagccaca gcagaggcct gacctggctg ttgatgttct agagaggaca     660
gcagacaagg ccacagtcaa tggacttcct gagaaggaca gagagacgga cacctcggcc     720
ctggctgcag ggagttccca ggaggtgacg tatgctcagc tggaccactg ggccctcaca     780
cagaggacag cccgggctgt gtccccacag tccacaaagc ccatggccga gtccatcacg     840
tatgcagccg ttgccagaca ctga                                            864

<210> SEQ ID NO 250
<211> LENGTH: 287
<212> TYPE: PRT
<213> ORGANISM: Homo sapiens

<400> SEQUENCE: 250

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
                20                  25                  30

Ala Glu Pro Gly Thr Val Ile Pro Leu Gly Ser His Val Thr Phe Val
            35                  40                  45

Cys Arg Gly Pro Val Gly Val Gln Thr Phe Arg Leu Glu Arg Glu Ser
        50                  55                  60

Arg Ser Thr Tyr Asn Asp Thr Glu Asp Val Ser Gln Ala Ser Pro Ser
65                  70                  75                  80
```

```
Glu Ser Glu Ala Arg Phe Arg Ile Asp Ser Val Ser Glu Gly Asn Ala
                85                  90                  95

Gly Pro Tyr Arg Cys Ile Tyr Tyr Lys Pro Pro Lys Trp Ser Glu Gln
            100                 105                 110

Ser Asp Tyr Leu Glu Leu Leu Val Lys Glu Thr Ser Gly Gly Pro Asp
            115                 120                 125

Ser Pro Asp Thr Glu Pro Gly Ser Ser Ala Gly Pro Thr Gln Arg Pro
130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
            195                 200                 205

Arg Pro Asp Leu Ala Val Asp Val Leu Glu Arg Thr Ala Asp Lys Ala
210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
            275                 280                 285

<210> SEQ ID NO 251
<211> LENGTH: 144
<212> TYPE: PRT
<213> ORGANISM: Homo sapiens

<400> SEQUENCE: 251

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
                20                  25                  30

Gly Val Gln Thr Phe Arg Leu Glu Arg Glu Ser Arg Ser Thr Tyr Asn
            35                  40                  45

Asp Thr Glu Asp Val Ser Gln Ala Ser Pro Ser Glu Ser Glu Ala Arg
        50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
            115                 120                 125

Asn Glu His Ala Pro Ala Ser Gln Gly Leu Lys Ala Glu His Leu Tyr
        130                 135                 140

<210> SEQ ID NO 252
<211> LENGTH: 792
<212> TYPE: DNA
<213> ORGANISM: Mus musculus
```

<400> SEQUENCE: 252

```
atgtcacttc atccagttat cctgctggtg cttgtgctgt gcctgggatg gaaaattaac    60
acacaggagg ttctctgcc tgatattacc atcttcccta attcaagtct tatgatctcc   120
caagggactt ttgtaactgt tgtgtgctca tactctgata aacacgactt gtataacatg   180
gtccgcctgg agaaggacgg cagcaccttt atggaaaaga gcactgagcc ttataaaaca   240
gaggatgaat ttgagattgg ccagtgaat gaaaccatta ctggacatta tagctgtatc   300
tattcgaagg ggattacctg gtccgaacgt agtaagacgc tggagctaaa ggtgatcaaa   360
gaaaatgtca tccagactcc tgccccaggt ccaacctcag atacatcttg gctaaagaca   420
tacagcattt acatttttac tgtggtctct gtgattttcc tcctttgtct ttccgccctt   480
ctgttctgct tcctcaggca ccgtcagaaa aagcagggac tcccaaacaa caaaagacag   540
cagcagaggc cagaagagag gctaaatcta gctactaatg gcctggagat gactccagac   600
atagttgcag atgacaggct tcctgaggac agatggacaa aaacctggac cccagttgca   660
ggagaccttc aagaggtgac gtatatccag ctggaccatc actccctcac acagagggca   720
gtcggagctg tgacctcaca gagcacagat atggctgagt ccagcacata tgcagccatc   780
atcagacact ga                                                      792
```

<210> SEQ ID NO 253
<211> LENGTH: 263
<212> TYPE: PRT
<213> ORGANISM: Mus musculus

<400> SEQUENCE: 253

```
Met Ser Leu His Pro Val Ile Leu Leu Val Leu Val Leu Cys Leu Gly
1               5                   10                  15

Trp Lys Ile Asn Thr Gln Glu Gly Ser Leu Pro Asp Ile Thr Ile Phe
            20                  25                  30

Pro Asn Ser Ser Leu Met Ile Ser Gln Gly Thr Phe Val Thr Val Val
        35                  40                  45

Cys Ser Tyr Ser Asp Lys His Asp Leu Tyr Asn Met Val Arg Leu Glu
    50                  55                  60

Lys Asp Gly Ser Thr Phe Met Glu Lys Ser Thr Glu Pro Tyr Lys Thr
65                  70                  75                  80

Glu Asp Glu Phe Glu Ile Gly Pro Val Asn Glu Thr Ile Thr Gly His
                85                  90                  95

Tyr Ser Cys Ile Tyr Ser Lys Gly Ile Thr Trp Ser Glu Arg Ser Lys
            100                 105                 110

Thr Leu Glu Leu Lys Val Ile Lys Glu Asn Val Ile Gln Thr Pro Ala
        115                 120                 125

Pro Gly Pro Thr Ser Asp Thr Ser Trp Leu Lys Thr Tyr Ser Ile Tyr
    130                 135                 140

Ile Phe Thr Val Val Ser Val Ile Phe Leu Leu Cys Leu Ser Ala Leu
145                 150                 155                 160

Leu Phe Cys Phe Leu Arg His Arg Gln Lys Lys Gln Gly Leu Pro Asn
                165                 170                 175

Asn Lys Arg Gln Gln Arg Pro Glu Glu Arg Leu Asn Leu Ala Thr
            180                 185                 190

Asn Gly Leu Glu Met Thr Pro Asp Ile Val Ala Asp Asp Arg Leu Pro
        195                 200                 205

Glu Asp Arg Trp Thr Glu Thr Trp Thr Pro Val Ala Gly Asp Leu Gln
```

```
                210                 215                 220
Glu Val Thr Tyr Ile Gln Leu Asp His His Ser Leu Thr Gln Arg Ala
225                 230                 235                 240

Val Gly Ala Val Thr Ser Gln Ser Thr Asp Met Ala Glu Ser Thr
                245                 250                 255

Tyr Ala Ala Ile Ile Arg His
            260

<210> SEQ ID NO 254
<211> LENGTH: 123
<212> TYPE: PRT
<213> ORGANISM: Mus musculus

<400> SEQUENCE: 254

Gln Glu Gly Ser Leu Pro Asp Ile Thr Ile Phe Pro Asn Ser Ser Leu
1               5                   10                  15

Met Ile Ser Gln Gly Thr Phe Val Thr Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
    50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr
        115                 120

<210> SEQ ID NO 255
<211> LENGTH: 1470
<212> TYPE: DNA
<213> ORGANISM: Homo sapiens

<400> SEQUENCE: 255 atgacccca tcgtcacagt cctgatctgt ctcaggctga gtctgggccc ccggacccac      60
gtgcaggcag ggaccctccc caagcccaca ctctgggctg agccaggctc tgtgatcacc     120
caggggagtc ccgtgaccct ctggtgtcag gggatcctgg agacccagga gtaccgtctg    180
tatagagaaa agaaaacagc acctggatt acacggatcc acaggagat tgtgaagaag       240 ggccagttcc ccatcccatc catcacctgg aacacacag ggcggtatcg ctgtttctac      300
ggtagccaca ctgcaggctg gtcagagccc agtgaccccc tggagctggt ggtgacagga    360
gcctacatca aacccaccct ctcagctcta cccagccctg tggtgacctc aggagggaac   420 gtgacctcc attgtgtctc acaggtggca tttggcagct tcattctgtg taaggaagga    480
gaagatgaac acccacaatg cctgaactca agccccgta cccatgggtg gtcccgggcc    540
atcttctctg tgggccccgt gagcccgagt cgcaggtggt cgtacaggtg ctatgcttat   600
gactcgaact ctccccatgt gtggtctcta cccagtgatc tcctggagct cctggtccta   660
ggtgtttcta agaagccatc actctcagtg cagccaggtc ctatagtggc cctggggag     720 agcctgaccc tccagtgtgt ttctgatgtc agctacgaca gatttgttct gtataaggag   780
ggagaacgtg acttcctcca gctccctggc ccacagcccc aggctgggct ctcccaggcc   840
```

```
aacttcaccc tgggccctgt gagccgctcc tacgggggcc agtacagatg ctccggtgca    900
tacaacctct cctccgagtg gtcggccccc agcgaccccc tggacatcct gatcgcagga    960
cagttccgtg gcagacccct catctcggtg catccgggcc cacggtggc ctcaggagag    1020 aacgtgaccc tgctgtgtca gtcatggggg ccgttccaca ctttccttct gaccaaggcg    1080
ggagcagctg atgccccct ccgtctcaga tcaatacacg aatatcctaa gtaccaggct    1140
gaattcccta tgagtcctgt gacctcagcc cactcgggga cctacaggtg ctacggctca    1200
ctcagctcca accctacct gctgtctcac cccagtgact ccctggagct catggtctca    1260
ggagcagctg agaccctcag cccaccacaa aacaagtccg attccaaggc tggagcagct    1320
aacaccctca gcccatcaca aacaagact gcctcacacc cccaggatta cacagtggag    1380
aatctcatcc gcatgggcat agctggcttg gtcctggtgg tcctcgggat tctgctattt    1440
gaggctcagc acagccagag aagcctctga                                    1470
```

<210> SEQ ID NO 256
<211> LENGTH: 489
<212> TYPE: PRT
<213> ORGANISM: Homo sapiens

<400> SEQUENCE: 256

```
Met Thr Pro Ile Val Thr Val Leu Ile Cys Leu Arg Leu Ser Leu Gly
1               5                   10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
        35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
                245                 250                 255

Leu Tyr Lys Glu Gly Glu Arg Asp Phe Leu Gln Leu Pro Gly Pro Gln
```

```
                260                 265                 270
Pro Gln Ala Gly Leu Ser Gln Ala Asn Phe Thr Leu Gly Pro Val Ser
            275                 280                 285

Arg Ser Tyr Gly Gly Gln Tyr Arg Cys Ser Gly Ala Tyr Asn Leu Ser
        290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
                325                 330                 335

Ala Ser Gly Glu Asn Val Thr Leu Leu Cys Gln Ser Trp Gly Pro Phe
            340                 345                 350

His Thr Phe Leu Leu Thr Lys Ala Gly Ala Ala Asp Ala Pro Leu Arg
        355                 360                 365

Leu Arg Ser Ile His Glu Tyr Pro Lys Tyr Gln Ala Glu Phe Pro Met
    370                 375                 380

Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
                405                 410                 415

Leu Met Val Ser Gly Ala Ala Glu Thr Leu Ser Pro Pro Gln Asn Lys
            420                 425                 430

Ser Asp Ser Lys Ala Gly Ala Asn Thr Leu Ser Pro Ser Gln Asn
        435                 440                 445

Lys Thr Ala Ser His Pro Gln Asp Tyr Thr Val Glu Asn Leu Ile Arg
    450                 455                 460

Met Gly Ile Ala Gly Leu Val Leu Val Val Leu Gly Ile Leu Leu Phe
465                 470                 475                 480

Glu Ala Gln His Ser Gln Arg Ser Leu
                485

<210> SEQ ID NO 257
<211> LENGTH: 445
<212> TYPE: PRT
<213> ORGANISM: Homo sapiens

<400> SEQUENCE: 257

Pro Arg Thr His Val Gln Ala Gly Thr Leu Pro Lys Pro Thr Leu Trp
1               5                   10                  15

Ala Glu Pro Gly Ser Val Ile Thr Gln Gly Ser Pro Val Thr Leu Trp
            20                  25                  30

Cys Gln Gly Ile Leu Glu Thr Gln Glu Tyr Arg Leu Tyr Arg Glu Lys
        35                  40                  45

Lys Thr Ala Pro Trp Ile Thr Arg Ile Pro Gln Glu Ile Val Lys Lys
    50                  55                  60

Gly Gln Phe Pro Ile Pro Ser Ile Thr Trp Glu His Thr Gly Arg Tyr
65                  70                  75                  80

Arg Cys Phe Tyr Gly Ser His Thr Ala Gly Trp Ser Glu Pro Ser Asp
                85                  90                  95

Pro Leu Glu Leu Val Val Thr Gly Ala Tyr Ile Lys Pro Thr Leu Ser
            100                 105                 110

Ala Leu Pro Ser Pro Val Val Thr Ser Gly Gly Asn Val Thr Leu His
        115                 120                 125

Cys Val Ser Gln Val Ala Phe Gly Ser Phe Ile Leu Cys Lys Glu Gly
    130                 135                 140
```

-continued

```
Glu Asp Glu His Pro Gln Cys Leu Asn Ser Gln Pro Arg Thr His Gly
145                 150                 155                 160
Trp Ser Arg Ala Ile Phe Ser Val Gly Pro Val Ser Pro Ser Arg Arg
                165                 170                 175
Trp Ser Tyr Arg Cys Tyr Ala Tyr Asp Ser Asn Ser Pro His Val Trp
            180                 185                 190
Ser Leu Pro Ser Asp Leu Leu Glu Leu Leu Val Leu Gly Val Ser Lys
        195                 200                 205
Lys Pro Ser Leu Ser Val Gln Pro Gly Pro Ile Val Ala Pro Gly Glu
    210                 215                 220
Ser Leu Thr Leu Gln Cys Val Ser Asp Val Ser Tyr Asp Arg Phe Val
225                 230                 235                 240
Leu Tyr Lys Glu Gly Glu Arg Asp Phe Leu Gln Leu Pro Gly Pro Gln
                245                 250                 255
Pro Gln Ala Gly Leu Ser Gln Ala Asn Phe Thr Leu Gly Pro Val Ser
            260                 265                 270
Arg Ser Tyr Gly Gly Gln Tyr Arg Cys Ser Gly Ala Tyr Asn Leu Ser
        275                 280                 285
Ser Glu Trp Ser Ala Pro Ser Asp Pro Leu Asp Ile Leu Ile Ala Gly
    290                 295                 300
Gln Phe Arg Gly Arg Pro Phe Ile Ser Val His Pro Gly Pro Thr Val
305                 310                 315                 320
Ala Ser Gly Glu Asn Val Thr Leu Leu Cys Gln Ser Trp Gly Pro Phe
                325                 330                 335
His Thr Phe Leu Leu Thr Lys Ala Gly Ala Ala Asp Ala Pro Leu Arg
            340                 345                 350
Leu Arg Ser Ile His Glu Tyr Pro Lys Tyr Gln Ala Glu Phe Pro Met
        355                 360                 365
Ser Pro Val Thr Ser Ala His Ser Gly Thr Tyr Arg Cys Tyr Gly Ser
    370                 375                 380
Leu Ser Ser Asn Pro Tyr Leu Ser His Pro Ser Asp Ser Leu Glu
385                 390                 395                 400
Leu Met Val Ser Gly Ala Ala Glu Thr Leu Ser Pro Pro Gln Asn Lys
                405                 410                 415
Ser Asp Ser Lys Ala Gly Ala Ala Asn Thr Leu Ser Pro Ser Gln Asn
            420                 425                 430
Lys Thr Ala Ser His Pro Gln Asp Tyr Thr Val Glu Asn
        435                 440                 445

<210> SEQ ID NO 258
<211> LENGTH: 1452
<212> TYPE: DNA
<213> ORGANISM: Homo sapiens

<400> SEQUENCE: 258 atgacccca tcctcacggt cctgatctgt ctcgggctga gtctgggccc caggacccac     60
gtgcaggcag ggcacctccc caagcccacc ctctgggctg agccaggctc tgtgatcatc    120
cagggaagtc ctgtgaccct caggtgtcag gggagccttc aggctgagga gtaccatcta    180
tatagggaaa acaaatcagc atcctgggtt agacggatac aagagcctgg gaagaatggc    240
cagttcccca tcccatccat cacctgggaa cacgcagggc ggtatcactg tcagtactac    300
agccacaatc actcatcaga gtacagtgac cccctggagc tggtggtgac aggagcctac    360
agcaaaccca ccctctcagc tctgccagc cctgtggtga cctcaggagg gaacgtgacc    420
```

-continued

```
ctccagtgtg tctcacaggt ggcatttgac ggcttcattc tgtgtaagga aggagaagat   480
gaacacccac aacgcctgaa ctcccattcc catgcccgtg ggtggtcctg ggccatcttc   540
tccgtgggcc ccgtgagccc gagtcgcagg tggtcgtaca ggtgctatgc ttatgactcg   600
aactctccct atgtgtggtc tctacccagt gatctcctgg agctcctggt cccaggtgtt   660
tctaagaagc catcactctc agtgcagcca ggtcctatgg tggcccctgg ggagagcctg   720
accctccagt gtgtctctga tgtcggctac gacagatttg ttctgtataa ggagggagaa   780
cgtgacttcc tccagcgccc tggttggcag ccccaggctg ggctctccca ggccaacttc   840
accctgggcc ctgtgagccc ctcccacggg ggccagtaca gatgctacag tgcacacaac   900
ctctcctccg agtggtcggc ccccagtgac cccctggaca tcctgatcac aggacagttc   960
tatgacagac cctctctctc ggtgcagccg tccccacag tagccccagg aaagaacgtg   1020
accctgctgt gtcagtcacg ggggcagttc cacactttcc ttctgaccaa ggagggggca   1080
ggccatcccc cactgcatct gagatcagag caccaagctc agcagaacca ggctgaattc   1140
cgcatgggtc ctgtgacctc agcccacgtg ggacctaca gatgctacag ctcactcagc   1200
tccaaccccr acctgctgtc tctccccagt gaccccctgg agctcgtggt ctcagaagca   1260
gctgagaccc tcagcccatc acaaaacaag acagactcca cgactacatc cctaggccaa   1320
cacccccagg attacacagt ggagaatctc atccgcatgg gtgtggctgg cttggtcctg   1380
gtggtcctcg ggattctgct atttgaggct cagcacagcc agagaagcct acaagatgca   1440
gccgggaggt ga                                                         1452
```

<210> SEQ ID NO 259
<211> LENGTH: 483
<212> TYPE: PRT
<213> ORGANISM: Homo sapiens

<400> SEQUENCE: 259

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190

```
Tyr Arg Cys Tyr Ala Tyr Asp Ser Asn Ser Pro Tyr Val Trp Ser Leu
            195                 200                 205

Pro Ser Asp Leu Leu Glu Leu Leu Val Pro Gly Val Ser Lys Lys Pro
210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
            245                 250                 255

Lys Glu Gly Glu Arg Asp Phe Leu Gln Arg Pro Gly Trp Gln Pro Gln
                260                 265                 270

Ala Gly Leu Ser Gln Ala Asn Phe Thr Leu Gly Pro Val Ser Pro Ser
            275                 280                 285

His Gly Gly Gln Tyr Arg Cys Tyr Ser Ala His Asn Leu Ser Ser Glu
290                 295                 300

Trp Ser Ala Pro Ser Asp Pro Leu Asp Ile Leu Ile Thr Gly Gln Phe
305                 310                 315                 320

Tyr Asp Arg Pro Ser Leu Ser Val Gln Pro Val Pro Thr Val Ala Pro
            325                 330                 335

Gly Lys Asn Val Thr Leu Leu Cys Gln Ser Arg Gly Gln Phe His Thr
                340                 345                 350

Phe Leu Leu Thr Lys Glu Gly Ala Gly His Pro Pro Leu His Leu Arg
            355                 360                 365

Ser Glu His Gln Ala Gln Gln Asn Gln Ala Glu Phe Arg Met Gly Pro
370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
            405                 410                 415

Val Ser Glu Ala Ala Glu Thr Leu Ser Pro Ser Gln Asn Lys Thr Asp
                420                 425                 430

Ser Thr Thr Thr Ser Leu Gly Gln His Pro Gln Asp Tyr Thr Val Glu
            435                 440                 445

Asn Leu Ile Arg Met Gly Val Ala Gly Leu Val Leu Val Val Leu Gly
            450                 455                 460

Ile Leu Leu Phe Glu Ala Gln His Ser Gln Arg Ser Leu Gln Asp Ala
465                 470                 475                 480

Ala Gly Arg

<210> SEQ ID NO 260
<211> LENGTH: 426
<212> TYPE: PRT
<213> ORGANISM: Homo sapiens

<400> SEQUENCE: 260

Gly His Leu Pro Lys Pro Thr Leu Trp Ala Glu Pro Gly Ser Val Ile
1               5                   10                  15

Ile Gln Gly Ser Pro Val Thr Leu Arg Cys Gln Gly Ser Leu Gln Ala
                20                  25                  30

Glu Glu Tyr His Leu Tyr Arg Glu Asn Lys Ser Ala Ser Trp Val Arg
            35                  40                  45

Arg Ile Gln Glu Pro Gly Lys Asn Gly Gln Phe Pro Ile Pro Ser Ile
        50                  55                  60

Thr Trp Glu His Ala Gly Arg Tyr His Cys Gln Tyr Tyr Ser His Asn
65                  70                  75                  80
```

```
His Ser Ser Glu Tyr Ser Asp Pro Leu Glu Leu Val Val Thr Gly Ala
                85                  90                  95
Tyr Ser Lys Pro Thr Leu Ser Ala Leu Pro Ser Pro Val Val Thr Leu
            100                 105                 110
Gly Gly Asn Val Thr Leu Gln Cys Val Ser Gln Val Ala Phe Asp Gly
            115                 120                 125
Phe Ile Leu Cys Lys Glu Gly Glu Asp Glu His Pro Gln Arg Leu Asn
130                 135                 140
Ser His Ser His Ala Arg Gly Trp Ser Trp Ala Ile Phe Ser Val Gly
145                 150                 155                 160
Pro Val Ser Pro Ser Arg Arg Trp Ser Tyr Arg Cys Tyr Ala Tyr Asp
                165                 170                 175
Ser Asn Ser Pro Tyr Val Trp Ser Leu Pro Ser Asp Leu Leu Glu Leu
            180                 185                 190
Leu Val Pro Gly Val Ser Lys Lys Pro Ser Leu Ser Val Gln Pro Gly
            195                 200                 205
Pro Met Val Ala Pro Gly Glu Ser Leu Thr Leu Gln Cys Val Ser Asp
210                 215                 220
Val Gly Tyr Asp Arg Phe Val Leu Tyr Lys Glu Gly Glu Arg Asp Phe
225                 230                 235                 240
Leu Gln Arg Pro Gly Trp Gln Pro Gln Ala Gly Leu Ser Gln Ala Asn
                245                 250                 255
Phe Thr Leu Gly Pro Val Ser Pro Ser His Gly Gly Gln Tyr Arg Cys
            260                 265                 270
Tyr Ser Ala His Asn Leu Ser Ser Glu Trp Ser Ala Pro Ser Asp Pro
            275                 280                 285
Leu Asp Ile Leu Ile Thr Gly Gln Phe Tyr Asp Arg Pro Ser Leu Ser
290                 295                 300
Val Gln Pro Val Pro Thr Val Ala Pro Gly Lys Asn Val Thr Leu Leu
305                 310                 315                 320
Cys Gln Ser Arg Gly Gln Phe His Thr Phe Leu Leu Thr Lys Glu Gly
                325                 330                 335
Ala Gly His Pro Pro Leu His Leu Arg Ser Glu His Gln Ala Gln Gln
            340                 345                 350
Asn Gln Ala Glu Phe Arg Met Gly Pro Val Thr Ser Ala His Val Gly
            355                 360                 365
Thr Tyr Arg Cys Tyr Ser Ser Leu Ser Ser Asn Pro Tyr Leu Leu Ser
370                 375                 380
Leu Pro Ser Asp Pro Leu Glu Leu Val Val Ser Glu Ala Ala Glu Thr
385                 390                 395                 400
Leu Ser Pro Ser Gln Asn Lys Thr Asp Ser Thr Thr Thr Ser Leu Gly
                405                 410                 415
Gln His Pro Gln Asp Tyr Thr Val Glu Asn
            420                 425

<210> SEQ ID NO 261
<211> LENGTH: 1320
<212> TYPE: DNA
<213> ORGANISM: Homo sapiens

<400> SEQUENCE: 261 atgacccca tcctcacggt cctgatctgt ctcgggctga gcctggaccc caggacccac        60
gtgcaggcag ggcccctccc caagcccacc ctctgggctg agccaggctc tgtgatcacc       120
```

```
caagggagtc ctgtgaccct caggtgtcag gggagcctgg agacgcagga gtaccatcta    180
tatagagaaa agaaaacagc actctggatt acacggatcc cacaggagct tgtgaagaag    240
ggccagttcc ccatcctatc catcacctgg gaacatgcag ggcggtattg ctgtatctat    300
ggcagccaca ctgcaggcct ctcagagagc agtgaccccc tggagctggt ggtgacagga    360
gcctacagca aacccaccct ctcagctctg cccagccctg tggtgacctc aggagggaat    420
gtgaccatcc agtgtgactc acaggtggca tttgatggct tcattctgtg taaggaagga    480
gaagatgaac acccacaatg cctgaactcc cattcccatg cccgtgggtc atcccgggcc    540
atcttctccg tgggccccgt gagcccaagt cgcaggtggt cgtacaggtg ctatggttat    600
gactcgcgcg ctccctatgt gtggtctcta cccagtgatc tcctggggct cctggtccca    660 ggtgttttcta agaagccatc actctcagtg cagccgggtc ctgtcgtggc ccctggggag    720
aagctgacct tccagtgtgg ctctgatgcc ggctacgaca gatttgttct gtacaaggag    780
tggggacgtg acttcctcca gcgcctggc cggcagcccc aggctgggct ctcccaggcc    840
aacttcaccc tgggccctgt gagccgctcc tacggggggca gtacacatg ctccggtgca    900 tacaacctct cctccgagtg gtcggccccc agcgaccccc tggacatcct gatcacagga    960
cagatccgtg ccagaccctt cctctccgtg cggccgggcc ccacagtggc ctcaggagag   1020
aacgtgaccc tgctgtgtca gtcacaggga gggatgcaca ctttccttttt gaccaaggag   1080 gggggcagctg attccccgct gcgtctaaaa tcaaagcgcc aatctcataa gtaccaggct   1140
gaattcccca tgagtcctgt gacctcggcc cacgcgggga cctacaggtg ctacggctca   1200
ctcagctcca cccctacct gctgactcac cccagtgacc cctggagct cgtggtctca   1260 ggagcagctg agaccctcag cccaccacaa aacaagtccg actccaaggc tggtgagtga   1320
```

<210> SEQ ID NO 262
<211> LENGTH: 439
<212> TYPE: PRT
<213> ORGANISM: Homo sapiens

<400> SEQUENCE: 262

```
Met Thr Pro Ile Leu Thr Val Leu Ile Cys Leu Gly Leu Ser Leu Asp
 1               5                  10                  15

Pro Arg Thr His Val Gln Ala Gly Pro Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Ser Leu Glu Thr Gln Glu Tyr His Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Leu Ser Ile Thr Trp Glu His Ala Gly Arg Tyr
                85                  90                  95

Cys Cys Ile Tyr Gly Ser His Thr Ala Gly Leu Ser Glu Ser Ser Asp
            100                 105                 110

Pro Leu Glu Leu Val Val Thr Gly Ala Tyr Ser Lys Pro Thr Leu Ser
        115                 120                 125

Ala Leu Pro Ser Pro Val Val Thr Ser Gly Gly Asn Val Thr Ile Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
```

```
                165                 170                 175
Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
            195                 200                 205

Ser Leu Pro Ser Asp Leu Leu Gly Leu Leu Val Pro Gly Val Ser Lys
            210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
            245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
            275                 280                 285

Arg Ser Tyr Gly Gly Gln Tyr Thr Cys Ser Gly Ala Tyr Asn Leu Ser
            290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Gly Pro Thr Val
            325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
            355                 360                 365

Leu Lys Ser Lys Arg Gln Ser His Lys Tyr Gln Ala Glu Phe Pro Met
            370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
            405                 410                 415

Leu Val Val Ser Gly Ala Ala Glu Thr Leu Ser Pro Pro Gln Asn Lys
            420                 425                 430

Ser Asp Ser Lys Ala Gly Glu
            435

<210> SEQ ID NO 263
<211> LENGTH: 416
<212> TYPE: PRT
<213> ORGANISM: Homo sapiens

<400> SEQUENCE: 263

Gly Pro Leu Pro Lys Pro Thr Leu Trp Ala Glu Pro Gly Ser Val Ile
1               5                   10                  15

Thr Gln Gly Ser Pro Val Thr Leu Arg Cys Gln Gly Ser Leu Glu Thr
            20                  25                  30

Gln Glu Tyr His Leu Tyr Arg Glu Lys Lys Thr Ala Leu Trp Ile Thr
            35                  40                  45

Arg Ile Pro Gln Glu Leu Val Lys Lys Gly Gln Phe Pro Ile Leu Ser
50                  55                  60

Ile Thr Trp Glu His Ala Gly Arg Tyr Cys Cys Ile Tyr Gly Ser His
65                  70                  75                  80

Thr Ala Gly Leu Ser Glu Ser Ser Asp Pro Leu Glu Leu Val Val Thr
            85                  90                  95
```

Gly Ala Tyr Ser Lys Pro Thr Leu Ser Ala Leu Pro Ser Pro Val Val
            100                 105                 110

Thr Ser Gly Gly Asn Val Thr Ile Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser His Ser His Ala Arg Gly Ser Ser Arg Ala Ile Phe Ser
145                 150                 155                 160

Val Gly Pro Val Ser Pro Ser Arg Arg Trp Ser Tyr Arg Cys Tyr Gly
                165                 170                 175

Tyr Asp Ser Arg Ala Pro Tyr Val Trp Ser Leu Pro Ser Asp Leu Leu
            180                 185                 190

Gly Leu Leu Val Pro Gly Val Ser Lys Lys Pro Ser Leu Ser Val Gln
        195                 200                 205

Pro Gly Pro Val Val Ala Pro Gly Glu Lys Leu Thr Phe Gln Cys Gly
    210                 215                 220

Ser Asp Ala Gly Tyr Asp Arg Phe Val Leu Tyr Lys Glu Trp Gly Arg
225                 230                 235                 240

Asp Phe Leu Gln Arg Pro Gly Arg Gln Pro Gln Ala Gly Leu Ser Gln
                245                 250                 255

Ala Asn Phe Thr Leu Gly Pro Val Ser Arg Ser Tyr Gly Gly Gln Tyr
            260                 265                 270

Thr Cys Ser Gly Ala Tyr Asn Leu Ser Ser Glu Trp Ser Ala Pro Ser
        275                 280                 285

Asp Pro Leu Asp Ile Leu Ile Thr Gly Gln Ile Arg Ala Arg Pro Phe
    290                 295                 300

Leu Ser Val Arg Pro Gly Pro Thr Val Ala Ser Gly Glu Asn Val Thr
305                 310                 315                 320

Leu Leu Cys Gln Ser Gln Gly Gly Met His Thr Phe Leu Leu Thr Lys
                325                 330                 335

Glu Gly Ala Ala Asp Ser Pro Leu Arg Leu Lys Ser Lys Arg Gln Ser
            340                 345                 350

His Lys Tyr Gln Ala Glu Phe Pro Met Ser Pro Val Thr Ser Ala His
        355                 360                 365

Ala Gly Thr Tyr Arg Cys Tyr Gly Ser Leu Ser Ser Asn Pro Tyr Leu
    370                 375                 380

Leu Thr His Pro Ser Asp Pro Leu Glu Leu Val Val Ser Gly Ala Ala
385                 390                 395                 400

Glu Thr Leu Ser Pro Pro Gln Asn Lys Ser Asp Ser Lys Ala Gly Glu
                405                 410                 415

<210> SEQ ID NO 264
<211> LENGTH: 1500
<212> TYPE: DNA
<213> ORGANISM: Homo sapiens

<400> SEQUENCE: 264
atgaccctca ttctcacaag cctgctcttc tttgggctga gcctgggccc caggacccgg      60
gtgcaggcag aaaacctact caaacccatc ctgtgggccg agccaggtcc cgtgatcacc     120
tggcataacc ccgtgaccat ctggtgtcag ggcaccctgg aggcccaggg gtaccgtctg     180
gataaagagg gaaactcaat gtcgaggcac atattaaaaa cactggagtc tgaaaacaag     240
gtcaaactct ccatcccatc catgatgtgg gaacatgcag ggcgatatca ctgttactat     300
cagagccctg caggctggtc agagcccagc gaccccctgg agctggtggt gacagcctac     360

```
agcagaccca ccctgtccgc actgccaagc cctgtggtga cctcaggagt gaacgtgacc    420
ctccggtgtg cctcacggct gggactgggc aggttcactc tgattgagga aggagaccac    480
aggctctcct ggaccctgaa ctcacaccaa cacaaccatg gaaagttcca ggccctgttc    540
cccatgggcc ccctgacctt cagcaacagg ggtacattca gatgctacgg ctatgaaaac    600
aacaccccat acgtgtggtc ggaacccagt gaccccctgc agctactggt gtcaggcgtg    660
tctaggaagc cctccctcct gaccctgcag ggccctgtcg tgaccccgg agagaatctg     720
accctccagt gtggctctga tgtcggctac atcagataca ctctgtacaa ggaggggcc     780
gatggcctcc cccagcgccc tggccggcag ccccaggctg gctctcccca ggccaacttc    840
accctgagcc ctgtgagccg ctcctacggg ggccagtaca gatgctacgg cgcacacaac    900
gtctcctccg agtggtcggc ccccagtgac ccctgata tcctgatcgc aggacagatc     960
tctgacagac cctccctctc agtgcagccg ggcccacgg tgacctcagg agagaaggtg     1020
accctgctgt gtcagtcatg ggacccgatg ttcactttcc ttctgaccaa ggagggggca    1080
gcccatcccc cgttgcgtct gagatcaatg tacggagctc ataagtacca ggctgaattc    1140
cccatgagtc ctgtgacctc agcccacgcg gggacctaca ggtgctacgg ctcacgcagc    1200
tccaaccct acctgctgtc tcaccccagt gagcccctgg agctcgtggt ctcaggagca     1260
actgagaccc tcaatccagc acaaaagaag tcagattcca agactgcccc acacctccag    1320
gattacacag tggagaatct catccgcatg ggtgtggctg gcttggtcct gctgttcctc    1380
gggattctgt tatttgaggc tcagcacagc cagagaagcc ccccaaggtg cagccaggag    1440
gcaaacagca gaaaggacaa tgcacccttc agagtggtgg agccttggga acagatctga    1500
```

<210> SEQ ID NO 265
<211> LENGTH: 499
<212> TYPE: PRT
<213> ORGANISM: Homo sapiens

<400> SEQUENCE: 265

```
Met Thr Leu Ile Leu Thr Ser Leu Leu Phe Phe Gly Leu Ser Leu Gly
1               5                   10                  15

Pro Arg Thr Arg Val Gln Ala Glu Asn Leu Pro Lys Pro Ile Leu Trp
                20                  25                  30

Ala Glu Pro Gly Pro Val Ile Thr Trp His Asn Pro Val Thr Ile Trp
            35                  40                  45

Cys Gln Gly Thr Leu Glu Ala Gln Gly Tyr Arg Leu Asp Lys Glu Gly
        50                  55                  60

Asn Ser Met Ser Arg His Ile Leu Lys Thr Leu Glu Ser Glu Asn Lys
65                  70                  75                  80

Val Lys Leu Ser Ile Pro Ser Met Met Trp Glu His Ala Gly Arg Tyr
                85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
        115                 120                 125

Pro Ser Pro Val Val Thr Ser Gly Val Asn Val Thr Leu Arg Cys Ala
    130                 135                 140

Ser Arg Leu Gly Leu Gly Arg Phe Thr Leu Ile Glu Glu Gly Asp His
145                 150                 155                 160

Arg Leu Ser Trp Thr Leu Asn Ser His Gln His Asn His Gly Lys Phe
                165                 170                 175
```

```
Gln Ala Leu Phe Pro Met Gly Pro Leu Thr Phe Ser Asn Arg Gly Thr
            180                 185                 190

Phe Arg Cys Tyr Gly Tyr Glu Asn Asn Thr Pro Tyr Val Trp Ser Glu
        195                 200                 205

Pro Ser Asp Pro Leu Gln Leu Leu Val Ser Gly Val Ser Arg Lys Pro
    210                 215                 220

Ser Leu Leu Thr Leu Gln Gly Pro Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
            260                 265                 270

Ala Gly Leu Ser Gln Ala Asn Phe Thr Leu Ser Pro Val Ser Arg Ser
        275                 280                 285

Tyr Gly Gly Gln Tyr Arg Cys Tyr Gly Ala His Asn Val Ser Ser Glu
    290                 295                 300

Trp Ser Ala Pro Ser Asp Pro Leu Asp Ile Leu Ile Ala Gly Gln Ile
305                 310                 315                 320

Ser Asp Arg Pro Ser Leu Ser Val Gln Pro Gly Pro Thr Val Thr Ser
                325                 330                 335

Gly Glu Lys Val Thr Leu Leu Cys Gln Ser Trp Asp Pro Met Phe Thr
            340                 345                 350

Phe Leu Leu Thr Lys Glu Gly Ala Ala His Pro Pro Leu Arg Leu Arg
        355                 360                 365

Ser Met Tyr Gly Ala His Lys Tyr Gln Ala Glu Phe Pro Met Ser Pro
    370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
            420                 425                 430

Ser Lys Thr Ala Pro His Leu Gln Asp Tyr Thr Val Glu Asn Leu Ile
        435                 440                 445

Arg Met Gly Val Ala Gly Leu Val Leu Leu Phe Leu Gly Ile Leu Leu
    450                 455                 460

Phe Glu Ala Gln His Ser Gln Arg Ser Pro Pro Arg Cys Ser Gln Glu
465                 470                 475                 480

Ala Asn Ser Arg Lys Asp Asn Ala Pro Phe Arg Val Val Glu Pro Trp
                485                 490                 495

Glu Gln Ile

<210> SEQ ID NO 266
<211> LENGTH: 423
<212> TYPE: PRT
<213> ORGANISM: Homo sapiens

<400> SEQUENCE: 266

Glu Asn Leu Pro Lys Pro Ile Leu Trp Ala Glu Pro Gly Pro Val Ile
1               5                   10                  15

Thr Trp His Asn Pro Val Thr Ile Trp Cys Gln Gly Thr Leu Glu Ala
            20                  25                  30

Gln Gly Tyr Arg Leu Asp Lys Glu Gly Asn Ser Met Ser Arg His Ile
        35                  40                  45
```

```
Leu Lys Thr Leu Glu Ser Glu Asn Lys Val Lys Leu Ser Ile Pro Ser
 50                  55                  60

Met Met Trp Glu His Ala Gly Arg Tyr His Cys Tyr Tyr Gln Ser Pro
 65                  70                  75                  80

Ala Gly Trp Ser Glu Pro Ser Asp Pro Leu Glu Leu Val Val Thr Ala
                 85                  90                  95

Tyr Ser Arg Pro Thr Leu Ser Ala Leu Pro Ser Pro Val Val Thr Ser
            100                 105                 110

Gly Val Asn Val Thr Leu Arg Cys Ala Ser Arg Leu Gly Leu Gly Arg
        115                 120                 125

Phe Thr Leu Ile Glu Glu Gly Asp His Arg Leu Ser Trp Thr Leu Asn
130                 135                 140

Ser His Gln His Asn His Gly Lys Phe Gln Ala Leu Phe Pro Met Gly
145                 150                 155                 160

Pro Leu Thr Phe Ser Asn Arg Gly Thr Phe Arg Cys Tyr Gly Tyr Glu
                165                 170                 175

Asn Asn Thr Pro Tyr Val Trp Ser Glu Pro Ser Asp Pro Leu Gln Leu
            180                 185                 190

Leu Val Ser Gly Val Ser Arg Lys Pro Ser Leu Leu Thr Leu Gln Gly
        195                 200                 205

Pro Val Val Thr Pro Gly Glu Asn Leu Thr Leu Gln Cys Gly Ser Asp
210                 215                 220

Val Gly Tyr Ile Arg Tyr Thr Leu Tyr Lys Glu Gly Ala Asp Gly Leu
225                 230                 235                 240

Pro Gln Arg Pro Gly Arg Gln Pro Gln Ala Gly Leu Ser Gln Ala Asn
                245                 250                 255

Phe Thr Leu Ser Pro Val Ser Arg Ser Tyr Gly Gly Tyr Arg Cys
            260                 265                 270

Tyr Gly Ala His Asn Val Ser Ser Glu Trp Ser Ala Pro Ser Asp Pro
        275                 280                 285

Leu Asp Ile Leu Ile Ala Gly Gln Ile Ser Asp Arg Pro Ser Leu Ser
290                 295                 300

Val Gln Pro Gly Pro Thr Val Thr Ser Gly Glu Lys Val Thr Leu Leu
305                 310                 315                 320

Cys Gln Ser Trp Asp Pro Met Phe Thr Phe Leu Leu Thr Lys Glu Gly
                325                 330                 335

Ala Ala His Pro Pro Leu Arg Leu Arg Ser Met Tyr Gly Ala His Lys
            340                 345                 350

Tyr Gln Ala Glu Phe Pro Met Ser Pro Val Thr Ser Ala His Ala Gly
        355                 360                 365

Thr Tyr Arg Cys Tyr Gly Ser Arg Ser Ser Asn Pro Tyr Leu Leu Ser
370                 375                 380

His Pro Ser Glu Pro Leu Glu Leu Val Val Ser Gly Ala Thr Glu Thr
385                 390                 395                 400

Leu Asn Pro Ala Gln Lys Lys Ser Asp Ser Lys Thr Ala Pro His Leu
                405                 410                 415

Gln Asp Tyr Thr Val Glu Asn
            420

<210> SEQ ID NO 267
<211> LENGTH: 900
<212> TYPE: DNA
<213> ORGANISM: Homo sapiens
```

<400> SEQUENCE: 267

```
atggcaccat ggtctcatcc atctgcacag ctgcagccag tgggaggaga cgccgtgagc      60
cctgccctca tggttctgct ctgcctcggg ctgagtctgg gccccaggac ccacgtgcag     120
gcagggaacc tctccaaagc caccctctgg gctgagccag gctctgtgat cagccggggg     180
aactctgtga ccatccggtg tcaggggacc ctggaggccc aggaataccg tctggttaaa     240
gagggaagcc cagaaccctg gacacacag aacccactgg agcccaagaa caaggccaga      300
ttctccatcc catccatgac agagcaccat gcagggagat accgctgtta ctactacagc     360
cctgcaggct ggtcagagcc cagcgacccc ctggagctgg tggtgacagg attctacaac     420
aaacccaccc tctcagccct gcccagtcct gtggtgacct caggagagaa cgtgaccctc     480
cagtgtggct cacggctgag attcgacagg ttcattctga ctgaggaagg agaccacaag     540
ctctcctgga ccttggactc acagctgacc cccagtgggc agttccaggc cctgttccct     600
gtgggccctg tgaccccag ccacaggtgg atgctcagat gctatggctc tcgcaggcat      660
atcctgcagg tatggtcaga acccagtgac ctcctggaga ttccggtctc aggagcagct     720
gataacctca gtccgtcaca aaacaagtct gactctggga ctgcctcaca ccttcaggat     780
tacgcagtag agaatctcat ccgcatgggc atggccggct tgatcctggt ggtccttggg     840
attctgatat ttcaggattg gcacagccag agaagccccc aagctgcagc tggaaggtga     900
```

<210> SEQ ID NO 268
<211> LENGTH: 299
<212> TYPE: PRT
<213> ORGANISM: Homo sapiens

<400> SEQUENCE: 268

```
Met Ala Pro Trp Ser His Pro Ser Ala Gln Leu Gln Pro Val Gly Gly
1               5                   10                  15

Asp Ala Val Ser Pro Ala Leu Met Val Leu Leu Cys Leu Gly Leu Ser
                20                  25                  30

Leu Gly Pro Arg Thr His Val Gln Ala Gly Asn Leu Ser Lys Ala Thr
            35                  40                  45

Leu Trp Ala Glu Pro Gly Ser Val Ile Ser Arg Gly Asn Ser Val Thr
        50                  55                  60

Ile Arg Cys Gln Gly Thr Leu Glu Ala Gln Glu Tyr Arg Leu Val Lys
65                  70                  75                  80

Glu Gly Ser Pro Glu Pro Trp Asp Thr Gln Asn Pro Leu Glu Pro Lys
                85                  90                  95

Asn Lys Ala Arg Phe Ser Ile Pro Ser Met Thr Glu His His Ala Gly
            100                 105                 110

Arg Tyr Arg Cys Tyr Tyr Tyr Ser Pro Ala Gly Trp Ser Glu Pro Ser
        115                 120                 125

Asp Pro Leu Glu Leu Val Val Thr Gly Phe Tyr Asn Lys Pro Thr Leu
    130                 135                 140

Ser Ala Leu Pro Ser Pro Val Val Thr Ser Gly Glu Asn Val Thr Leu
145                 150                 155                 160

Gln Cys Gly Ser Arg Leu Arg Phe Asp Arg Phe Ile Leu Thr Glu Glu
                165                 170                 175

Gly Asp His Lys Leu Ser Trp Thr Leu Asp Ser Gln Leu Thr Pro Ser
            180                 185                 190

Gly Gln Phe Gln Ala Leu Phe Pro Val Gly Pro Val Thr Pro Ser His
        195                 200                 205
```

```
Arg Trp Met Leu Arg Cys Tyr Gly Ser Arg Arg His Ile Leu Gln Val
    210                 215                 220

Trp Ser Glu Pro Ser Asp Leu Leu Glu Ile Pro Val Ser Gly Ala Ala
225                 230                 235                 240

Asp Asn Leu Ser Pro Ser Gln Asn Lys Ser Asp Ser Gly Thr Ala Ser
                245                 250                 255

His Leu Gln Asp Tyr Ala Val Glu Asn Leu Ile Arg Met Gly Met Ala
            260                 265                 270

Gly Leu Ile Leu Val Val Leu Gly Ile Leu Ile Phe Gln Asp Trp His
        275                 280                 285

Ser Gln Arg Ser Pro Gln Ala Ala Ala Gly Arg
    290                 295
```

<210> SEQ ID NO 269
<211> LENGTH: 227
<212> TYPE: PRT
<213> ORGANISM: Homo sapiens

<400> SEQUENCE: 269

```
Gly Asn Leu Ser Lys Ala Thr Leu Trp Ala Glu Pro Gly Ser Val Ile
1               5                   10                  15

Ser Arg Gly Asn Ser Val Thr Ile Arg Cys Gln Gly Thr Leu Glu Ala
            20                  25                  30

Gln Glu Tyr Arg Leu Val Lys Glu Gly Ser Pro Glu Pro Trp Asp Thr
        35                  40                  45

Gln Asn Pro Leu Glu Pro Lys Asn Lys Ala Arg Phe Ser Ile Pro Ser
    50                  55                  60

Met Thr Glu His His Ala Gly Arg Tyr Arg Cys Tyr Tyr Tyr Ser Pro
65                  70                  75                  80

Ala Gly Trp Ser Glu Pro Ser Asp Pro Leu Glu Leu Val Val Thr Gly
                85                  90                  95

Phe Tyr Asn Lys Pro Thr Leu Ser Ala Leu Pro Ser Pro Val Val Thr
            100                 105                 110

Ser Gly Glu Asn Val Thr Leu Gln Cys Gly Ser Arg Leu Arg Phe Asp
        115                 120                 125

Arg Phe Ile Leu Thr Glu Glu Gly Asp His Lys Leu Ser Trp Thr Leu
    130                 135                 140

Asp Ser Gln Leu Thr Pro Ser Gly Gln Phe Gln Ala Leu Phe Pro Val
145                 150                 155                 160

Gly Pro Val Thr Pro Ser His Arg Trp Met Leu Arg Cys Tyr Gly Ser
                165                 170                 175

Arg Arg His Ile Leu Gln Val Trp Ser Glu Pro Ser Asp Leu Leu Glu
            180                 185                 190

Ile Pro Val Ser Gly Ala Ala Asp Asn Leu Ser Pro Ser Gln Asn Lys
        195                 200                 205

Ser Asp Ser Gly Thr Ala Ser His Leu Gln Asp Tyr Ala Val Glu Asn
    210                 215                 220

Leu Ile Arg
225
```

<210> SEQ ID NO 270
<211> LENGTH: 1446
<212> TYPE: DNA
<213> ORGANISM: Homo sapiens

<400> SEQUENCE: 270

```
atgacccca cccctcgcagc cctgctctgc ctagggctga gtctgggccc caggacccac    60
gtgcaggcag ggcccttccc caaacccacc ctctgggctg agccaggctc tgtgatcagc   120
tggggagcc ccgtgaccat ctggtgtcag gggagcctgg aggcccagga gtaccgactg   180
gataaagagg gaagcccaga gccctgggac agaaataacc cactggaacc caagaacaag   240
gccagattct ccatcccatc cataacagag caccatgcgg ggagataccg ctgccactat   300
tacagctctg caggctggtc agagcccagc gaccccctgg agctggtgat gacaggagcc   360
tatagcaaac ccaccctctc agccctgccc agccctgtgg tggcctcagg ggggaatatg   420
accctccaat gtggctcaca aagggatat caccattttg ttctgatgaa ggaaggagaa   480
caccagctcc cccggaccct ggactcacag cagctccaca gtgggggggtt ccaggccctg   540
ttccctgtgg ccccgtgaa ccccagccac aggtggaggt tcacatgcta ttactattat   600
atgaacaccc cccgggtgtg gtcccacccc agtgaccccc tggagattct gccctcaggc   660
gtgtctagga agccctccct cctgaccctg cagggccctg tcctggcccc tgggcagagc   720
ctgaccctcc agtgtggctc tgatgtcggc tacgacagat ttgttctgta taaggagggg   780
gaacgtgact tcctccagcg ccctggccag cagccccagg ctgggctctc ccaggccaac   840
ttcaccctgg ccctgtgag cccctcccac gggggccagt acaggtgcta tggtgcacac   900
aacctctcct ccgagtggtc ggccccagc gaccccctga catcctgat ggcaggacag   960
atctatgaca ccgtctccct gtcagcacag ccgggcccca cagtggcctc aggagagaac  1020
gtgaccctgc tgtgtcagtc atggtggcag tttgacactt tccttctgac caaagaaggg  1080
gcagcccatc ccccactgcg tctgagatca atgtacggag ctcataagta ccaggctgaa  1140
ttccccatga gtcctgtgac ctcagcccac gcggggacct acaggtgcta cggctcatac  1200
agctccaacc cccacctgct gtctttcccc agtgagcccc tggaactcat ggtctcagga  1260
cactctggag gctccagcct cccacccaca gggccgccct ccacacctgc tcacacgcc   1320
aaggattaca cagtggagaa tctcatccgc atgggcatgg caggcttggt cctggtgttc  1380
ctcgggattc tgttatttga ggctcagcac agccagagaa accccaaga tgcagccggg  1440
aggtga                                                              1446
```

<210> SEQ ID NO 271
<211> LENGTH: 481
<212> TYPE: PRT
<213> ORGANISM: Homo sapiens

<400> SEQUENCE: 271

```
Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Gln Leu Asp Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Gln His His Ala Gly Arg Tyr
                85                  90                  95

Arg Cys His Tyr Tyr Ser Ser Ala Gly Trp Ser Glu Pro Ser Asp Pro
            100                 105                 110
```

```
Leu Glu Leu Val Met Thr Gly Phe Tyr Asn Lys Pro Thr Leu Ser Ala
            115                 120                 125

Leu Pro Ser Pro Val Val Ala Ser Gly Gly Asn Met Thr Leu Arg Cys
        130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Leu His Ser Gly Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Thr Asn Thr Pro Arg Val Trp Ser
        195                 200                 205

His Pro Ser Asp Pro Leu Glu Ile Leu Pro Ser Gly Val Ser Arg Lys
210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Arg Gly Tyr Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Ser Ser Leu Pro Pro Thr Gly Pro
            420                 425                 430

Pro Ser Thr Pro Ala Ser His Ala Lys Asp Tyr Thr Val Glu Asn Leu
        435                 440                 445

Ile Arg Met Gly Met Ala Gly Leu Val Leu Val Phe Leu Gly Ile Leu
450                 455                 460

Leu Phe Glu Ala Gln His Ser Gln Arg Asn Pro Gln Asp Ala Ala Gly
465                 470                 475                 480

Arg

<210> SEQ ID NO 272
<211> LENGTH: 424
<212> TYPE: PRT
<213> ORGANISM: Homo sapiens

<400> SEQUENCE: 272
```

```
Gly Pro Phe Pro Lys Pro Thr Leu Trp Ala Glu Pro Gly Ser Val Ile
1               5                   10                  15

Ser Trp Gly Ser Pro Val Thr Ile Trp Cys Gln Gly Ser Leu Glu Ala
            20                  25                  30

Gln Glu Tyr Gln Leu Asp Lys Glu Gly Ser Pro Glu Pro Leu Asp Arg
        35                  40                  45

Asn Asn Pro Leu Glu Pro Lys Asn Lys Ala Arg Phe Ser Ile Pro Ser
    50                  55                  60

Met Thr Gln His His Ala Gly Arg Tyr Arg Cys His Tyr Tyr Ser Ser
65                  70                  75                  80

Ala Gly Trp Ser Glu Pro Ser Asp Pro Leu Glu Leu Val Met Thr Gly
                85                  90                  95

Phe Tyr Asn Lys Pro Thr Leu Ser Ala Leu Pro Ser Pro Val Val Ala
            100                 105                 110

Ser Gly Gly Asn Met Thr Leu Arg Cys Gly Ser Gln Lys Gly Tyr His
        115                 120                 125

His Phe Val Leu Met Lys Glu Gly Glu His Gln Leu Pro Arg Thr Leu
    130                 135                 140

Asp Ser Gln Gln Leu His Ser Gly Gly Phe Gln Ala Leu Phe Pro Val
145                 150                 155                 160

Gly Pro Val Thr Pro Ser His Arg Trp Arg Phe Thr Cys Tyr Tyr Tyr
                165                 170                 175

Tyr Thr Asn Thr Pro Arg Val Trp Ser His Pro Ser Asp Pro Leu Glu
            180                 185                 190

Ile Leu Pro Ser Gly Val Ser Arg Lys Pro Ser Leu Leu Thr Leu Gln
        195                 200                 205

Gly Pro Val Leu Ala Pro Gly Gln Ser Leu Thr Leu Gln Cys Gly Ser
210                 215                 220

Asp Val Gly Tyr Asp Arg Phe Val Leu Tyr Lys Glu Gly Glu Arg Asp
225                 230                 235                 240

Phe Leu Gln Arg Pro Gly Gln Gln Pro Gln Ala Gly Leu Ser Gln Ala
            245                 250                 255

Asn Phe Thr Leu Gly Pro Val Ser Pro Ser His Gly Gly Gln Tyr Arg
        260                 265                 270

Cys Tyr Gly Ala His Asn Leu Ser Ser Glu Trp Ser Ala Pro Ser Asp
    275                 280                 285

Pro Leu Asn Ile Leu Met Ala Gly Gln Ile Tyr Asp Thr Val Ser Leu
290                 295                 300

Ser Ala Gln Pro Gly Pro Thr Val Ala Ser Gly Glu Asn Val Thr Leu
305                 310                 315                 320

Leu Cys Gln Ser Arg Gly Tyr Phe Asp Thr Phe Leu Leu Thr Lys Glu
            325                 330                 335

Gly Ala Ala His Pro Pro Leu Arg Leu Arg Ser Met Tyr Gly Ala His
        340                 345                 350

Lys Tyr Gln Ala Glu Phe Pro Met Ser Pro Val Thr Ser Ala His Ala
    355                 360                 365

Gly Thr Tyr Arg Cys Tyr Gly Ser Tyr Ser Ser Asn Pro His Leu Leu
370                 375                 380

Ser Phe Pro Ser Glu Pro Leu Glu Leu Met Val Ser Gly His Ser Gly
385                 390                 395                 400

Gly Ser Ser Leu Pro Pro Thr Gly Pro Pro Ser Thr Pro Ala Ser His
            405                 410                 415

Ala Lys Asp Tyr Thr Val Glu Asn
```

<210> SEQ ID NO 273
<211> LENGTH: 675
<212> TYPE: DNA
<213> ORGANISM: Mus musculus

<400> SEQUENCE: 273

```
atggctttgc tgatctcgct tcctggaggg actccagcca tggctcaggt cctgcttctg      60
ctctcatcag gctgtctgca tgctggaaat tcagaaagat acaacagaaa aaatggcttt     120
ggggtcaacc aacctgaacg ctgctctgga gtccagggtg gctccatcga catccccttc     180
tccttctatt tcccctggaa gttggccaag gatccacaga tgagcatagc ctggaaatgg     240
aaggatttcc atggggaagt catctacaac tcctccctgc ctttcataca tgagcacttc     300
aagggccggc tcatcctgaa ctggacacag gtcagacat ctggagtcct cagaatcctg     360
aacttgaagg agtctgacca agcccagtac tttagtcgag ttaatctgca gtcgacagaa     420
ggcatgaagt tgtggcagtc aattcctgga acccaactca acgtgaccca agcactcaac     480
accaccatga ggagcccctt catcgtcacc tctgaattca ccacagctgg cctggagcac     540
acaagcgacc agaggaatcc ttcactgatg aacctgggag ccatggtcac gatgctcctg     600
gctaaagttt tggtcatagt cctagtctat ggatggatga tcttcctgag gtggaagcaa     660
aggccagcac actaa                                                      675
```

<210> SEQ ID NO 274
<211> LENGTH: 224
<212> TYPE: PRT
<213> ORGANISM: Mus musculus

<400> SEQUENCE: 274

```
Met Ala Leu Leu Ile Ser Leu Pro Gly Gly Thr Pro Ala Met Ala Gln
1               5                   10                  15

Val Leu Leu Leu Ser Ser Gly Cys Leu His Ala Gly Asn Ser Glu
            20                  25                  30

Arg Tyr Asn Arg Lys Asn Gly Phe Gly Val Asn Gln Pro Glu Arg Cys
        35                  40                  45

Ser Gly Val Gln Gly Gly Ser Ile Asp Ile Pro Phe Ser Phe Tyr Phe
    50                  55                  60

Pro Trp Lys Leu Ala Lys Asp Pro Gln Met Ser Ile Ala Trp Lys Trp
65                  70                  75                  80

Lys Asp Phe His Gly Glu Val Ile Tyr Asn Ser Ser Leu Pro Phe Ile
                85                  90                  95

His Glu His Phe Lys Gly Arg Leu Ile Leu Asn Trp Thr Gln Gly Gln
            100                 105                 110

Thr Ser Gly Val Leu Arg Ile Leu Asn Leu Lys Glu Ser Asp Gln Ala
        115                 120                 125

Gln Tyr Phe Ser Arg Val Asn Leu Gln Ser Thr Glu Gly Met Lys Leu
    130                 135                 140

Trp Gln Ser Ile Pro Gly Thr Gln Leu Asn Val Thr Gln Ala Leu Asn
145                 150                 155                 160

Thr Thr Met Arg Ser Pro Phe Ile Val Thr Ser Glu Phe Thr Thr Ala
                165                 170                 175

Gly Leu Glu His Thr Ser Asp Gln Arg Asn Pro Ser Leu Met Asn Leu
            180                 185                 190

Gly Ala Met Val Thr Met Leu Leu Ala Lys Val Leu Val Ile Val Leu
```

```
              195                 200                 205
Val Tyr Gly Trp Met Ile Phe Leu Arg Trp Lys Gln Arg Pro Ala His
            210                 215                 220
```

<210> SEQ ID NO 275
<211> LENGTH: 24
<212> TYPE: DNA
<213> ORGANISM: Mus musculus

<400> SEQUENCE: 275
aggtggaagc aaaggccagc acac                                           24

<210> SEQ ID NO 276
<211> LENGTH: 8
<212> TYPE: PRT
<213> ORGANISM: Mus musculus

<400> SEQUENCE: 276

```
Arg Trp Lys Gln Arg Pro Ala His
1               5
```

<210> SEQ ID NO 277
<211> LENGTH: 900
<212> TYPE: DNA
<213> ORGANISM: Artificial Sequence
<220> FEATURE:
<223> OTHER INFORMATION: Synthetic

<400> SEQUENCE: 277

| | |
|---|---|
| atggatccca aaggatccct ttcctggaga atacttctgt ttctctccct ggcttttgag | 60 |
| ttgagctacg gactcgagca ggcagggccc ctccccaaac ccaccctctg ggctgagcca | 120 |
| ggctctgtga tcagctgggg gaactctgtg accatctggt gtcaggggac cctggaggct | 180 |
| cgggagtacc gtctggataa agaggaaagc ccagcaccct gggacagaca gaacccactg | 240 |
| gagcccaaga acaaggccag attctccatc ccatccatga cagaggacta tgcagggaga | 300 |
| taccgctgtt actatcgcag ccctgtaggc tggtcacagc ccagtgaccc cctggagctg | 360 |
| gtgatgacag gagcctacag taaacccacc ctttcagccc tgccgagtcc tcttgtgacc | 420 |
| tcaggaaaga gcgtgaccct gctgtgtcag tcacggagcc aatggacac tttcttctg | 480 |
| atcaaggagc gggcagccca tccctactg catctgagat cagagcacgg agctcagcag | 540 |
| caccaggctg aattccccat gagtcctgtg acctcagtgc acgggggac ctacaggtgc | 600 |
| ttcagctcac acggcttctc ccactacctg ctgtcacacc ccagtgaccc cctggagctc | 660 |
| atagtctcag gatccttgga gggtcccagg ccctcaccca aaggtccgt ctcaacagct | 720 |
| gcaggccctg aggaccagcc cctcatgcct acagggtcag tccccacag tggtctgaga | 780 |
| aggcactggg agctcgagct gggagccatg gtcacgatgc tcctggctaa agttttggtc | 840 |
| atagtcctag tctatggatg gatgatcttc ctgaggtgga agcaaaggcc agcacactaa | 900 |

<210> SEQ ID NO 278
<211> LENGTH: 299
<212> TYPE: PRT
<213> ORGANISM: Artificial Sequence
<220> FEATURE:
<223> OTHER INFORMATION: Synthetic peptide

<400> SEQUENCE: 278

```
Met Asp Pro Lys Gly Ser Leu Ser Trp Arg Ile Leu Leu Phe Leu Ser
1               5                   10                  15
```

```
Leu Ala Phe Glu Leu Ser Tyr Gly Leu Glu Gln Ala Gly Pro Leu Pro
                20                  25                  30

Lys Pro Thr Leu Trp Ala Glu Pro Gly Ser Val Ile Ser Trp Gly Asn
            35                  40                  45

Ser Val Thr Ile Trp Cys Gln Gly Thr Leu Glu Ala Arg Glu Tyr Arg
50                  55                  60

Leu Asp Lys Glu Glu Ser Pro Ala Pro Trp Asp Arg Gln Asn Pro Leu
65                  70                  75                  80

Glu Pro Lys Asn Lys Ala Arg Phe Ser Ile Pro Ser Met Thr Glu Asp
                85                  90                  95

Tyr Ala Gly Arg Tyr Arg Cys Tyr Tyr Arg Ser Pro Val Gly Trp Ser
            100                 105                 110

Gln Pro Ser Asp Pro Leu Glu Leu Val Met Thr Gly Ala Tyr Ser Lys
        115                 120                 125

Pro Thr Leu Ser Ala Leu Pro Ser Pro Leu Val Thr Ser Gly Lys Ser
    130                 135                 140

Val Thr Leu Leu Cys Gln Ser Arg Ser Pro Met Asp Thr Phe Leu Leu
145                 150                 155                 160

Ile Lys Glu Arg Ala Ala His Pro Leu Leu His Leu Arg Ser Glu His
                165                 170                 175

Gly Ala Gln Gln His Gln Ala Glu Phe Pro Met Ser Pro Val Thr Ser
            180                 185                 190

Val His Gly Gly Thr Tyr Arg Cys Phe Ser Ser His Gly Phe Ser His
        195                 200                 205

Tyr Leu Leu Ser His Pro Ser Asp Pro Leu Glu Leu Ile Val Ser Gly
    210                 215                 220

Ser Leu Glu Asp Pro Arg Pro Ser Pro Thr Arg Ser Val Ser Thr Ala
225                 230                 235                 240

Ala Gly Pro Glu Asp Gln Pro Leu Met Pro Thr Gly Ser Val Pro His
                245                 250                 255

Ser Gly Leu Arg Arg His Trp Glu Leu Glu Leu Gly Ala Met Val Thr
            260                 265                 270

Met Leu Leu Ala Lys Val Leu Val Ile Val Leu Val Tyr Gly Trp Met
        275                 280                 285

Ile Phe Leu Arg Trp Lys Gln Arg Pro Ala His
    290                 295

<210> SEQ ID NO 279
<211> LENGTH: 18
<212> TYPE: DNA
<213> ORGANISM: Mus musculus

<400> SEQUENCE: 279
tgaaaatgaa aatgaaaa                                                    18

<210> SEQ ID NO 280
<211> LENGTH: 954
<212> TYPE: DNA
<213> ORGANISM: Homo sapiens

<400> SEQUENCE: 280
atgaaggttc tgtgggctgc gttgctggtc acattcctgg caggatgcca ggccaaggtg      60
gagcaagcgg tggagacaga gccggagccc gagctgcgcc agcagaccga gtggcagagc     120
ggccagcgct gggaactggc actgggtcgc ttttgggatt acctgcgctg ggtgcagaca     180
ctgtctgagc aggtgcagga ggagctgctc agctcccagg tcacccagga actgaggcg      240
```

```
ctgatggacg agaccatgaa ggagttgaag gcctacaaat cggaactgga ggaacaactg    300
accccggtgg cggaggagac gcgggcacgg ctgtccaagg agctgcaggc ggcgcaggcc    360
cggctgggcg cggacatgga ggacgtgtgc ggccgcctgg tgcagtaccg cggcgaggtg    420
caggccatgc tcggccagag caccgaggag ctgcgggtgc gcctcgcctc ccacctgcgc    480
aagctgcgta gcggctcct ccgcgatgcc gatgacctgc agaagcgcct ggcagtgtac    540
caggccgggg cccgcgaggg cgccgagcgc ggcctcagcg ccatccgcga gcgcctgggg    600
cccctggtgg aacagggccg cgtgcgggcc gccactgtgg gctccctggc cggccagccg    660
ctacaggagc gggcccaggc ctggggcgag cggctgcgcg cgcggatgga ggagatgggc    720
agccggaccc gcgaccgcct ggacgaggtg aaggagcagg tggcggaggt gcgcgccaag    780
ctggaggagc aggcccagca gatacgcctg caggccgagg ccttccaggc ccgcctcaag    840
agctggttcg agcccctggt ggaagacatg cagcgccagt gggccgggct ggtggagaag    900
gtgcaggctg ccgtgggcac cagcgccgcc cctgtgccca gcgacaatca ctga          954
```

<210> SEQ ID NO 281
<211> LENGTH: 317
<212> TYPE: PRT
<213> ORGANISM: Homo sapiens

<400> SEQUENCE: 281

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
```

```
            245                 250                 255
Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 282
<211> LENGTH: 299
<212> TYPE: PRT
<213> ORGANISM: Homo sapiens

<400> SEQUENCE: 282

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295
```

<210> SEQ ID NO 283
<211> LENGTH: 7
<212> TYPE: PRT
<213> ORGANISM: Artificial sequence
<220> FEATURE:
<223> OTHER INFORMATION: Synthetic peptide

<400> SEQUENCE: 283

```
Pro Glu Asp Gln Pro Leu Met
1               5
```

<210> SEQ ID NO 284
<211> LENGTH: 6
<212> TYPE: PRT
<213> ORGANISM: Artificial sequence
<220> FEATURE:
<223> OTHER INFORMATION: Synthetic peptide

<400> SEQUENCE: 284

```
Pro Thr Gly Ser Val Pro
1               5
```

<210> SEQ ID NO 285
<211> LENGTH: 12
<212> TYPE: PRT
<213> ORGANISM: Artificial sequence
<220> FEATURE:
<223> OTHER INFORMATION: Synthetic peptide

<400> SEQUENCE: 285

```
Gly Phe Ser His Tyr Leu Leu Ser His Pro Ser Asp
1               5                   10
```

<210> SEQ ID NO 286
<211> LENGTH: 12
<212> TYPE: PRT
<213> ORGANISM: Artificial sequence
<220> FEATURE:
<223> OTHER INFORMATION: Synthetic peptide

<400> SEQUENCE: 286

```
Leu Pro Ser Pro Leu Val Thr Ser Gly Lys Ser Val
1               5                   10
```

<210> SEQ ID NO 287
<211> LENGTH: 12
<212> TYPE: PRT
<213> ORGANISM: Artificial sequence
<220> FEATURE:
<223> OTHER INFORMATION: Synthetic peptide

<400> SEQUENCE: 287

```
Gly Ser Leu Glu Asp Pro Arg Pro Ser Pro Thr Arg
1               5                   10
```

<210> SEQ ID NO 288
<211> LENGTH: 12
<212> TYPE: PRT
<213> ORGANISM: Artificial sequence
<220> FEATURE:
<223> OTHER INFORMATION: Synthetic peptide

<400> SEQUENCE: 288

```
Ala Gln Gln His Gln Ala Glu Phe Pro Met Ser Pro
1               5                   10
```

```
<210> SEQ ID NO 289
<211> LENGTH: 12
<212> TYPE: PRT
<213> ORGANISM: Artificial sequence
<220> FEATURE:
<223> OTHER INFORMATION: Synthetic peptide

<400> SEQUENCE: 289

Pro Glu Pro Leu Asp Arg Asn Asn Pro Leu Glu Pro
1               5                   10

<210> SEQ ID NO 290
<211> LENGTH: 12
<212> TYPE: PRT
<213> ORGANISM: Artificial sequence
<220> FEATURE:
<223> OTHER INFORMATION: Synthetic peptide

<400> SEQUENCE: 290

Pro Asp Ser Val Ile Thr Gln Gly Ser Pro Val Thr
1               5                   10

<210> SEQ ID NO 291
<211> LENGTH: 12
<212> TYPE: PRT
<213> ORGANISM: Artificial sequence
<220> FEATURE:
<223> OTHER INFORMATION: Synthetic peptide

<400> SEQUENCE: 291

Pro Ser Pro Val Val Ala Ser Gly Gly Asn Met Thr
1               5                   10

<210> SEQ ID NO 292
<211> LENGTH: 12
<212> TYPE: PRT
<213> ORGANISM: Artificial sequence
<220> FEATURE:
<223> OTHER INFORMATION: Synthetic peptide

<400> SEQUENCE: 292

Thr Phe Leu Leu Thr Lys Ala Gly Ala Ala Asp Ala
1               5                   10

<210> SEQ ID NO 293
<211> LENGTH: 12
<212> TYPE: PRT
<213> ORGANISM: Artificial sequence
<220> FEATURE:
<223> OTHER INFORMATION: Synthetic peptide

<400> SEQUENCE: 293

Asp Ala Pro Leu Arg Leu Arg Ser Ile His Glu Tyr
1               5                   10

<210> SEQ ID NO 294
<211> LENGTH: 12
<212> TYPE: PRT
<213> ORGANISM: Artificial sequence
<220> FEATURE:
<223> OTHER INFORMATION: Synthetic peptide

<400> SEQUENCE: 294

Asp Pro Leu Glu Ile Leu Pro Ser Gly Val Ser Arg
1               5                   10

<210> SEQ ID NO 295
```

```
<211> LENGTH: 21
<212> TYPE: DNA
<213> ORGANISM: Artificial sequence
<220> FEATURE:
<223> OTHER INFORMATION: Synthetic primer

<400> SEQUENCE: 295
gaacgactag ttaggcgtgt a                                            21

<210> SEQ ID NO 296
<211> LENGTH: 20
<212> TYPE: DNA
<213> ORGANISM: Artificial sequence
<220> FEATURE:
<223> OTHER INFORMATION: Synthetic primer

<400> SEQUENCE: 296
tgttactatc gcagccctgt                                              20

<210> SEQ ID NO 297
<211> LENGTH: 20
<212> TYPE: DNA
<213> ORGANISM: Artificial sequence
<220> FEATURE:
<223> OTHER INFORMATION: Synthetic primer

<400> SEQUENCE: 297
gtaggtcccc ccgtgcactg                                              20

<210> SEQ ID NO 298
<211> LENGTH: 20
<212> TYPE: DNA
<213> ORGANISM: Artificial sequence
<220> FEATURE:
<223> OTHER INFORMATION: Synthetic primer

<400> SEQUENCE: 298
cctgtgacct cagtgcacgg                                              20

<210> SEQ ID NO 299
<211> LENGTH: 60
<212> TYPE: PRT
<213> ORGANISM: Artificial sequence
<220> FEATURE:
<223> OTHER INFORMATION: Synthetic peptide

<400> SEQUENCE: 299

Gly Thr Leu Glu Ala Arg Glu Tyr Arg Leu Asp Lys Glu Ser Pro
 1               5                  10                  15

Ala Pro Trp Asp Arg Gln Asn Pro Leu Glu Pro Lys Asn Lys Ala Arg
            20                  25                  30

Phe Ser Ile Pro Ser Met Thr Glu Asp Tyr Ala Gly Tyr Arg Cys
        35                  40                  45

Tyr Tyr Arg Ser Pro Val Gly Trp Ser Gln Pro Ser
    50                  55                  60

<210> SEQ ID NO 300
<211> LENGTH: 61
<212> TYPE: PRT
<213> ORGANISM: Artificial sequence
<220> FEATURE:
<223> OTHER INFORMATION: Synthetic peptide

<400> SEQUENCE: 300

Gly Gly Gln Glu Thr Gln Glu Tyr Arg Leu Tyr Arg Glu Lys Lys Thr
```

```
                1               5                   10                  15
Ala Leu Trp Ile Thr Arg Ile Pro Gln Glu Leu Val Lys Lys Gly Gln
                20                  25                  30

Phe Pro Ile Pro Ser Ile Thr Trp Glu His Ala Gly Arg Tyr Arg Cys
                35                  40                  45

Tyr Tyr Gly Ser Asp Thr Ala Gly Arg Ser Glu Ser Ser
    50                  55                  60
```

<210> SEQ ID NO 301
<211> LENGTH: 60
<212> TYPE: PRT
<213> ORGANISM: Artificial sequence
<220> FEATURE:
<223> OTHER INFORMATION: Synthetic peptide

<400> SEQUENCE: 301

```
Gly Ser Leu Glu Ala Gln Glu Tyr Arg Leu Tyr Arg Glu Lys Lys Ser
1               5                   10                  15

Ala Ser Trp Ile Thr Arg Ile Arg Pro Glu Leu Val Lys Asn Gly Gln
                20                  25                  30

Phe His Ile Pro Ser Ile Thr Trp Glu His Thr Gly Arg Tyr Gly Cys
                35                  40                  45

Gln Tyr Tyr Ser Arg Ala Arg Trp Ser Glu Leu Ser
    50                  55                  60
```

<210> SEQ ID NO 302
<211> LENGTH: 60
<212> TYPE: PRT
<213> ORGANISM: Artificial sequence
<220> FEATURE:
<223> OTHER INFORMATION: Synthetic peptide

<400> SEQUENCE: 302

```
Gly Ser Leu Glu Ala Gln Glu Tyr Gln Leu Asp Lys Glu Gly Ser Pro
1               5                   10                  15

Glu Pro Trp Asp Arg Asn Asn Pro Leu Glu Pro Lys Asn Lys Ala Arg
                20                  25                  30

Phe Ser Ile Pro Ser Met Thr Gln His His Ala Gly Arg Tyr Arg Cys
                35                  40                  45

His Tyr Tyr Ser Ser Ala Gly Trp Ser Glu Pro Ser
    50                  55                  60
```

<210> SEQ ID NO 303
<211> LENGTH: 60
<212> TYPE: PRT
<213> ORGANISM: Artificial sequence
<220> FEATURE:
<223> OTHER INFORMATION: Synthetic peptide

<400> SEQUENCE: 303

```
Gly Pro Leu Glu Thr Glu Glu Tyr Arg Leu Asp Lys Glu Gly Leu Pro
1               5                   10                  15

Trp Ala Arg Lys Arg Gln Asn Pro Leu Glu Pro Gly Ala Lys Ala Lys
                20                  25                  30

Phe His Ile Pro Ser Thr Val Tyr Asp Ser Ala Gly Arg Tyr Arg Cys
                35                  40                  45

Tyr Tyr Glu Thr Pro Ala Gly Trp Ser Glu Pro Ser
    50                  55                  60
```

<210> SEQ ID NO 304

<211> LENGTH: 40
<212> TYPE: PRT
<213> ORGANISM: Artificial sequence
<220> FEATURE:
<223> OTHER INFORMATION: Synthetic peptide

<400> SEQUENCE: 304

Ser Leu Glu Gly Pro Arg Pro Ser Pro Thr Arg Ser Val Ser Thr Ala
1               5                   10                  15

Ala Gly Pro Glu Asp Gln Pro Leu Met Pro Thr Gly Ser Val Pro His
            20                  25                  30

Ser Gly Leu Arg Arg His Trp Glu
        35                  40

<210> SEQ ID NO 305
<211> LENGTH: 39
<212> TYPE: PRT
<213> ORGANISM: Artificial sequence
<220> FEATURE:
<223> OTHER INFORMATION: Synthetic peptide

<400> SEQUENCE: 305

Pro Ser Gly Gly Pro Ser Ser Pro Thr Thr Gly Pro Thr Ser Thr Ser
1               5                   10                  15

Gly Pro Glu Asp Gln Pro Leu Thr Pro Thr Gly Ser Asp Pro Gln Ser
            20                  25                  30

Gly Leu Gly Arg His Leu Gly
        35

<210> SEQ ID NO 306
<211> LENGTH: 40
<212> TYPE: PRT
<213> ORGANISM: Artificial sequence
<220> FEATURE:
<223> OTHER INFORMATION: Synthetic peptide

<400> SEQUENCE: 306

Pro Ser Met Gly Ser Ser Pro Pro Thr Gly Pro Ile Ser Thr Pro
1               5                   10                  15

Ala Gly Pro Glu Asp Gln Pro Leu Thr Pro Thr Gly Ser Asp Pro Gln
            20                  25                  30

Ser Gly Leu Gly Arg His Leu Gly
        35                  40

<210> SEQ ID NO 307
<211> LENGTH: 23
<212> TYPE: PRT
<213> ORGANISM: Artificial sequence
<220> FEATURE:
<223> OTHER INFORMATION: Synthetic peptide

<400> SEQUENCE: 307

His Ser Gly Gly Ser Ser Leu Pro Pro Thr Gly Pro Pro Ser Thr Pro
1               5                   10                  15

Gly Leu Gly Arg Tyr Leu Glu
            20

<210> SEQ ID NO 308
<211> LENGTH: 39
<212> TYPE: PRT
<213> ORGANISM: Artificial sequence
<220> FEATURE:
<223> OTHER INFORMATION: Synthetic peptide

```
<400> SEQUENCE: 308

Pro Ser Gly Asp Pro Ser Leu Ser Pro Thr Gly Ser Thr Pro Thr Pro
1               5                   10                  15

Gly Pro Glu Asp Gln Pro Leu Thr Pro Thr Gly Leu Asp Pro Gln Ser
                20                  25                  30

Gly Leu Gly Arg His Leu Gly
            35
```